US010800833B2

(12) United States Patent
Jantz et al.

(10) Patent No.: US 10,800,833 B2
(45) Date of Patent: *Oct. 13, 2020

(54) CO-STIMULATORY DOMAINS FOR USE IN GENETICALLY-MODIFIED CELLS

(71) Applicant: Precision BioSciences, Inc., Durham, NC (US)

(72) Inventors: Derek Jantz, Durham, NC (US); Aaron Martin, Carrboro, NC (US); Daniel T. MacLeod, Durham, NC (US)

(73) Assignee: Precision BioSciences, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/600,074

(22) Filed: Oct. 11, 2019

(65) Prior Publication Data

US 2020/0031904 A1    Jan. 30, 2020

Related U.S. Application Data

(63) Continuation of application No. 16/339,699, filed as application No. PCT/US2017/055133 on Oct. 4, 2017.

(60) Provisional application No. 62/556,199, filed on Sep. 8, 2017, provisional application No. 62/501,475, filed on May 4, 2017, provisional application No. 62/403,880, filed on Oct. 4, 2016.

(51) Int. Cl.
| | |
|---|---|
| *C07K 14/705* | (2006.01) |
| *C07K 19/00* | (2006.01) |
| *C07K 16/30* | (2006.01) |
| *C12N 15/62* | (2006.01) |
| *C12N 15/86* | (2006.01) |
| *C12N 5/10* | (2006.01) |
| *A61K 35/12* | (2015.01) |
| *C07K 14/715* | (2006.01) |
| *C07K 14/725* | (2006.01) |
| *C07K 16/28* | (2006.01) |
| *A61P 35/00* | (2006.01) |
| *A61K 35/17* | (2015.01) |
| *C12N 5/0783* | (2010.01) |
| *C12N 7/00* | (2006.01) |
| *C12N 9/90* | (2006.01) |
| *A61K 38/00* | (2006.01) |
| *A61K 39/00* | (2006.01) |

(52) U.S. Cl.
CPC .......... *C07K 14/7151* (2013.01); *A61K 35/17* (2013.01); *A61P 35/00* (2018.01); *C07K 14/7051* (2013.01); *C07K 14/70517* (2013.01); *C07K 14/70521* (2013.01); *C07K 14/70578* (2013.01); *C07K 16/2803* (2013.01); *C12N 5/0636* (2013.01); *C12N 7/00* (2013.01); *C12N 9/90* (2013.01); *C12Y 502/01008* (2013.01); *A61K 38/00* (2013.01); *A61K 2039/505* (2013.01); *C07K 2317/622* (2013.01); *C07K 2319/00* (2013.01); *C07K 2319/02* (2013.01); *C07K 2319/03* (2013.01); *C07K 2319/30* (2013.01); *C07K 2319/33* (2013.01); *C12N 2501/2302* (2013.01); *C12N 2740/15043* (2013.01); *C12N 2750/14143* (2013.01)

(58) Field of Classification Search
None
See application file for complete search history.

(56) References Cited

U.S. PATENT DOCUMENTS

| | | |
|---|---|---|
| 4,873,192 A | 10/1989 | Kunkel |
| 5,350,674 A | 9/1994 | Boenisch et al. |
| 5,585,362 A | 12/1996 | Wilson et al. |
| 5,789,538 A | 8/1998 | Rebar et al. |
| 5,925,523 A | 7/1999 | Dove et al. |
| 5,994,136 A | 11/1999 | Naldini et al. |
| 6,007,988 A | 12/1999 | Choo et al. |
| 6,013,453 A | 1/2000 | Choo et al. |
| 6,013,516 A | 1/2000 | Verma et al. |
| 6,015,832 A | 1/2000 | Baker, Jr. et al. |
| 6,200,759 B1 | 3/2001 | Dove et al. |
| 6,326,193 B1 | 12/2001 | Liu et al. |
| 6,506,803 B1 | 1/2003 | Baker, Jr. et al. |
| 6,559,189 B2 | 5/2003 | Baker, Jr. et al. |
| 6,635,676 B2 | 10/2003 | Baker, Jr. et al. |
| 8,399,645 B2 | 3/2013 | Campana et al. |
| 9,605,049 B2 | 3/2017 | Campana et al. |
| 9,834,590 B2 | 12/2017 | Campana et al. |
| 9,856,322 B2 | 1/2018 | Campana et al. |

(Continued)

FOREIGN PATENT DOCUMENTS

| | | |
|---|---|---|
| WO | WO 95/19431 A1 | 7/1995 |
| WO | WO 96/06166 A1 | 2/1996 |

(Continued)

OTHER PUBLICATIONS

U.S. Appl. No. 16/339,699, filed Apr. 4, 2019, Jantz et al.

(Continued)

*Primary Examiner* — Ilia I Ouspenski
(74) *Attorney, Agent, or Firm* — Wolf, Greenfield & Sacks, P.C.

(57) ABSTRACT

The present disclosure provides novel co-stimulatory domains useful in genetically-modified cells to promote cell proliferation and/or promote cytokine secretion after antigen recognition. For example, disclosed herein are genetically-modified cells comprising a chimeric antigen receptor or an inducible regulatory construct incorporating the co-stimulatory domains disclosed herein. Also disclosed herein are plasmids and viral vectors comprising a nucleic acid sequence encoding the co-stimulatory domains, and methods of administering compositions comprising the novel co-stimulatory domains to subjects in order to reduce the symptoms, progression, or occurrence of disease, such as cancer.

23 Claims, 32 Drawing Sheets

Specification includes a Sequence Listing.

(56) References Cited

U.S. PATENT DOCUMENTS

| | | |
|---|---|---|
| 2002/0045667 A1 | 4/2002 | Baker, Jr. et al. |
| 2003/0232410 A1 | 12/2003 | Liljedahl et al. |
| 2004/0043041 A1 | 3/2004 | Baker, Jr. et al. |
| 2005/0026157 A1 | 2/2005 | Baltimore et al. |
| 2005/0064474 A1 | 3/2005 | Urnov et al. |
| 2005/0208489 A1 | 9/2005 | Carroll et al. |
| 2006/0188987 A1 | 8/2006 | Guschin et al. |
| 2011/0145940 A1 | 6/2011 | Voytas et al. |
| 2013/0117869 A1 | 5/2013 | Duchateau et al. |
| 2017/0283482 A1 | 10/2017 | Campana et al. |
| 2018/0118845 A1 | 5/2018 | Campana et al. |
| 2019/0233500 A1* | 8/2019 | Jantz .................. C07K 14/7051 |

FOREIGN PATENT DOCUMENTS

| | | |
|---|---|---|
| WO | WO 98/53057 A1 | 11/1998 |
| WO | WO 98/54311 A1 | 12/1998 |
| WO | WO 00/27878 A1 | 5/2000 |
| WO | WO 01/29058 A1 | 4/2001 |
| WO | WO 01/60970 A2 | 8/2001 |
| WO | WO 01/88197 A2 | 11/2001 |
| WO | WO 01/96584 A2 | 12/2001 |
| WO | WO 02/12514 A2 | 2/2002 |
| WO | WO 02/099084 A2 | 12/2002 |
| WO | WO 2007/014275 A2 | 2/2007 |
| WO | WO 2007/047859 A2 | 4/2007 |
| WO | WO 2010/079430 A1 | 7/2010 |
| WO | WO 2011/041093 A1 | 4/2011 |
| WO | WO 2013/063419 A2 | 5/2013 |
| WO | WO 2016/016341 A1 | 2/2016 |

OTHER PUBLICATIONS

PCT/US2017/055133, Jan. 22, 2018, International Search Report and Written Opinion.

PCT/US2017/055133, Apr. 18, 2019, International Preliminary Report on Patentability.

International Search Report and Written Opinion for Application No. PCT/US2017/055133 dated Jan. 22, 2018.

International Preliminary Report on Patentability for Application No. PCT/US2017/055133 dated Apr. 18, 2019.

Altschul et al., Basic local alignment search tool. J Mol Biol. Oct. 5, 1990;215(3):403-10.

Altschul et al., Gapped BLAST and PSI-BLAST: a new generation of protein database search programs. Nucleic Acids Res. Sep. 1, 1997;25(17):3389-402.

Boch et al., Breaking the code of DNA binding specificity of TAL-type III effectors. Science. Dec. 11, 2009;326(5959):1509-12. doi: 10.1126/science.1178811.

Cahill et al., Mechanisms of eukaryotic DNA double strand break repair. Front Biosci. May 1, 2006;11:1958-76.

Cheng et al., Dendrimers as drug carriers: applications in different routes of drug administration. J Pharm Sci. Jan. 2008;97(1):123-43.

Christian et al., Targeting DNA double-strand breaks with TAL effector nucleases. Genetics. Oct. 2010;186(2):757-61. doi: 10.1534/genetics.110.120717. Epub Jul. 26, 2010.

Cots et al., Helper dependent adenovirus vectors: progress and future prospects. Curr Gene Ther. Oct. 2013;13(5):370-81.

Database Accession No. AZZ24509 "Sus scrofa 4-1BB receptor (CD137) variant 2 sequence, SEQ ID 4", dated Oct. 25, 2012. 1 page.

Database Accession No. BAN89557 "Human 4-1BB ligand, SEQ ID 19", dated Jun. 20, 2013. 1 page.

Dull et al., A third-generation lentivirus vector with a conditional packaging system. J Virol. Nov. 1998;72(11):8463-71.

Ellebrecht et al., Reengineering chimeric antigen receptor T cells for targeted therapy of autoimmune disease. Science. Jul. 8, 2016;353(6295):179-84. doi: 10.1126/science.aaf6756. Epub Jun. 30, 2016.

Gish et al., Identification of protein coding regions by database similarity search. Nat Genet. Mar. 1993;3(3):266-72.

Jiang et al., Cationic core-shell liponanoparticles for ocular gene delivery. Biomaterials. Oct. 2012;33(30):7621-30. doi: 10.1016/j.biomaterials.2012.06.079. Epub Jul. 11, 2012.

Karvelis et al, Methods for decoding Cas9 protospacer adjacent motif (PAM) sequences: A brief overview. Methods. May 15, 2017;121-122:3-8. doi: 10.1016/j.ymeth.2017.03.006. Epub Mar. 24, 2017.

Kunkel et al., Rapid and efficient site-specific mutagenesis without phenotypic selection. Methods Enzymol. 1987;154:367-82.

Kunkel, Rapid and efficient site-specific mutagenesis without phenotypic selection. Proc Natl Acad Sci U S A. Jan. 1985;82(2):488-92.

Linsley et al., Coexpression and functional cooperation of CTLA-4 and CD28 on activated T lymphocytes. J Exp Med. Dec. 1, 1992;176(6):1595-604.

Madden et al., Applications of network BLAST server. Methods Enzymol. 1996;266:131-41.

Mastorakos et al., Hydroxyl PAMAM dendrimer-based gene vectors for transgene delivery to human retinal pigment epithelial cells. Nanoscale. Mar. 7, 2015;7(9):3845-56. doi: 10.1039/c4nr04284k.

McCarty et al., Self-complementary recombinant adeno-associated virus (scAAV) vectors promote efficient transduction independently of DNA synthesis. Gene Ther. Aug. 2001;8(16):1248-54.

Mishra et al., Recent applications of liposomes in ophthalmic drug delivery. J Drug Deliv. 2011;2011:863734. doi: 10.1155/2011/863734. Epub Mar. 1, 2011.

Moscou et al., A simple cipher governs DNA recognition by TAL effectors. Science. Dec. 11, 2009;326(5959):1501. doi: 10.1126/science.1178817.

Naldini et al., In vivo gene delivery and stable transduction of nondividing cells by a lentiviral vector. Science. Apr. 12, 1996;272(5259):263-7.

Naldini, Lentiviruses as gene transfer agents for delivery to non-dividing cells. Curr Opin Biotechnol. Oct. 1998;9(5):457-63.

Rosenberg et al., Use of tumor-infiltrating lymphocytes and interleukin-2 in the immunotherapy of patients with metastatic melanoma. A preliminary report. N Engl J Med. Dec. 22, 1988;319(25):1676-80.

Sanchez-Paulete et al., Deciphering CD137 (4-1BB) signaling in T-cell costimulation for translation into successful cancer immunotherapy. Eur J Immunol. Mar. 2016;46(3):513-22. doi: 10.1002/eji.201445388. Epub Feb. 9, 2016.

Sequence 6 from Patent WO 2011/041093, Database Accession No. JA314238, dated May 9, 2011. 1 page.

Sequence 8 from Patent WO 2016/016341, Database Accession No. LQ101275, dated Feb. 22, 2016. 1 page.

Sharma et al., Formulation and optimization of polymeric nanoparticles for intranasal delivery of lorazepam using Box-Behnken design: in vitro and in vivo evaluation. Biomed Res Int. 2014;2014:156010. doi: 10.1155/2014/156010. Epub Jul. 14, 2014.

Sharma et al., Next generation delivery system for proteins and genes of therapeutic purpose: why and how? Biomed Res Int. 2014;2014:327950. doi: 10.1155/2014/327950. Epub Jul. 15, 2014.

Tamboli et al., Polymeric vectors for ocular gene delivery. Ther Deliv. Apr. 2011;2(4):523-36. doi: 10.4155/tde.11.20. Author manuscript.

Tong et al., Eye drop delivery of nano-polymeric micelle formulated genes with cornea-specific promoters. J Gene Med. Nov. 2007;9(11):956-66.

Vannucci et al., Viral vectors: a look back and ahead on gene transfer technology. New Microbiol. Jan. 2013;36(1):1-22. Epub Jan. 1, 2013.

Vinay et al., 4-1BB (CD137), an inducible costimulatory receptor, as a specific target for cancer therapy. BMB Rep. Mar. 2014;47(3):122-9.

Zhang et al., A greedy algorithm for aligning DNA sequences. J Comput Biol. Feb.-Apr. 2000;7(1-2):203-14.

Zufferey et al., Multiply attenuated lentiviral vector achieves efficient gene delivery in vivo. Nat Biotechnol. Sep. 1997;15(9):871-5.

(56) References Cited

OTHER PUBLICATIONS

Zuris et al., Cationic lipid-mediated delivery of proteins enables efficient protein-based genome editing in vitro and in vivo. Nat Biotechnol. Jan. 2015;33(1):73-80. doi: 10.1038/nbt.3081. Epub Oct. 30, 2014.

* cited by examiner

| Domain | | | | | | | | | | | | | | TRAF2 | | | | | | | TRAF1 | | | SEQ ID NO: |
|---|---|---|---|---|---|---|---|---|---|---|---|---|---|---|---|---|---|---|---|---|---|---|---|---|
| Novel1 | K | H | S | R | K | F | V | H | L | L | K | R | P | F | I | K | T | T | I | G | A | A | Q | M | E | D | A | S | C | R | P | Q | E | E | E | G | E | C | D | L | 5 |
| Novel3 | K | W | G | R | K | L | L | Y | L | F | K | R | P | F | A | Q | P | I | R | T | A | Q | E | E | D | A | S | C | R | F | P | E | E | E | G | N | C | E | I | 6 |
| Novel5 | K | H | S | R | K | I | I | E | L | L | K | N | P | F | M | K | P | T | N | S | A | Q | E | E | D | A | S | C | R | F | P | Q | E | E | E | G | D | C | D | L | 7 |
| Novel6 | K | A | S | R | K | A | A | A | A | A | K | S | P | F | A | S | P | A | S | S | A | Q | E | E | D | A | S | C | R | A | P | S | E | E | E | G | S | C | E | L | 8 |

FIGURE 1

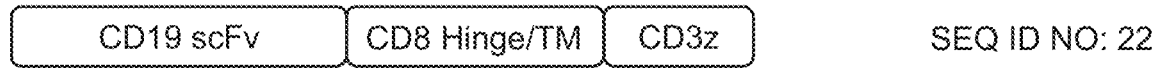
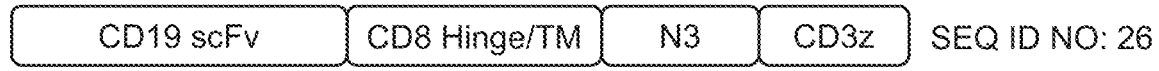
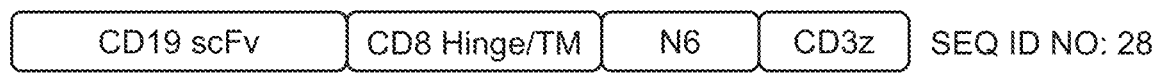
FIGURE 2

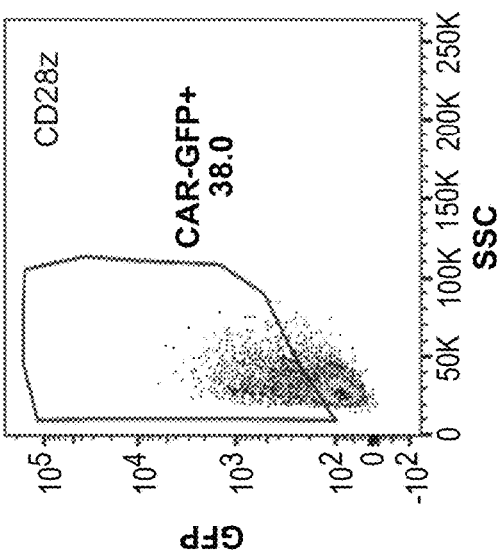
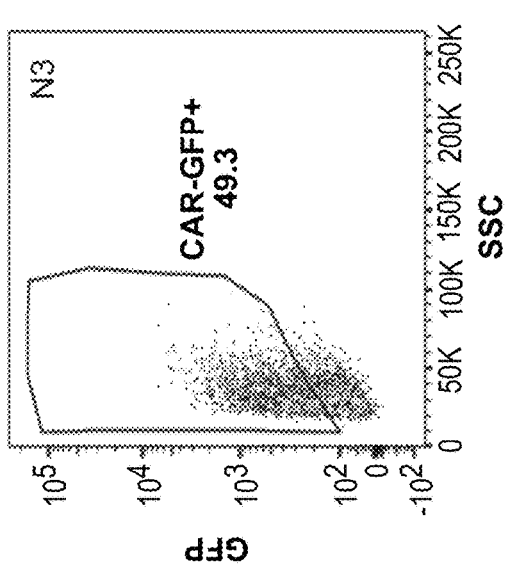
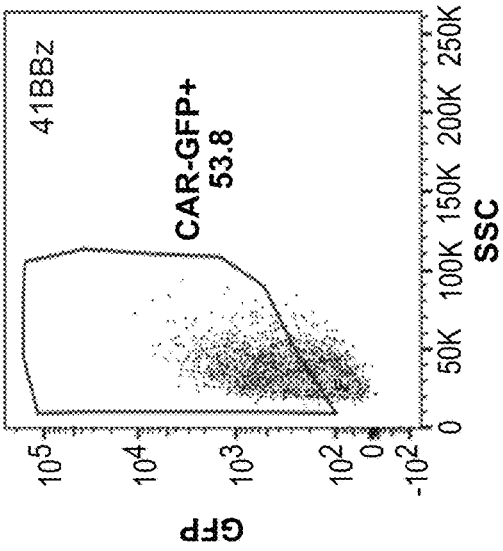
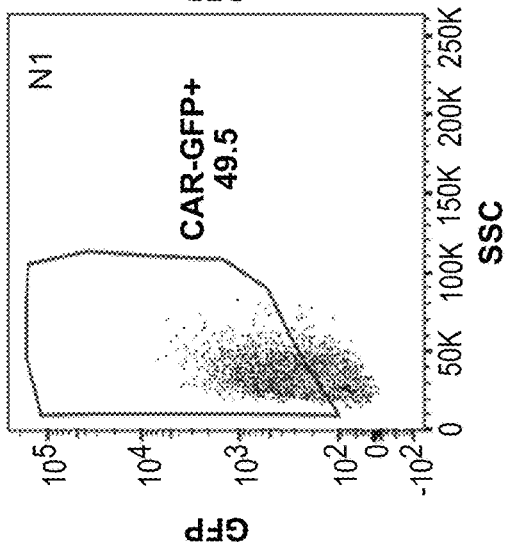
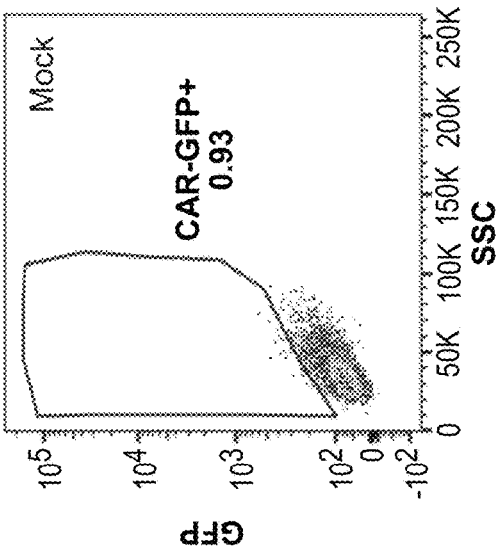
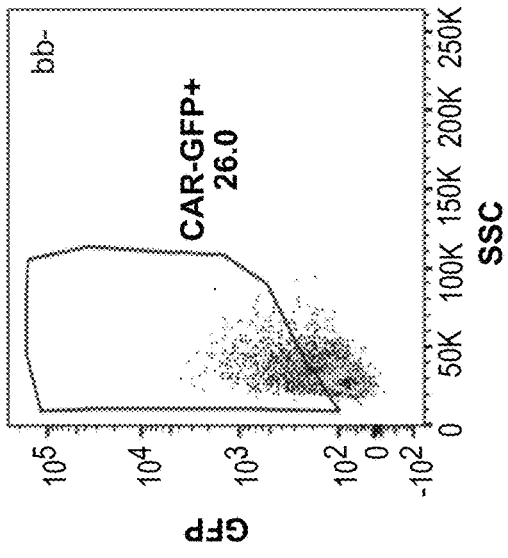
FIGURE 3

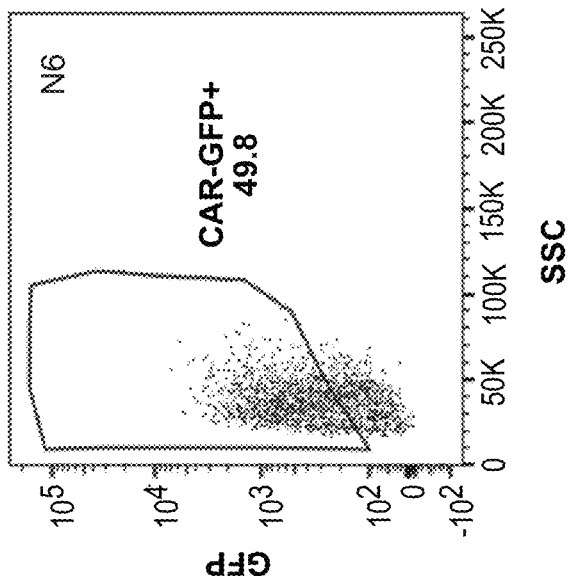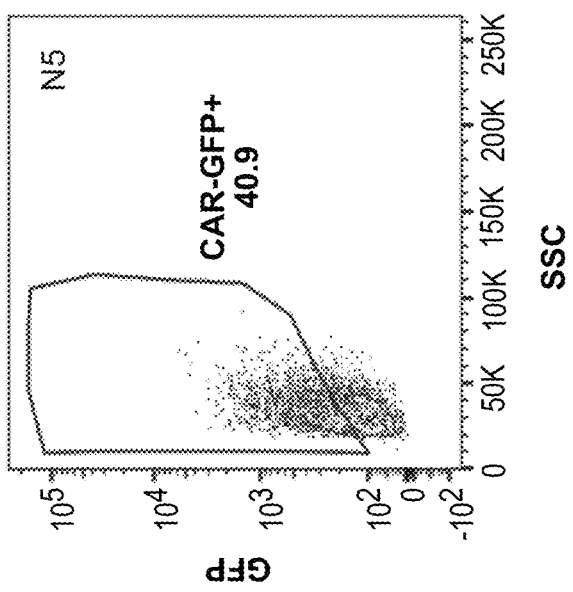

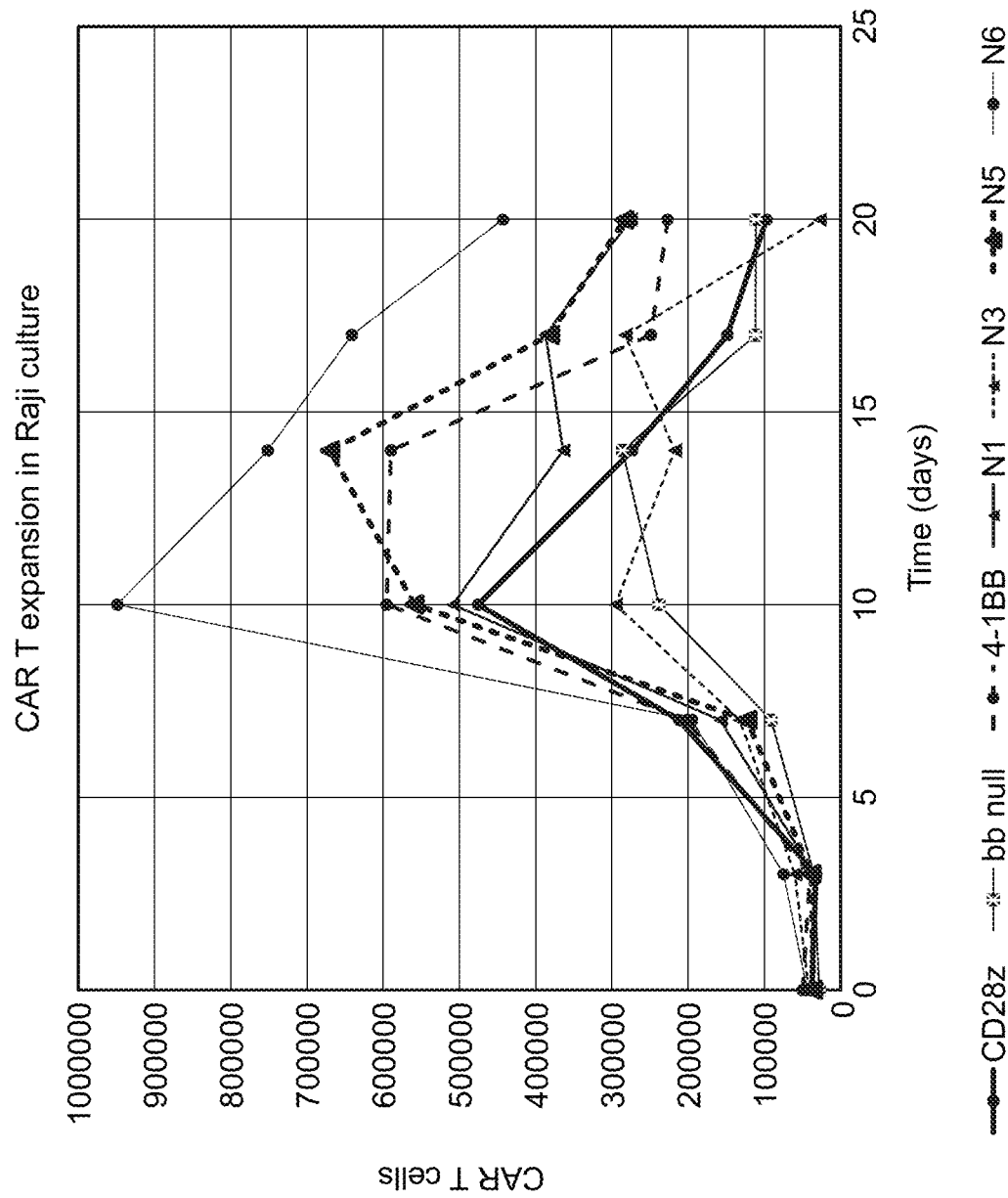

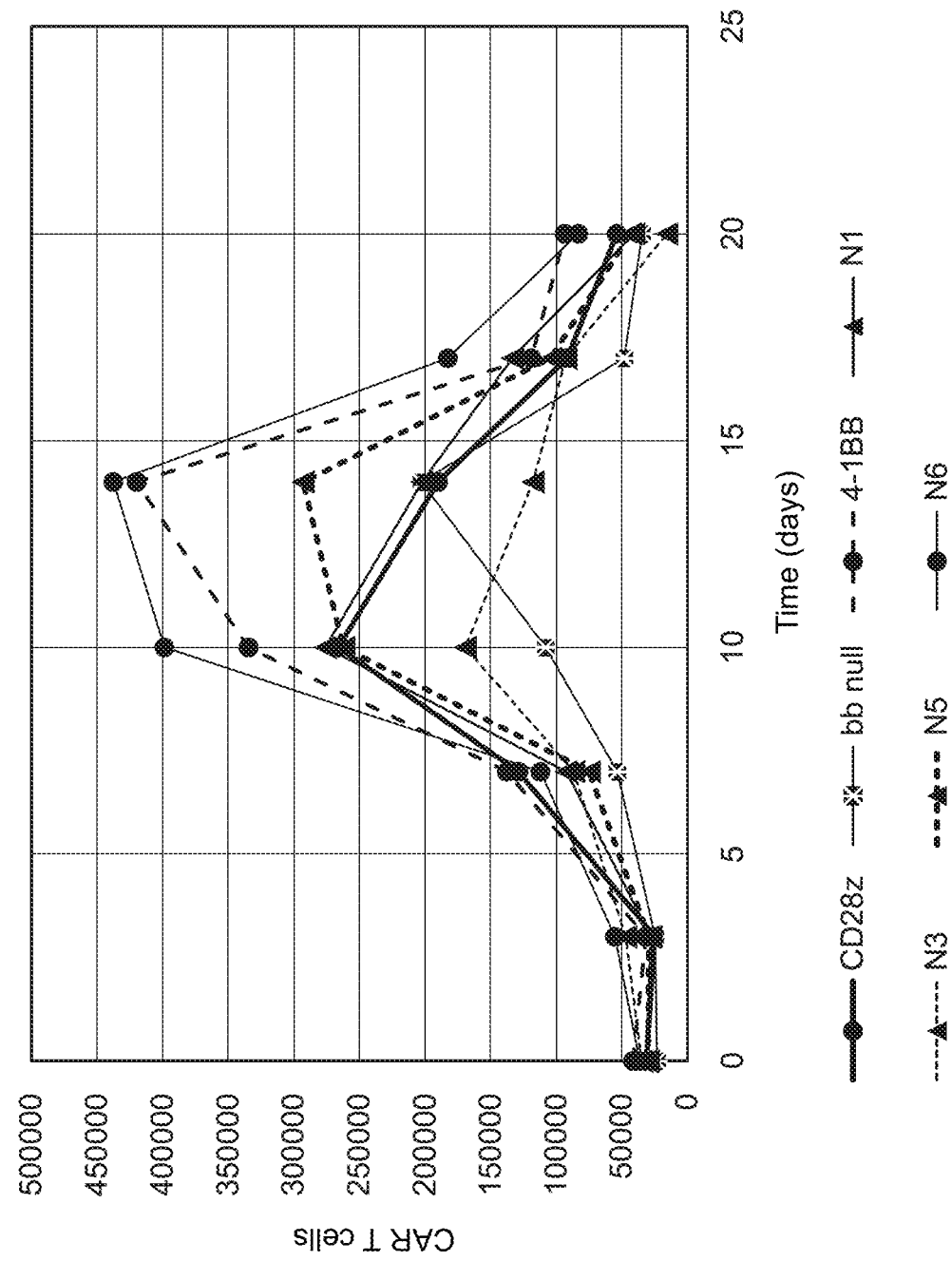

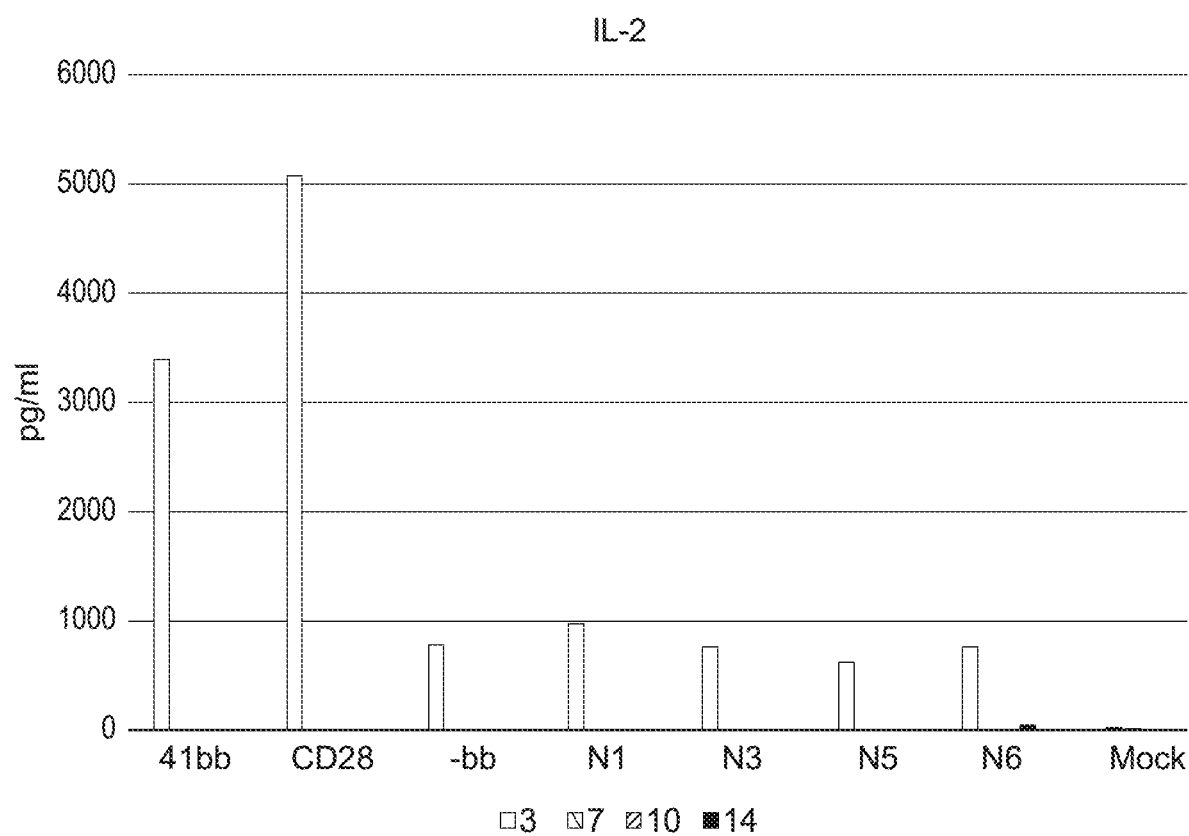

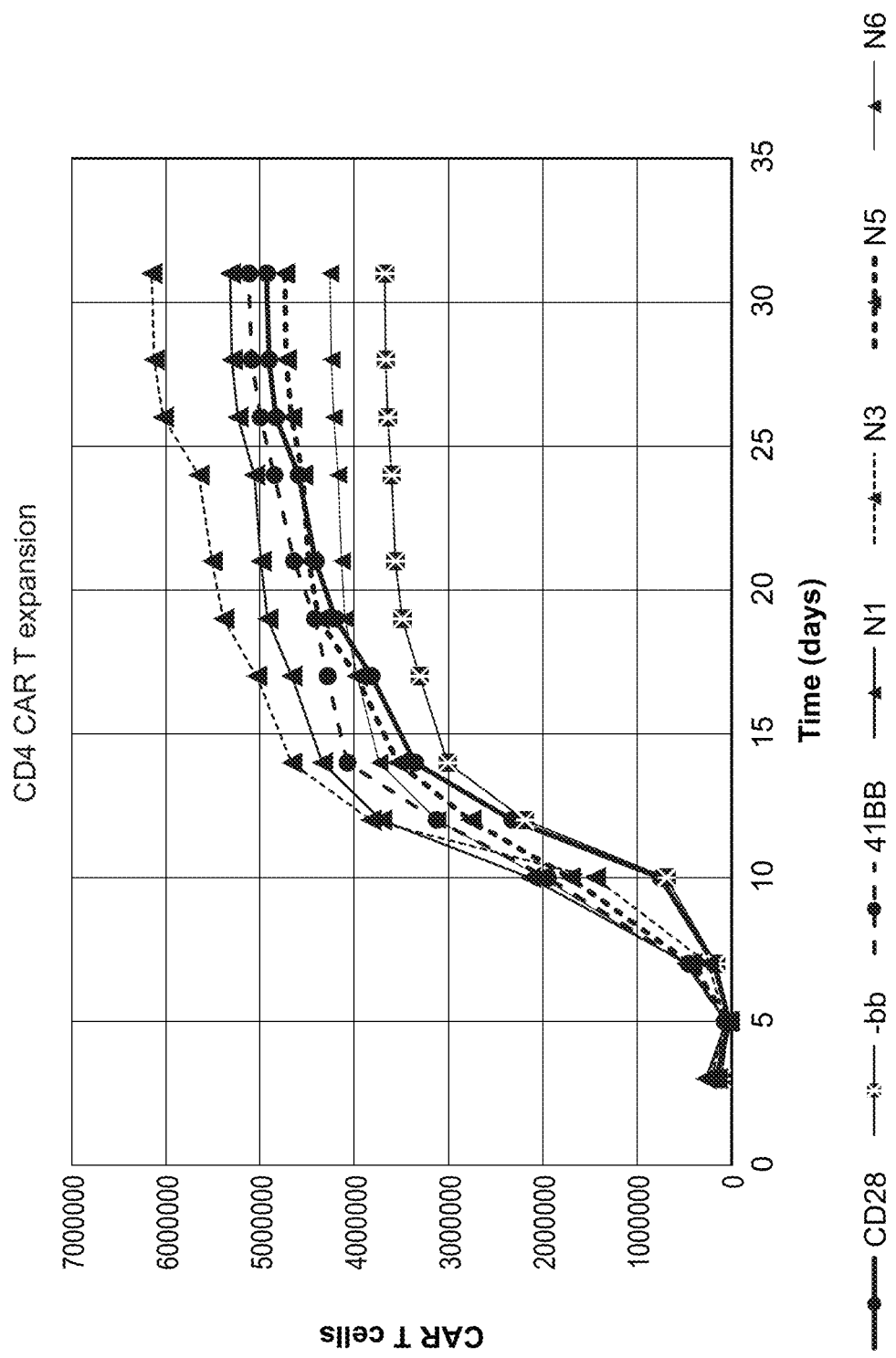

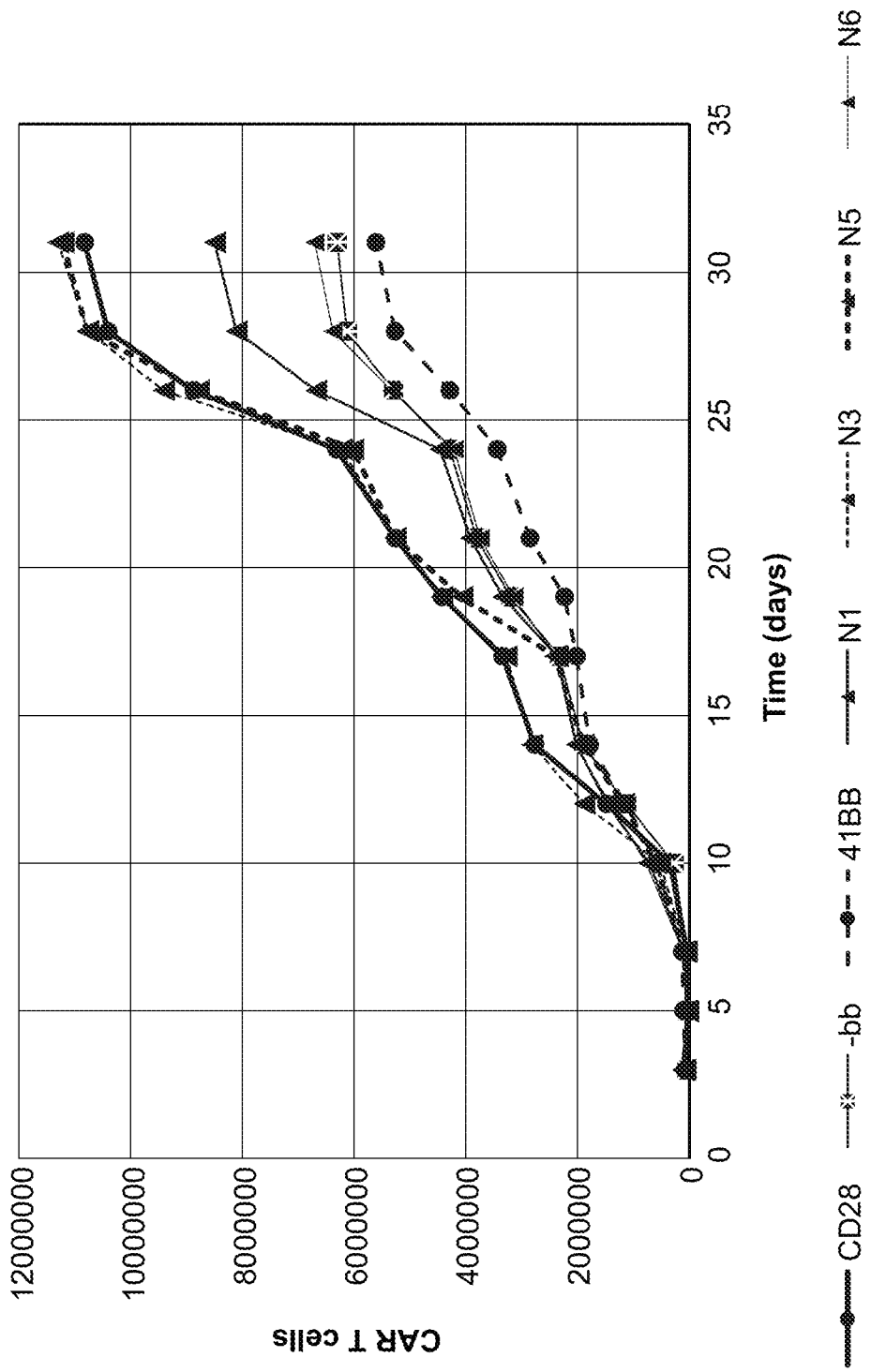

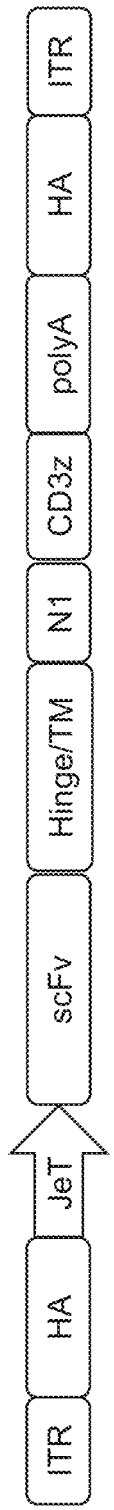
FIGURE 7

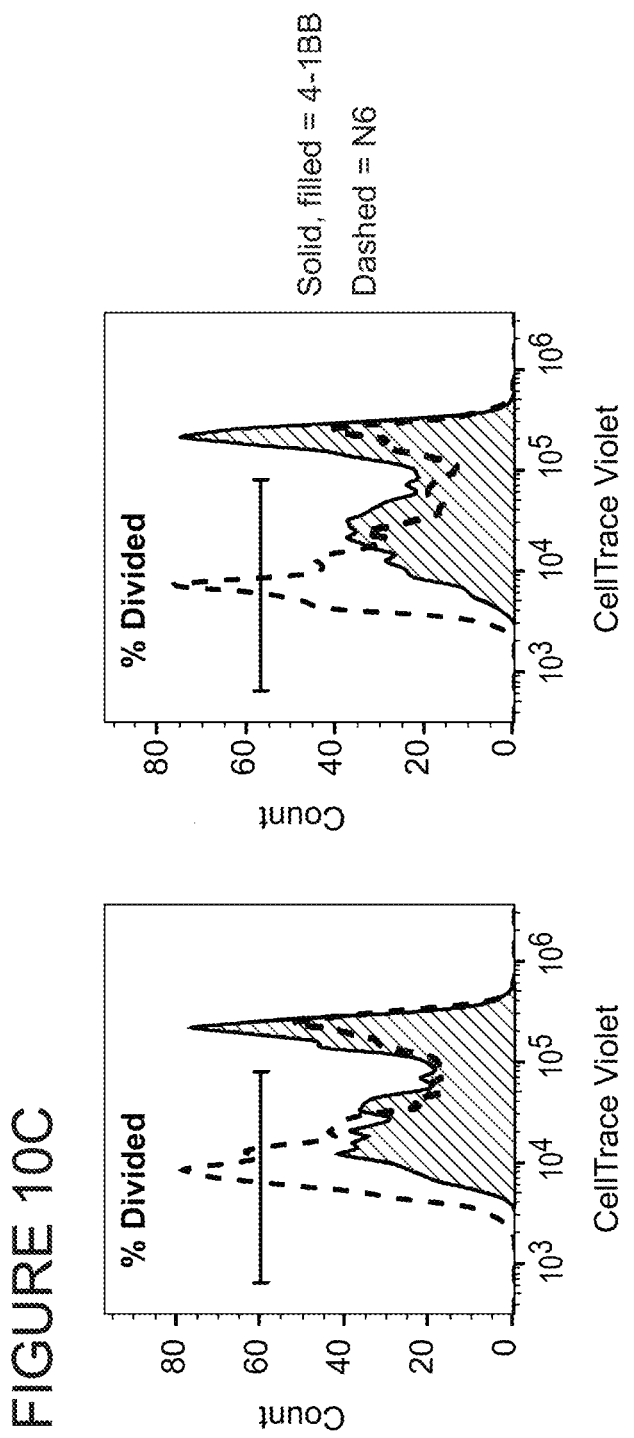

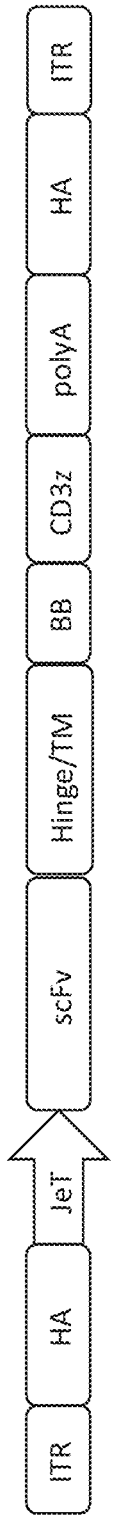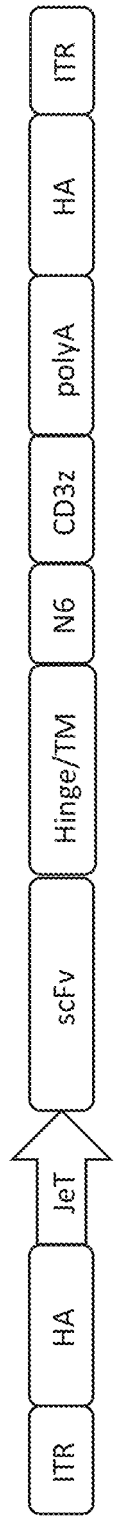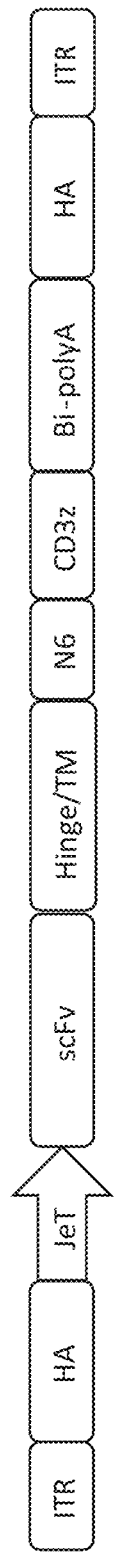
FIGURE 11

TRC Control - Ventral

7206 - Ventral

7205 - Ventral 4-1BB - Ventral

TRC Control

CD4+ T cells

CD8+ T cells

N6 CAR

CD4+ T cells

CD8+ T cells

MyD88/N6 CAR

CD4+ T cells

CD8+ T cells

TRC Control
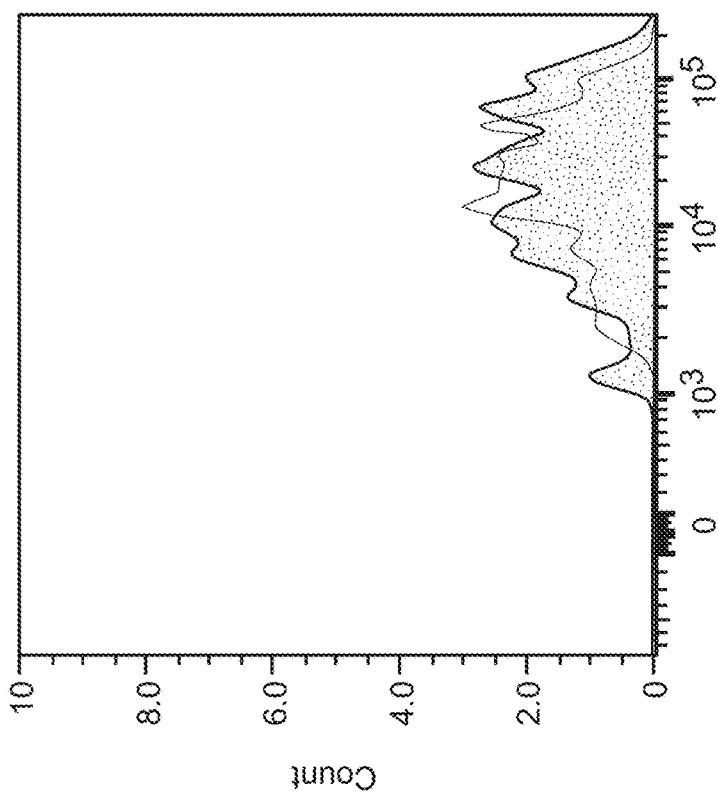
FIGURE 18A  CD4+ T cells
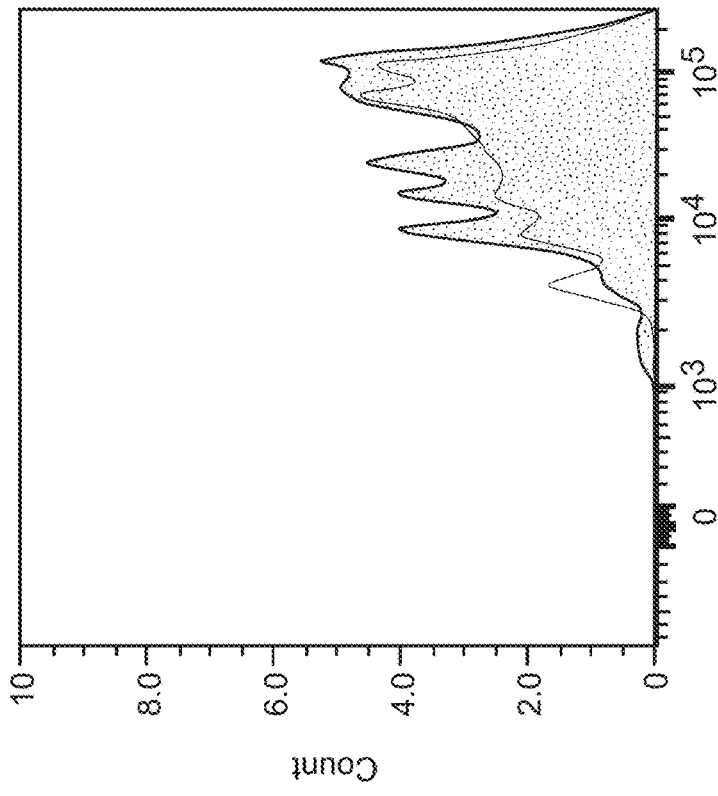
FIGURE 18B  CD8+ T cells N6 CAR – CD4⁺T cells

K19/K562

K19 +/- Rimiducid

N6 CAR – CD8⁺ T cells

K19/K562

K19 +/- Rimiducid iMyD88/N6 – CD4$^+$ T cells

K19/K562

K19 +/- Rimiducid iMyD88/N6 – CD4$^+$ T cells

K19/K562

K19 +/- Rimiducid

SEQUENCE LISTING

```
<160> NUMBER OF SEQ ID NOS: 42

<210> SEQ ID NO 1
<211> LENGTH: 126
<212> TYPE: DNA
<213> ORGANISM: Artificial Sequence
<220> FEATURE:
<223> OTHER INFORMATION: Synthetic polynucleotide

<400> SEQUENCE: 1
aaacatagcc gcaaaaaatt tgtgcatctg ctgaaacgcc cgtttattaa aaccaccggc      60
gcggcgcaga tggaagatgc gagcagctgc cgctgcccgc aggaagaaga aggcgaatgc     120
gatctg                                                                126

<210> SEQ ID NO 2
<211> LENGTH: 126
<212> TYPE: DNA
<213> ORGANISM: Artificial Sequence
<220> FEATURE:
<223> OTHER INFORMATION: Synthetic polynucleotide

<400> SEQUENCE: 2
aaatggggcc gcaaaaaact gctgtatctg tttaaacgcc cgtttgcgca gccgattcgc      60
accgcgcagg aagaagatgc gagcagctgc cgctttccgg aagaagaaga aggcaactgc     120
gaactg                                                                126

<210> SEQ ID NO 3
<211> LENGTH: 126
<212> TYPE: DNA
<213> ORGANISM: Artificial Sequence
<220> FEATURE:
<223> OTHER INFORMATION: Synthetic polynucleotide

<400> SEQUENCE: 3
aaacatagcc gcaaaaaaat tattttctg tataaaaacc cgtttatgaa accgaccaac       60
agcgcgcagg aagaagatgc gagcagctgc cgctttccgc aggaagaaga aggcgattgc     120
gatctg                                                                126

<210> SEQ ID NO 4
<211> LENGTH: 126
<212> TYPE: DNA
<213> ORGANISM: Artificial Sequence
<220> FEATURE:
<223> OTHER INFORMATION: Synthetic polynucleotide

<400> SEQUENCE: 4
aaagcgagcc gcaaaaaagc ggcggcggcg gcgaaaagcc cgtttgcgag cccggcgagc      60
agcgcgcagg aagaagatgc gagcagctgc cgcgcgccga gcgaagaaga aggcagctgc     120
gaactg                                                                126
```

```
<210> SEQ ID NO 5
<211> LENGTH: 42
<212> TYPE: PRT
<213> ORGANISM: Artificial Sequence
<220> FEATURE:
<223> OTHER INFORMATION: Synthetic polypeptide

<400> SEQUENCE: 5

Lys His Ser Arg Lys Lys Phe Val His Leu Leu Lys Arg Pro Phe Ile
1               5                   10                  15

Lys Thr Thr Gly Ala Ala Gln Met Glu Asp Ala Ser Ser Cys Arg Cys
            20                  25                  30

Pro Gln Glu Glu Glu Gly Glu Cys Asp Leu
        35                  40

<210> SEQ ID NO 6
<211> LENGTH: 42
<212> TYPE: PRT
<213> ORGANISM: Artificial Sequence
<220> FEATURE:
<223> OTHER INFORMATION: Synthetic polypeptide

<400> SEQUENCE: 6

Lys Trp Gly Arg Lys Lys Leu Leu Tyr Leu Phe Lys Arg Pro Phe Ala
1               5                   10                  15

Gln Pro Ile Arg Thr Ala Gln Glu Glu Asp Ala Ser Ser Cys Arg Phe
            20                  25                  30

Pro Glu Glu Glu Glu Gly Asn Cys Glu Leu
        35                  40

<210> SEQ ID NO 7
<211> LENGTH: 42
<212> TYPE: PRT
<213> ORGANISM: Artificial Sequence
<220> FEATURE:
<223> OTHER INFORMATION: Synthetic polypeptide

<400> SEQUENCE: 7

Lys His Ser Arg Lys Lys Ile Ile Phe Leu Tyr Lys Asn Pro Phe Met
1               5                   10                  15

Lys Pro Thr Asn Ser Ala Gln Glu Glu Asp Ala Ser Ser Cys Arg Phe
            20                  25                  30

Pro Gln Glu Glu Glu Gly Asp Cys Asp Leu
        35                  40

<210> SEQ ID NO 8
<211> LENGTH: 42
<212> TYPE: PRT
<213> ORGANISM: Artificial Sequence
<220> FEATURE:
<223> OTHER INFORMATION: Synthetic polypeptide

<400> SEQUENCE: 8

Lys Ala Ser Arg Lys Lys Ala Ala Ala Ala Ala Lys Ser Pro Phe Ala
1               5                   10                  15

Ser Pro Ala Ser Ser Ala Gln Glu Glu Asp Ala Ser Ser Cys Arg Ala
            20                  25                  30

Pro Ser Glu Glu Glu Gly Ser Cys Glu Leu
        35                  40
```

```
<210> SEQ ID NO 9
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 9

Gln Met Glu Asp
1

<210> SEQ ID NO 10
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 10

Gln Glu Glu Asp
1

<210> SEQ ID NO 11
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 11

Glu Glu Glu Gly
1

<210> SEQ ID NO 12
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 12

Ala Ser Ser Cys Arg Cys Pro Gln
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 13

Ala Ser Ser Cys Arg Phe Pro Glu
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 14

Ala Ser Ser Cys Arg Phe Pro Gln
1               5
```

<210> SEQ ID NO 15
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 15

Ala Ser Ser Cys Arg Ala Pro Ser
1               5

<210> SEQ ID NO 16
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 16

Met Ala Leu Pro Val Thr Ala Leu Leu Leu Pro Leu Ala Leu Leu Leu
1               5                   10                  15

His Ala Ala Arg Pro
            20

<210> SEQ ID NO 17
<211> LENGTH: 242
<212> TYPE: PRT
<213> ORGANISM: Artificial Sequence
<220> FEATURE:
<223> OTHER INFORMATION: Synthetic polypeptide

<400> SEQUENCE: 17

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Ser Glu Val Lys Leu Gln Glu
        115                 120                 125

Ser Gly Pro Gly Leu Val Ala Pro Ser Gln Ser Leu Ser Val Thr Cys
    130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
    210                 215                 220

```
Gly Ser Tyr Ala Met Asp Tyr Trp Gly Gln Gly Thr Ser Val Thr Val
225                 230                 235                 240

Ser Ser

<210> SEQ ID NO 18
<211> LENGTH: 69
<212> TYPE: PRT
<213> ORGANISM: Artificial Sequence
<220> FEATURE:
<223> OTHER INFORMATION: Synthetic polypeptide

<400> SEQUENCE: 18

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile Tyr Ile
            35                  40                  45

Trp Ala Pro Leu Ala Gly Thr Cys Gly Val Leu Leu Leu Ser Leu Val
        50                  55                  60

Ile Thr Leu Tyr Cys
65

<210> SEQ ID NO 19
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 19

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110

<210> SEQ ID NO 20
<211> LENGTH: 41
<212> TYPE: PRT
<213> ORGANISM: Artificial Sequence
<220> FEATURE:
<223> OTHER INFORMATION: Synthetic polypeptide

<400> SEQUENCE: 20

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
                20                  25                  30

Pro Arg Asp Phe Ala Ala Tyr Arg Ser
            35                  40
```

```
<210> SEQ ID NO 21
<211> LENGTH: 42
<212> TYPE: PRT
<213> ORGANISM: Artificial Sequence
<220> FEATURE:
<223> OTHER INFORMATION: Synthetic polypeptide

<400> SEQUENCE: 21

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 22
<211> LENGTH: 444
<212> TYPE: PRT
<213> ORGANISM: Artificial Sequence
<220> FEATURE:
<223> OTHER INFORMATION: Synthetic polypeptide

<400> SEQUENCE: 22

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Ser Gly Gly Gly Gly Ser Glu
    130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270
```

```
Thr Pro Ala Pro Thr Ile Ala Ser Gln Pro Leu Ser Leu Arg Pro Glu
            275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Arg Val Lys Phe
                325                 330                 335

Ser Arg Ser Ala Asp Ala Pro Ala Tyr Gln Gln Gly Gln Asn Gln Leu
                340                 345                 350

Tyr Asn Glu Leu Asn Leu Gly Arg Arg Glu Glu Tyr Asp Val Leu Asp
                355                 360                 365

Lys Arg Arg Gly Arg Asp Pro Glu Met Gly Gly Lys Pro Arg Arg Lys
                370                 375                 380

Asn Pro Gln Glu Gly Leu Tyr Asn Glu Leu Gln Lys Asp Lys Met Ala
385                 390                 395                 400

Glu Ala Tyr Ser Glu Ile Gly Met Lys Gly Glu Arg Arg Arg Gly Lys
                405                 410                 415

Gly His Asp Gly Leu Tyr Gln Gly Leu Ser Thr Ala Thr Lys Asp Thr
                420                 425                 430

Tyr Asp Ala Leu His Met Gln Ala Leu Pro Pro Arg
                435                 440

<210> SEQ ID NO 23
<211> LENGTH: 485
<212> TYPE: PRT
<213> ORGANISM: Artificial Sequence
<220> FEATURE:
<223> OTHER INFORMATION: Synthetic polypeptide

<400> SEQUENCE: 23

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
                20                  25                  30

Ser Ala Ser Leu Gly Asp Arg Val Thr Ile Ser Cys Arg Ala Ser Gln
            35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
                100                 105                 110

Asn Thr Leu Pro Tyr Thr Phe Gly Gly Gly Thr Lys Leu Glu Ile Thr
            115                 120                 125

Gly Gly Gly Gly Ser Gly Gly Gly Gly Ser Gly Gly Gly Gly Ser Glu
    130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
                180                 185                 190
```

Val Ile Trp Gly Ser Glu Thr Thr Tyr Tyr Asn Ser Ala Leu Lys Ser
195                 200                 205

Arg Leu Thr Ile Ile Lys Asp Asn Ser Lys Ser Gln Val Phe Leu Lys
210                 215                 220

Met Asn Ser Leu Gln Thr Asp Asp Thr Ala Ile Tyr Tyr Cys Ala Lys
225                 230                 235                 240

His Tyr Tyr Tyr Gly Ser Tyr Ala Met Asp Tyr Trp Gly Gln Gly
            245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
            275                 280                 285

Ala Cys Arg Pro Ala Ala Gly Gly Ala Val His Thr Arg Gly Leu Asp
            290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Arg Ser Lys Arg
            325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
            355                 360                 365

Ala Ala Tyr Arg Ser Arg Val Lys Phe Ser Arg Ser Ala Asp Ala Pro
            370                 375                 380

Ala Tyr Gln Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
            405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
            435                 440                 445

Met Lys Gly Glu Arg Arg Arg Gly Lys Gly His Asp Gly Leu Tyr Gln
450                 455                 460

Gly Leu Ser Thr Ala Thr Lys Asp Thr Tyr Asp Ala Leu His Met Gln
465                 470                 475                 480

Ala Leu Pro Pro Arg
            485

<210> SEQ ID NO 24
<211> LENGTH: 486
<212> TYPE: PRT
<213> ORGANISM: Artificial Sequence
<220> FEATURE:
<223> OTHER INFORMATION: Synthetic polypeptide

<400> SEQUENCE: 24

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
            35                  40                  45

Asp Ile Ser Lys Tyr Leu Asn Trp Tyr Gln Gln Lys Pro Asp Gly Thr
        50                  55                  60

-continued

```
Val Lys Leu Leu Ile Tyr His Thr Ser Arg Leu His Ser Gly Val Pro
 65                  70                  75                  80

Ser Arg Phe Ser Gly Ser Gly Ser Gly Thr Asp Tyr Ser Leu Thr Ile
             85                  90                  95

Ser Asn Leu Glu Gln Glu Asp Ile Ala Thr Tyr Phe Cys Gln Gln Gly
        100                 105                 110

Asn Thr Leu Pro Tyr Thr Phe Gly Gly Gly Thr Lys Leu Glu Ile Thr
    115                 120                 125

Gly Gly Gly Gly Ser Gly Gly Gly Ser Gly Gly Gly Gly Ser Glu
130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
             165                 170                 175

Val Ser Trp Ile Arg Gln Pro Pro Arg Lys Gly Leu Glu Trp Leu Gly
             180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
             245                 250                 255

Thr Ser Val Thr Val Ser Ser Thr Thr Thr Pro Ala Pro Arg Pro Pro
             260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
             325                 330                 335

Lys Lys Leu Leu Tyr Ile Phe Lys Gln Pro Phe Met Arg Pro Val Gln
        340                 345                 350

Thr Thr Gln Glu Glu Asp Gly Cys Ser Cys Arg Phe Pro Glu Glu Glu
    355                 360                 365

Glu Gly Gly Cys Glu Leu Arg Val Lys Phe Ser Arg Ser Ala Asp Ala
    370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Gly Arg Asp
             405                 410                 415

Pro Glu Met Gly Gly Lys Pro Arg Arg Lys Asn Pro Gln Glu Gly Leu
        420                 425                 430

Tyr Asn Glu Leu Gln Lys Asp Lys Met Ala Glu Ala Tyr Ser Glu Ile
    435                 440                 445

Gly Met Lys Gly Glu Arg Arg Arg Gly Lys Gly His Asp Gly Leu Tyr
450                 455                 460
```

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 25
<211> LENGTH: 486
<212> TYPE: PRT
<213> ORGANISM: Artificial Sequence
<220> FEATURE:
<223> OTHER INFORMATION: Synthetic polypeptide

<400> SEQUENCE: 25

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
                20                  25                  30

Ser Ala Ser Leu Gly Asp Arg Val Thr Ile Ser Cys Arg Ala Ser Gln
            35                  40                  45

Asp Ile Ser Lys Tyr Leu Asn Trp Tyr Gln Gln Lys Pro Asp Gly Thr
        50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
                100                 105                 110

Asn Thr Leu Pro Tyr Thr Phe Gly Gly Gly Thr Lys Leu Glu Ile Thr
            115                 120                 125

Gly Gly Gly Gly Ser Gly Gly Gly Ser Gly Gly Gly Gly Ser Glu
130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
                180                 185                 190

Val Ile Trp Gly Ser Glu Thr Thr Tyr Tyr Asn Ser Ala Leu Lys Ser
            195                 200                 205

Arg Leu Thr Ile Ile Lys Asp Asn Ser Lys Ser Gln Val Phe Leu Lys
        210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
                260                 265                 270

Thr Pro Ala Pro Thr Ile Ala Ser Gln Pro Leu Ser Leu Arg Pro Glu
            275                 280                 285

Ala Cys Arg Pro Ala Ala Gly Gly Ala Val His Thr Arg Gly Leu Asp
        290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys His Ser Arg
                325                 330                 335

-continued

```
Lys Lys Phe Val His Leu Leu Lys Arg Pro Phe Ile Lys Thr Thr Gly
            340                 345                 350

Ala Ala Gln Met Glu Asp Ala Ser Ser Cys Arg Cys Pro Gln Glu Glu
        355                 360                 365

Glu Gly Glu Cys Asp Leu Arg Val Lys Phe Ser Arg Ser Ala Asp Ala
    370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
                485
```

<210> SEQ ID NO 26
<211> LENGTH: 486
<212> TYPE: PRT
<213> ORGANISM: Artificial Sequence
<220> FEATURE:
<223> OTHER INFORMATION: Synthetic polypeptide

<400> SEQUENCE: 26

```
Met Ala Leu Pro Val Thr Ala Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Ser Gly Gly Gly Gly Ser Glu
    130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205
```

Arg Leu Thr Ile Ile Lys Asp Asn Ser Lys Ser Gln Val Phe Leu Lys
210                 215                 220

Met Asn Ser Leu Gln Thr Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
            245                 250                 255

Thr Ser Val Thr Val Ser Ser Thr Thr Pro Ala Pro Arg Pro Pro
            260                 265                 270

Thr Pro Ala Pro Thr Ile Ala Ser Gln Pro Leu Ser Leu Arg Pro Glu
            275                 280                 285

Ala Cys Arg Pro Ala Ala Gly Gly Ala Val His Thr Arg Gly Leu Asp
290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Trp Gly Arg
            325                 330                 335

Lys Lys Leu Leu Tyr Leu Phe Lys Arg Pro Phe Ala Gln Pro Ile Arg
            340                 345                 350

Thr Ala Gln Glu Glu Asp Ala Ser Ser Cys Arg Phe Pro Glu Glu Glu
            355                 360                 365

Glu Gly Asn Cys Glu Leu Arg Val Lys Phe Ser Arg Ser Ala Asp Ala
370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Gly Arg Asp
            405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
            435                 440                 445

Gly Met Lys Gly Glu Arg Arg Arg Gly Lys Gly His Asp Gly Leu Tyr
            450                 455                 460

Gln Gly Leu Ser Thr Ala Thr Lys Asp Thr Tyr Asp Ala Leu His Met
465                 470                 475                 480

Gln Ala Leu Pro Pro Arg
            485

<210> SEQ ID NO 27
<211> LENGTH: 486
<212> TYPE: PRT
<213> ORGANISM: Artificial Sequence
<220> FEATURE:
<223> OTHER INFORMATION: Synthetic polypeptide

<400> SEQUENCE: 27

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

```
Ser Arg Phe Ser Gly Ser Gly Ser Gly Thr Asp Tyr Ser Leu Thr Ile
                85              90                  95
Ser Asn Leu Glu Gln Glu Asp Ile Ala Thr Tyr Phe Cys Gln Gln Gly
            100                 105                 110
Asn Thr Leu Pro Tyr Thr Phe Gly Gly Gly Thr Lys Leu Glu Ile Thr
            115                 120                 125
Gly Gly Gly Gly Ser Gly Gly Gly Ser Gly Gly Gly Ser Glu
130             135                 140
Val Lys Leu Gln Glu Ser Gly Pro Gly Leu Val Ala Pro Ser Gln Ser
145                 150                 155                 160
Leu Ser Val Thr Cys Thr Val Ser Gly Val Ser Leu Pro Asp Tyr Gly
                165                 170                 175
Val Ser Trp Ile Arg Gln Pro Pro Arg Lys Gly Leu Glu Trp Leu Gly
                180                 185                 190
Val Ile Trp Gly Ser Glu Thr Thr Tyr Tyr Asn Ser Ala Leu Lys Ser
                195                 200                 205
Arg Leu Thr Ile Ile Lys Asp Asn Ser Lys Ser Gln Val Phe Leu Lys
        210                 215                 220
Met Asn Ser Leu Gln Thr Asp Asp Thr Ala Ile Tyr Tyr Cys Ala Lys
225                 230                 235                 240
His Tyr Tyr Tyr Gly Gly Ser Tyr Ala Met Asp Tyr Trp Gly Gln Gly
                245                 250                 255
Thr Ser Val Thr Val Ser Ser Thr Thr Pro Ala Pro Arg Pro Pro
            260                 265                 270
Thr Pro Ala Pro Thr Ile Ala Ser Gln Pro Leu Ser Leu Arg Pro Glu
            275                 280                 285
Ala Cys Arg Pro Ala Ala Gly Gly Ala Val His Thr Arg Gly Leu Asp
        290                 295                 300
Phe Ala Cys Asp Ile Tyr Ile Trp Ala Pro Leu Ala Gly Thr Cys Gly
305                 310                 315                 320
Val Leu Leu Leu Ser Leu Val Ile Thr Leu Tyr Cys Lys His Ser Arg
                325                 330                 335
Lys Lys Ile Ile Phe Leu Tyr Lys Asn Pro Phe Met Lys Pro Thr Asn
                340                 345                 350
Ser Ala Gln Glu Glu Asp Ala Ser Ser Cys Arg Phe Pro Gln Glu Glu
            355                 360                 365
Glu Gly Asp Cys Asp Leu Arg Val Lys Phe Ser Arg Ser Ala Asp Ala
        370                 375                 380
Pro Ala Tyr Gln Gln Gly Gln Asn Gln Leu Tyr Asn Glu Leu Asn Leu
385                 390                 395                 400
Gly Arg Arg Glu Glu Tyr Asp Val Leu Asp Lys Arg Arg Gly Arg Asp
                405                 410                 415
Pro Glu Met Gly Gly Lys Pro Arg Arg Lys Asn Pro Gln Glu Gly Leu
            420                 425                 430
Tyr Asn Glu Leu Gln Lys Asp Lys Met Ala Glu Ala Tyr Ser Glu Ile
        435                 440                 445
Gly Met Lys Gly Glu Arg Arg Arg Gly Lys Gly His Asp Gly Leu Tyr
            450                 455                 460
Gln Gly Leu Ser Thr Ala Thr Lys Asp Thr Tyr Asp Ala Leu His Met
465                 470                 475                 480
Gln Ala Leu Pro Pro Arg
                485
```

```
<210> SEQ ID NO 28
<211> LENGTH: 486
<212> TYPE: PRT
<213> ORGANISM: Artificial Sequence
<220> FEATURE:
<223> OTHER INFORMATION: Synthetic polypeptide

<400> SEQUENCE: 28
```

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Ser Gly Gly Gly Gly Ser Glu
    130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Ala Ser Arg
                325                 330                 335

Lys Lys Ala Ala Ala Ala Ala Lys Ser Pro Phe Ala Ser Pro Ala Ser
            340                 345                 350

Ser Ala Gln Glu Glu Asp Ala Ser Ser Cys Arg Ala Pro Ser Glu Glu
        355                 360                 365

```
Glu Gly Ser Cys Glu Leu Arg Val Lys Phe Ser Arg Ser Ala Asp Ala
    370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
                420                 425                 430

Tyr Asn Glu Leu Gln Lys Asp Lys Met Ala Glu Ala Tyr Ser Glu Ile
            435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
                485
```

```
<210> SEQ ID NO 29
<211> LENGTH: 7464
<212> TYPE: DNA
<213> ORGANISM: Artificial Sequence
<220> FEATURE:
<223> OTHER INFORMATION: Synthetic polynucleotide

<400> SEQUENCE: 29
cagcagctgg cgtaatagcg aagaggcccg caccgatcgc ccttcccaac agttgcgcag      60
cctgaatggc gaatggaatt ccagacgatt gagcgtcaaa atgtaggtat ttccatgagc     120
gtttttcctg ttgcaatggc tggcggtaat attgttctgg atattaccag caaggccgat     180
agtttgagtt cttctactca ggcaagtgat gttattacta atcaaagaag tattgcgaca     240
acggttaatt tgcgtgatgg acagactctt ttactcggtg gcctcactga ttataaaaac     300
acttctcagg attctggcgt accgttcctg tctaaaatcc ctttaatcgg cctcctgttt     360
agctcccgct ctgattctaa cgaggaaagc acgttatacg tgctcgtcaa agcaaccata     420
gtacgcgccc tgtagcggcg cattaagcgc ggcgggtgtg gtggttacgc gcagcgtgac     480
cgctacactt gccagcgccc tagcgcccgc tcctttcgct ttcttccctt cctttctcgc     540
cacgttcgcc ggctttcccc gtcaagctct aaatcggggg ctcccttag ggttccgatt     600 tagtgcttta cggcacctcg accccaaaaa acttgattag ggtgatggtt cacgtagtgg     660
gccatcgccc tgatagacgg ttttttcgcc tttgacgttg gagtccacgt tctttaatag     720
tggactcttg ttccaaactg gaacaacact caaccctatc tcggtctatt cttttgattt     780
ataagggatt ttgccgattt cggcctattg gttaaaaaat gagctgattt aacaaaaatt     840
taacgcgaat tttaacaaaa tattaacgtt tacaatttaa atatttgctt atacaatctt     900 cctgttttg gggcttttct gattatcaac cggggtacat atgattgaca tgctagtttt     960
acggcgcgcc gggttggcca ctccctctct gcgcgctcgc tcgctcactg aggccgggcg    1020
accaaaggtc gcccgacgcc cgggctttgc ccgggcggcc tcagtgagcg agcgagcgcg    1080
cagagaggga gtggccaact ccatcactag gggttcctac gctagatctc catattctgg    1140
cagggtcagt ggctccaact aacatttgtt tggtactttca gtttattaa aatagatgtt    1200 tatatgagaa agctctcatt tctttctcag aagagcctgg ctaggaaggt ggatgaggca    1260
ccatattcat tttgcaggtg aaattcctga atgtaagga gctgctgtga cttgctcaag    1320
gccttatatc gagtaaacgg tagcgctggg gcttagacgc aggtgttctg atttatagtt    1380
```

-continued

```
caaaacctct atcaatgaga gagcaatctc ctggtaatgt gatagatttc ccaacttaat      1440
gccaacatac cataaacctc ccattctgct aatgcccagc ctaagttggg gagaccactc      1500
cagattccaa gatgtacagt ttgctttgct gggccttttt cccatgcctg cctttactct      1560
gccagagtta tattgctggg gttttgaaga agatcctatt aaataaaaga ataagcagta      1620
ttattaagta gccctgcatt tcaggtttcc ttgagtggca ggccaggcct ggccgtgaac      1680
gttcactgaa atcatggcct cttggccaag attgatagct tgtgcctgtc cctgagtccc      1740
agtccatcac gagcagctgg tttctaagat gctatttccc gtataaagca tgagaccgtg      1800
acttgccagc cccacagagc cccgcccttg tccatcactg gcatctggac tccagcctgg      1860 gttgggcaa agagggaaat gagatcatgt cctaaccctg atcctcttgt cccacagata      1920
tccagaaccc tgaccctgcc gtgtaccagc tgagagactc taaatccagt gacaagtctg      1980
tctgcctatt caccgatttt gattctcaaa caaatgtgtc acaaagtaag gattctgatg      2040
tgtatatcac agacaaaact gtgctagaca tgaggtctat ggacttcaag agcaacagtg      2100
ctgtggcctg gagcaactag tgggcggagt tagggcggag ccaatcagcg tgcgccgttc      2160
cgaaagttgc cttttatggc tgggcggaga atgggcggtg aacgccgatg attatataag      2220
gacgcgccgg gtgtggcaca gctagttccg tcgcagccgg gatttgggtc gcggttcttg      2280
tttgttccgg aaagccacca tggcgctccc agtgacagcc ttacttttac ctctggcgtt      2340
attattgcac gcggctcgtc ctgacataca gatgactcag actacctctt ccctatctgc      2400
ttctttaggc gaccgagtaa caatatcttg ccgggccagc caggacatct caaaatactt      2460
aaactggtat cagcagaagc cggacggaac agttaagttg ctcatttacc acacgtcgag      2520
attacactca ggcgttccta gccgatttc gggttccggt tccggtacgg actacagcct      2580
gacaatcagt aaccttgagc aggaggacat cgccacctac ttctgtcagc agggcaacac      2640
gctcccgtac acattcggtg ggggaactaa gctggagatt accggaggcg gtggcagcgg      2700
tggcggcggc agcggggtg gcggctcgga ggtcaagtta caggagagcg gacccggctt      2760
ggtcgcacct agccagagcc tctcagtcac gtgcactgtg tctggagtca gtctcccaga      2820 ctacgggta tcatggatac gacagccgcc tagaaagggc ttagagtggc tggggggttat      2880 ctggggaagt gaaaccacat actacaactc agctctcaag agccgcctca ccatcattaa      2940
ggacaacagt aagtcgcagg ttttcttaaa gatgaactct ctccagactg acgacaccgc      3000
tatttactac tgcgcgaagc actactacta cggcgggagt tacgcaatgg actactgggg      3060
tcagggcact tctgtgaccg tatccagcac tactacccca gccccacgtc ccccacgcc      3120 agctccaacg atagcaagtc agcccttatc tcttcgccct gaggcttgca ggcccgcggc      3180
gggcggcgcc gttcacacgc gaggactaga cttcgcctgc gacatctaca tctgggcacc      3240
actagccggg acttgcggag tgttgttgtt gagcttggta ataacgctct actgcaagcg      3300
tgggagaaag aagctcttgt acatttttcaa gcagccattc atgcgtcccg ttcagacgac      3360
tcaggaggag gacggctgct cgtgccgatt cccggaggag gaggagggcg gttgcgaact      3420
cagagtgaag ttctctcgct ccgcggacgc accgcttac cagcagggtc agaaccagct      3480
atacaacagt ttaaacctgg ggcgccggga ggagtacgac gtgttagaca gcgtagagg      3540 tagggacccg gagatgggag gcaagcctcg gagaaagaac cccaggagg gcctgtacaa      3600 cgaactccag aaggacaaga tggctgaggc gtactcggag attggtatga agggcgagag      3660
acgtcgcgga aagggacacg acggcttata ccagggcctt ccaccgcgca ccaaggacac      3720
atacgacgcg ctgcacatgc aagccttacc acctcgatga ggtaccagcg gccgcttcga      3780
```

```
gcagacatga taagatacat tgatgagttt ggacaaacca caactagaat gcagtgaaaa    3840
aaatgcttta tttgtgaaat ttgtgatgct attgctttat ttgtaaccat tataagctgc    3900
aataaacaag ttaacaacaa caattcgaat ttaaatcgga tccgcaacaa atctgacttt    3960
gcatgtgcaa acgccttcaa caacagcatt attccagaag acaccttctt ccccagccca    4020
ggtaagggca gctttggtgc cttcgcaggc tgtttccttg cttcaggaat ggccaggttc    4080
tgcccagagc tctggtcaat gatgtctaaa actcctctga ttggtggtct cggccttatc    4140
cattgccacc aaaaccctct ttttactaag aaacagtgag ccttgttctg gcagtccaga    4200
gaatgacacg ggaaaaaagc agatgaagag aaggtggcag gagagggcac gtggcccagc    4260
ctcagtctct ccaactgagt tcctgcctgc ctgcctttgc tcagactgtt tgccccttac    4320
tgctcttcta ggcctcattc taagccccct ctccaagttg cctctcctta tttctccctg    4380
tctgccaaaa aatctttccc agctcactaa gtcagtctca cgcagtcact cattaaccca    4440
ccaatcactg attgtgccgg cacatgaatg caccaggtgt tgaagtggag gaattaaaaa    4500
gtcagatgag gggtgtgccc agaggaagca ccattctagt tggggagcc catctgtcag    4560 ctggaaaaag tccaaataac ttcagattgg aatgtgtttt aactcagggt tgagaaaaca    4620
gccaccttca ggacaaaagt cagggaaggg ctctctgaag aaatgctact tgaagatacc    4680
agccctacca agggcaggga gaggaccaat tgatggagtt ggccactccc tctctgcgcg    4740
ctcgctcgct cactgaggcc gcccgggcaa agcccgggcg tcgggcgacc tttggtcgcc    4800
cggcctcagt gagcgagcga gcgcgcagag agggagtggc caacggcgcg cctgcaggtc    4860
tcaaaaatag ctaccctctc cggcatgaat ttatcagcta gaacggttga atatcatatt    4920
gatggtgatt tgactgtctc cggccttcct cacccgtttg aatctttacc tacacattac    4980
tcaggcattg catttaaaat atatgagggt tctaaaaatt tttatccttg cgttgaaata    5040
aaggcttctc ccgcaaaagt attacagggt cataatgttt ttggtacaac cgatttagct    5100
ttatgctctg aggctttatt gcttaatttt gctaattctt tgccttgcct gtatgattta    5160
ttggatgttg gaattcctga tgcggtattt tctccttacg catctgtgcg gtatttcaca    5220
ccgcatatgg tgcactctca gtacaatctg ctctgatgcc gcatagttaa gccagccccg    5280
acacccgcca cacccgctg acgcgccctg acgggcttgt ctgctcccgg catccgctta    5340
cagacaagct gtgaccgtct ccgggagctg catgtgtcag aggttttcac cgtcatcacc    5400
gaaacgcgcg agacgaaagg gcctcgtgat acgcctattt ttataggtta atgtcatgat    5460
aataatggtt tcttagacgt caggtggcac ttttcgggga atgtgcgcg gaaccccctat    5520 ttgtttattt ttctaaatac attcaaatat gtatccgctc atgagacaat aaccctgata    5580
aatgcttcaa taatattgaa aaaggaagag tatgagtatt caacatttcc gtgtcgccct    5640
tattcccttt tttgcggcat tttgccttcc tgttttgct cacccagaaa cgctggtgaa    5700
agtaaaagat gctgaagatc agttgggtgc acgagtgggt tacatcgaac tggatctcaa    5760
cagcggtaag atccttgaga gttttcgccc cgaagaacgt tttccaatga tgagcacttt    5820
taaagttctg ctatgtggcg cggtattatc ccgtattgac gccgggcaag agcaactcgg    5880
tcgccgcata cactattctc agaatgactt ggttgagtac tcaccagtca cagaaaagca    5940
tcttacggat ggcatgacag taagagaatt atgcagtgct gccataacca tgagtgataa    6000
cactgcggcc aacttacttc tgacaacgat cggaggaccg aaggagctaa ccgcttttttt    6060 gcacaacatg gggatcatg taactcgcct tgatcgttgg gaaccggagc tgaatgaagc    6120
cataccaaac gacgagcgtg acaccacgat gcctgtagca atggcaacaa cgttgcgcaa    6180
```

| | |
|---|---|
| actattaact ggcgaactac ttactctagc ttcccggcaa caattaatag actggatgga | 6240 |
| ggcggataaa gttgcaggac cacttctgcg ctcggccctt ccggctggct ggtttattgc | 6300 |
| tgataaatct ggagccggtg agcgtgggtc tcgcggtatc attgcagcac tggggccaga | 6360 |
| tggtaagccc tcccgtatcg tagttatcta cacgacgggg agtcaggcaa ctatggatga | 6420 |
| acgaaataga cagatcgctg agataggtgc ctcactgatt aagcattggt aactgtcaga | 6480 |
| ccaagtttac tcatatatac tttagattga tttaaaactt catttttaat ttaaaaggat | 6540 |
| ctaggtgaag atcctttttg ataatctcat gaccaaaatc ccttaacgtg agttttcgtt | 6600 |
| ccactgagcg tcagaccccg tagaaaagat caaaggatct tcttgagatc ctttttttct | 6660 |
| gcgcgtaatc tgctgcttgc aaacaaaaaa accaccgcta ccagcggtgg tttgtttgcc | 6720 |
| ggatcaagag ctaccaactc tttttccgaa ggtaactggc ttcagcagag cgcagatacc | 6780 |
| aaatactgtc cttctagtgt agccgtagtt aggccaccac ttcaagaact ctgtagcacc | 6840 |
| gcctacatac ctcgctctgc taatcctgtt accagtggct gctgccagtg gcgataagtc | 6900 |
| gtgtcttacc gggttggact caagacgata gttaccggat aaggcgcagc ggtcgggctg | 6960 |
| aacggggggt tcgtgcacac agcccagctt ggagcgaacg acctacaccg aactgagata | 7020 |
| cctacagcgt gagctatgag aaagcgccac gcttcccgaa gggagaaagg cggacaggta | 7080 |
| tccggtaagc ggcagggtcg gaacaggaga gcgcacgagg gagcttccag ggggaaacgc | 7140 |
| ctggtatctt tatagtcctg tcgggtttcg ccacctctga cttgagcgtc gatttttgtg | 7200 |
| atgctcgtca gggggggcgga gcctatggaa aaacgccagc aacgcggcct ttttacggtt | 7260 |
| cctggccttt tgctggcctt tgctcacat gttctttcct gcgttatccc ctgattctgt | 7320 |
| ggataaccgt attaccgcct ttgagtgagc tgataccgct cgccgcagcc gaacgaccga | 7380 |
| gcgcagcgag tcagtgagcg aggaagcgga agagcgccca atacgcaaac cgcctctccc | 7440 |
| cgcgcgttgg ccgattcatt aatg | 7464 |

<210> SEQ ID NO 30
<211> LENGTH: 7464
<212> TYPE: DNA
<213> ORGANISM: Artificial Sequence
<220> FEATURE:
<223> OTHER INFORMATION: Synthetic polynucleotide

<400> SEQUENCE: 30

| | |
|---|---|
| cagcagctgg cgtaatagcg aagaggcccg caccgatcgc ccttcccaac agttgcgcag | 60 |
| cctgaatggc gaatggaatt ccagacgatt gagcgtcaaa atgtaggtat ttccatgagc | 120 |
| gttttttcctg ttgcaatggc tggcggtaat attgttctgg atattaccag caaggccgat | 180 |
| agtttgagtt cttctactca ggcaagtgat gttattacta atcaaagaag tattgcgaca | 240 |
| acggttaatt tgcgtgatgg acagactctt ttactcggtg gcctcactga ttataaaaac | 300 |
| acttctcagg attctggcgt accgttcctg tctaaaatcc ctttaatcgg cctcctgttt | 360 |
| agctcccgct ctgattctaa cgaggaaagc acgttatacg tgctcgtcaa agcaaccata | 420 |
| gtacgcgccc tgtagcggcg cattaagcgc ggcgggtgtg gtggttacgc gcagcgtgac | 480 |
| cgctacactt gccagcgccc tagcgcccgc tcctttcgct ttcttccctt cctttctcgc | 540 |
| cacgttcgcc ggctttcccc gtcaagctct aaatcggggg ctccctttag ggttccgatt | 600 |
| tagtgcttta cggcacctcg accccaaaaa acttgattag ggtgatggtt cacgtagtgg | 660 |
| gccatcgccc tgatagacgg ttttcgccc tttgacgttg gagtccacgt tctttaatag | 720 |
| tggactcttg ttccaaactg gaacaacact caaccctatc tcggtctatt cttttgattt | 780 |

```
ataagggatt ttgccgattt cggcctattg gttaaaaaat gagctgattt aacaaaaatt      840
taacgcgaat tttaacaaaa tattaacgtt tacaatttaa atatttgctt atacaatctt      900
cctgtttttg gggcttttct gattatcaac cggggtacat atgattgaca tgctagtttt      960
acggcgcgcc gggttggcca ctccctctct gcgcgctcgc tcgctcactg aggccgggcg     1020
accaaaggtc gcccgacgcc cgggctttgc ccgggcggcc tcagtgagcg agcgagcgcg     1080
cagagaggga gtggccaact ccatcactag gggttcctac gcgtagatct catattctgg     1140
cagggtcagt ggctccaact aacatttgtt tggtacttta cagtttatta aatagatgtt     1200
tatatggaga agctctcatt tctttctcag aagagcctgg ctaggaaggt ggatgaggca     1260
ccatattcat tttgcaggtg aaattcctga gatgtaagga gctgctgtga cttgctcaag     1320
gccttatatc gagtaaacgg tagcgctggg gcttagacgc aggtgttctg atttatagtt     1380
caaaacctct atcaatgaga gagcaatctc ctggtaatgt gatagatttc ccaacttaat     1440
gccaacatac cataaacctc ccattctgct aatgcccagc ctaagttggg gagaccactc     1500
cagattccaa gatgtacagt ttgctttgct gggccttttt cccatgcctg cctttactct     1560
gccagagtta tattgctggg gttttgaaga agatcctatt aaataaaaga ataagcagta     1620
ttattaagta gccctgcatt tcaggtttcc ttgagtggca ggccaggcct ggccgtgaac     1680
gttcactgaa atcatggcct cttggccaag attgatagct tgtgcctgtc cctgagtccc     1740
agtccatcac gagcagctgg tttctaagat gctatttccc gtataaagca tgagaccgtg     1800
acttgccagc cccacagagc ccgcccttg tccatcactg gcatctggac tccagcctgg     1860
gttggggcaa agagggaaat gagatcatgt cctaaccctg atcctcttgt cccacagata     1920
tccagaaccc tgaccctgcc gtgtaccagc tgagagactc taaatccagt gacaagtctg     1980
tctgcctatt caccgatttt gattctcaaa caaatgtgtc acaaagtaag gattctgatg     2040
tgtatatcac agacaaaact gtgctagaca tgaggtctat ggacttcaag agcaacagtg     2100
ctgtggcctg gagcaactag tgggcggagt tagggcggag ccaatcagcg tgcgccgttc     2160
cgaaagttgc cttttatggc tgggcggaga atgggcggtg aacgccgatg attatataag     2220
gacgcgccgg gtgtggcaca gctagttccg tcgcagccgg gatttgggtc gcggttcttg     2280
tttgttccgg aaagccacca tggcgctccc agtgacagcc ttacttttac ctctggcgtt     2340
attattgcac gcggctcgtc ctgacataca gatgactcag actacctctt ccctatctgc     2400
ttctttaggc gaccgagtaa caatatcttg ccgggccagc caggacatct caaaatactt     2460
aaactggtat cagcagaagc cggacggaac agttaagttg ctcatttacc acacgtcgag     2520
attacactca ggcgttccta gccgattttc gggttccggt tccggtacgg actacagcct     2580
gacaatcagt aaccttgagc aggaggacat cgccacctac ttctgtcagc agggcaacac     2640
gctcccgtac acattcggtg ggggaactaa gctggagatt accggaggcg gtggcagcgg     2700
tggcggcggc agcggggtg gcggctcgga ggtcaagtta caggagagcg gacccggctt     2760
ggtcgcacct agccagagcc tctcagtcac gtgcactgtg tctggagtca gtctcccaga     2820
ctacggggta tcatggatac gacagccgcc tagaaagggc ttagagtggc tgggggttat     2880
ctggggaagt gaaaccacat actacaactc agctctcaag agccgcctca ccatcattaa     2940
ggacaacagt aagtcgcagg ttttcttaaa gatgaactct ctccagactg acgacaccgc     3000
tatttactac tgcgcgaagc actactacta cggcgggagt tacgcaatgg actactgggg     3060
tcagggcact tctgtgaccg tatccagcac tactacccca gccccacgtc ccccacgcc     3120 agctccaacg atagcaagtc agcccttatc tcttcgccct gaggcttgca ggcccgcggc     3180
```

```
gggcggcgcc gttcacacgc gaggactaga cttcgcctgc gacatctaca tctgggcacc   3240
actagccggg acttgcggag tgttgttgtt gagcttggta ataacgctct actgcaaaca   3300
tagccgcaaa aaatttgtgc atctgctgaa acgcccgttt attaaaacca ccggcgcggc   3360
gcagatggaa gatgcgagca gctgccgctg cccgcaggaa gaagaaggcg aatgcgatct   3420
gagagtgaag ttctctcgct ccgcggacgc acccgcttac cagcagggtc agaaccagct   3480
atacaacgag ttaaacctgg ggcgccggga ggagtacgac gtgttagaca agcgtagagg   3540
tagggacccg gagatgggag gcaagcctcg gagaaagaac ccccaggagg gcctgtacaa   3600
cgaactccag aaggacaaga tggctgaggc gtactcggag attggtatga agggcgagag   3660
acgtcgcgga aagggacacg acggcttata ccaggggctt ccaccgcga ccaaggacac    3720 atacgacgcg ctgcacatgc aagccttacc acctcgatga ggtaccagcg gccgcttcga   3780
gcagacatga taagatacat tgatgagttt ggacaaacca caactagaat gcagtgaaaa   3840
aaatgcttta tttgtgaaat ttgtgatgct attgctttat ttgtaaccat tataagctgc   3900
aataaacaag ttaacaacaa caattcgaat ttaaatcgga tccgcaacaa atctgacttt   3960
gcatgtgcaa acgccttcaa caacagcatt attccagaag acaccttctt ccccagccca   4020
ggtaagggca gctttggtgc cttcgcaggc tgtttccttg cttcaggaat ggccaggttc   4080
tgcccagagc tctggtcaat gatgtctaaa actcctctga ttggtggtct cggccttatc   4140
cattgccacc aaaaccctct ttttactaag aaacagtgag ccttgttctg gcagtccaga   4200
gaatgacacg ggaaaaaagc agatgaagag aaggtggcag gagagggcac gtggcccagc   4260
ctcagtctct ccaactgagt tcctgcctgc ctgcctttgc tcagactgtt tgccccttac   4320
tgctcttcta ggcctcattc taagccccct ctccaagttg cctctcctta tttctccctg   4380
tctgccaaaa aatctttccc agctcactaa gtcagtctca cgcagtcact cattaaccca   4440
ccaatcactg attgtgccgg cacatgaatg caccaggtgt tgaagtggag gaattaaaaa   4500
gtcagatgag gggtgtgccc agaggaagca ccattctagt tgggggagcc catctgtcag   4560
ctgggaaaag tccaaataac ttcagattgg aatgtgtttt aactcagggt tgagaaaaca   4620
gccaccttca ggacaaaagt cagggaaggg ctctctgaag aaatgctact tgaagatacc   4680
agccctacca agggcaggga gaggaccaat tgatggagtt ggccactccc tctctgcgcg   4740
ctcgctcgct cactgaggcc gcccgggcaa agcccgggcg tcgggcgacc tttggtcgcc   4800
cggcctcagt gagcgagcga gcgcgcagag agggagtggc caacggcgcg cctgcaggtc   4860
tcaaaaatag ctaccctctc cggcatgaat ttatcagcta gaacggttga atatcatatt   4920
gatggtgatt tgactgtctc cggcctttct cacccgtttg aatctttacc tacacattac   4980
tcaggcattg catttaaaat atatgagggt tctaaaaatt tttatccttg cgttgaaata   5040
aaggcttctc ccgcaaaagt attacagggt cataatgttt ttggtacaac cgatttagct   5100
ttatgctctg aggctttatt gcttaatttt gctaattctt tgccttgcct gtatgattta   5160
ttggatgttg gaattcctga tgcggtattt tctccttacg catctgtgcg gtatttcaca   5220
ccgcatatgg tgcactctca gtacaatctg ctctgatgcc gcatagttaa gccagccccg   5280
acacccgcca cacccgctg acgcgccctg acgggcttgt ctgctcccgg catccgctta   5340
cagacaagct gtgaccgtct ccgggagctg catgtgtcag aggttttcac cgtcatcacc   5400
gaaacgcgcg agacgaaagg gcctcgtgat acgcctattt ttataggtta atgtcatgat   5460
aataatggtt tcttagacgt caggtggcac ttttcgggga aatgtgcgcg gaaccctat    5520 ttgtttattt ttctaaatac attcaaatat gtatccgctc atgagacaat aaccctgata   5580
```

```
aatgcttcaa taatattgaa aaaggaagag tatgagtatt caacatttcc gtgtcgccct   5640 tattccctttt tttgcggcat tttgccttcc tgttttgct cacccagaaa cgctggtgaa    5700
agtaaaagat gctgaagatc agttgggtgc acgagtgggt tacatcgaac tggatctcaa   5760
cagcggtaag atccttgaga gttttcgccc cgaagaacgt tttccaatga tgagcacttt   5820
taaagttctg ctatgtggcg cggtattatc ccgtattgac gccgggcaag agcaactcgg   5880
tcgccgcata cactattctc agaatgactt ggttgagtac tcaccagtca cagaaaagca   5940
tcttacggat ggcatgacag taagagaatt atgcagtgct gccataacca tgagtgataa   6000
cactgcggcc aacttacttc tgacaacgat cggaggaccg aaggagctaa ccgcttttttt  6060 gcacaacatg ggggatcatg taactcgcct tgatcgttgg aaccggagc tgaatgaagc    6120 cataccaaac gacgagcgtg acaccacgat gcctgtagca atggcaacaa cgttgcgcaa   6180
actattaact ggcgaactac ttactctagc ttcccggcaa caattaatag actggatgga   6240
ggcggataaa gttgcaggac cacttctgcg ctcggccctt ccggctggct ggtttattgc   6300
tgataaatct ggagccggtg agcgtgggtc tcgcggtatc attgcagcac tggggccaga   6360
tggtaagccc tcccgtatcg tagttatcta cacgacgggg agtcaggcaa ctatggatga   6420
acgaaataga cagatcgctg agataggtgc ctcactgatt aagcattggt aactgtcaga   6480
ccaagtttac tcatatatac tttagattga tttaaaactt catttttaat ttaaaaggat   6540
ctaggtgaag atcctttttg ataatctcat gaccaaaatc ccttaacgtg agttttcgtt   6600
ccactgagcg tcagaccccg tagaaaagat caaaggatct tcttgagatc ctttttttct   6660
gcgcgtaatc tgctgcttgc aaacaaaaaa accaccgcta ccagcggtgg tttgtttgcc   6720
ggatcaagag ctaccaactc tttttccgaa ggtaactggc ttcagcagag cgcagatacc   6780
aaatactgtc cttctagtgt agccgtagtt aggccaccac ttcaagaact ctgtagcacc   6840
gcctacatac ctcgctctgc taatcctgtt accagtggct gctgccagtg gcgataagtc   6900
gtgtcttacc gggttggact caagacgata gttaccggat aaggcgcagc ggtcgggctg   6960
aacggggggt tcgtgcacac agcccagctt ggagcgaacg acctacaccg aactgagata   7020
cctacagcgt gagctatgag aaagcgccac gcttcccgaa gggagaaagg cggacaggta   7080
tccggtaagc ggcagggtcg gaacaggaga gcgcacgagg gagcttccag ggggaaacgc   7140
ctggtatctt tatagtcctg tcgggtttcg ccacctctga cttgagcgtc gatttttgtg   7200
atgctcgtca ggggggcgga gcctatggaa aaacgccagc aacgcggcct ttttacggtt   7260
cctggccttt tgctggcctt ttgctcacat gttctttcct gcgttatccc ctgattctgt   7320
ggataaccgt attaccgcct ttgagtgagc tgataccgct cgccgcagcc gaacgaccga   7380
gcgcagcgag tcagtgagcg aggaagcgga agagcgccca atacgcaaac cgcctctccc   7440
cgcgcgttgg ccgattcatt aatg                                         7464
```

<210> SEQ ID NO 31
<211> LENGTH: 7464
<212> TYPE: DNA
<213> ORGANISM: Artificial Sequence
<220> FEATURE:
<223> OTHER INFORMATION: Synthetic polynucleotide

<400> SEQUENCE: 31

```
cagcagctgg cgtaatagcg aagaggcccg caccgatcgc ccttcccaac agttgcgcag     60
cctgaatggc gaatggaatt ccagacgatt gagcgtcaaa atgtaggtat ttccatgagc    120 gttttttcctg ttgcaatggc tggcggtaat attgttctgg atattaccag caaggccgat   180
```

```
agtttgagtt cttctactca ggcaagtgat gttattacta atcaaagaag tattgcgaca    240
acggttaatt tgcgtgatgg acagactctt ttactcggtg gcctcactga ttataaaaac    300
acttctcagg attctggcgt accgttcctg tctaaaatcc ctttaatcgg cctcctgttt    360
agctcccgct ctgattctaa cgaggaaagc acgttatacg tgctcgtcaa agcaaccata    420
gtacgcgccc tgtagcggcg cattaagcgc ggcgggtgtg gtggttacgc gcagcgtgac    480
cgctacactt gccagcgccc tagcgcccgc tcctttcgct ttcttccctt cctttctcgc    540
cacgttcgcc ggctttcccc gtcaagctct aaatcggggg ctcccttag ggttccgatt    600 tagtgcttta cggcacctcg accccaaaaa acttgattag ggtgatggtt cacgtagtgg    660
gccatcgccc tgatagacgg ttttcgccc tttgacgttg gagtccacgt tctttaatag    720
tggactcttg ttccaaactg gaacaacact caacccatc tcggtctatt cttttgattt    780
ataagggatt ttgccgattt cggcctattg gttaaaaaat gagctgattt aacaaaaatt    840
taacgcgaat tttaacaaaa tattaacgtt tacaatttaa atatttgctt atacaatctt    900 cctgttttg gggcttttct gattatcaac cggggtacat atgattgaca tgctagtttt    960
acggcgcgcc gggttggcca ctccctctct gcgcgctcgc tcgctcactg aggccgggcg   1020
accaaaggtc gcccgacgcc cgggctttgc ccgggcggcc tcagtgagcg agcgagcgcg   1080
cagagaggga gtggccaact ccatcactag gggttcctac gcgtagatct catattctgg   1140
cagggtcagt ggctccaact aacatttgtt tggtacttta cagttattta aatagatgtt   1200
tatatggaga agctctcatt tctttctcag aagagcctgg ctaggaaggt ggatgaggca   1260
ccatattcat tttgcaggtg aaattcctga gatgtaagga gctgctgtga cttgctcaag   1320
gccttatatc gagtaaacgg tagcgctggg gcttagacgc aggtgttctg atttatagtt   1380
caaaacctct atcaatgaga gagcaatctc ctggtaatgt gatagatttc ccaacttaat   1440
gccaacatac cataaaccctc ccattctgct aatgcccagc ctaagttggg gagaccactc   1500
cagattccaa gatgtacagt ttgctttgct gggccttttt cccatgcctg cctttactct   1560
gccagagtta tattgctggg gttttgaaga agatcctatt aaataaaaga ataagcagta   1620
ttattaagta gccctgcatt tcaggtttcc ttgagtggca ggccaggcct ggccgtgaac   1680
gttcactgaa atcatggcct cttggccaag attgatagct tgtgcctgtc cctgagtccc   1740
agtccatcac gagcagctgg tttctaagat gctatttccc gtataaagca tgagaccgtg   1800
acttgccagc cccacagagc cccgcccttg tccatcactg gcatctggac tccagcctgg   1860 gttgggcaa agagggaaat gagatcatgt cctaaccctg atcctcttgt cccacagata   1920
tccagaaccc tgaccctgcc gtgtaccagc tgagagactc taaatccagt gacaagtctg   1980
tctgcctatt caccgatttt gattctcaaa caaatgtgtc acaaagtaag gattctgatg   2040
tgtatatcac agacaaaact gtgctagaca tgaggtctat ggacttcaag agcaacagtg   2100
ctgtggcctg gagcaactag tgggcggagt tagggcggag ccaatcagcg tgcgccgttc   2160
cgaaagttgc cttttatggc tgggcggaga atgggcggtg aacgccgatg attatataag   2220
gacgcgccgg gtgtggcaca gctagttccg tcgcagccgg gatttgggtc gcggttcttg   2280
tttgttccgg aaagccacca tggcgctccc agtgacagcc ttactttac ctctggcgtt   2340 attattgcac gcggctcgtc ctgacataca gatgactcag actacctctt ccctatctgc   2400
ttctttaggc gaccgagtaa caatatcttt ccgggccagc caggacatct caaaatactt   2460
aaactggtat cagcagaagc cggacggaac agttaagttg ctcatttacc acacgtcgag   2520
attacactca ggcgttccta gccgattttc gggttccggt tccggtacgg actacagcct   2580
```

```
gacaatcagt aaccttgagc aggaggacat cgccacctac ttctgtcagc agggcaacac    2640
gctcccgtac acattcggtg ggggaactaa gctggagatt accggaggcg gtggcagcgg    2700
tggcggcggc agcgggggtg gcggctcgga ggtcaagtta caggagagcg gaccgggctt    2760
ggtcgcacct agccagagcc tctcagtcac gtgcactgtg tctggagtca gtctcccaga    2820
ctacggggta tcatggatac gacagccgcc tagaaagggc ttagagtggc tgggggttat    2880
ctggggaagt gaaaccacat actacaactc agctctcaag agccgcctca ccatcattaa    2940
ggacaacagt aagtcgcagg ttttcttaaa gatgaactct ctccagactg acgacaccgc    3000
tatttactac tgcgcgaagc actactacta cggcgggagt tacgcaatgg actactgggg    3060
tcagggcact tctgtgaccg tatccagcac tactacccca gccccacgtc cccccacgcc    3120
agctccaacg atagcaagtc agcccttatc tcttcgccct gaggcttgca ggcccgcggc    3180
gggcggcgcc gttcacacgc aggactagac ttcgcctgc gacatctaca tctgggcacc    3240
actagccggg acttgcggag tgttgttgtt gagcttggta ataacgctct actgcaaagc    3300
gagccgcaaa aaagcggcgg cggcggcgaa aagcccgttt gcgagcccgg cgagcagcgc    3360
gcaggaagaa gatgcgagca gctgccgcgc gccgagcgaa aagaaggca gctgcgaact    3420 gagagtgaag ttctctcgct ccgcggacgc acccgcttac cagcagggtc agaaccagct    3480
atacaacgag ttaaacctgg ggcgccggga ggagtacgac gtgttagaca agcgtagagg    3540
tagggacccg gagatgggag gcaagcctcg gagaaagaac ccccaggagg gcctgtacaa    3600
cgaactccag aaggacaaga tggctgaggc gtactcggag attggtatga agggcgagag    3660
acgtcgcgga aagggacacg acggcttata ccaggggctt tccaccgcga ccaaggacac    3720
atacgacgcg ctgcacatgc aagccttacc acctcgatga ggtaccagcg gccgcttcga    3780
gcagacatga taagatacat tgatgagttt ggacaaacca caactagaat gcagtgaaaa    3840
aaatgcttta tttgtgaaat ttgtgatgct attgctttat ttgtaaccat tataagctgc    3900
aataaacaag ttaacaacaa caattcgaat ttaaatcgga tccgcaacaa atctgacttt    3960
gcatgtgcaa acgccttcaa caacagcatt attccagaag acaccttctt ccccagccca    4020
ggtaagggca gctttggtgc cttcgcaggc tgtttccttg cttcaggaat ggccaggttc    4080
tgcccagagc tctggtcaat gatgtctaaa actcctctga ttggtggtct cggccttatc    4140
cattgccacc aaaaccctct ttttactaag aaacagtgag ccttgttctg gcagtccaga    4200
gaatgacacg ggaaaaaagc agatgaagag aaggtggcag gagagggcac gtggcccagc    4260
ctcagtctct ccaactgagt tcctgcctgc ctgcctttgc tcagactgtt tgccccttac    4320
tgctcttcta ggcctcattc taagcccctt ctccaagttg cctctcctta tttctccctg    4380
tctgccaaaa aatctttccc agctcactaa gtcagtctca cgcagtcact cattaaccca    4440
ccaatcactg attgtgccgg cacatgaatg caccaggtgt tgaagtggag gaattaaaaa    4500
gtcagatgag gggtgtgccc agaggaagca ccattctagt tggggagcc catctgtcag    4560 ctgggaaaag tccaaataac ttcagattgg aatgtgtttt aactcagggt tgagaaaaca    4620
gccaccttca ggacaaaagt cagggaaggg ctctctgaag aaatgctact tgaagatacc    4680
agccctacca agggcaggga gaggaccaat tgatggagtt ggccactccc tctctgcgcg    4740
ctcgctcgct cactgaggcc gcccgggcaa agcccgggcg tcgggcgacc tttggtcgcc    4800
cggcctcagt gagcgagcga gcgcgcagag agggagtggc caacggcgcg cctgcaggtc    4860
tcaaaaatag ctaccctctc cggcatgaat ttatcagcta gaacggttga atatcatatt    4920
gatggtgatt tgactgtctc cggcctttct cacccgtttg aatctttacc tacacattac    4980
```

```
tcaggcattg catttaaaat atatgagggt tctaaaaatt tttatccttg cgttgaaata    5040
aaggcttctc ccgcaaaagt attacagggt cataatgttt ttggtacaac cgatttagct    5100
ttatgctctg aggctttatt gcttaatttt gctaattctt tgccttgcct gtatgattta    5160
ttggatgttg gaattcctga tgcggtattt tctccttacg catctgtgcg gtatttcaca    5220
ccgcatatgg tgcactctca gtacaatctg ctctgatgcc gcatagttaa gccagccccg    5280
acacccgcca cacccgctg acgcgccctg acgggcttgt ctgctcccgg catccgctta    5340
cagacaagct gtgaccgtct ccgggagctg catgtgtcag aggttttcac cgtcatcacc    5400
gaaacgcgcg agacgaaagg gcctcgtgat acgcctattt ttataggtta atgtcatgat    5460
aataatggtt tcttagacgt caggtggcac ttttcgggga atgtgcgcg gaaccnctat    5520
ttgtttattt ttctaaatac attcaaatat gtatccgctc atgagacaat aaccctgata    5580
aatgcttcaa taatattgaa aaggaagag tatgagtatt caacatttcc gtgtcgccct    5640
tattcccttt tttgcggcat tttgccttcc tgttttgct cacccagaaa cgctggtgaa    5700
agtaaaagat gctgaagatc agttgggtgc acagtgggt tacatcgaac tggatctcaa    5760
cagcggtaag atccttgaga gttttcgccc cgaagaacgt tttccaatga tgagcacttt    5820
taaagttctg ctatgtggcg cggtattatc ccgtattgac gccgggcaag agcaactcgg    5880
tcgccgcata cactattctc agaatgactt ggttgagtac tcaccagtca cagaaaagca    5940
tcttacggat ggcatgacag taagagaatt atgcagtgct gccataacca tgagtgataa    6000
cactgcggcc aacttacttc tgacaacgat cggaggaccg aaggagctaa ccgcttttt    6060
gcacaacatg gggatcatg taactcgcct tgatcgttgg gaaccggagc tgaatgaagc    6120
cataccaaac gacgagcgtg acaccacgat gcctgtagca atggcaacaa cgttgcgcaa    6180
actattaact ggcgaactac ttactctagc ttcccggcaa caattaatag actggatgga    6240
ggcggataaa gttgcaggac cacttctgcg ctcggccctt ccggctggct ggtttattgc    6300
tgataaatct ggagccggtg agcgtgggtc tcgcggtatc attgcagcac tggggccaga    6360
tggtaagccc tcccgtatcg tagttatcta cacgacgggg agtcaggcaa ctatggatga    6420
acgaaataga cagatcgctg agataggtgc ctcactgatt aagcattggt aactgtcaga    6480
ccaagtttac tcatatatac tttagattga tttaaaactt catttttaat ttaaaaggat    6540
ctaggtgaag atcctttttg ataatctcat gaccaaaatc ccttaacgtg agttttcgtt    6600
ccactgagcg tcagaccccg tagaaaagat caaaggatct tcttgagatc ctttttttct    6660
gcgcgtaatc tgctgcttgc aaacaaaaaa accaccgcta ccagcggtgg tttgtttgcc    6720
ggatcaagag ctaccaactc tttttccgaa ggtaactggc ttcagcagag cgcagatacc    6780
aaatactgtc cttctagtgt agccgtagtt aggccaccac ttcaagaact ctgtagcacc    6840
gcctacatac ctcgctctgc taatcctgtt accagtggct gctgccagtg gcgataagtc    6900
gtgtcttacc gggttggact caagacgata gttaccggat aaggcgcagc ggtcgggctg    6960
aacggggggt tcgtgcacac agcccagctt ggagcgaacg acctacaccg aactgagata    7020
cctacagcgt gagctatgag aaagcgccac gcttcccgaa gggagaaagg cggacaggta    7080
tccggtaagc ggcagggtcg gaacaggaga gcgcacgagg gagcttccag ggggaaacgc    7140
ctggtatctt tatagtcctg tcgggtttcg ccacctctga cttgagcgtc gatttttgtg    7200
atgctcgtca gggggggcgga gcctatggaa aaacgccagc aacgcggcct ttttacggtt    7260
cctggccttt tgctggcctt ttgctcacat gttcttcct gcgttatccc ctgattctgt    7320
ggataaccgt attaccgcct ttgagtgagc tgataccgct cgccgcagcc gaacgaccga    7380
```

```
gcgcagcgag tcagtgagcg aggaagcgga agagcgccca atacgcaaac cgcctctccc    7440
cgcgcgttgg ccgattcatt aatg                                           7464
```

<210> SEQ ID NO 32
<211> LENGTH: 164
<212> TYPE: DNA
<213> ORGANISM: Artificial Sequence
<220> FEATURE:
<223> OTHER INFORMATION: Synthetic polynucleotide

<400> SEQUENCE: 32

```
gggcggagtt agggcggagc caatcagcgt gcgccgttcc gaaagttgcc ttttatggct     60
gggcggagaa tgggcggtga acgccgatga ttatataagg acgcgccggg tgtggcacag    120
ctagttccgt cgcagccggg atttgggtcg cggttcttgt ttgt                     164
```

<210> SEQ ID NO 33
<211> LENGTH: 122
<212> TYPE: DNA
<213> ORGANISM: Artificial Sequence
<220> FEATURE:
<223> OTHER INFORMATION: Synthetic polynucleotide

<400> SEQUENCE: 33

```
taagatacat tgatgagttt ggacaaacca caactagaat gcagtgaaaa aaatgcttta     60
tttgtgaaat ttgtgatgct attgctttat ttgtaaccat tataagctgc aataaacaag    120
tt                                                                   122
```

<210> SEQ ID NO 34
<211> LENGTH: 135
<212> TYPE: DNA
<213> ORGANISM: Artificial Sequence
<220> FEATURE:
<223> OTHER INFORMATION: Synthetic polynucleotide

<400> SEQUENCE: 34

```
gatccagaca tgataagata cattgatgag tttggacaaa ccacaactag aatgcagtga     60 aaaaatgct ttatttgtga aatttgtgat gctattgctt tatttgtaac cattataagc    120
tgcaataaac aagtt                                                     135
```

<210> SEQ ID NO 35
<211> LENGTH: 181
<212> TYPE: DNA
<213> ORGANISM: Artificial Sequence
<220> FEATURE:
<223> OTHER INFORMATION: Synthetic polynucleotide

<400> SEQUENCE: 35

```
tgagtttgga caaaccacaa ctagaatgca gtgaaaaaaa tgctttattt gtgaaatttg     60
tgatgctatt gctttatttg taaccattat aagctgcaat aaacaagtta acaacaacaa    120
ttgcattcat tttatgtttc aggttcaggg ggaggtgtgg gaggtttttt aaagcaagta    180
a                                                                    181
```

<210> SEQ ID NO 36
<211> LENGTH: 7521
<212> TYPE: DNA
<213> ORGANISM: Artificial Sequence
<220> FEATURE:
<223> OTHER INFORMATION: Synthetic polynucleotide

<400> SEQUENCE: 36

```
cagcagctgg cgtaatagcg aagaggcccg caccgatcgc ccttcccaac agttgcgcag      60
cctgaatggc gaatggaatt ccagacgatt gagcgtcaaa atgtaggtat ttccatgagc     120
gtttttcctg ttgcaatggc tggcggtaat attgttctgg atattaccag caaggccgat     180
agtttgagtt cttctactca ggcaagtgat gttattacta atcaaagaag tattgcgaca     240
acggttaatt tgcgtgatgg acagactctt ttactcggtg ccctcactga ttataaaaac     300
acttctcagg attctggcgt accgttcctg tctaaaatcc ctttaatcgg cctcctgttt     360
agctcccgct ctgattctaa cgaggaaagc acgttatacg tgctcgtcaa agcaaccata     420
gtacgcgccc tgtagcggcg cattaagcgc ggcgggtgtg gtggttacgc gcagcgtgac     480
cgctacactt gccagcgccc tagcgcccgc tcctttcgct ttcttccctt cctttctcgc     540
cacgttcgcc ggctttcccc gtcaagctct aaatcggggg ctccctttag ggttccgatt     600
tagtgcttta cggcacctcg accccaaaaa acttgattag ggtgatggtt cacgtagtgg     660
gccatcgccc tgatagacgg ttttcgccc tttgacgttg gagtccacgt tctttaatag     720
tggactcttg ttccaaactg gaacaacact caaccctatc tcggtctatt cttttgattt     780
ataagggatt ttgccgattt cggcctattg gttaaaaaat gagctgattt aacaaaaatt     840
taacgcgaat tttaacaaaa tattaacgct tacaatttaa atatttgctt atacaatctt     900
cctgttttg gggcttttct gattatcaac cggggtacat atgattgaca tgctagtttt     960
acggcgcgcc gggttggcca ctccctctct gcgcgctcgc tcgctcactg aggccgggcg    1020
accaaaggtc gcccgacgcc cgggctttgc ccgggcggcc tcagtgagcg agcgagcgcg    1080
cagagaggga gtggccaact ccatcactag gggttcctac gcgtagatct catattctgg    1140
cagggtcagt ggctccaact aacatttgtt tggtacttta cagtttatta atagatgtt    1200
tatatggaga agctctcatt tctttctcag aagagcctgg ctaggaaggt ggatgaggca    1260
ccatattcat tttgcaggtg aaattcctga gatgtaagga gctgctgtga cttgctcaag    1320
gccttatatc gagtaaacgg tagcgctggg gcttagacgc aggtgttctg atttatagtt    1380
caaaacctct atcaatgaga gagcaatctc ctggtaatgt gatagatttc ccaacttaat    1440
gccaacatac cataaacctc ccattctgct aatgcccagc ctaagttggg gagaccactc    1500
cagattccaa gatgtacagt ttgctttgct gggcttttt cccatgcctg cctttactct    1560
gccagagtta tattgctggg gttttgaaga agatcctatt aaataaaaga ataagcagta    1620
ttattaagta gccctgcatt tcaggttttcc ttgagtggca ggccaggcct ggccgtgaac    1680
gttcactgaa atcatggcct cttggccaag attgatagct tgtgcctgtc cctgagtccc    1740
agtccatcac gagcagctgg tttctaagat gctatttccc gtataaagca tgagaccgtg    1800
acttgccagc cccacagagc cccgcccttg tccatcactg gcatctggac tccagcctgg    1860
gttgggcaa agagggaaat gagatcatgt cctaaccctg atcctcttgt cccacagata    1920
tccagaaccc tgaccctgcc gtgtaccagc tgagagactc taaatccagt gacaagtctg    1980
tctgcctatt caccgatttt gattctcaaa caaatgtgtc acaaagtaag gattctgatg    2040
tgtatatcac agacaaaact gtgctagaca tgaggtctat ggacttcaag agcaacagtg    2100
ctgtggcctg gagcaactag tgggcggagt tagggcggag ccaatcagcg tgcgccgttc    2160
cgaaagttgc cttttatggc tgggcggaga atgggcggtg aacgccgatg attatataag    2220
gacgcgccgt gtgtggcaca gctagttccg tcgcagccgg gatttgggtc gcggttcttg    2280
tttgttccgg aaagccacat ggcgctccca gtgacagcct tactttacc tctggcgtta    2340
```

```
ttattgcacg cggctcgtcc tgacatacag atgactcaga ctacctcttc cctatctgct    2400
tctttaggcg accgagtaac aatatcttgc cgggccagcc aggacatctc aaaatactta    2460
aactggtatc agcagaagcc ggacggaaca gttaagttgc tcatttacca cacgtcgaga    2520
ttacactcag gcgttcctag ccgattttcg ggttccggtt ccggtacgga ctacagcctg    2580
acaatcagta accttgagca ggaggacatc gccacctact tctgtcagca gggcaacacg    2640
ctcccgtaca cattcggtgg gggaactaag ctggagatta ccggaggcgg tggcagcggt    2700
ggcggcggca gcggggtgg cggctcggag gtcaagttac aggagagcgg accgggcttg    2760
gtcgcaccta gccagagcct ctcagtcacg tgcactgtgt ctggagtcag tctcccagac    2820
tacggggtat catggatacg acagccgcct agaaagggct tagagtggct gggggttatc    2880
tggggaagtg aaaccacata ctacaactca gctctcaaga gccgcctcac catcattaag    2940
gacaacagta agtcgcaggt tttcttaaag atgaactctc tccagactga cgacaccgct    3000
atttactact gcgcgaagca ctactactac ggcgggagtt acgcaatgga ctactggggt    3060
cagggcactt ctgtgaccgt atccagcact actaccccag ccccacgtcc ccccacgcca    3120
gctccaacga tagcaagtca gcccttatct cttcgccctg aggcttgcag gcccgcggcg    3180
ggcggcgccg ttcacacgcg aggactagac ttcgcctgcg acatctacat ctgggcacca    3240
ctagccggga cttgcggagt gttgttgttg agcttggtaa taacgctcta ctgcaagcgt    3300
gggagaaaga agctcttgta cattttcaag cagccattca tgcgtcccgt tcagacgact    3360
caggaggagg acggctgctc gtgccgattc ccggaggagg aggagggcgg ttgcgaactc    3420
agagtgaagt tctctcgctc cgcggacgca cccgcttacc agcagggtca gaaccagcta    3480
tacaacgagt taaacctggg gcgccgggag gagtacgacg tgttagacaa gcgtagaggt    3540
agggaccccg agatgggagg caagcctcgg agaaagaacc cccaggaggg cctgtacaac    3600
gaactccaga aggacaagat ggctgaggcg tactcggaga ttggtatgaa gggcgagaga    3660
cgtcgcggaa agggacacga cggcttatac caggggcttt ccaccgcgac caaggacaca    3720
tacgacgcgc tgcacatgca agccttacca cctcgatgag gtaccagcgg ccgcgatcca    3780
gacatgataa gatacattga tgagtttgga caaaccacaa ctagaatgca gtgaaaaaaa    3840
tgctttattt gtgaaatttg tgatgctatt gctttatttg taaccattat aagctgcaat    3900
aaacaagtta acaacaacaa ttgcattcat tttatgtttc aggttcaggg ggaggtgtgg    3960
gaggtttttt aaagcaagta aactggtact agtacggatc cgcaacaaat ctgactttgc    4020
atgtgcaaac gccttcaaca acagcattat tccagaagac accttcttcc ccagcccagg    4080
taagggcagc tttggtgcct tcgcaggctg tttccttgct tcaggaatgg ccaggttctg    4140
cccagagctc tggtcaatga tgtctaaaac tcctctgatt ggtggtctcg gccttatcca    4200
ttgccaccaa aaccctcttt ttactaagaa acagtgagcc ttgttctggc agtccagaga    4260
atgcacggg aaaaagcag atgaagagaa ggtggcagga gagggcacgt ggcccagcct    4320
cagtctctcc aactgagttc ctgcctgcct gcctttgctc agactgtttg ccccttactg    4380
ctcttctagg cctcattcta agccccttct ccaagttgcc tctccttatt tctccctgtc    4440
tgccaaaaaa tctttcccag ctcactaagt cagtctcacg cagtcactca ttaacccacc    4500
aatcactgat tgtgccggca catgaatgca ccaggtgttg aagtggagga attaaaaagt    4560
cagatgaggg gtgtgcccag aggaagcacc attctagttg ggggagccca tctgtcagct    4620
gggaaaagtc caaataactt cagattggaa tgtgttttaa ctcaggggttg agaaaacagc    4680
caccttcagg acaaaagtca gggaagggct ctctgaagaa atgctacttg aagataccag    4740
```

```
ccctaccaag ggcagggaga ggaccaattg atggagttgg ccactccctc tctgcgcgct    4800
cgctcgctca ctgaggccgc ccgggcaaag cccgggcgtc gggcgacctt tggtcgcccg    4860
gcctcagtga gcgagcgagc gcgcagagag ggagtggcca acggcgcgcc tgcaggttca    4920
aaaatagcta ccctctccgg catgaattta tcagctagaa cggttgaata tcatattgat    4980
ggtgatttga ctgtctccgg cctttctcac ccgtttgaat ctttacctac acattactca    5040
ggcattgcat ttaaaatata tgagggttct aaaaattttt atccttgcgt tgaaataaag    5100
gcttctcccg caaaagtatt acagggtcat aatgttttg gtacaaccga tttagcttta    5160
tgctctgagg ctttattgct taattttgct aattctttgc cttgcctgta tgatttattg    5220
gatgttggaa ttcctgatgc ggtattttct ccttacgcat ctgtgcggta tttcacaccg    5280
catatggtgc actctcagta caatctgctc tgatgccgca tagttaagcc agccccgaca    5340
cccgccaaca cccgctgacg cgccctgacg ggcttgtctg ctcccggcat ccgcttacag    5400
acaagctgtg accgtctccg ggagctgcat gtgtcagagg ttttcaccgt catcaccgaa    5460
acgcgcgaga cgaaagggcc tcgtgatacg cctatttta taggttaatg tcatgataat    5520
aatggtttct tagacgtcag gtggcacttt tcggggaaat gtgcgcggaa cccctatttg    5580 tttattttc taaatacatt caaatatgta tccgctcatg agacaataac cctgataaat    5640
gcttcaataa tattgaaaaa ggaagagtat gagtattcaa catttccgtg tcgcccttat    5700
tccctttttt gcggcatttt gccttcctgt ttttgctcac ccagaaacgc tggtgaaagt    5760
aaaagatgct gaagatcagt tgggtgcacg agtgggttac atcgaactgg atctcaacag    5820
cggtaagatc cttgagagtt ttcgccccga gaacgttttt ccaatgatga gcacttttaa    5880
agttctgcta tgtggcgcgg tattatcccg tattgacgcc gggcaagagc aactcggtcg    5940
ccgcatacac tattctcaga atgacttggt tgagtactca ccagtcacag aaaagcatct    6000
tacggatggc atgacagtaa gagaattatg cagtgctgcc ataaccatga gtgataacac    6060
tgcggccaac ttacttctga caacgatcgg aggaccgaag gagctaaccg cttttttgca    6120
caacatgggg gatcatgtaa ctcgccttga tcgttgggaa ccggagctga atgaagccat    6180
accaaacgac gagcgtgaca ccacgatgcc tgtagcaatg gcaacaacgt tgcgcaaact    6240
attaactggc gaactactta ctctagcttc ccggcaacaa ttaatagact ggatggaggc    6300
ggataaagtt gcaggaccac ttctgcgctc ggcccttccg gctggctggt ttattgctga    6360
taaatctgga gccggtgagc gtgggtctcg cggtatcatt gcagcactgg ggccagatgg    6420
taagccctcc cgtatcgtag ttatctacac gacggggagt caggcaacta tggatgaacg    6480
aaatagacag atcgctgaga taggtgcctc actgattaag cattggtaac tgtcagacca    6540
agtttactca tatatacttt agattgattt aaaacttcat ttttaattta aaaggatcta    6600
ggtgaagatc ctttttgata atctcatgac caaaatccct taacgtgagt tttcgttcca    6660
ctgagcgtca gacccgtag aaaagatcaa aggatcttct tgagatcctt tttttctgcg    6720
cgtaatctgc tgcttgcaaa caaaaaaacc accgctacca gcggtggttt gtttgccgga    6780
tcaagagcta ccaactcttt ttccgaaggt aactggcttc agcagagcgc agataccaaa    6840
tactgtcctt ctagtgtagc cgtagttagg ccaccacttc aagaactctg tagcaccgcc    6900
tacatacctc gctctgctaa tcctgttacc agtggctgct gccagtggcg ataagtcgtg    6960
tcttaccggg ttggactcaa gacgatagtt accggataag gcgcagcggt cgggctgaac    7020
ggggggttcg tgcacacagc ccagcttgga gcgaacgacc tacaccgaac tgagatacct    7080
acagcgtgag ctatgagaaa gcgccacgct tcccgaaggg agaaaggcgg acaggtatcc    7140
```

```
ggtaagcggc agggtcggaa caggagagcg cacgagggag cttccagggg gaaacgcctg    7200
gtatctttat agtcctgtcg ggtttcgcca cctctgactt gagcgtcgat ttttgtgatg    7260
ctcgtcaggg gggcggagcc tatggaaaaa cgccagcaac gcggcctttt tacggttcct    7320
ggccttttgc tggccttttg ctcacatgtt ctttcctgcg ttatccctg attctgtgga     7380 taaccgtatt accgcctttg agtgagctga taccgctcgc cgcagccgaa cgaccgagcg    7440
cagcgagtca gtgagcgagg aagcggaaga gcgcccaata cgcaaaccgc ctctccccgc    7500
gcgttggccg attcattaat g                                              7521

<210> SEQ ID NO 37
<211> LENGTH: 7464
<212> TYPE: DNA
<213> ORGANISM: Artificial Sequence
<220> FEATURE:
<223> OTHER INFORMATION: Synthetic polynucleotide

<400> SEQUENCE: 37
cagcagctgg cgtaatagcg aagaggcccg caccgatcgc ccttcccaac agttgcgcag      60
cctgaatggc gaatggaatt ccagacgatt gagcgtcaaa atgtaggtat ttccatgagc     120 gttttttcctg ttgcaatggc tggcggtaat attgttctgg atattaccag caaggccgat   180
agtttgagtt cttctactca ggcaagtgat gttattacta atcaaagaag tattgcgaca    240
acggttaatt tgcgtgatgg acagactctt ttactcggtg gcctcactga ttataaaaac    300
acttctcagg attctggcgt accgttcctg tctaaaatcc ctttaatcgg cctcctgttt    360
agctcccgct ctgattctaa cgaggaaagc acgttatacg tgctcgtcaa agcaaccata    420
gtacgcgccc tgtagcggcg cattaagcgc ggcgggtgtg gtggttacgc gcagcgtgac    480
cgctacactt gccagcgccc tagcgcccgc tcctttcgct ttcttccctt cctttctcgc    540
cacgttcgcc ggctttcccc gtcaagctct aaatcggggg ctcccttag ggttccgatt     600 tagtgcttta cggcacctcg accccaaaaa acttgattag ggtgatggtt cacgtagtgg    660
gccatcgccc tgatagacgg ttttcgccc tttgacgttg gagtccacgt tctttaatag    720
tggactcttg ttccaaactg gaacaacact caacccatc tcggtctatt cttttgattt     780
ataagggatt ttgccgattt cggcctattg gttaaaaaat gagctgattt aacaaaaatt    840
taacgcgaat tttaacaaaa tattaacgtt acaatttaa atatttgctt atacaatctt     900 cctgttttg gggctttttct gattatcaac cggggtacat atgattgaca tgctagtttt    960
acggcgcgcc gggttggcca ctccctctct gcgcgctcgc tcgctcactg aggccgggcg   1020
accaaaggtc gcccgacgcc cgggctttgc ccgggcggcc tcagtgagcg agcgagcgcg   1080
cagagaggga gtggccaact ccatcactag gggttcctac gcgtagatct catattctgg   1140
cagggtcagt ggctccaact aacatttgtt tggtacttta cagtttatta aatagatgtt   1200
tatatggaga agctctcatt tctttctcag aagagcctgg ctaggaaggt ggatgaggca   1260
ccatattcat tttgcaggtg aaattcctga gatgtaagga gctgctgtga cttgctcaag   1320
gccttatatc gagtaaacgg tagcgctggg gcttagacgc aggtgttctg atttatagtt   1380 caaaaccctct atcaatgaga gagcaatctc ctggtaatgt gatagatttc caacttaat   1440 gccaacatac cataaacctc ccattctgct aatgcccagc ctaagttggg gagaccactc   1500
cagattccaa gatgtacagt ttgctttgct gggccttttt cccatgcctg cctttactct   1560
gccagagtta tattgctggg gttttgaaga agatcctatt aaataaaaga ataagcagta   1620
ttattaagta gccctgcatt tcaggttttcc ttgagtggca ggccaggcct ggccgtgaac   1680
```

-continued

| | |
|---|---|
| gttcactgaa atcatggcct cttggccaag attgatagct tgtgcctgtc cctgagtccc | 1740 |
| agtccatcac gagcagctgg tttctaagat gctatttccc gtataaagca tgagaccgtg | 1800 |
| acttgccagc cccacagagc cccgcccttg tccatcactg gcatctggac tccagcctgg | 1860 |
| gttgggcaa agagggaaat gagatcatgt cctaaccctg atcctcttgt cccacagata | 1920 |
| tccagaaccc tgaccctgcc gtgtaccagc tgagagactc taaatccagt gacaagtctg | 1980 |
| tctgcctatt caccgatttt gattctcaaa caaatgtgtc acaaagtaag gattctgatg | 2040 |
| tgtatatcac agacaaaact gtgctagaca tgaggtctat ggacttcaag agcaacagtg | 2100 |
| ctgtggcctg gagcaactag tgggcggagt tagggcggag ccaatcagcg tgcgccgttc | 2160 |
| cgaaagttgc cttttatggc tgggcggaga atgggcggtg aacgccgatg attatataag | 2220 |
| gacgcgccgg gtgtggcaca gctagttccg tcgcagccgg gatttgggtc gcggttcttg | 2280 |
| tttgttccgg aaagccacca tggcgctccc agtgacagcc ttactttac ctctggcgtt | 2340 |
| attattgcac gcggctcgtc ctgacataca gatgactcag actacctctt ccctatctgc | 2400 |
| ttctttaggc gaccgagtaa caatatcttg ccgggccagc aggacatct caaaatactt | 2460 |
| aaactggtat cagcagaagc cggacggaac agttaagttg ctcatttacc acacgtcgag | 2520 |
| attacactca ggcgttccta gccgatttc gggttccggt tccggtacgg actacagcct | 2580 |
| gacaatcagt aaccttgagc aggaggacat cgccacctac ttctgtcagc agggcaacac | 2640 |
| gctcccgtac acattcggtg ggggaactaa gctggagatt accggaggcg gtggcagcgg | 2700 |
| tggcggcggc agcggggtg gcggctcgga ggtcaagtta caggagagcg accgggctt | 2760 |
| ggtcgcacct agccagagcc tctcagtcac gtgcactgtg tctggagtca gtctcccaga | 2820 |
| ctacggggta tcatggatac gacagccgcc tagaaagggc ttagagtggc tgggggttat | 2880 |
| ctggggaagt gaaaccacat actacaactc agctctcaag agccgcctca ccatcattaa | 2940 |
| ggacaacagt aagtcgcagg ttttcttaaa gatgaactct ctccagactg acgacaccgc | 3000 |
| tatttactac tgcgcgaagc actactacta cggcggagt tacgcaatgg actactgggg | 3060 |
| tcagggcact tctgtgaccg tatccagcac tactacccca gccccacgtc ccccacgcc | 3120 |
| agctccaacg atagcaagtc agcccttatc tcttcgccct gaggcttgca ggcccgcggc | 3180 |
| gggcggcgcc gttcacacgc gaggactaga cttcgcctgc gacatctaca tctgggcacc | 3240 |
| actagccggg acttgcggag tgttgttgtt gagcttggta ataacgctct actgcaaagc | 3300 |
| gagccgcaaa aaagcggcgg cggcggcgaa aagcccgttt gcgagcccgg cgagcagcgc | 3360 |
| gcaggaagaa gatgcgagca gctgccgcgc gccgagcgaa aagaaggca gctgcgaact | 3420 |
| gagagtgaag ttctctcgct ccgcggacgc acccgcttac cagcagggtc agaaccagct | 3480 |
| atacaacgag ttaaacctgg ggcgccggga ggagtacgac gtgttagaca gcgtagagg | 3540 |
| tagggacccg gagatgggag gcaagcctcg gagaaagaac ccccaggagg gcctgtacaa | 3600 |
| cgaactccag aaggacaaga tggctgaggc gtactcggag attggtatga agggcgagag | 3660 |
| acgtcgcgga aagggacacg acggcttata ccagggctt tccaccgcga ccaaggacac | 3720 |
| atacgacgcg ctgcacatgc aagccttacc acctcgatga ggtaccagcg gccgcttcga | 3780 |
| gcagacatga taagatacat tgatgagttt ggacaaacca caactagaat gcagtgaaaa | 3840 |
| aaatgcttta tttgtgaaat tgtgatgct attgctttat ttgtaaccat tataagctgc | 3900 |
| aataaacaag ttaacaacaa caattcgaat ttaaatcgga tccgcaacaa atctgacttt | 3960 |
| gcatgtgcaa acgccttcaa caacagcatt attccagaag acaccttctt ccccagccca | 4020 |
| ggtaagggca gctttggtgc cttcgcaggc tgtttccttg cttcaggaat ggccaggttc | 4080 |

```
tgcccagagc tctggtcaat gatgtctaaa actcctctga ttggtggtct cggccttatc    4140
cattgccacc aaaaccctct ttttactaag aaacagtgag ccttgttctg gcagtccaga    4200
gaatgacacg ggaaaaaagc agatgaagag aaggtggcag gagagggcac gtggcccagc    4260
ctcagtctct ccaactgagt tcctgcctgc ctgcctttgc tcagactgtt tgccccttac    4320
tgctcttcta ggcctcattc taagccccett ctccaagttg cctctcctta tttctccctg    4380
tctgccaaaa aatctttccc agctcactaa gtcagtctca cgcagtcact cattaaccca    4440
ccaatcactg attgtgccgg cacatgaatg caccaggtgt tgaagtggag gaattaaaaa    4500
gtcagatgag gggtgtgccc agaggaagca ccattctagt tgggggagcc catctgtcag    4560
ctgggaaaag tccaaataac ttcagattgg aatgtgtttt aactcagggt tgagaaaaca    4620
gccaccttca ggacaaaagt cagggaaggg ctctctgaag aaatgctact tgaagatacc    4680
agccctacca agggcaggga gaggaccaat tgatggagtt ggccactccc tctctgcgcg    4740
ctcgctcgct cactgaggcc gcccgggcaa agcccgggcg tcgggcgacc tttggtcgcc    4800
cggcctcagt gagcgagcga gcgcgcagag agggagtggc caacggcgcg cctgcaggtc    4860
tcaaaaatag ctaccctctc cggcatgaat ttatcagcta gaacggttga atatcatatt    4920
gatggtgatt tgactgtctc cggccttcct cacccgtttg aatctttacc tacacattac    4980
tcaggcattg catttaaaat atatgagggt tctaaaaatt tttatccttg cgttgaaata    5040
aaggcttctc ccgcaaaagt attacagggt cataatgttt ttggtacaac cgatttagct    5100
ttatgctctg aggctttatt gcttaatttt gctaattctt tgccttgcct gtatgattta    5160
ttggatgttg gaattcctga tgcggtattt tctccttacg catctgtgcg gtatttcaca    5220
ccgcatatgg tgcactctca gtacaatctg ctctgatgcc gcatagttaa gccagccccg    5280
acacccgcca cacccgctg acgcgccctg acgggcttgt ctgctcccgg catccgctta    5340
cagacaagct gtgaccgtct ccgggagctg catgtgtcag aggttttcac cgtcatcacc    5400
gaaacgcgcg agacgaaagg gcctcgtgat acgcctattt ttataggtta atgtcatgat    5460
aataatggtt tcttagacgt caggtggcac ttttcgggga aatgtgcgcg gaacccctat    5520
ttgtttattt ttctaaatac attcaaatat gtatccgctc atgagacaat aaccctgata    5580
aatgcttcaa taatattgaa aaaggaagag tatgagtatt caacatttcc gtgtcgccct    5640
tattcccttt tttgcggcat tttgccttcc tgttttgct cacccagaaa cgctggtgaa    5700
agtaaaagat gctgaagatc agttgggtgc acgagtgggt tacatcgaac tggatctcaa    5760
cagcggtaag atccttgaga gttttcgccc cgaagaacgt tttccaatga tgagcacttt    5820
taaagttctg ctatgtggcg cggtattatc ccgtattgac gccgggcaag agcaactcgg    5880
tcgccgcata cactattctc agaatgactt ggttgagtac tcaccagtca cagaaaagca    5940
tcttacggat ggcatgacag taagagaatt atgcagtgct gccataacca tgagtgataa    6000
cactgcggcc aacttacttc tgacaacgat cggaggaccg aaggagctaa ccgcttttt    6060 gcacaacatg gggatcatg taactcgcct tgatcgttgg gaaccggagc tgaatgaagc    6120
cataccaaac gacgagcgtg acaccacgat gcctgtagca atggcaacaa cgttgcgcaa    6180
actattaact ggcgaactac ttactctagc ttcccggcaa caattaatag actggatgga    6240
ggcggataaa gttgcaggac cacttctgcg ctcggccctt ccggctggct ggtttattgc    6300
tgataaatct ggagccggtg agcgtgggtc tcgcggtatc attgcagcac tggggccaga    6360
tggtaagccc tcccgtatcg tagttatcta cacgacgggg agtcaggcaa ctatggatga    6420
acgaaataga cagatcgctg agataggtgc ctcactgatt aagcattggt aactgtcaga    6480
```

```
ccaagtttac tcatatatac tttagattga tttaaaactt catttttaat ttaaaaggat      6540
ctaggtgaag atccttttg ataatctcat gaccaaaatc ccttaacgtg agttttcgtt       6600
ccactgagcg tcagaccccg tagaaaagat caaaggatct tcttgagatc ctttttttct     6660
gcgcgtaatc tgctgcttgc aaacaaaaaa accaccgcta ccagcggtgg tttgtttgcc     6720
ggatcaagag ctaccaactc tttttccgaa ggtaactggc ttcagcagag cgcagatacc     6780
aaatactgtc cttctagtgt agccgtagtt aggccaccac ttcaagaact ctgtagcacc     6840
gcctacatac ctcgctctgc taatcctgtt accagtggct gctgccagtg gcgataagtc     6900
gtgtcttacc gggttggact caagacgata gttaccggat aaggcgcagc ggtcgggctg     6960
aacggggggt tcgtgcacac agcccagctt ggagcgaacg acctacaccg aactgagata     7020
cctacagcgt gagctatgag aaagcgccac gcttcccgaa gggagaaagg cggacaggta     7080
tccggtaagc ggcagggtcg aacaggaga gcgcacgagg gagcttccag ggggaaacgc      7140
ctggtatctt tatagtcctg tcgggtttcg ccacctctga cttgagcgtc gatttttgtg     7200
atgctcgtca gggggcgga gcctatggaa aaacgccagc aacgcggcct ttttacggtt      7260
cctggccttt tgctggcctt ttgctcacat gttctttcct gcgttatccc ctgattctgt     7320
ggataaccgt attaccgcct ttgagtgagc tgataccgct cgccgcagcc gaacgaccga     7380
gcgcagcgag tcagtgagcg aggaagcgga agagcgccca atacgcaaac cgcctctccc     7440
cgcgcgttgg ccgattcatt aatg                                            7464

<210> SEQ ID NO 38
<211> LENGTH: 7523
<212> TYPE: DNA
<213> ORGANISM: Artificial Sequence
<220> FEATURE:
<223> OTHER INFORMATION: Synthetic polynucleotide

<400> SEQUENCE: 38
cagcagctgg cgtaatagcg aagaggcccg caccgatcgc ccttcccaac agttgcgcag       60
cctgaatggc gaatggaatt ccagacgatt gagcgtcaaa atgtaggtat ttccatgagc      120
gtttttcctg ttgcaatggc tggcggtaat attgttctgg atattaccag caaggccgat      180
agtttgagtt cttctactca ggcaagtgat gttattacta atcaaagaag tattgcgaca     240
acggttaatt tgcgtgatgg acagactctt ttactcggtg gcctcactga ttataaaaac     300
acttctcagg attctggcgt accgttcctg tctaaaatcc ctttaatcgg cctcctgttt     360
agctcccgct ctgattctaa cgaggaaagc acgttatacg tgctcgtcaa agcaaccata     420
gtacgcgccc tgtagcggcg cattaagcgc ggcgggtgtg gtggttacgc gcagcgtgac     480
cgctacactt gccagcgccc tagcgcccgc tcctttcgct ttcttccctt cctttctcgc     540
cacgttcgcc ggctttcccc gtcaagctct aaatcggggg ctccctttag ggttccgatt     600
tagtgcttta cggcacctcg accccaaaaa acttgattag ggtgatggtt cacgtagtgg     660
gccatcgccc tgatagacgg ttttcgccc tttgacgttg gagtccacgt tctttaatag      720
tggactcttg ttccaaactg gaacaacact caaccctatc tcggtctatt cttttgattt     780
ataagggatt ttgccgattt cggcctattg gttaaaaaat gagctgattt aacaaaaatt     840
taacgcgaat tttaacaaaa tattaacgtt tacaatttaa atatttgctt atacaatctt     900
cctgtttttg ggcttttct gattatcaac cggggtacat atgattgaca tgctagtttt      960
acggcgcgcc gggttggcca ctccctctct gcgcgctcgc tcgctcactg aggccgggcg    1020
accaaaggtc gcccgacgcc cgggctttgc ccgggcggcc tcagtgagcg agcgagcgcg    1080
```

```
cagagaggga gtggccaact ccatcactag gggttcctac gcgtagatct catattctgg      1140
cagggtcagt ggctccaact aacatttgtt tggtacttta cagttttatta aatagatgtt     1200
tatatggaga agctctcatt tctttctcag aagagcctgg ctaggaaggt ggatgaggca      1260
ccatattcat tttgcaggtg aaattcctga gatgtaagga gctgctgtga cttgctcaag     1320
gccttatatc gagtaaacgg tagcgctggg gcttagacgc aggtgttctg atttatagtt     1380
caaaacctct atcaatgaga gagcaatctc ctggtaatgt gatagatttc ccaacttaat     1440
gccaacatac cataaacctc ccattctgct aatgcccagc taagttggg gagaccactc      1500
cagattccaa gatgtacagt ttgctttgct gggccttttt cccatgcctg cctttactct     1560
gccagagtta tattgctggg gttttgaaga agatccttatt aaataaaaga ataagcagta    1620
ttattaagta gccctgcatt tcaggtttcc ttgagtggca ggccaggcct ggccgtgaac     1680
gttcactgaa atcatggcct cttggccaag attgatagct tgtgcctgtc cctgagtccc     1740
agtccatcac gagcagctgg tttctaagat gctatttccc gtataaagca tgagaccgtg     1800
acttgccagc cccacagagc cccgcccttg tccatcactg gcatctggac tccagcctgg     1860
gttggggcaa agagggaaat gagatcatgt cctaaccctg atcctcttgt cccacagata     1920
tccagaaccc tgaccctgcc gtgtaccagc tgagagactc taaatccagt gacaagtctg     1980
tctgcctatt caccgatttt gattctcaaa caaatgtgtc acaaagtaag gattctgatg     2040
tgtatatcac agacaaaact gtgctagaca tgaggtctat ggacttcaag agcaacagtg     2100
ctgtggcctg gagcaactag tgggcggagt tagggcggag ccaatcagcg tgcgccgttc     2160
cgaaagttgc cttttatggc tgggcggaga atgggcggtg aacgccgatg attatataag     2220
gacgcgccgg gtgtggcaca gctagttccg tcgcagccgg gatttgggtc gcggttcttg     2280
tttgttccgg aaagccacca tggcgctccc agtgacagcc ttactttac ctctggcgtt      2340
attattgcac gcggctcgtc ctgacataca gatgactcag actacctctt ccctatctgc     2400
ttctttaggc gaccgagtaa caatatcttg ccgggccagc caggacatct caaaatactt     2460
aaactggtat cagcagaagc cggacggaac agttaagttg ctcatttacc acacgtcgag     2520
attacactca ggcgttccta gccgattttc gggttccggt tccggtacgg actacagcct     2580
gacaatcagt aaccttgagc aggaggacat cgccacctac ttctgtcagc agggcaacac     2640
gctcccgtac acattcggtg ggggaactaa gctggagatt accggaggcg gtggcagcgg     2700
tggcggcggc agcggggggtg gcggctcgga ggtcaagtta caggagagcg gacccggctt    2760
ggtcgcacct agccagagcc tctcagtcac gtgcactgtg tctggagtca gtctcccaga     2820
ctacggggta tcatggatac gacagccgcc tagaaagggc ttagagtggc tgggggttat     2880
ctggggaagt gaaaccacat actacaactc agctctcaag agccgcctca ccatcattaa     2940
ggacaacagt aagtcgcagg ttttcttaaa gatgaactct ctccagactg acgacaccgc     3000
tatttactac tgcgcgaagc actactacta cggcggagt tacgcaatgg actactgggg      3060
tcagggcact tctgtgaccg tatccagcac tactaccccca gccccacgtc cccccacgcc    3120
agctccaacg atagcaagtc agcccttatc tcttcgccct gaggcttgca ggcccgcggc     3180
gggcggcgcc gttcacacgc gaggactaga cttcgcctgc gacatctaca tctgggcacc     3240
actagccggg acttgcggag tgttgttgtt gagcttggta ataacgctct actgcaaagc     3300
gagccgcaaa aaagcggcgg cggcggcgaa aagcccgttt gcgagccgg cgagcagcgc      3360
gcaggaagaa gatgcgagca gctgccgcgc gccgagcgaa aagaaggca gctgcgaact      3420
gagagtgaag ttctctcgct ccgcggacgc acccgcttac cagcagggtc agaaccagct    3480
```

```
atacaacgag ttaaacctgg ggcgccggga ggagtacgac gtgttagaca agcgtagagg    3540
tagggacccg gagatgggag gcaagcctcg gagaaagaac ccccaggagg gcctgtacaa    3600
cgaactccag aaggacaaga tggctgaggc gtactcggag attggtatga agggcgagag    3660
acgtcgcgga aagggacacg acggcttata ccaggggctt ccaccgcga ccaaggacac     3720
atacgacgcg ctgcacatgc aagccttacc acctcgatga ggtaccagcg gccgcgatcc    3780
agacatgata agatacattg atgagtttgg acaaaccaca actagaatgc agtgaaaaaa    3840
atgctttatt tgtgaaattt gtgatgctat tgctttattt gtaaccatta taagctgcaa    3900
taaacaagtt aacaacaaca attgcattca ttttatgttt caggttcagg gggaggtgtg    3960
ggaggttttt taaagcaagt aaactggtac tagtacggat ccgcaacaaa tctgactttg    4020
catgtgcaaa cgccttcaac aacagcatta ttccagaaga caccttcttc cccagcccag    4080
gtaagggcag ctttggtgcc ttcgcaggct gtttccttgc ttcaggaatg gccaggttct    4140
gcccagagct ctggtcaatg atgtctaaaa ctcctctgat tggtggtctc ggccttatcc    4200
attgccacca aaaccctctt tttactaaga aacagtgagc cttgttctgg cagtccagag    4260
aatgacacgg gaaaaagca gatgaagaga aggtggcagg agagggcacg tggcccagcc     4320
tcagtctctc caactgagtt cctgcctgcc tgcctttgct cagactgttt gccccttact    4380
gctcttctag gcctcattct aagccccttc tccaagttgc ctctccttat ttctccctgt    4440
ctgccaaaaa atctttccca gctcactaag tcagtctcac gcagtcactc attaacccac    4500
caatcactga ttgtgccggc acatgaatgc accaggtgtt gaagtggagg aattaaaaag    4560
tcagatgagg ggtgtgccca gaggaagcac cattctagtt gggggagccc atctgtcagc    4620
tgggaaaagt ccaaataact tcagattgga atgtgtttta actcagggtt gagaaaacag    4680
ccaccttcag gacaaaagtc agggaaggc tctctgaaga aatgctactt gaagatacca     4740
gccctaccaa gggcagggag aggaccaatt gatggagttg gccactccct ctctgcgcgc    4800
tcgctcgctc actgaggccg cccgggcaaa gcccgggcgt cgggcgacct ttggtcgccc    4860
ggcctcagtg agcgagcgag cgcgcagaga gggagtggcc aacggcgcgc ctgcaggtct    4920
caaaaatagc taccctctcc ggcatgaatt tatcagctag aacggttgaa tatcatattg    4980
atggtgattt gactgtctcc ggcctttctc acccgtttga atctttacct acacattact    5040
caggcattgc atttaaaata tatgagggtt ctaaaaattt ttatccttgc gttgaaataa    5100
aggcttctcc cgcaaaagta ttacagggtc ataatgtttt tggtacaacc gatttagctt    5160
tatgctctga ggcttattg cttaattttg ctaattcttt gccttgcctg tatgatttat      5220
tggatgttgg aattcctgat gcggtatttt ctccttacgc atctgtgcgg tatttcacac    5280
cgcatatggt gcactctcag tacaatctgc tctgatgccg catagttaag ccagccccga    5340
cacccgccaa cacccgctga cgcgccctga cgggcttgtc tgctcccggc atccgcttac    5400
agacaagctg tgaccgtctc cgggagctgc atgtgtcaga ggttttcacc gtcatcaccg    5460
aaacgcgcga gacgaaaggg cctcgtgata cgcctatttt tataggttaa tgtcatgata    5520
ataatggttt cttagacgtc aggtggcact tttcggggaa atgtgcgcgg aacccctatt    5580
tgtttatttt tctaaataca ttcaaatatg tatccgctca tgagacaata accctgataa    5640
atgcttcaat aatattgaaa aaggaagagt atgagtattc aacatttccg tgtcgccctt    5700
attcccttttt tgcggcatt ttgccttcct gtttttgctc acccagaaac gctggtgaaa     5760
gtaaaagatg ctgaagatca gttgggtgca cgagtgggtt acatcgaact ggatctcaac    5820
agcggtaaga tccttgagag ttttcgcccc gaagaacgtt ttccaatgat gagcactttt    5880
```

-continued

```
aaagttctgc tatgtggcgc ggtattatcc cgtattgacg ccgggcaaga gcaactcggt    5940
cgccgcatac actattctca gaatgacttg gttgagtact caccagtcac agaaaagcat    6000
cttacggatg gcatgacagt aagagaatta tgcagtgctg ccataaccat gagtgataac    6060
actgcggcca acttacttct gacaacgatc ggaggaccga aggagctaac cgcttttttg    6120
cacaacatgg gggatcatgt aactcgcctt gatcgttggg aaccggagct gaatgaagcc    6180
ataccaaacg acgagcgtga caccacgatg cctgtagcaa tggcaacaac gttgcgcaaa    6240
ctattaactg gcgaactact tactctagct tcccggcaac aattaataga ctggatggag    6300
gcggataaag ttgcaggacc acttctgcgc tcggcccttc cggctggctg gtttattgct    6360
gataaatctg gagccggtga gcgtgggtct cgcggtatca ttgcagcact ggggccagat    6420
ggtaagccct cccgtatcgt agttatctac acgacgggga gtcaggcaac tatggatgaa    6480
cgaaatagac agatcgctga gataggtgcc tcactgatta gcattggta actgtcagac    6540 caagtttact catatatact ttagattgat ttaaaacttc atttttaatt taaaaggatc    6600
taggtgaaga tcctttttga taatctcatg accaaaatcc cttaacgtga gttttcgttc    6660
cactgagcgt cagaccccgt agaaaagatc aaaggatctt cttgagatcc ttttttttctg    6720 cgcgtaatct gctgcttgca acaaaaaaaa ccaccgctac cagcggtggt ttgtttgccg    6780
gatcaagagc taccaactct ttttccgaag gtaactggct tcagcagagc gcagatacca    6840
aatactgtcc ttctagtgta gccgtagtta ggccaccact tcaagaactc tgtagcaccg    6900
cctacatacc tcgctctgct aatcctgtta ccagtggctg ctgccagtgg cgataagtcg    6960
tgtcttaccg ggttggactc aagacgatag ttaccggata aggcgcagcg gtcgggctga    7020
acggggggtt cgtgcacaca gcccagcttg gagcgaacga cctacaccga actgagatac    7080
ctacagcgtg agctatgaga aagcgccacg cttcccgaag ggagaaaggc ggacaggtat    7140
ccggtaagcg gcagggtcgg aacaggagag cgcacgaggg agcttccagg gggaaacgcc    7200
tggtatcttt atagtcctgt cgggtttcgc cacctctgac ttgagcgtcg attttgtga    7260 tgctcgtcag gggggcggag cctatggaaa aacgccagca acgcggcctt tttacggttc    7320
ctggcctttt gctggccttt tgctcacatg ttctttcctg cgttatcccc tgattctgtg    7380
gataaccgta ttaccgcctt tgagtgagct gataccgctc gccgcagccg aacgaccgag    7440
cgcagcgagt cagtgagcga ggaagcggaa gagcgcccaa tacgcaaacc gcctctcccc    7500
gcgcgttggc cgattcatta atg                                          7523
```

<210> SEQ ID NO 39
<211> LENGTH: 172
<212> TYPE: PRT
<213> ORGANISM: Artificial Sequence
<220> FEATURE:
<223> OTHER INFORMATION: Synthetic polypeptide

<400> SEQUENCE: 39

```
Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
            20                  25                  30

Leu Ser Leu Phe Leu Asn Val Arg Thr Gln Val Ala Ala Asp Trp Thr
        35                  40                  45

Ala Leu Ala Glu Glu Met Asp Phe Glu Tyr Leu Glu Ile Arg Gln Leu
    50                  55                  60
```

```
Glu Thr Gln Ala Asp Pro Thr Gly Arg Leu Leu Asp Ala Trp Gln Gly
 65                  70                  75                  80

Arg Pro Gly Ala Ser Val Gly Arg Leu Leu Asp Leu Leu Thr Lys Leu
                 85                  90                  95

Gly Arg Asp Asp Val Leu Leu Glu Leu Gly Pro Ser Ile Glu Glu Asp
            100                 105                 110

Cys Gln Lys Tyr Ile Leu Lys Gln Gln Gln Glu Glu Ala Glu Lys Pro
        115                 120                 125

Leu Gln Val Ala Ala Val Asp Ser Ser Val Pro Arg Thr Ala Glu Leu
    130                 135                 140

Ala Gly Ile Thr Thr Leu Asp Asp Pro Leu Gly His Met Pro Glu Arg
145                 150                 155                 160

Phe Asp Ala Phe Ile Cys Tyr Cys Pro Ser Asp Ile
                165                 170
```

<210> SEQ ID NO 40
<211> LENGTH: 8044
<212> TYPE: DNA
<213> ORGANISM: Artificial Sequence
<220> FEATURE:
<223> OTHER INFORMATION: Synthetic polynucleotide

<400> SEQUENCE: 40

```
cagcagctgg cgtaatagcg aagaggcccg caccgatcgc ccttcccaac agttgcgcag      60
cctgaatggc gaatggaatt ccagacgatt gagcgtcaaa atgtaggtat tccatgagc     120
gttttcctg ttgcaatggc tggcggtaat attgttctgg atattaccag caaggccgat     180
agtttgagtt cttctactca ggcaagtgat gttattacta atcaaagaag tattgcgaca     240
acggttaatt tgcgtgatgg acagactctt ttactcggtg gcctcactga ttataaaaac     300
acttctcagg attctggcgt accgttcctg tctaaaatcc ctttaatcgg cctcctgttt     360
agctcccgct ctgattctaa cgaggaaagc acgttatacg tgctcgtcaa agcaaccata     420
gtacgcgccc tgtagcggcg cattaagcgc ggcgggtgtg gtggttacgc gcagcgtgac     480
cgctacactt gccagcgccc tagcgcccgc tcctttcgct ttcttccctt cctttctcgc     540
cacgttcgcc ggctttcccc gtcaagctct aaatcggggg ctccctttag ggttccgatt     600
tagtgcttta cggcacctcg accccaaaaa acttgattag ggtgatggtt cacgtagtgg     660
gccatcgccc tgatagacgg ttttcgccc tttgacgttg gagtccacgt tctttaatag     720
tggactcttg ttccaaactg gaacaacact caaccctatc tcggtctatt cttttgattt     780
ataagggatt tgccgatttc ggcctattg gttaaaaaat gagctgattt aacaaaaatt     840
taacgcgaat tttaacaaaa tattaacgtt acaatttaa atatttgctt atacaatctt     900
cctgttttg gggcttttct gattatcaac cggggtacat atgattgaca tgctagtttt     960
acggcgcgcc gggttggcca ctccctctct gcgcgctcgc tcgctcactg aggccgggcg    1020
accaaaggtc gcccgacgcc cgggctttgc ccggcggcc tcagtgagcg agcgagcgcg    1080
cagagaggga gtggccaact ccatcactag gggttcctac gcgtagatct catattctgg    1140
cagggtcagt ggctccaact aacatttgtt tggtacttta cagtttatta atagatgtt    1200
tatatggaga agctctcatt tctttctcag aagagcctgg ctaggaaggt ggatgaggca    1260
ccatattcat tttgcaggtg aaattcctga gatgtaagga gctgctgtga cttgctcaag    1320
gccttatatc gagtaaacgg tagcgctggg cttagacgc aggtgttctg atttatagtt    1380
caaaacctct atcaatgaga gagcaatctc ctggtaatgt gatagatttc caacttaat    1440
```

```
gccaacatac cataaacctc ccattctgct aatgcccagc ctaagttggg gagaccactc    1500
cagattccaa gatgtacagt ttgctttgct gggcctttt cccatgcctg cctttactct    1560
gccagagtta tattgctggg gttttgaaga agatcctatt aaataaaaga ataagcagta   1620
ttattaagta gccctgcatt tcaggtttcc ttgagtggca ggccaggcct ggccgtgaac   1680
gttcactgaa atcatggcct cttggccaag attgatagct tgtgcctgtc cctgagtccc   1740
agtccatcac gagcagctgg tttctaagat gctatttccc gtataaagca tgagaccgtg   1800
acttgccagc cccacagagc cccgcccttg tccatcactg gcatctggac tccagcctgg   1860 gttgggcaa agagggaaat gagatcatgt cctaaccctg atcctcttgt cccacagata    1920
tccagaaccc tgaccctgcc gtgtaccagc tgagagactc taaatccagt gacaagtctg   1980
tctgcctatt caccgatttt gattctcaaa caaatgtgtc acaaagtaag gattctgatg   2040
tgtatatcac agacaaaact gtgctagaca tgaggtctat ggacttcaag agcaacagtg   2100
ctgtggcctg gagcaactag tgggcggagt tagggcggag ccaatcagcg tgcgccgttc   2160
cgaaagttgc ctttatggc tgggcggaga atggcggtaa acgccgatg attatataag     2220 gacgcgccgg gtgtggcaca gctagttccg tcgcagccgg gatttgggtc gcggttcttg   2280
tttgttccgg aaagccacca tggcgctccc agtgacagcc ttacttttac ctctggcgtt   2340
attattgcac gcggctcgtc ctgacataca gatgactcag actacctctt ccctatctgc   2400
ttctttaggc gaccgagtaa caatatcttg ccgggccagc caggacatct caaaatactt   2460
aaactggtat cagcagaagc cggacggaac agttaagttg ctcatttacc acacgtcgag   2520
attacactca ggcgttccta gccgatttc gggttccggt tccggtacgg actacagcct    2580
gacaatcagt aaccttgagc aggaggacat cgccacctac ttctgtcagc agggcaacac   2640
gctcccgtac acattcggtg ggggaactaa gctggagatt accggaggcg gtggcagcgg   2700
tggcggcggc agcggggtg gcggctcgga ggtcaagtta caggagagcg gaccgggctt    2760
ggtcgcacct agccagagcc tctcagtcac gtgcactgtg tctggagtca gtctcccaga   2820
ctacggggta tcatggatac gacagccgcc tagaaagggc ttagagtggc tgggggttat   2880
ctggggaagt gaaaccacat actacaactc agctctcaag agccgcctca ccatcattaa   2940
ggacaacagt aagtcgcagg ttttcttaaa gatgaactct ctccagactg acgacaccgc   3000
tatttactac tgcgcgaagc actactacta cggcggagt tacgcaatgg actactgggg   3060
tcagggcact tctgtgaccg tatccagcac tactacccca gccccacgtc cccccacgcc   3120
agctccaacg atagcaagtc agcccttatc tcttcgccct gaggcttgca ggcccgcggc   3180
gggcggcgcc gttcacacgc gaggactaga cttcgcctgc gacatctaca tctgggcacc   3240
actagccggg acttgcggag tgttgttgtt gagcttggta ataacgctct actgcatggc   3300
tgcaggaggt cccggcgcgg ggtctgcggc cccggtctcc tccacatcct cccttcccct   3360
ggctgctctc aacatgcgag tgcgcgccgc cctgtctctg ttcttgaacg tgcggacaca   3420
ggtggcggcc gactggaccg cgctggcgga ggagatggac tttgagtact ggagatccg    3480 gcaactggag acacaagcgg accccactgg caggctgctg gacgcctggc agggacgccc   3540
tggcgcctct gtaggccgac tgctcgatct gcttaccaag ctgggccgcg acgacgtgct   3600
gctggagctg ggacccagca ttgaggagga ttgccaaaag tatatcttga agcagcagca   3660
ggaggaggct gagaagcctt tacaggtggc cgctgtagac agcagtgtcc cacggacagc   3720
agagctggcg ggcatcacca cacttgatga ccccctgggg catatgcctg agcgtttcga   3780
tgccttcatc tgctattgcc ccagcgacat cgtcgagaaa gcgagccgca aaaaagcggc   3840
```

```
ggcggcggcg aaaagcccgt tgcgagccc ggcgagcagc gcgcaggaag aagatgcgag    3900
cagctgccgc gcgccgagcg aagaagaagg cagctgcgaa ctgagagtga agttctctcg    3960
ctccgcggac gcacccgctt accagcaggg tcagaaccag ctatacaacg agttaaacct    4020
ggggcgccgg gaggagtacg acgtgttaga caagcgtaga ggtagggacc cggagatggg    4080
aggcaagcct cggagaaaga accccagga gggcctgtac aacgaactcc agaaggacaa    4140
gatggctgag gcgtactcgg agattggtat gaagggcgag agacgtcgcg gaaagggaca    4200
cgacggctta taccaggggc tttccaccgc gaccaaggac acatacgacg cgctgcacat    4260
gcaagcctta ccacctcgat gaggtaccag cggccgcgat ccagacatga taagatacat    4320
tgatgagttt ggacaaacca caactagaat gcagtgaaaa aaatgctttta tttgtgaaat    4380
ttgtgatgct attgctttat ttgtaaccat tataagctgc aataaacaag ttaacaacaa    4440
caattgcatt cattttatgt ttcaggttca gggggaggtg tgggaggttt tttaaagcaa    4500
gtaaactggt actagtacgg atccgcaaca aatctgactt tgcatgtgca aacgccttca    4560
acaacagcat tattccagaa gacaccttct tccccagccc aggtaagggc agctttggtg    4620
ccttcgcagg ctgtttcctt gcttcaggaa tggccaggtt ctgcccagag ctctggtcaa    4680
tgatgtctaa aactcctctg attggtggtc tcggccttat ccattgccac caaaaccctc    4740
tttttactaa gaaacagtga gccttgttct ggcagtccag agaatgacac gggaaaaaag    4800
cagatgaaga gaaggtggca ggagagggca cgtggcccag cctcagtctc tccaactgag    4860
ttcctgcctg cctgcctttg ctcagactgt tgccccctta ctgctcttct aggcctcatt    4920
ctaagcccct tctccaagtt gcctctcctt atttctccct gtctgccaaa aaatctttcc    4980
cagctcacta agtcagtctc acgcagtcac tcattaaccc accaatcact gattgtgccg    5040
gcacatgaat gcaccaggtg ttgaagtgga ggaattaaaa agtcagatga ggggtgtgcc    5100
cagaggaagc accattctag ttgggggagc ccatctgtca gctgggaaaa gtccaaataa    5160
cttcagattg gaatgtgttt taactcaggg ttgagaaaac agccaccttc aggacaaaag    5220
tcagggaagg gctctctgaa gaaatgctac ttgaagatac cagccctacc aagggcaggg    5280
agaggaccaa ttgatggagt tggccactcc ctctctgcgc gctcgctcgc tcactgaggc    5340
cgccccgggca aagcccgggc gtcgggcgac ctttggtcgc ccggcctcag tgagcgagcg    5400
agcgcgcaga gagggagtgg ccaacggcgc gcctgcaggt tcaaaaatag ctaccctctc    5460
cggcatgaat ttatcagcta gaacggttga atatcatatt gatggtgatt tgactgtctc    5520
cggcctttct cacccgtttg aatctttacc tacacattac tcaggcattg catttaaaat    5580
atatgagggt tctaaaaatt tttatccttg cgttgaaata aaggcttctc ccgcaaaagt    5640
attacagggt cataatgttt ttggtacaac cgatttagct ttatgctctg aggctttatt    5700
gcttaatttt gctaattctt tgccttgcct gtatgattta ttggatgttg gaattcctga    5760
tgcggtattt tctccttacg catctgtgcg gtatttcaca ccgcatatgg tgcactctca    5820
gtacaatctg ctctgatgcc gcatagttaa gccagccccg acacccgcca acacccgctg    5880
acgcgccctg acgggcttgt ctgctcccgg catccgctta cagacaagct gtgaccgtct    5940
ccgggagctg catgtgtcag aggttttcac cgtcatcacc gaaacgcgcg agacgaaagg    6000
gcctcgtgat acgcctattt ttataggtta atgtcatgat aataatggtt tcttagacgt    6060
caggtggcac ttttcgggga atgtgcgcg gaacccctat ttgtttattt ttctaaatac    6120
attcaaatat gtatccgctc atgagacaat aaccctgata aatgcttcaa taatattgaa    6180
aaaggaagag tatgagtatt caacatttcc gtgtcgccct tattcccttt tttgcggcat    6240
```

| | | | | | |
|---|---|---|---|---|---|
| tttgccttcc | tgtttttgct | cacccagaaa | cgctggtgaa | agtaaaagat | gctgaagatc | 6300 |
| agttgggtgc | acgagtgggt | tacatcgaac | tggatctcaa | cagcggtaag | atccttgaga | 6360 |
| gttttcgccc | cgaagaacgt | tttccaatga | tgagcacttt | taaagttctg | ctatgtggcg | 6420 |
| cggtattatc | ccgtattgac | gccgggcaag | agcaactcgg | tcgccgcata | cactattctc | 6480 |
| agaatgactt | ggttgagtac | tcaccagtca | cagaaaagca | tcttacggat | ggcatgacag | 6540 |
| taagagaatt | atgcagtgct | gccataacca | tgagtgataa | cactgcggcc | aacttacttc | 6600 |
| tgacaacgat | cggaggaccg | aaggagctaa | ccgcttttt | gcacaacatg | ggggatcatg | 6660 |
| taactcgcct | tgatcgttgg | gaaccggagc | tgaatgaagc | cataccaaac | gacgagcgtg | 6720 |
| acaccacgat | gcctgtagca | atggcaacaa | cgttgcgcaa | actattaact | ggcgaactac | 6780 |
| ttactctagc | ttcccggcaa | caattaatag | actggatgga | ggcggataaa | gttgcaggac | 6840 |
| cacttctgcg | ctcggccctt | ccggctggct | ggtttattgc | tgataaatct | ggagccggtg | 6900 |
| agcgtgggtc | tcgcggtatc | attgcagcac | tggggccaga | tggtaagccc | tcccgtatcg | 6960 |
| tagttatcta | cacgacgggg | agtcaggcaa | ctatggatga | acgaaataga | cagatcgctg | 7020 |
| agataggtgc | ctcactgatt | aagcattggt | aactgtcaga | ccaagtttac | tcatatatac | 7080 |
| tttagattga | tttaaaactt | cattttaat | ttaaaaggat | ctaggtgaag | atcctttttg | 7140 |
| ataatctcat | gaccaaaatc | ccttaacgtg | agttttcgtt | ccactgagcg | tcagaccccg | 7200 |
| tagaaaagat | caaaggatct | cttgagatc | ctttttttct | gcgcgtaatc | tgctgcttgc | 7260 |
| aaacaaaaaa | accaccgcta | ccagcggtgg | tttgtttgcc | ggatcaagag | ctaccaactc | 7320 |
| tttttccgaa | ggtaactggc | ttcagcagag | cgcagatacc | aaatactgtc | cttctagtgt | 7380 |
| agccgtagtt | aggccaccac | ttcaagaact | ctgtagcacc | gcctacatac | ctcgctctgc | 7440 |
| taatcctgtt | accagtggct | gctgccagtg | gcgataagtc | gtgtcttacc | gggttggact | 7500 |
| caagacgata | gttaccggat | aaggcgcagc | ggtcgggctg | aacggggggt | tcgtgcacac | 7560 |
| agcccagctt | ggagcgaacg | acctacaccg | aactgagata | cctacagcgt | gagctatgag | 7620 |
| aaagcgccac | gcttcccgaa | gggagaaagg | cggacaggta | tccggtaagc | ggcagggtcg | 7680 |
| gaacaggaga | gcgcacgagg | gagcttccag | ggggaaacgc | ctggtatctt | tatagtcctg | 7740 |
| tcgggtttcg | ccacctctga | cttgagcgtc | gatttttgtg | atgctcgtca | ggggggcgga | 7800 |
| gcctatggaa | aaacgccagc | aacgcggcct | ttttacggtt | cctggccttt | tgctggcctt | 7860 |
| ttgctcacat | gttctttcct | gcgttatccc | ctgattctgt | ggataaccgt | attaccgcct | 7920 |
| ttgagtgagc | tgataccgct | cgccgcagcc | gaacgaccga | gcgcagcgag | tcagtgagcg | 7980 |
| aggaagcgga | agagcgccca | atacgcaaac | cgcctctccc | cgcgcgttgg | ccgattcatt | 8040 |
| aatg | | | | | 8044 |

<210> SEQ ID NO 41
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 41

```
Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30
```

```
Gly Lys Lys Val Asp Ser Ser Arg Asp Arg Asn Lys Pro Phe Lys Phe
             35                  40                  45

Met Leu Gly Lys Gln Glu Val Ile Arg Gly Trp Glu Glu Gly Val Ala
 50                  55                  60

Gln Met Ser Val Gly Gln Arg Ala Lys Leu Thr Ile Ser Pro Asp Tyr
 65                  70                  75                  80

Ala Tyr Gly Ala Thr Gly His Pro Gly Ile Ile Pro Pro His Ala Thr
                 85                  90                  95

Leu Val Phe Asp Val Glu Leu Leu Lys Leu Val Glu Gly Val Gln
             100                 105                 110

Val Glu Thr Ile Ser Pro Gly Asp Gly Arg Thr Phe Pro Lys Arg Gly
             115                 120                 125

Gln Thr Cys Val Val His Tyr Thr Gly Met Leu Glu Asp Gly Lys Lys
130                 135                 140

Val Asp Ser Ser Arg Asp Arg Asn Lys Pro Phe Lys Phe Met Leu Gly
145                 150                 155                 160

Lys Gln Glu Val Ile Arg Gly Trp Glu Glu Gly Val Ala Gln Met Ser
                165                 170                 175

Val Gly Gln Arg Ala Lys Leu Thr Ile Ser Pro Asp Tyr Ala Tyr Gly
            180                 185                 190

Ala Thr Gly His Pro Gly Ile Ile Pro Pro His Ala Thr Leu Val Phe
        195                 200                 205

Asp Val Glu Leu Leu Lys Leu Glu
    210                 215

<210> SEQ ID NO 42
<211> LENGTH: 7760
<212> TYPE: DNA
<213> ORGANISM: Artificial Sequence
<220> FEATURE:
<223> OTHER INFORMATION: Synthetic polynucleotide

<400> SEQUENCE: 42
cagcagctgg cgtaatagcg aagaggcccg caccgatcgc ccttcccaac agttgcgcag    60
cctgaatggc gaatggaatt ccagacgatt gagcgtcaaa atgtaggtat ttccatgagc   120 gttttcctg ttgcaatggc tggcggtaat attgttctgg atattaccag caaggccgat   180
agtttgagtt cttctactca ggcaagtgat gttattacta atcaaagaag tattgcgaca   240
acggttaatt tgcgtgatgg acagactctt ttactcggtg gcctcactga ttataaaaac   300
acttctcagg attctggcgt accgttcctg tctaaaatcc ctttaatcgg cctcctgttt   360
agctcccgct ctgattctaa cgaggaaagc acgttatacg tgctcgtcaa agcaaccata   420
gtacgcgccc tgtagcggcg cattaagcgc ggcgggtgtg gtggttacgc gcagcgtgac   480
cgctacactt gccagcgccc tagcgcccgc tcctttcgct ttcttccctt cctttctcgc   540
cacgttcgcc ggctttcccc gtcaagctct aaatcggggg ctccctttag ggttccgatt   600
tagtgcttta cggcacctcg accccaaaaa acttgattag ggtgatggtt cacgtagtgg   660
gccatcgccc tgatagacgg ttttcgccc tttgacgttg gagtccacgt tctttaatag   720
tggactcttg ttccaaactg gaacaacact caacccatc tcggtctatt cttttgattt   780
ataagggatt ttgccgattt cggcctattg gttaaaaaat gagctgattt aacaaaaatt   840
taacgcgaat tttaacaaaa tattaacgct tacaatttaa atatttgctt atacaatctt   900 cctgttttg gggcttttct gattatcaac cggggtacat atgattgaca tgctagtttt   960
acggcgcgcc gggttggcca ctccctctct gcgcgctcgc tcgctcactg aggccgggcg  1020
```

```
accaaaggtc gcccgacgcc cgggcttttgc ccgggcggcc tcagtgagcg agcgagcgcg      1080
cagagaggga gtggccaact ccatcactag gggttcctac gcgtagatct catcacgagc      1140
agctggtttc taagatgcta tttcccgtat aaagcatgag accgtgactt gccagcccca      1200
cagagccccg cccttgtcca tcactggcat ctggactcca gctgggttg gggcaaagag       1260
ggaaatgaga tcatgtccta accctgatcc tcttgtccca cagatatcca gaaccctgac      1320
cctgccgtgt accagctgag agactctaaa tccagtgaca gtctgtctg cctattcacc       1380
gattttgatt ctcaaacaaa tgtgtcacaa agtaaggatt ctgatgtgta tatcacagac      1440
aaaactgtgc tagacatgag gtctatggac ttcaagagca acagtgctgt ggcctggagc      1500
aactagtggg cggagttagg gcggagccaa tcagcgtgcg ccgttccgaa agttgccttt      1560
tatggctggg cggagaatgg gcggtgaacg ccgatgatta tataaggacg cgccgggtgt      1620
ggcacagcta gttccgtcgc agccgggatt tgggtcgcgg ttcttgtttg ttccctcgag      1680
ccaccatggc tgcaggaggt cccggcgcgg ggtctgcggc cccggtctcc tccacatcct      1740
cccttcccct ggctgctctc aacatgcgag tgcggcgccg cctgtctctg ttcttgaacg      1800
tgcggacaca ggtggcggcc gactggaccg cgctggcgga ggagatggac tttgagtact      1860
tggagatccg gcaactggag acacaagcgg accccactgg caggctgctg gacgcctggc      1920
agggacgccc tggcgcctct gtaggccgac tgctcgatct gcttaccaag ctgggccgcg      1980
acgacgtgct gctggagctg ggacccagca ttgaggagga ttgccaaaag tatatcttga      2040
agcagcagca ggaggaggct gagaagcctt acaggtggc cgctgtagac agcagtgtcc       2100
cacgacagc agagctggcg ggcatcacca cacttgatga cccctgggg catatgcctg        2160
agcgtttcga tgccttcatc tgctattgcc ccagcgacat cgtcgagaaa gcgagccgca      2220
aaaagcggc ggcggcggcg aaagcccgt ttgcgagccc ggcgagcagc gcgcaggaag         2280
aagatgcgag cagctgccgc gcgccgagcg aagaagaagg cagctgcgaa ctggtcgagg      2340
gcgtccaagt cgaaaccatt agtcccggcg atggcagaac atttcctaaa agggacaaa       2400
catgtgtcgt ccattataca ggcatgttgg aggacggcaa aaaggtggac agtagtagag      2460
atcgcaataa accttttcaaa ttcatgttgg gaaaacaaga agtcattagg ggatgggagg     2520
agggcgtggc tcaaatgtcc gtcggccaac gcgctaagct caccatcagc cccgactacg      2580
catacggcgc taccggacat cccggaatta ttccccctca cgctaccttg gtgtttgacg      2640
tcgaactgtt gaagctcgaa gtcgagggag tgcaggtgga gactatctcc ccaggagacg      2700
ggcgcacctt ccccaagcgc ggccagacct gcgtggtgca ctacaccggg atgcttgaag      2760
atggaaagaa agttgattcc tcccgggaca gaaacaagcc ctttaagttt atgctaggca     2820
agcaggaggt gatccgaggc tgggaagaag gggttgccca gatgagtgtg ggtcagagag      2880
ccaaactgac tatatctcca gattatgcct atggtgccac tgggcaccca ggcatcatcc      2940
caccacatgc cactctcgtc ttcgatgtgg agcttctaaa actggaaccg cgggaaggcc      3000
gagggagcct gctgacatgt ggcgatgtgg aggaaaaccc aggaccacca tggatggcgc      3060
tcccagtgac agccttactt ttacctctgg cgttattatt gcacgcggct cgtcctgaca      3120
tacagatgac tcagactacc tcttcccttat ctgcttcttt aggcgaccga gtaacaatat     3180
cttgccgggc cagccaggac atctcaaaat acttaaactg gtatcagcag aagccggacg      3240
gaacagttaa gttgctcatt taccacacgt cgagattaca ctcaggcgtt cctagccgat      3300
tttcgggttc cggttccggt acggactaca gcctgacaat cagtaacctt gagcaggagg      3360
acatcgccac ctacttctgt cagcagggca acacgctccc gtacacattc ggtgggggaa      3420
```

```
ctaagctgga gattaccgga ggcggtggca gcggtggcgg cggcagcggg ggtggcggct    3480
cggaggtcaa gttacaggag agcggaccgg gcttggtcgc acctagccag agcctctcag    3540
tcacgtgcac tgtgtctgga gtcagtctcc cagactacgg ggtatcatgg atacgacagc    3600
cgcctagaaa gggcttagag tggctggggg ttatctgggg aagtgaaacc acatactaca    3660
actcagctct caagagccgc ctcaccatca ttaaggacaa cagtaagtcg caggttttct    3720
taaagatgaa ctctctccag actgacgaca ccgctattta ctactgcgcg aagcactact    3780
actacggcgg gagttacgca atggactact ggggtcaggg cacttctgtg accgtatcca    3840
gcactactac cccagcccca cgtcccccca cgccagctcc aacgatagca agtcagccct    3900
tatctcttcg ccctgaggct tgcaggcccg cggcgggcgg cgccgttcac acgcgaggac    3960
tagacttcgc ctgcgacatc tacatctggg caccactagc cgggacttgc ggagtgttgt    4020
tgttgagctt ggtaataacg ctctactgca gagtgaagtt ctctcgctcc gcggacgcac    4080
ccgcttacca gcagggtcag aaccagctat acaacgagtt aaacctgggg cgccgggagg    4140
agtacgacgt gttagacaag cgtagaggta gggacccgga gatgggaggc aagcctcgga    4200
gaaagaaccc ccaggagggc ctgtacaacg aactccagaa ggacaagatg gctgaggcgt    4260
actcggagat tggtatgaag ggcgagagac gtcgcgaaaa gggacacgac ggcttatacc    4320
aggggctttc caccgcgacc aaggacacat acgacgcgct gcacatgcaa gccttaccac    4380
ctcgatgagg taccagcgcg gccgcgatcc agacatgata agatacattg atgagtttgg    4440
acaaaccaca actagaatgc agtgaaaaaa atgctttatt tgtgaaattt gtgatgctat    4500
tgctttattt gtaaccatta taagctgcaa taaacaagtt aacaacaaca attgcattca    4560
ttttatgttt caggttcagg gggaggtgtg ggaggttttt taaagcaagt aaactggtac    4620
tagtacggat ccgcaacaaa tctgactttg catgtgcaaa cgccttcaac aacagcatta    4680
ttccagaaga caccttcttc cccagcccag gtaagggcag cttttggtgc cttcgcaggct   4740
gtttccttgc ttcaggaatg gccaggttct gcccagagct ctggtcaatg atgtctaaaa    4800
ctcctctgat tggtggtctc ggccttatcc attgccacca aaaccctctt tttactaaga    4860
aacagtgagc cttgttctgg cagtccagag aatgacacgg gaaaaaagca gatgaagaga    4920
aggtggcagg agagggcacg tgggccagcc tcagtctctc caactgagtt cctgcctgcc    4980
tgcctttgct cagactgttt gcccaattga tggagttggc cactccctct ctgcgcgctc    5040
gctcgctcac tgaggccgcc cgggcaaagc ccgggcgtcg ggcgaccttt ggtcgcccgg    5100
cctcagtgag cgagcgagcg cgcagagagg gagtggccaa cggcgcgcct gcaggttcaa    5160
aaatagctac cctctccggc atgaatttat cagctagaac ggttgaatat catattgatg    5220
gtgatttgac tgtctccggc ctttctcacc cgtttgaatc tttacctaca cattactcag    5280
gcattgcatt taaaatatat gagggttcta aaaatttta tccttgcgtt gaaataaagg    5340
cttctcccgc aaaagtatta cagggtcata atgtttttgg tacaaccgat ttagctttat    5400
gctctgaggc tttattgctt aattttgcta attctttgcc ttgcctgtat gatttattgg    5460
atgttggaat tcctgatgcg gtattttctc cttacgcatc tgtgcggtat ttcacaccgc    5520
atatggtgca ctctcagtac aatctgctct gatgccgcat agttaagcca gccccgacac    5580
ccgccaacac ccgctgacgc gccctgacgg gcttgtctgc tcccggcatc cgcttacaga    5640
caagctgtga ccgtctccgg gagctgcatg tgtcagaggt tttcaccgtc atcaccgaaa    5700
cgcgcgagac gaaagggcct cgtgatacgc ctattttat aggttaatgt catgataata    5760
atggtttctt agacgtcagg tggcactttt cggggaaatg tgcgcggaac ccctatttgt    5820
```

```
ttatttttct aaatacattc aaatatgtat ccgctcatga gacaataacc ctgataaatg    5880
cttcaataat attgaaaaag gaagagtatg agtattcaac atttccgtgt cgcccttatt    5940
cccttttttg cggcattttg ccttcctgtt tttgctcacc cagaaacgct ggtgaaagta    6000
aaagatgctg aagatcagtt gggtgcacga gtgggttaca tcgaactgga tctcaacagc    6060
ggtaagatcc ttgagagttt tcgccccgaa gaacgttttc caatgatgag cacttttaaa    6120
gttctgctat gtggcgcggt attatcccgt attgacgccg ggcaagagca actcggtcgc    6180
cgcatacact attctcagaa tgacttggtt gagtactcac cagtcacaga aaagcatctt    6240
acggatggca tgacagtaag agaattatgc agtgctgcca taaccatgag tgataacact    6300
gcggccaact tacttctgac aacgatcgga ggaccgaagg agctaaccgc ttttttgcac    6360
aacatggggg atcatgtaac tcgccttgat cgttgggaac cggagctgaa tgaagccata    6420
ccaaacgacg agcgtgacac cacgatgcct gtagcaatgg caacaacgtt gcgcaaacta    6480
ttaactggcg aactacttac tctagcttcc cggcaacaat taatagactg gatggaggcg    6540
gataaagttg caggaccact tctgcgctcg gcccttccgg ctggctggtt tattgctgat    6600
aaatctggag ccggtgagcg tgggtctcgc ggtatcattg cagcactggg gccagatggt    6660
aagccctccc gtatcgtagt tatctacacg acggggagtc aggcaactat ggatgaacga    6720
aatagacaga tcgctgagat aggtgcctca ctgattaagc attggtaact gtcagaccaa    6780
gtttactcat atatacttta gattgattta aaacttcatt tttaatttaa aaggatctag    6840
gtgaagatcc tttttgataa tctcatgacc aaaatccctt aacgtgagtt ttcgttccac    6900
tgagcgtcag accccgtaga aaagatcaaa ggatcttctt gagatccttt ttttctgcgc    6960
gtaatctgct gcttgcaaac aaaaaaacca ccgctaccag cggtggtttg tttgccggat    7020
caagagctac caactctttt tccgaaggta actggcttca gcagagcgca gataccaaat    7080
actgtccttc tagtgtagcc gtagttaggc caccacttca agaactctgt agcaccgcct    7140
acatacctcg ctctgctaat cctgttacca gtggctgctg ccagtggcga taagtcgtgt    7200
cttaccgggt tggactcaag acgatagtta ccggataagg cgcagcggtc gggctgaacg    7260
gggggttcgt gcacacagcc cagcttggag cgaacgacct acaccgaact gagataccta    7320
cagcgtgagc tatgagaaag cgccacgctt cccgaaggga gaaaggcgga caggtatccg    7380
gtaagcggca gggtcggaac aggagagcgc acgagggagc ttccaggggg aaacgcctgg    7440
tatctttata gtcctgtcgg gtttcgccac ctctgacttg agcgtcgatt tttgtgatgc    7500
tcgtcagggg ggcggagcct atggaaaaac gccagcaacg cggccttttt acggttcctg    7560
gccttttgct ggccttttgc tcacatgttc tttcctgcgt tatcccctga ttctgtggat    7620
aaccgtatta ccgcctttga gtgagctgat accgctcgcc gcagccgaac gaccgagcgc    7680
agcgagtcag tgagcgagga agcggaagag cgcccaatac gcaaaccgcc tctccccgcg    7740
cgttggccga ttcattaatg                                                7760
```

CO-STIMULATORY DOMAINS FOR USE IN GENETICALLY-MODIFIED CELLS

RELATED APPLICATIONS

The present invention is a continuation of U.S. application Ser. No. 16/339,699, filed Apr. 4, 2019, which is a national stage filing under 35 U.S.C. § 371 of international PCT application, PCT/US2017/055133, filed Oct. 4, 2017, which claims priority under 35 U.S.C. § 119(e) to U.S. provisional patent application No. 62/556,199, filed Sep. 8, 2017, U.S. provisional patent application No. 62/501,475, filed May 4, 2017, U.S. provisional patent application No. 62/403,880, filed Oct. 4, 2016, the entire contents of each of which are incorporated herein by reference.

FIELD OF THE INVENTION

The present disclosure relates to the field of molecular biology and recombinant nucleic acid technology. In particular, the present disclosure relates to novel co-stimulatory domains engineered to stimulate T cell proliferation and avert T cell exhaustion. The present disclosure further relates to genetically-modified cells comprising the novel co-stimulatory domains and the use of such cells in treatment of disease, such as cancer.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Oct. 11, 2019, is named P109070017US04-SEQ-MJT.txt, and is 124,908 bytes in size.

BACKGROUND OF THE INVENTION

T cell adoptive immunotherapy is a promising approach for cancer treatment. This strategy utilizes isolated human T cells that have been genetically-modified to enhance their specificity for a specific tumor associated antigen. Genetic modification may involve the expression of a chimeric antigen receptor (CAR) or an exogenous T cell receptor to graft antigen specificity onto the T cell. In contrast to exogenous T cell receptors, CARs derive their specificity from the variable domains of a monoclonal antibody. Thus, T cells expressing CARs induce tumor immunoreactivity in a major histocompatibility complex (MHC) non-restricted manner. To date, T cell adoptive immunotherapy has been utilized as a clinical therapy for a number of cancers, including B cell malignancies (e.g., acute lymphoblastic leukemia (ALL), B cell non-Hodgkin lymphoma (NHL), and chronic lymphocytic leukemia), multiple myeloma, neuroblastoma, glioblastoma, advanced gliomas, ovarian cancer, mesothelioma, melanoma, and pancreatic cancer.

T cell activation is initiated by the endogenous T cell receptor, which also provides antigen specificity to the cell. Signaling by the T cell is amplified by cell-surface co-stimulatory receptors, such as CD28. In the absence of co-stimulation, stimulation via the T cell receptor can be insufficient to drive T cell proliferation, resulting in cell anergy. Co-stimulation also serves a role in averting T cell exhaustion and some forms of activation-induced cell death. Early chimeric T cell-activating receptors were generated by fusing the ξ-chain of CD3 to the extracellular domain of T cell co-receptors, including CD4, CD8, and CD25.

So called "first generation" chimeric antigen receptors were then generated by fusing the CD3 ξ-chain to a single-chain variable fragment (scFv), which afforded antigen specificity and antigen-induced T cell activation. Although first generation CARs were able to mediate cytotoxicity, they were unable to direct antigen-induced expansion of modified primary T cells. Indeed, studies in early transgenic mouse models revealed that T cells expressing first generation CARs only produced a moderate effect on tumor progression in vivo due to anergy and the production of low amounts of interferon gamma (IFN-γ). "Second generation" chimeric antigen receptors were generated by further fusing a single co-stimulatory domain in cis with the cytoplasmic CD3 ξ-chain. Studies demonstrated that the addition of the co-stimulatory domain allowed for expansion of primary CAR-T cells following repeated antigen exposure, as well as increased secretion of cytokines such as IFN-γ. Indeed, early clinical trials utilizing second-generation CAR-T cells displayed significantly enhanced persistence and expansion in patients with B-cell lymphoma, CLL, and B-cell ALL. A number of co-stimulatory domains have been introduced into CARs, such as CD28, 4-1BB, or OX-40 elements, which have been utilized in CAR-T cells administered to patients with B cell malignancies. So called "third generation" chimeric antigen receptors introduced two co-stimulatory domains in tandem with the cytoplasmic CD3 ξ-chain to allow for further enhancement of cell expansion and/or cytokine secretion following repeated antigen exposure.

In addition to the use of co-stimulatory domains within CAR constructs, groups have also incorporated co-stimulatory domains into various "safety switches" that can be separate from the CAR. One such safety switch comprises MyD88 and CD40 signaling domains, fused to a binding domain which dimerizes when bound by a small molecule such as rimiducid. This safety switch is used in tandem with a CAR construct that only comprises a cytoplasmic CD3 ξ-chain to promote cell activation. By administering the small molecule, the safety switch dimerizes and allows for MyD88/CD40 co-stimulatory signaling to promote CAR-T cell expansion and cytokine secretion following antigen recognition by the separate CAR construct.

A number of co-stimulatory domains have been previously disclosed in both patents and in the literature. For example, U.S. Pat. No. 8,399,645 claims a polynucleotide encoding chimeric antigen receptor comprising both the 4-1BB signaling domain and a CD3 ξ signaling domain. However, none have disclosed the domains of the present disclosure or any domains having even 80% sequence identity to the domains of the present disclosure.

SUMMARY OF THE INVENTION

The present disclosure provides novel co-stimulatory domains that are useful in providing genetically-modified cells to promote cell proliferation and/or promote cytokine secretion. The present disclosure advances the art by providing new co-stimulatory domains which promote different degrees of cell proliferation and/or cytokine secretion following antigen-induced cell activation. For example, the co-stimulatory domains disclosed herein provide superior activity when compared to those domains, such as 4-1BB and CD28. Also disclosed herein are genetically-modified cells that comprise a chimeric antigen receptor (CAR) that incorporates one or more co-stimulatory domains disclosed herein. In other examples, genetically-modified cells disclosed herein comprise an inducible regulatory construct that incorporates one or more co-stimulatory domains disclosed herein. Also provided herein are nucleic acid molecules, recombinant DNA constructs (e.g., plasmids), and viral vectors comprising a nucleic acid sequence encoding the co-stimulatory domains, and methods of administering compositions comprising the novel co-stimulatory domains to subjects in order to reduce the symptoms, progression, or occurrence of disease. In some embodiments, genetically-modified cells comprising the novel co-stimulatory domains disclosed herein are formulated as pharmaceutical compositions and used, for example, as immunotherapy in the treatment of cancer.

Thus, in one aspect, the present disclosure provides a nucleic acid molecule comprising a nucleotide sequence encoding a co-stimulatory domain or active variant or fragment thereof having at least 80% sequence identity to an amino acid sequence set forth in any one of SEQ ID NOs: 5-8. In the various aspects of the present disclosure, an active variant or fragment of the co-stimulatory domain disclosed herein has at least 80%, at least 85%, at least 90%, at least 95%, at least 96%, at least 97%, at least 98%, or at least 99% sequence identity to an amino acid sequence set forth in any one of SEQ ID NOs: 5-8.

In some embodiments, the active variant or fragment amino acid sequence encoding a co-stimulatory domain comprises at least one TRAF-binding motif. In certain embodiments, the TRAF-binding motif is selected from the group consisting of SEQ ID NOs: 9-11. In specific embodiments, the active variant or fragment amino acid sequence encoding a co-stimulatory domain comprises two TRAF-binding motifs separated by a spacer sequence. In some such embodiments, the spacer sequence is selected from the group consisting of SEQ ID NOs: 12-15. In certain embodiments, the variant or fragment amino acid sequence encoding a co-stimulatory domain comprises two TRAF-binding motifs selected from the group consisting of SEQ ID NOs: 9-11 separated by a spacer sequence, wherein the spacer sequence is selected from the group consisting of SEQ ID NOs: 12-15.

In particular embodiments, the variant or fragment amino acid sequence encoding a co-stimulatory domain comprises the TRAF binding motifs of SEQ ID NOs: 9 and 11, separated by a spacer sequence, such as the spacer sequence set forth in SEQ ID NO: 12. In some embodiments, the variant or fragment amino acid sequence encoding the co-stimulatory domain comprises the TRAF binding motifs of SEQ ID NOs: 10 and 11, separated by a spacer sequence, such as the spacer sequence set forth in any of SEQ ID NOs: 13-15.

In specific embodiments, the nucleic acid molecule comprises a nucleotide sequence encoding a co-stimulatory domain comprising an amino acid sequence set forth in any one of SEQ ID NOs: 5-8.

In some embodiments, the nucleic acid molecule comprises a nucleotide sequence set forth in any one of SEQ ID NOs: 1-4, or a variant or fragment thereof having at least 80% identity to a nucleotide sequence set forth in any one of SEQ ID NOs: 1-4, wherein the nucleotide sequence encodes a co-stimulatory domain. In some embodiments, the nucleic acid molecule comprises a nucleotide sequence comprising a variant or fragment of any one of SEQ ID NOs: 1-4 having at least 80%, at least 85%, at least 90%, at least 95%, at least 96%, at least 97%, at least 98%, or at least 99% sequence identity to the nucleic acid sequence set forth in any one of SEQ ID NOs: 1-4, wherein the nucleotide sequence encodes an active co-stimulatory domain.

In some embodiments, the nucleic acid molecule comprises a nucleotide sequence encoding a chimeric antigen receptor (CAR), wherein the CAR comprises at least one co-stimulatory domain or active variant or fragment thereof described herein having at least 80% sequence identity to an amino acid sequence set forth in any one of SEQ ID NOs: 5-8. In some such embodiments, the nucleic acid molecule comprises a nucleotide sequence encoding a CAR comprising at least one co-stimulatory domain comprising an amino acid sequence set forth in any one of SEQ ID NOs: 5-8.

In other such embodiments, the CAR comprises an extracellular antigen-binding domain. In particular embodiments, the extracellular antigen-binding domain is a single-chain variable fragment (scFv). In various embodiments, the antigen-binding domain has specificity for a cancer or tumor antigen. In specific embodiments, the encoded CAR comprises a CD19-specific antigen-binding domain.

In further such embodiments, the encoded CAR comprises at least two co-stimulatory domains. In such embodiments, the at least two co-stimulatory domains are co-stimulatory domains described herein or, alternatively, are at least one co-stimulatory domain described herein and at least one additional co-stimulatory domain known in the art (e.g., 4-1BB, CD28, OX40, ICOS). In some embodiments, the encoded CAR further comprises at least one intracellular signaling domain. In particular embodiments, the at least one intracellular signaling domain is a CD3 ξ domain.

In other embodiments, the nucleic acid molecule comprises a nucleotide sequence encoding an inducible regulatory construct that comprises at least one co-stimulatory domain or active variant or fragment thereof having at least 80% sequence identity to an amino acid sequence set forth in any one of SEQ ID NOs: 5-8. In some embodiments, the nucleic acid molecule comprises a nucleotide sequence encoding an inducible regulatory construct comprising at least one co-stimulatory domain comprising an amino acid sequence set forth in any one of SEQ ID NOs: 5-8. In particular embodiments, the encoded inducible regulatory construct further comprises a binding domain which allows two inducible regulatory constructs to dimerize, wherein dimerization initiates a co-stimulatory signal to a cell. In some embodiments, the binding domain binds a small molecule (e.g., rimiducid), an antibody, or other molecule which allows for dimerization. In particular embodiments wherein the binding domain binds a small molecule, the binding domain comprises an analogue of FKBP12 (e.g., comprising an F36V substitution) and the small molecule is rimiducid (i.e., AP1903).

In particular embodiments, the nucleic acid molecule is an mRNA, a recombinant DNA construct (e.g., plasmid), or included within a viral genome of a viral vector.

In another aspect, the present disclosure provides a recombinant DNA construct, wherein the recombinant DNA construct comprises the nucleic acid molecule described herein which comprises a nucleotide sequence encoding at least one co-stimulatory domain or active variant or fragment thereof having at least 80% sequence identity to an amino acid sequence set forth in any one of SEQ ID NOs: 5-8. In specific embodiments, the recombinant DNA construct comprises a nucleotide sequence encoding a co-stimulatory domain comprising an amino acid sequence set forth in any one of SEQ ID NOs: 5-8. In some embodiments, the recombinant DNA construct comprises a nucleotide sequence encoding a CAR described herein, wherein the CAR comprises at least one co-stimulatory domain or active variant or fragment thereof having at least 80% sequence identity to an amino acid sequence set forth in any one of SEQ ID NOs: 5-8. In other embodiments, the recombinant DNA construct comprises a nucleotide sequence encoding an inducible regulatory construct described herein which comprises at least one co-stimulatory domain or active variant or fragment thereof having at least 80% sequence identity to an amino acid sequence set forth in any one of SEQ ID NOs: 5-8.

In some such embodiments, the recombinant DNA construct encodes a viral vector which comprises a nucleotide sequence encoding at least one co-stimulatory domain or active variant or fragment thereof having at least 80% sequence identity to an amino acid sequence set forth in any one of SEQ ID NOs: 5-8. In some embodiments, the viral vector is a retroviral vector, a lentiviral vector, an adenoviral vector, or an adeno-associated virus (AAV) vector. In a specific embodiment, the viral vector is a recombinant AAV vector.

In some aspects, the present disclosure provides a viral vector comprising the nucleic acid molecule described herein which comprises a nucleotide sequence encoding at least one co-stimulatory domain or active variant or fragment thereof having at least 80% sequence identity to an amino acid sequence set forth in any one of SEQ ID NOs: 5-8. In specific embodiments, the viral vector comprises a nucleotide sequence encoding a co-stimulatory domain comprising an amino acid sequence set forth in any one of SEQ ID NOs: 5-8. In some embodiments, the viral vector comprises a nucleotide sequence encoding a CAR described herein, wherein the CAR comprises at least one co-stimulatory domain or active variant or fragment thereof having at least 80% sequence identity to an amino acid sequence set forth in any one of SEQ ID NOs: 5-8. In other embodiments, the viral vector comprises a nucleotide sequence encoding an inducible regulatory construct described herein which comprises at least one co-stimulatory domain or active variant or fragment thereof having at least 80% sequence identity to an amino acid sequence set forth in any one of SEQ ID NOs: 5-8.

In particular embodiments, the viral vector is a retroviral vector, a lentiviral vector, an adenoviral vector, or an adeno-associated virus (AAV) vector. In a specific embodiment, the viral vector is a recombinant AAV vector.

In another aspect, the present disclosure provides a genetically-modified cell, wherein the genetically-modified cell comprises the nucleic acid molecule described herein which comprises a nucleotide sequence encoding at least one co-stimulatory domain or active variant or fragment thereof having at least 80% sequence identity to an amino acid sequence set forth in any one of SEQ ID NOs: 5-8. In some embodiments, the genetically-modified cell comprises an expression cassette comprising a nucleotide sequence encoding a CAR described herein, wherein the CAR comprises at least one co-stimulatory domain or active variant or fragment thereof having at least 80% sequence identity to an amino acid sequence set forth in any one of SEQ ID NOs: 5-8. In particular embodiments, the genetically-modified cell comprises an expression cassette comprising a nucleotide sequence encoding an inducible regulatory construct described herein, wherein the inducible regulatory construct comprises at least one co-stimulatory domain or active variant or fragment thereof having at least 80% sequence identity to an amino acid sequence set forth in any one of SEQ ID NOs: 5-8. In some such embodiments, the nucleic acid molecule described herein, or the expression cassette described herein, is present within the genome of the genetically-modified cell or, alternatively, is not integrated into the genome of the cell. In some such embodiments, the nucleic acid molecule described herein, or the expression cassette described herein, is present in the genetically-modified cell in a recombinant DNA construct, in an mRNA, or in a viral genome, which is not integrated into the genome of the cell.

In further embodiments, the genetically-modified cell comprises: (i) a CAR expression cassette comprising a nucleotide sequence encoding a CAR that does not comprise a co-stimulatory domain described herein, and (ii) a regulatory expression cassette encoding an inducible regulatory construct described herein which comprises at least one co-stimulatory domain or active variant or fragment thereof having at least 80% sequence identity to an amino acid sequence set forth in any one of SEQ ID NOs: 5-8. Thus, in a particular embodiment, the genetically-modified cell comprises: (i) a CAR that does not incorporate a co-stimulatory domain described herein, and (ii) an inducible regulatory domain which comprises at least one co-stimulatory domain described herein. In some embodiments, the genetically-modified cell comprises an expression cassette comprising: (i) a nucleotide sequence encoding a CAR that does not comprise a co-stimulatory domain described herein, and (ii) a nucleotide sequence encoding an inducible regulatory domain which comprises at least one co-stimulatory domain described herein. In each embodiment, the CAR expression cassette and/or the regulatory expression cassette are within the genome of the genetically-modified eukaryotic cell or, alternatively, are not integrated into the genome of the cell. In some such embodiments, the CAR expression cassette and/or the regulatory expression cassette is present in the genetically-modified eukaryotic cell in a recombinant DNA construct, in an mRNA, or in a viral genome, which are not integrated into the genome of the cell.

In some embodiments, the genetically-modified cell described herein is a genetically-modified eukaryotic cell. In particular embodiments, the cell is a T cell or a natural killer (NK) cell. In other embodiments, the genetically-modified cell is a primary human T cell or primary human NK cell. In further embodiments, the genetically-modified cell is a human CAR-T cell or human CAR-NK cell.

In particular embodiments, the genetically-modified cell described herein exhibits increased proliferation and/or cytokine secretion compared to a control cell that does not comprise a co-stimulatory domain described herein. In some embodiments, the increased proliferation and/or cytokine secretion is exhibited in vitro and/or in vivo. In particular embodiments, increased cytokine secretion comprises an increase in IFN-γ, IL-2, TNF-alpha, or other cytokines associated with cell activation and/or proliferation compared to a control cell that does not comprise a co-stimulatory domain described herein.

In another aspect, the present disclosure provides a method for producing a genetically-modified cell comprising at least one co-stimulatory domain or an active variant or fragment thereof described herein, the method comprising introducing into a cell at least one nucleic acid molecule described herein encoding at least one co-stimulatory domain or active variant or fragment thereof having at least 80% sequence identity to an amino acid sequence set forth in any one of SEQ ID NOs: 5-8.

In some embodiments of the method, the introduced nucleic acid molecule encodes a CAR described herein comprising at least one co-stimulatory domain or active variant or fragment thereof having at least 80% sequence identity to an amino acid sequence set forth in any one of SEQ ID NOs: 5-8.

In some embodiments of the method, the introduced nucleic acid molecule encodes an inducible regulatory construct described herein comprising at least one co-stimulatory domain or active variant or fragment thereof having at least 80% sequence identity to an amino acid sequence set forth in any one of SEQ ID NOs: 5-8.

In some embodiments, the method further comprises introducing into the cell: (i) a second nucleic acid molecule encoding an engineered nuclease, wherein the engineered nuclease is expressed in the cell, or (ii) an engineered nuclease protein; wherein the engineered nuclease recognizes and cleaves a recognition sequence to produce a cleavage site in the genome of the cell, and wherein the nucleic acid encoding the at least one co-stimulatory domain or active variant or fragment thereof is inserted into the genome at the cleavage site. In some embodiments, the engineered nuclease is an engineered meganuclease, a recombinant zinc-finger nuclease (ZFN), a recombinant transcription activator-like effector nuclease (TALEN), a CRISPR/Cas nuclease, or a megaTAL nuclease. In a particular embodiment of the method, the engineered nuclease is an engineered meganuclease. In a specific embodiment, the engineered meganuclease is a single-chain meganuclease.

In one such embodiment of the method, the nucleic acid molecule encoding at least one co-stimulatory domain or active variant or fragment thereof having at least 80% sequence identity to an amino acid sequence set forth in any one of SEQ ID NOs: 5-8 introduced into the cell further comprises sequences homologous to sequences flanking the nuclease cleavage site, such that the nucleic acid molecule is inserted into the genome at the cleavage site by homologous recombination. In another such embodiment of the method, the nucleic acid molecule lacks substantial homology to the nuclease cleavage site such that the nucleic acid molecule is inserted into the genome by non-homologous end joining.

In some embodiments of the method, the cell is a eukaryotic cell. In particular embodiments, the cell is a T cell or a natural killer (NK) cell, such as a primary human T cell or a primary human NK cell. In certain embodiments, the genetically-modified cell produced by the method is a human CAR-T cell or human CAR-NK cell.

In specific embodiments of the method, the nucleic acid molecule encoding at least one co-stimulatory domain or active variant or fragment thereof having at least 80% sequence identity to an amino acid sequences set forth in any one of SEQ ID NOs: 5-8 is introduced into the cell using an mRNA described herein, a recombinant DNA construct described herein, or a viral vector described herein.

In some embodiments, introduction of the at least one nucleic acid molecule described herein encoding at least one co-stimulatory domain or active variant or fragment thereof having at least 80% sequence identity to an amino acid sequence set forth in any one of SEQ ID NOs: 5-8 increases the activation, proliferation, and/or cytokine secretion of the genetically-modified cell. In specific embodiments, increased cytokine secretion comprises an increased secretion of IFN-γ, IL-2, TNF-alpha, or any other cytokine associated with cell activation and/or proliferation when compared to a control cell that does not comprise a co-stimulatory domain described herein.

In another aspect, the present disclosure provides a pharmaceutical composition comprising a pharmaceutically-acceptable carrier and genetically-modified cells described herein which comprise at least one co-stimulatory domain or active variant or fragment thereof having at least 80% sequence identity to an amino acid sequence set forth in any one of SEQ ID NOs: 5-8. In particular embodiments, the genetically-modified cells comprise a CAR described herein which comprises at least one co-stimulatory domain or active variant or fragment thereof having at least 80% sequence identity to an amino acid sequence set forth in any one of SEQ ID NOs: 5-8. In other embodiments, the genetically-modified cells comprise an inducible regulatory construct described herein which comprises at least one co-stimulatory domain or active variant or fragment thereof having at least 80% sequence identity to an amino acid sequence set forth in any one of SEQ ID NOs: 5-8.

In specific embodiments, the genetically-modified cells are CAR-T cells. In some such embodiments, the CAR-T cells comprise a CAR which includes a co-stimulatory domain or active variant or fragment thereof described herein having at least 80% sequence identity to an amino acid sequence set forth in any one of SEQ ID NOs: 5-8. In other such embodiments, the CAR-T cells comprise a CAR which does not include a co-stimulatory domain or active variant or fragment thereof described herein, and further comprise an inducible regulatory construct comprising at least one co-stimulatory domain or active variant or fragment thereof described herein having at least 80% sequence identity to an amino acid sequence set forth in any one of SEQ ID NOs: 5-8. In various embodiments, the CAR-T cells have specificity for a cancer or tumor-specific antigen, and the pharmaceutical composition is useful in methods of cancer immunotherapy.

In another aspect, the present disclosure provides a method of administering genetically-modified cells to a subject, wherein the genetically-modified cells are those described herein which comprise at least one co-stimulatory domain or active variant or fragment thereof having at least 80% sequence identity to an amino acid sequence set forth in any one of SEQ ID NOs: 5-8. In some embodiments of the method, the genetically-modified cells comprise a CAR described herein comprising at least one co-stimulatory domain or active variant or fragment thereof having at least 80% sequence identity to an amino acid sequence set forth in any one of SEQ ID NOs: 5-8. In other embodiments of the method, the genetically-modified cells comprise an inducible regulatory construct described herein comprising at least one co-stimulatory domain or active variant or fragment thereof having at least 80% sequence identity to an amino acid sequence set forth in any one of SEQ ID NOs: 5-8.

In particular embodiments of the method, the subject administered the genetically-modified cells has a disease, such as cancer. In some embodiments of the method, the genetically-modified cells are CAR-T cells. In some such embodiments, the CAR-T cells have specificity for a cancer or tumor-specific antigen and are useful in methods of cancer immunotherapy. In some embodiments, the cancer is a B cell malignancy (e.g., acute lymphoblastic leukemia (ALL), B cell non-Hodgkin lymphoma (NHL), or chronic lymphocytic leukemia), multiple myeloma, neuroblastoma, glioblastoma, advanced gliomas, ovarian cancer, mesothelioma, melanoma, or pancreatic cancer. In particular embodiments, the cancer is a B cell lymphoma.

In another aspect, the present disclosure provides genetically-modified cells described herein for use as a medicament. The present disclosure further provides the use of genetically-modified cells described herein in the manufacture of a medicament for treating a disease in a subject in need thereof. In one such aspect, the medicament is useful for cancer immunotherapy in subjects in need thereof.

In another aspect, the present disclosure provides a method of immunotherapy for treating cancer in a subject in need thereof comprising administering to the subject a pharmaceutical composition comprising a genetically-modified cell produced by the methods disclosed herein and a pharmaceutically acceptable carrier.

In some embodiments, the cancer is selected from the group consisting of a cancer of carcinoma, lymphoma, sarcoma, blastomas, and leukemia.

In some embodiments, the cancer is selected from the group consisting of a cancer of B-cell origin, breast cancer, gastric cancer, neuroblastoma, osteosarcoma, lung cancer, melanoma, prostate cancer, colon cancer, renal cell carcinoma, ovarian cancer, rhabdomyo sarcoma, leukemia, and Hodgkin's lymphoma. In some embodiments, the cancer of B-cell origin is selected from the group consisting of B-lineage acute lymphoblastic leukemia, B-cell chronic lymphocytic leukemia, and B-cell non-Hodgkin's lymphoma.

The foregoing and other aspects and embodiments of the present invention can be more fully understood by reference to the following detailed description and claims. Certain features of the invention, which are, for clarity, described in the context of separate embodiments, may also be provided in combination in a single embodiment. All combinations of the embodiments are specifically embraced by the present invention and are disclosed herein just as if each and every combination was individually and explicitly disclosed. Conversely, various features of the invention, which are, for brevity, described in the context of a single embodiment, may also be provided separately or in any suitable sub-combination. All sub-combinations of features listed in the embodiments are also specifically embraced by the present invention and are disclosed herein just as if each and every such sub-combination was individually and explicitly disclosed herein. Embodiments of each aspect of the present invention disclosed herein apply to each other aspect of the invention mutatis mutandis.

BRIEF DESCRIPTION OF THE FIGURES

FIG. 1 shows the alignment of novel co-stimulatory domains Novel1 (SEQ ID NO: 5), Novel3 (SEQ ID NO: 6), Novel5 (SEQ ID NO: 7), and Novel6 (SEQ ID NO: 8). Individual TRAF-binding motifs are identified, and spacer regions can be found between the TRAF-binding motifs within each listed co-stimulatory domain.

FIG. 2 shows CAR constructs comprising an anti-CD19 scFv, a CD8 hinge and transmembrane domain, a co-stimulatory domain, and a CD3 ξ intracellular signaling domain. The co-stimulatory domains shown include CD28, 4-1BB, Novel1 (N1), Novel3 (N3), Novel5 (N5), and Novel6 (N6). Also shown is a CAR construct lacking a co-stimulatory domain.

FIGS. 3A-3H report the results of a GFP analysis that demonstrates CAR expression following lentivirus transduction of donor human T cells. Results are reported for each of the novel co-stimulatory domains Novel1 (N1), Novel3 (N3), Novel5 (N5), and Novel6 (N6). FIG. 3A) Mock-transduced. FIG. 3B) Transduced with CAR comprising 4-1BB co-stimulatory domain. FIG. 3C) Transduced with CAR comprising CD28 co-stimulatory domain. FIG. 3D) Transduced with CAR comprising no co-stimulatory domain (BB-). FIG. 3E) Transduced with CAR comprising Novel1 (N1) co-stimulatory domain. FIG. 3F) Transduced with CAR comprising Novel3 (N3) co-stimulatory domain. FIG. 3G) Transduced with CAR comprising Novel5 (N5) co-stimulatory domain. FIG. 3H) Transduced with CAR comprising Novel6 (N6) co-stimulatory domain.

FIGS. 4A, 4B, and 4C show CAR-T cell expansion numbers measured over time following repeated antigen-induced activation in Raji culture. Results are reported for each of the novel co-stimulatory domains Novel1 (N1), Novel3 (N3), Novel5 (N5), and Novel6 (N6). FIG. 4A shows results obtained for mixed population of CD4+ and CD8+ CAR-T cells. FIG. 4B shows results obtained for CD4+ CAR-T cell population. FIG. 4C shows results obtained for CD8+ CAR-T cell population.

FIGS. 5A, 5B and 5C show cytokine secretion in each transduced CAR-T cell population at 3, 7, 10, and 14 days post-transduction. FIG. 5A shows Interferon-gamma (IFN-γ) secretion. FIG. 5B shows TNF-alpha (TNF-α) secretion. FIG. 5C shows IL-2 secretion.

FIGS. 6A, 6B, and 6C show CAR-T cell expansion numbers measured over time following repeated antigen-induced activation in Raji culture using more frequent antigen encounter and a higher target:effector ratio. Results are reported for each of the novel co-stimulatory domains Novel1 (N1), Novel3 (N3), Novel5 (N5), and Novel6 (N6). FIG. 5A shows results obtained for mixed population of CD4+ and CD8+ CAR-T cells. FIG. 5B shows results obtained for CD4+ CAR-T cell population. FIG. 5C shows results obtained for CD8+ CAR-T cell population.

FIG. 7 shows donor template constructs comprising, from 5' to 3', a 5' inverted terminal repeat (ITR), a 5' homology arm, a promoter, coding sequences for an anti-CD19 scFv, a CD8 hinge and transmembrane domain, a co-stimulatory domain, and a CD3 ξ intracellular signaling domain, an SV40 polyA signal, a 3' homology arm, and a 3' ITR. The co-stimulatory domains shown include 4-1BB, Novel1 (N1), and Novel6 (N6).

FIG. 8A shows results using CAR-T cells prepared from Donor K799. FIG. 8B shows results using CAR-T cells prepared from donor z4100.

FIG. 9A shows CAR-T cells prepared from donor K799. FIG. 9B shows CAR-T cells prepared from donor z4100.

FIGS. 10A, 10B, and 10C show histograms of the results of the cell proliferation assay used to determine relative proliferation of CAR-T cells comprising the 4-1BB, N1, or N6 co-stimulatory domains in response to CD19+ target cells. FIG. 10A shows proliferation of CAR-4-1BB CAR-T cells compared to the negative control TRC KO T cells at two different E:T ratios. FIG. 10B shows proliferation of CAR-4-1BB T cells compared to CAR-N1 T cells.

FIG. 10C shows proliferation of CAR-4-1BB T cells compared to CAR-N6 T cells.

FIG. 11 shows the 7241, 7205, and 7206 donor template constructs comprising, from 5' to 3', a 5' inverted terminal repeat (ITR), a 5' homology arm, a promoter, coding sequences for an anti-CD19 scFv, a CD8 hinge and transmembrane domain, a co-stimulatory domain, and a CD3 ξ intracellular signaling domain, an SV40 polyA signal or SV40 bi-polyA signal, a 3' homology arm, and a 3' ITR. The co-stimulatory domains shown include 4-1BB (construct 7241) and Novel 6 (N6; constructs 7205 and 7206).

FIG. 12A shows dorsal flux following treatment with TCR KO cells. FIG. 12B shows dorsal flux following treatment with 7205 CAR T cells. FIG. 12C shows dorsal flux following treatment with 7206 CAR T cells. FIG. 12D shows dorsal flux following treatment with 4-1BB CAR T cells. FIG. 12E shows ventral flux following treatment with TCR KO cells. FIG. 12F shows ventral flux following treatment with 7205 CAR T cells. FIG. 12G shows ventral flux following treatment with 7206 CAR T cells.

FIG. 13A shows imaging of dorsal flux on days 7, 10, and 16 in groups treated with TCR KO cells, 7205 CAR T cells, 7206 CART cells, and 4-1BB CART cells. FIG. 13B shows imaging of dorsal flux on days 24, 31, and 38 in groups treated with 7205 CART cells, 7206 CART cells, and 4-1BB CAR T cells. FIG. 13C shows imaging of ventral flux on days 7, 10, and 16 in groups treated with TCR KO cells, 7205 CAR T cells, 7206 CAR T cells, and 4-1BB CAR T cells. FIG. 13D shows imaging of ventral flux on days 24, 31, and 38 in groups treated with 7205 CAR T cells, 7206 CAR T cells, and 4-1BB CAR T cells.

FIG. 16A shows CD4+ cells transfected with the TRC 1-2×0.87EE meganuclease only. FIG. 16B shows CD8+ cells transfected with the TRC 1-2×0.87EE meganuclease only. FIG. 16C shows CD4+ cells transfected with the TRC 1-2×0.87EE meganuclease and an N6 CAR donor template. FIG. 16D shows CD8+ cells transfected with the TRC 1-2×0.87EE meganuclease and an N6 CAR donor template. FIG. 16E shows CD4+ cells transfected with the TRC 1-2×0.87EE meganuclease and a MyD88/N6 CAR donor template. FIG. 16F shows CD8+ cells transfected with the TRC 1-2×0.87EE meganuclease and a MyD88/N6 CAR donor template.

FIGS. 18A and 18B show the results of a Cell Trace Violet proliferation assay using human T cells transfected to express the TRC 1-2×0.87EE meganuclease only without a donor template. Transfected cells were labeled with Cell Trace Violet and co-cultured with CD19-negative K562 cells or engineered CD19-positive K562 cells (K19 cells). Proliferation was assessed by flow cytometry for CD4+ and CD8+ subsets of T cells. FIG. 18A shows the CD4+ subset of cells. FIG. 18B shows the CD8+ subset of cells.

FIGS. 19A-9D show the show the results of a Cell Trace Violet proliferation assay using human T cells transfected to express an anti-CD19 CAR comprising a Novel6 (N6) domain. Transfected cells were labeled with Cell Trace Violet and co-cultured with CD19-negative K562 cells or engineered CD19-positive K562 cells (K19 cells). Proliferation was assessed by flow cytometry for CD4+ and CD8+ subsets of T cells. Further, cells were assessed in K19 co-culture in the presence or absence of rimiducid. FIG. 19A shows the CD4+ subset of cells cultured on K19 or K562 cells.

FIG. 20A shows the CD4+ subset of cells cultured on K19 or K562 cells. FIG. 20B shows the CD4+ subset of cells cultured on K19 cells in the presence or absence of rimiducid. FIG. 20C shows the CD8+ subset of cells cultured on K19 or K562 cells. FIG. 20D shows the CD8+ subset of cells cultured on K19 cells in the presence or absence of rimiducid.

BRIEF DESCRIPTION OF THE SEQUENCES

Figure 4C:
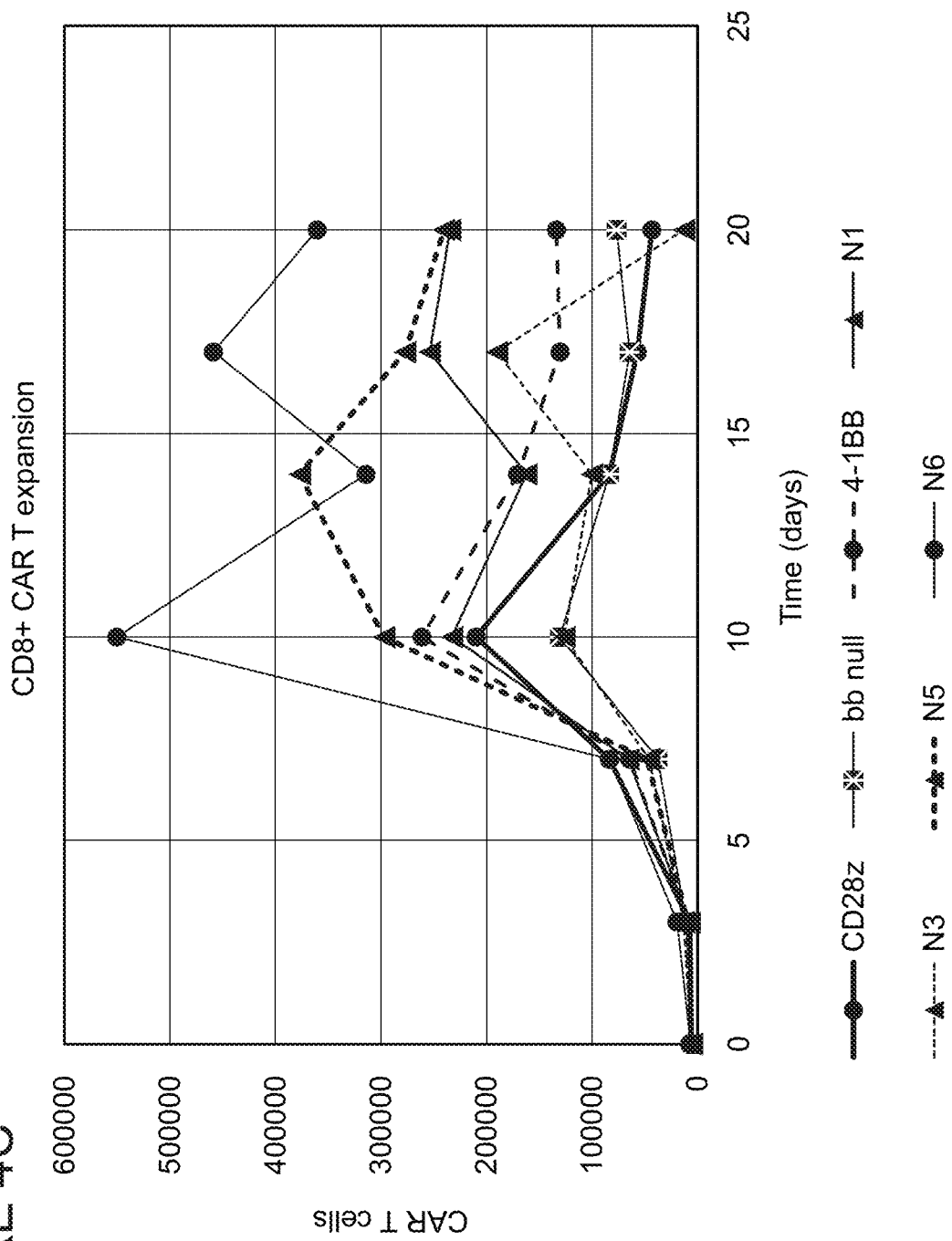

SEQ ID NO:1 sets forth the nucleic acid sequence encoding the Novel1 co-stimulatory domain.

SEQ ID NO:2 sets forth the nucleic acid sequence encoding the Novel3 co-stimulatory domain.

SEQ ID NO:3 sets forth the nucleic acid sequence encoding the Novel5 co-stimulatory domain.

SEQ ID NO:4 sets forth the nucleic acid sequence encoding the Novel6 co-stimulatory domain.

SEQ ID NO:5 sets forth the amino acid sequence of the Novel1 co-stimulatory domain.

SEQ ID NO:6 sets forth the amino acid sequence of the Novel3 co-stimulatory domain.

SEQ ID NO:7 sets forth the amino acid sequence of the Novel5 co-stimulatory domain.

SEQ ID NO:8 sets forth the amino acid sequence of the Novel6 co-stimulatory domain.

SEQ ID NO:9 sets forth the amino acid sequence of a TRAF-binding motif found in a novel co-stimulatory domain.

SEQ ID NO:10 sets forth the amino acid sequence of a TRAF-binding motif found in a novel co-stimulatory domain.

SEQ ID NO:11 sets forth the amino acid sequence of a TRAF-binding motif found in a novel co-stimulatory domain.

SEQ ID NO:12 sets forth the amino acid sequence of a spacer sequence found in a novel co-stimulatory domain.

SEQ ID NO:13 sets forth the amino acid sequence of a spacer sequence found in a novel co-stimulatory domain.

SEQ ID NO:14 sets forth the amino acid sequence of a spacer sequence found in a novel co-stimulatory domain.

SEQ ID NO:15 sets forth the amino acid sequence of a spacer sequence found in a novel co-stimulatory domain.

SEQ ID NO: 16 sets forth the amino acid sequence of a chimeric antigen receptor signal peptide.

SEQ ID NO: 17 sets forth the amino acid sequence of an anti-CD19 chimeric antigen receptor scFv.

SEQ ID NO: 18 sets forth the amino acid sequence of a chimeric antigen receptor CD8 hinge and transmembrane region.

SEQ ID NO: 19 sets forth the amino acid sequence of a CD3-ξ intracellular signaling domain.

SEQ ID NO: 20 sets forth the amino acid sequence of a CD28 co-stimulatory domain.

SEQ ID NO: 21 sets forth the amino acid sequence of a 4-1BB co-stimulatory domain.

SEQ ID NO: 22 sets forth the amino acid sequence of an anti-CD19 chimeric antigen receptor lacking a co-stimulatory domain.

SEQ ID NO: 23 sets forth the amino acid sequence of an anti-CD19 chimeric antigen receptor comprising a CD28 co-stimulatory domain.

SEQ ID NO: 24 sets forth the amino acid sequence of an anti-CD19 chimeric antigen receptor comprising a 4-1BB co-stimulatory domain.

SEQ ID NO: 25 sets forth the amino acid sequence of an anti-CD19 chimeric antigen receptor comprising a Novel1 co-stimulatory domain.

SEQ ID NO: 26 sets forth the amino acid sequence of an anti-CD19 chimeric antigen receptor comprising a Novel3 co-stimulatory domain.

SEQ ID NO: 27 sets forth the amino acid sequence of an anti-CD19 chimeric antigen receptor comprising a Novel5 co-stimulatory domain.

SEQ ID NO: 28 sets forth the amino acid sequence of an anti-CD19 chimeric antigen receptor comprising a Novel6 co-stimulatory domain.

SEQ ID NO: 29 sets forth the nucleic acid sequence of vector encoding an anti-CD19 CAR comprising a 4-1BB co-stimulatory domain.

SEQ ID NO: 30 sets forth the nucleic acid sequence of vector encoding an anti-CD19 CAR comprising a Novel1 co-stimulatory domain.

SEQ ID NO: 31 sets forth the nucleic acid sequence of vector encoding an anti-CD19 CAR comprising a Novel6 co-stimulatory domain.

SEQ ID NO: 32 sets forth the nucleic acid sequence of the JeT promoter.

SEQ ID NO: 33 sets forth the nucleic acid sequence of an SV40 polyA signal sequence.

SEQ ID NO: 34 sets forth the nucleic acid sequence of a first SV40 bi-polyA signal sequence.

SEQ ID NO: 35 sets forth the nucleic acid sequence of a second SV40 bi-polyA signal sequence.

SEQ ID NO: 36 sets forth the nucleic acid sequence of a vector encoding the 7241 anti-CD19 CAR construct comprising a 4-1BB co-stimulatory domain and an SV40 polyA signal.

SEQ ID NO: 37 sets forth the nucleic acid sequence of a vector encoding the 7205 anti-CD19 CAR construct comprising a Novel6 co-stimulatory domain and an SV40 polyA signal.

SEQ ID NO: 38 sets forth the nucleic acid sequence of a vector encoding the 7206 anti-CD19 CAR construct comprising a Novel6 co-stimulatory domain and an SV40 bi-polyA signal.

SEQ ID NO: 39 sets forth the amino acid sequence of a MyD88 co-stimulatory domain.

SEQ ID NO: 40 sets forth the nucleic acid sequence of a vector encoding the 7240 anti-CD19 CAR construct which comprises MyD88 and Novel6 co-stimulatory domains.

SEQ ID NO: 41 sets forth the amino acid sequence of tandem ligand-binding FKBP12v36 domains.

SEQ ID NO: 42 sets forth the nucleic acid sequence of a vector encoding the 7235 anti-CD19 CAR construct which encodes a first generation CAR and an inducible regulatory construct comprising MyD88 and Novel6 co-stimulatory domains and tandem ligand-binding FKBP12v36 domains.

DETAILED DESCRIPTION OF THE INVENTION 1.1 References and Definitions

The patent and scientific literature referred to herein establishes knowledge that is available to those of skill in the art. The issued US patents, allowed applications, published foreign applications, and references, including GenBank database sequences, which are cited herein are hereby incorporated by reference to the same extent as if each was specifically and individually indicated to be incorporated by reference.

The present disclosure can be embodied in different forms and should not be construed as limited to the embodiments set forth herein. Rather, these embodiments are provided so that this disclosure will be thorough and complete, and will fully convey the scope of the present disclosure to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the present disclosure.

Unless otherwise defined, all technical and scientific terms used herein have the same meaning as commonly understood by one of ordinary skill in the art to which this disclosure belongs. The terminology used in the description of the present disclosure herein is for the purpose of describing particular embodiments only and is not intended to be limiting of the present disclosure.

All publications, patent applications, patents, and other references mentioned herein are incorporated by reference herein in their entirety.

As used herein, "a," "an," or "the" can mean one or more than one. For example, "a" cell can mean a single cell or a multiplicity of cells.

As used herein, unless specifically indicated otherwise, the word "or" is used in the inclusive sense of "and/or" and not the exclusive sense of "either/or."

As used herein, a "co-stimulatory domain" refers to a polypeptide domain which transmits an intracellular proliferative and/or cell-survival signal upon activation. Activation of a co-stimulatory domain may occur following homodimerization of two co-stimulatory domain polypeptides. Activation may also occur, for example, following activation of a construct comprising the co-stimulatory domain (e.g., a chimeric antigen receptor or an inducible regulatory construct). Generally, a co-stimulatory domain can be derived from a transmembrane co-stimulatory receptor, particularly from an intracellular portion of a co-stimulatory receptor. Non-limiting examples of co-stimulatory polypeptides include, but are not limited to, those co-stimulatory domains described herein, 4-1BB, CD28, ICOS, OX-40, and CD27.

As used herein, a "chimeric antigen receptor" or "CAR" refers to an engineered receptor that grafts specificity for an antigen or other ligand or molecule onto an immune effector cell (e.g., a T cell or NK cell). A chimeric antigen receptor typically comprises at least an extracellular ligand-binding domain or moiety and an intracellular domain that comprises one or more signaling domains and/or co-stimulatory domains.

In some embodiments, the extracellular ligand-binding domain or moiety is in the form of a single-chain variable fragment (scFv) derived from a monoclonal antibody, which provides specificity for a particular epitope or antigen (e.g., an epitope or antigen preferentially present on the surface of a cell, such as a cancer cell or other disease-causing cell or particle). In some embodiments, the scFv is attached via a linker sequence. In some embodiments, the extracellular ligand-binding domain is specific for any antigen or epitope of interest. In some embodiments, the scFv is humanized. In some embodiments, the extracellular domain of a chimeric antigen receptor comprises an autoantigen (see, Payne et al. (2016) *Science*, Vol. 353 (6295): 179-184), which is recognized by autoantigen-specific B cell receptors on B lymphocytes, thus directing T cells to specifically target and kill autoreactive B lymphocytes in antibody-mediated autoimmune diseases. Such CARs can be referred to as chimeric autoantibody receptors (CAARs), and the incorporation of one or more co-stimulatory domains described herein into such CAARs is encompassed by the present disclosure.

Intracellular signaling domains are cytoplasmic domains which transmit an activation signal to the cell following binding of the extracellular domain. An intracellular signaling domain can be any intracellular signaling domain of interest that is known in the art. Such cytoplasmic signaling domains can include, without limitation, CD3 ξ.

In some embodiments, the intracellular domain also includes one or more intracellular co-stimulatory domains, such as those described herein, which transmit a co-stimulatory signal which promotes cell proliferation, cell survival, and/or cytokine secretion after binding of the extracellular domain. Such intracellular co-stimulatory domains can include, without limitation, any co-stimulatory domain disclosed herein or those domains known in the art, such as, for example, a CD28 domain, a 4-1BB domain, an OX-40 domain, an ICOS domain, or a CD27 domain. In some embodiments, a chimeric antigen receptor further includes additional structural elements, including a transmembrane domain which is attached to the extracellular ligand-binding domain via a hinge or junction sequence.

As used herein, an "inducible regulatory construct" refers to a transmembrane or intracellular construct expressed in a cell that provides an inducible co-stimulatory signal to promote cell proliferation, cell survival, and/or cytokine secretion. Such constructs comprise one or more co-stimulatory domains, such as those described herein and/or others known in the art, which provide a co-stimulatory signal upon activation. In some embodiments, a co-stimulatory signal is induced, for example, by homodimerization of two inducible regulatory construct polypeptides. An inducible regulatory construct generally comprises a binding domain which allows for homodimerization following binding of a small molecule, an antibody, or other molecule that allows for homodimerization of two construct polypeptides.

As used herein, a "co-stimulatory signal" refers to an intracellular signal induced by a co-stimulatory domain that promotes cell proliferation, expansion of a cell population in vitro and/or in vivo, promotes cell survival, modulates (e.g., upregulates or downregulates) the secretion of cytokines, and/or modulates the production and/or secretion of other immunomodulatory molecules. In some embodiments, a co-stimulatory signal is induced following homodimerization of two co-stimulatory domain polypeptides. In some embodiments, a co-stimulatory signal is induced following activation of a construct comprising the co-stimulatory domain (e.g., a chimeric antigen receptor or an inducible regulatory construct).

As used herein, the term "activation" refers to the state of a cell (e.g., a T cell) that has been sufficiently stimulated to induce detectable effector function. In some embodiments, activation is associated with induced cytokine production and/or induced cell proliferation and expansion.

As used herein, the term "anti-tumor activity" or "anti-tumor effect" refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the genetically-modified cells of the present disclosure in prevention of the occurrence of tumor in the first place.

As used herein, with respect to a protein, the term "engineered" or "recombinant" means having an altered amino acid sequence as a result of the application of genetic engineering techniques to nucleic acids which encode the protein, and cells or organisms which express the protein. With respect to a nucleic acid, the term "engineered" or "recombinant" means having an altered nucleic acid sequence as a result of the application of genetic engineering techniques. Genetic engineering techniques include, but are not limited to, PCR and DNA cloning technologies; transfection, transformation and other gene transfer technologies; homologous recombination; site-directed mutagenesis; and gene fusion. In accordance with this definition, a protein having an amino acid sequence identical to a naturally-occurring protein, but produced by cloning and expression in a heterologous host, is not considered recombinant.

As used herein, the term "wild-type" refers to the most common naturally-occurring polynucleotide or polypeptide sequence responsible for a given phenotype. Whereas a wild-type allele or polypeptide can confer a normal phenotype in an organism, a mutant or variant allele or polypeptide can, in some instances, confer an altered phenotype.

As used herein with respect to recombinant proteins, the term "modification" means any insertion, deletion or substitution of an amino acid residue in the recombinant sequence relative to a reference sequence (e.g., a wild-type or a native sequence).

As used herein, the term "homologous recombination" or "HR" refers to the natural, cellular process in which a double-stranded DNA-break is repaired using a homologous DNA sequence as a donor template (see, e.g. Cahill et al. (2006), *Front. Biosci.* 11:1958-1976). The homologous DNA sequence may be an endogenous chromosomal or episomal sequence or an exogenous nucleic acid that was delivered to the cell.

As used herein, the term "non-homologous end-joining" or "NHEJ" refers to the natural, cellular process in which a double-stranded DNA-break is repaired by the direct joining of two non-homologous DNA segments (see, e.g. Cahill et al. (2006), *Front. Biosci.* 11:1958-1976).

As used herein, the term "reduced" refers to any reduction in the symptoms or severity of a disease or any reduction in the proliferation or number of cancerous cells. In either case, such a reduction may be up to 5%, 10%, 20%, 30%, 40%, 50%, 60%, 70%, 80%, 90%, 95%, or up to 100%. Accordingly, the term "reduced" encompasses both a partial reduction and a complete reduction of a disease state.

As used herein, the term "increased" refers to any increase in the activation, proliferation, or cytokine signaling of a cell genetically-modified to comprise a co-stimulatory domain disclosed herein, or an active fragment or variant thereof. Such an increase may be up to 5%, 10%, 20%, 30%, 40%, 50%, 60%, 70%, 80%, 90%, 95%, or up to 100%, or more. Any method can be used to measure an increase in the activation, proliferation, or cytokine signaling of a cell. For example, increased activation and/or cytokine expression can encompass an increase of expression of any one of IFN-γ, IL-2, TNF-α, or any other cytokine that could be used to determine a change in cell activation and/or proliferation. In some embodiments, an increase in proliferation encompasses an increase in cell number or cell division, and includes an expansion of a cell population.

As used herein with respect to both amino acid sequences and nucleic acid sequences, the terms "percent identity," "sequence identity," "percentage similarity," "sequence similarity," and the like, refer to a measure of the degree of similarity of two sequences based upon an alignment of the sequences which maximizes similarity between aligned amino acid residues or nucleotides, and which is a function of the number of identical or similar residues or nucleotides, the number of total residues or nucleotides, and the presence and length of gaps in the sequence alignment. A variety of algorithms and computer programs are available for determining sequence similarity using standard parameters. As used herein, sequence similarity is measured using the BLASTp program for amino acid sequences and the BLASTn program for nucleic acid sequences, both of which are available through the National Center for Biotechnology Information (www.ncbi.nlm.nih.gov), and are described in, for example, Altschul et al. (1990), *J. Mol. Biol.* 215:403-410; Gish and States (1993), *Nature Genet.* 3:266-272; Madden et al. (1996), *Meth. Enzymol.* 266:131-141; Altschul et al. (1997), *Nucleic Acids Res.* 25:33 89-3402); Zhang et al. (2000), *J. Comput. Biol.* 7(1-2):203-14. As used herein, percent similarity of two amino acid sequences is the score based upon the following parameters for the BLASTp algorithm: word size=3; gap opening penalty=−11; gap extension penalty=−1; and scoring matrix=BLOSUM62. As used herein, percent similarity of two nucleic acid sequences is the score based upon the following parameters for the BLASTn algorithm: word size=11; gap opening penalty=−5; gap extension penalty=−2; match reward=1; and mismatch penalty=−3.

As used herein with respect to modifications of two proteins or amino acid sequences, the term "corresponding to" is used to indicate that a specified modification in the first protein is a substitution of the same amino acid residue as in the modification in the second protein, and that the amino acid position of the modification in the first proteins corresponds to or aligns with the amino acid position of the modification in the second protein when the two proteins are subjected to standard sequence alignments (e.g., using the BLASTp program). Thus, the modification of residue "X" to amino acid "A" in the first protein will correspond to the modification of residue "Y" to amino acid "A" in the second protein if residues X and Y correspond to each other in a sequence alignment, and despite the fact that X and Y may be different numbers.

The terms "recombinant DNA construct," "recombinant construct," "expression cassette," "expression construct," "chimeric construct," "construct," and "recombinant DNA fragment" are used interchangeably herein and are linear or circular nucleic acid molecules. A recombinant construct comprises an artificial or non-naturally-occurring combination of nucleic acid molecules, including, without limitation, regulatory and coding sequences. Although the recombinant construct as a whole does not occur in nature, portions of the construct may be found in nature. For example, a recombinant DNA construct may comprise regulatory sequences and coding sequences that are derived from different sources, or regulatory sequences and coding sequences derived from the same source and arranged in a manner different than that found in nature. Such a construct may be used by itself or may be used in conjunction with a vector.

As used herein, a "vector" or "recombinant DNA vector" may be a construct that includes a replication system and sequences that are capable of transcription and translation of a polypeptide-encoding sequence in a given host cell. If a vector is used then the choice of vector is dependent upon the method that will be used to transform host cells as is well known to those skilled in the art. Vectors can include, without limitation, plasmid vectors and recombinant lentiviral or recombinant AAV vectors, or any other vector known in that art suitable for delivering a gene encoding a co-stimulatory domain of the present disclosure to a target cell. The skilled artisan is well aware of the genetic elements that must be present on the vector in order to successfully transform, select and propagate host cells comprising any of the isolated nucleotides or nucleic acid sequences of the present disclosure.

As used herein, a "vector" can also refer to a viral vector. Viral vectors can include, without limitation, retroviral vectors, lentiviral vectors, adenoviral vectors, and adeno-associated viral vectors (AAV).

As used herein, the term "operably linked" is intended to mean a functional linkage between two or more elements. For example, an operable linkage between a nucleic acid sequence encoding a nuclease as disclosed herein and a regulatory sequence (e.g., a promoter) is a functional link that allows for expression of the nucleic acid sequence encoding the nuclease. Operably linked elements may be contiguous or non-contiguous. When used to refer to the joining of two protein coding regions, by operably linked is intended that the coding regions are in the same reading frame.

As used herein, "transfected" or "transformed" or "transduced" or "nucleofected" refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

As used herein, a "human T cell" or "T cell" refers to a T cell isolated from a human donor. Human T cells, and cells derived therefrom, include isolated T cells that have not been passaged in culture, T cells that have been passaged and maintained under cell culture conditions without immortalization, and T cells that have been immortalized and can be maintained under cell culture conditions indefinitely.

As used herein, a "human natural killer cell" or "human NK cell" or "natural killer cell" or "NK cell" refers to a type of cytotoxic lymphocyte critical to the innate immune system. The role NK cells play is analogous to that of cytotoxic T-cells in the vertebrate adaptive immune response. NK cells provide rapid responses to virally infected cells and respond to tumor formation, acting at around 3 days after infection. Human NK cells, and cells derived therefrom, include isolated NK cells that have not been passaged in culture, NK cells that have been passaged and maintained under cell culture conditions without immortalization, and NK cells that have been immortalized and can be maintained under cell culture conditions indefinitely.

As used herein, a "control" or "control cell" refers to a cell that provides a reference point for measuring changes in genotype or phenotype of a genetically-modified cell. A control cell may comprise, for example: (a) a wild-type cell, i.e., of the same genotype as the starting material for the genetic alteration which resulted in the genetically-modified cell; (b) a cell of the same genotype as the genetically-modified cell but which has been transformed with a null construct (i.e., with a construct which has no known effect on the trait of interest); or, (c) a cell genetically identical to the genetically-modified cell but which is not exposed to conditions, stimuli, or further genetic modifications that would induce expression of altered genotype or phenotype.

The term "effective amount" or "therapeutically effective amount" refers to an amount sufficient to effect beneficial or desirable biological and/or clinical results. The amount will vary depending on the therapeutic (e.g., genetically-modified cell, CAR-T cell, CAR-NK cell) formulation or composition, the disease and its severity, and the age, weight, physical condition and responsiveness of the subject to be treated. In specific embodiments, an effective amount of a cell comprising a co-stimulatory domain disclosed herein or pharmaceutical compositions disclosed herein reduces at least one symptom or the progression of a disease.

As used herein, the term "treat" or "treatment" means to reduce the frequency or severity of at least one sign or symptom of a disease or disorder experienced by a subject.

As used herein, the term "cancer" should be understood to encompass any neoplastic disease (whether or not invasive or metastatic) which is characterized by abnormal cell growth. Invasive or metastatic caners have the potential to spread to other parts of the body. Cancers with uncontrolled cell division can cause malignant growth or tumors whereas cancers with slowly dividing cells can cause benign growth or tumors.

As used herein, the term "carcinoma" refers to a malignant growth made up of epithelial cells.

As used herein, the term "leukemia" refers to malignancies of the hematopoietic organs/systems and is generally characterized by an abnormal proliferation and development of leukocytes and their precursors in the blood and bone marrow.

As used herein, the term "sarcoma" refers to a tumor which is made up of a substance like the embryonic connective tissue and is generally composed of closely packed cells embedded in a fibrillary, heterogeneous, or homogeneous substance.

As used herein, the term "melanoma" refers to a tumor arising from the melanocytic system of the skin and other organs.

As used herein, the term "lymphoma" refers to a group of blood cell tumors that develop from lymphocytes.

As used herein, the term "blastoma" refers to a type of cancer that is caused by malignancies in precursor cells or blasts (immature or embryonic tissue).

As used herein, the term "meganuclease" refers to an endonuclease that binds double-stranded DNA at a recognition sequence that is greater than 12 base pairs. In some embodiments, the recognition sequence for a meganuclease of the present disclosure is 22 base pairs. A meganuclease can be an endonuclease that is derived from I-CreI, and can refer to an engineered variant of I-CreI that has been modified relative to natural I-CreI with respect to, for example, DNA-binding specificity, DNA cleavage activity, DNA-binding affinity, or dimerization properties. Methods for producing such modified variants of I-CreI are known in the art (e.g. WO 2007/047859). A meganuclease as used herein binds to double-stranded DNA as a heterodimer. A meganuclease may also be a "single-chain meganuclease" in which a pair of DNA-binding domains are joined into a single polypeptide using a peptide linker. The term "homing endonuclease" is synonymous with the term "meganuclease." Meganucleases of the present disclosure are substantially non-toxic when expressed in cells, particularly in human T cells, such that cells can be transfected and maintained at 37° C. without observing deleterious effects on cell viability or significant reductions in meganuclease cleavage activity when measured using the methods described herein.

As used herein, the term "single-chain meganuclease" refers to a polypeptide comprising a pair of nuclease subunits joined by a linker. A single-chain meganuclease has the organization: N-terminal subunit-Linker-C-terminal subunit. The two meganuclease subunits will generally be non-identical in amino acid sequence and will recognize non-identical DNA sequences. Thus, single-chain meganucleases typically cleave pseudo-palindromic or non-palindromic recognition sequences. A single-chain meganuclease may be referred to as a "single-chain heterodimer" or "single-chain heterodimeric meganuclease" although it is not, in fact, dimeric. For clarity, unless otherwise specified, the term "meganuclease" can refer to a dimeric or single-chain meganuclease.

As used herein, the term "linker" refers to an exogenous peptide sequence used to join two meganuclease subunits into a single polypeptide. A linker may have a sequence that is found in natural proteins, or may be an artificial sequence that is not found in any natural protein. A linker may be flexible and lacking in secondary structure or may have a propensity to form a specific three-dimensional structure under physiological conditions. A linker can include, without limitation, any of those encompassed by U.S. Pat. Nos. 8,445,251 and 9,434,931.

As used herein, the term "zinc finger nuclease" or "ZFN" refers to chimeric proteins comprising a zinc finger DNA-binding domain fused to a nuclease domain from an endonuclease or exonuclease, including but not limited to a restriction endonuclease, homing endonuclease, 51 nuclease, mung bean nuclease, pancreatic DNAse I, micrococcal nuclease, and yeast HO endonuclease. Nuclease domains useful for the design of zinc finger nuclease include those from a Type IIs restriction endonuclease, including but not limited to FokI, FoM, StsI restriction enzyme. Additional Type IIs restriction endonucleases are described in International Publication No. WO 2007/014275, which is incorporated by reference in its entirety. The structure of a zinc finger domain is stabilized through coordination of a zinc ion. DNA binding proteins comprising one or more zinc finger domains bind DNA in a sequence-specific manner. The zinc finger domain can be a native sequence or can be redesigned through rational or experimental means to produce a protein which binds to a pre-determined DNA sequence ~18 basepairs in length. See, for example, U.S. Pat. Nos. 5,789,538, 5,925,523, 6,007,988, 6,013,453, 6,200,759, and International Publication Nos. WO 95/19431, WO 96/06166, WO 98/53057, WO 98/54311, WO 00/27878, WO 01/60970, WO 01/88197, and WO 02/099084, each of which is incorporated by reference in its entirety. By fusing this engineered protein domain to a nuclease domain, such as FokI nuclease, it is possible to target DNA breaks with genome-level specificity. The selection of target sites, zinc finger proteins and methods for design and construction of zinc finger nucleases are known to those of skill in the art and are described in detail in U.S. Publications Nos. 20030232410, 20050208489, 2005064474, 20050026157, 20060188987 and International Publication No. WO 07/014275, each of which is incorporated by reference in its entirety.

As used herein, the term "TALEN" refers to an endonuclease comprising a DNA-binding domain comprising a plurality of TAL domain repeats fused to a nuclease domain or an active portion thereof from an endonuclease or exonuclease, including but not limited to a restriction endonuclease, homing endonuclease, 51 nuclease, mung bean nuclease, pancreatic DNAse I, micrococcal nuclease, and yeast HO endonuclease. See, for example, Christian et al. (2010) Genetics 186:757-761, which is incorporated by reference in its entirety. Nuclease domains useful for the design of TALENs include those from a Type IIs restriction endonuclease, including but not limited to FokI, FoM, StsI, HhaI, HindIII, Nod, BbvCI, EcoRI, BglI, and AlwI. Additional Type IIs restriction endonucleases are described in International Publication No. WO 2007/014275. In some embodiments, the nuclease domain of the TALEN is a FokI nuclease domain or an active portion thereof. TAL domain repeats can be derived from the TALE (transcription activator-like effector) family of proteins used in the infection process by plant pathogens of the *Xanthomonas* genus. TAL domain repeats are 33-34 amino acid sequences with divergent $12^{th}$ and $13^{th}$ amino acids. These two positions, referred to as the repeat variable dipeptide (RVD), are highly variable and show a strong correlation with specific nucleotide recognition. Each base pair in the DNA target sequence is contacted by a single TAL repeat, with the specificity resulting from the RVD. In some embodiments, the TALEN comprises 16-22 TAL domain repeats. DNA cleavage by a TALEN requires two DNA recognition regions flanking a nonspecific central region (i.e., the "spacer"). The term "spacer" in reference to a TALEN refers to the nucleic acid sequence that separates the two nucleic acid sequences recognized and bound by each monomer constituting a TALEN. The TAL domain repeats can be native sequences from a naturally-occurring TALE protein or can be redesigned through rational or experimental means to produce a protein which binds to a pre-determined DNA sequence (see, for example, Boch et al. (2009) *Science* 326(5959): 1509-1512 and Moscou and Bogdanove (2009) *Science* 326(5959):1501, each of which is incorporated by reference in its entirety). See also, U.S. Publication No. 20110145940 and International Publication No. WO 2010/079430 for methods for engineering a TALEN to recognize a specific sequence and examples of RVDs and their corresponding target nucleotides. In some embodiments, each nuclease (e.g., FokI) monomer can be fused to a TAL effector sequence that recognizes a different DNA sequence, and only when the two recognition sites are in close proximity do the inactive monomers come together to create a functional enzyme.

As used herein, the term "compact TALEN" refers to an endonuclease comprising a DNA-binding domain with one or more TAL domain repeats fused in any orientation to any portion of the I-TevI homing endonuclease or any of the endonucleases listed in Table 2 in U.S. Application No. 20130117869 (which is incorporated by reference in its entirety), including but not limited to MmeI, EndA, End1, I-BasI, I-TevII, I-TevIII, I-TwoI, MspI, MvaI, NucA, and NucM. Compact TALENs do not require dimerization for DNA processing activity, alleviating the need for dual target sites with intervening DNA spacers. In some embodiments, the compact TALEN comprises 16-22 TAL domain repeats.

As used herein, the term "CRISPR" refers to a caspase-based endonuclease comprising a caspase, such as Cas9, and a guide RNA that directs DNA cleavage of the caspase by hybridizing to a recognition site in the genomic DNA. The caspase component of a CRISPR is an RNA-guided DNA endonuclease. In certain embodiments, the caspase is a class II Cas enzyme. In some of these embodiments, the caspase is a class II, type II enzyme, such as Cas9. In other embodiments, the caspase is a class II, type V enzyme, such as CpfI. The guide RNA comprises a direct repeat and a guide sequence (often referred to as a spacer in the context of an endogenous CRISPR system), which is complementary to the target recognition site. In certain embodiments, the CRISPR further comprises a tracrRNA (trans-activating CRISPR RNA) that is complementary (fully or partially) to a direct repeat sequence (sometimes referred to as a tracr-mate sequence) present on the guide RNA. In particular embodiments, the caspase can be mutated with respect to a corresponding wild-type enzyme such that the enzyme lacks the ability to cleave one strand of a target polynucleotide, functioning as a nickase, cleaving only a single strand of the target DNA. Non-limiting examples of caspase enzymes that function as a nickase include Cas9 enzymes with a D10A mutation within the RuvC I catalytic domain, or with a H840A, N854A, or N863A mutation.

As used herein, the term "megaTAL" refers to a single-chain nuclease comprising a transcription activator-like effector (TALE) DNA binding domain with an engineered, sequence-specific homing endonuclease.

As used herein, the term "recognition sequence" refers to a DNA sequence that is bound and cleaved by an endonuclease. In the case of a meganuclease, a recognition sequence comprises a pair of inverted, 9 base pair "half sites" which are separated by four basepairs. In the case of a single-chain meganuclease, the N-terminal domain of the protein contacts a first half-site and the C-terminal domain of the protein contacts a second half-site. Cleavage by a meganuclease produces four base pair 3' "overhangs". "Overhangs," or "sticky ends" are short, single-stranded DNA segments that can be produced by endonuclease cleavage of a double-stranded DNA sequence. In the case of meganucleases and single-chain meganucleases derived from I-CreI, the overhang comprises bases 10-13 of the 22 base pair recognition sequence. In the case of a compact TALEN, the recognition sequence can comprises a first CNNNGN sequence that is recognized by the I-TevI domain, followed by a non-specific spacer 4-16 basepairs in length, followed by a second sequence 16-22 bp in length that is recognized by the TAL-effector domain (this sequence typically has a 5' T base). Cleavage by a Compact TALEN produces two base pair 3' overhangs. In the case of a CRISPR, the recognition sequence is the sequence, typically 16-24 basepairs, to which the guide RNA binds to direct Cas9 cleavage. Full complementarity between the guide sequence and the recognition sequence is not necessarily required to effect cleavage. Cleavage by a CRISPR can produce blunt ends (such as by a class II, type II caspase) or overhanging ends (such as by a class II, type V caspase), depending on the caspase. In those embodiments wherein a Cpf1 caspase is utilized, cleavage by the CRISPR complex comprising the same will result in 5' overhangs and in certain embodiments, 5 nucleotide 5' overhangs. Each caspase enzyme also requires the recognition of a PAM (protospacer adjacent motif) sequence that is near the recognition sequence complementary to the guide RNA. The precise sequence, length requirements for the PAM, and distance from the target sequence differ depending on the caspase enzyme, but PAMs are typically 2-5 base pair sequences adjacent to the target/recognition sequence. PAM sequences for particular caspase enzymes are known in the art (see, for example, U.S. Pat. No. 8,697,359 and U.S. Publication No. 20160208243, each of which is incorporated by reference in its entirety) and PAM sequences for novel or engineered caspase enzymes can be identified using methods known in the art, such as a PAM depletion assay (see, for example, Karvelis et al. (2017) *Methods* 121-122:3-8, which is incorporated herein in its entirety).

As used herein, the term "target site" or "target sequence" refers to a region of the chromosomal DNA of a cell comprising a recognition sequence for a nuclease.

As used herein, the terms "T cell receptor alpha gene" or "TCR alpha gene" are interchangeable and refer to the locus in a T cell which encodes the T cell receptor alpha subunit. The T cell receptor alpha can refer to NCBI gene ID number 6955, before or after rearrangement. Following rearrangement, the T cell receptor alpha gene comprises an endogenous promoter, rearranged V and J segments, an endogenous splice donor site, an intron, an endogenous splice acceptor site, and the T cell receptor alpha constant region locus, which comprises the subunit coding exons.

As used herein, the term "T cell receptor alpha constant region gene" refers to the coding sequence of the T cell receptor alpha gene. The T cell receptor alpha constant region gene includes the wild-type sequence, and functional variants thereof, identified by NCBI Gen ID NO. 28755.

As used herein, the recitation of a numerical range for a variable is intended to convey that the present disclosure may be practiced with the variable equal to any of the values within that range. Thus, for a variable which is inherently discrete, the variable can be equal to any integer value within the numerical range, including the end-points of the range. Similarly, for a variable which is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, or any other real values 0 and 2 if the variable is inherently continuous.

2.1 Principle of the Invention

The present disclosure is based, in part, on the discovery that engineered co-stimulatory domains can demonstrate equivalent or superior activity compared to conventional co-stimulatory domains. In specific examples, the co-stimulatory domains disclosed herein have equivalent or superior co-stimulatory activity in terms of cell proliferation following antigen-induced activation and/or cytokine secretion. In some embodiments, a nucleic acid molecule is provided that comprises a nucleic acid sequence encoding one of the co-stimulatory domains disclosed herein. In some embodiments, the co-stimulatory domain is expressed in a genetically-modified cell as part of a construct such as, for example, a chimeric antigen receptor or an inducible regulatory construct. Accordingly, cells are provided comprising the novel co-stimulatory domains disclosed herein, as well as methods of making cells comprising the novel co-stimulatory domains. Further disclosed herein are methods of administering a genetically-modified cell comprising a co-stimulatory domain disclosed herein in order to reduce the symptoms or severity of a disease. In some embodiments, administration of genetically-modified cells comprising the co-stimulatory domains disclosed herein reduces the symptoms or severity of diseases, such cancers, autoimmune disorders, and other conditions which can be targeted by genetically-modified cells of the present disclosure. Also disclosed herein are methods of immunotherapy for treating cancer in a subject in need thereof comprising administering to the subject a pharmaceutical composition comprising a genetically-modified cell disclosed herein and a pharmaceutically acceptable carrier.

2.2 Nucleic Acid Molecules Encoding Co-Stimulatory Domains

Provided herein are nucleic acid molecules encoding novel co-stimulatory domains and variants thereof having co-stimulatory activity (i.e., active variants). The co-stimulatory activity of an individual domain can be determined using any method known in the art that measures the activation, proliferation, and cytokine secretion of cells, such as immune cells. One example of such a method is that disclosed in Linsley et al., *Journal of Experimental Medicine* 176 (1992), 1595-604. Further examples include those methods described herein for measuring cell proliferation and cytokine secretion.

Accordingly, nucleic acid molecules are provided comprising nucleic acid sequences that encode the co-stimulatory domains set forth in SEQ ID NOs: 5-8 and active variants thereof. Specifically, the nucleic acid sequence set forth in SEQ ID NO: 1 encodes the co-stimulatory domain of SEQ ID NO: 5, referred to herein as the Novel1 domain. The nucleic acid sequence set forth in SEQ ID NO: 2 encodes the co-stimulatory domain of SEQ ID NO: 6, referred to herein as the Novel3 domain. The nucleic acid sequence set forth in SEQ ID NO: 3 encodes the co-stimulatory domain of SEQ ID NO: 7, referred to herein as the Novel5 domain. The nucleic acid sequence set forth in SEQ ID NO: 4 encodes the co-stimulatory domain of SEQ ID NO: 8, referred to herein as the Novel6 domain.

Also provided herein are active variants of the nucleic acid sequences encoding the co-stimulatory domains disclosed herein, wherein the variant nucleic acid sequences encode a domain having co-stimulatory activity. Further provided are variants of the co-stimulatory domains disclosed herein that retain co-stimulatory activity. As used herein, "variants" is intended to mean substantially similar sequences. A "variant" polypeptide is intended to mean a polypeptide derived from the "native" polypeptide by deletion and/or addition of one or more amino acids at one or more internal sites in the native protein and/or substitution of one or more amino acids at one or more sites in the native polypeptide. Likewise, a "variant" polynucleotide is a polynucleotide derived from the "native" polynucleotide by deletion and/or addition of one or more nucleic acids at one or more sites in the native nucleotide sequence. As used herein, a "native" polynucleotide or polypeptide comprises a parental sequence from which variants are derived. In specific embodiments, the parental nucleic acid sequences of variant polynucleotides encoding co-stimulatory domains include SEQ ID NOs: 1-4. Likewise, in some embodiments, the parental polypeptide sequences of variant polypeptides encoding the novel co-stimulatory domains include SEQ ID NOs: 5-8.

Variant polypeptides encompassed by the embodiments are biologically active. That is, they continue to possess the desired biological activity of the native protein; i.e., co-stimulatory activity. Such variants may result, for example, from human manipulation. Biologically active variants of a native co-stimulatory domain of the embodiments (e.g., SEQ ID NOs: 5-8), or variants of the native nucleic acid sequences (e.g., SEQ ID NOs: 1-4) encoding the co-stimulatory domains disclosed herein, will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about 99%, sequence identity to the amino acid sequence of the native polypeptide or nucleic acid sequence of the native polynucleotide, as determined by sequence alignment programs and parameters described elsewhere herein. A biologically active variant of a co-stimulatory domain of the embodiments may differ from that co-stimulatory domain by as few as about 1-20 amino acid residues, as few as about 1-10, as few as about 1-5, as few as about 4, as few as 3, 2, or even 1 amino acid residue.

The polypeptides of the embodiments may be altered in various ways including amino acid substitutions, deletions, truncations, and insertions. Methods for such manipulations are generally known in the art. For example, amino acid sequence variants can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Depending on the context, "fragment" refers to a portion of the amino acid sequence of a polypeptide or protein, or polynucleotide encoding a portion of the amino acid sequence of a polypeptide or protein. Fragments may retain the activity of the original protein and hence, such "active" fragments include, for example, fragments of co-stimulatory domain, such as a fragment of any one of SEQ ID NO: 5-8 that retains co-stimulatory activity. A fragment of a nucleotide sequence encoding a co-stimulatory domain, such as a fragment of any one of SEQ ID NOs: 1-4 may encode a protein fragment that is biologically active. A biologically active nucleotide fragment can be prepared by isolating a portion of a nucleic acid sequence encoding a co-stimulatory domain, expressing the encoded portion of the co-stimulatory domain, and assessing the activity of the encoded portion of co-stimulatory domain. Fragments of co-stimulatory domains include fragments of SEQ ID NOS: 5-8. Fragments of co-stimulatory domains comprise at least about 15, 20, 30, 35, 36, 37, 38, 39, 40, 41, or 42 amino acids.

In specific embodiments, variants or fragments of the co-stimulatory domains disclosed herein comprise at least one TNFR-associated Factor (TRAF) binding motif, referred to herein as TRAF motifs. Examples of TRAF motifs provided herein include, but are not limited to, QMED (SEQ ID NO:9), QEED (SEQ ID NO:10), and EEEG (SEQ ID NO:11). For example, in some embodiments, active variants or fragments of the co-stimulatory domains disclosed herein comprise SEQ ID NO: 9 and 11 or SEQ ID NO: 10 and 11.

In some embodiments, the co-stimulatory domains or variants or fragments thereof comprise two TRAF motifs separated by a spacer region. As used herein, the term "spacer region" refers to the region between two predicted TRAF motifs of a co-stimulatory domain. In specific embodiments, the spacer region comprises one of the following amino acid sequences: ASSCRCPQ (SEQ ID NO: 12), ASSCRFPE (SEQ ID NO: 13), ASSCRFPQ (SEQ ID NO: 14), and ASSCRAPS (SEQ ID NO: 15). In specific active variant co-stimulatory domains, the spacer region of SEQ ID NO: 12 is located between the TRAF binding motifs of SEQ ID NO: 9 and SEQ ID NO: 11. In other active variant co-stimulatory domains, the spacer region of SEQ ID NO: 13 is located between the TRAF binding motifs of SEQ ID NO: 10 and SEQ ID NO: 11. In some active variant co-stimulatory domains, the spacer region of SEQ ID NO: 14 is located between the TRAF binding motifs of SEQ ID NO: 10 and SEQ ID NO: 11. In other active variant co-stimulatory domains, the spacer region of SEQ ID NO: 15 is located between the TRAF binding motifs of SEQ ID NO: 10 and SEQ ID NO: 11. Alternatively, the spacer region could be any sequence that maintains co-stimulatory activity of the variant domain.

In certain embodiments, expression cassettes or expression constructs are provided for the expression of at least one co-stimulatory domain disclosed herein, or active variant thereof, in a cell. In some embodiments, the cassette includes 5' and 3' regulatory sequences operably linked to a nucleic acid molecule provided herein encoding a novel co-stimulatory domain, or active variant thereof. "Operably linked" is intended to mean a functional linkage between two or more elements. For example, an operable linkage between a nucleic acid sequence encoding a co-stimulatory domain as disclosed herein and a regulatory sequence (e.g., a promoter) is a functional link that allows for expression of the nucleic acid sequence encoding the co-stimulatory domain. Operably linked elements may be contiguous or non-contiguous. When used to refer to the joining of two protein coding regions, by operably linked is intended that the coding regions are in the same reading frame.

In some embodiments, the cassette further comprises at least one additional gene to be co-transformed into a cell. In further embodiments, the additional gene(s) are provided on multiple expression cassettes. In some embodiments, such an expression cassette is provided with a plurality of restriction sites and/or recombination sites for insertion of a recombinant polynucleotide to be under the transcriptional regulation of the regulatory regions. In some embodiments, the expression cassette additionally contains selectable marker genes.

In some embodiments, the expression cassette includes in the 5'-3' direction of transcription, a transcriptional and translational initiation region (i.e., a promoter), a nucleic acid sequence encoding a co-stimulatory domain, or active variant thereof, as disclosed herein, and a transcriptional and translational termination region (i.e., termination region) functional in genetically-modified cells of the present disclosure. The regulatory regions (i.e., promoters, transcriptional regulatory regions, and translational termination regions) and/or a nucleic acid molecule provided herein may be native/analogous to the host cell or to each other. Alternatively, the regulatory regions and/or a nucleic acid molecule provided herein may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous nucleic acid molecule is from a species different from the species from which the nucleic acid molecule was derived, or, if from the same/analogous species, one or both are substantially modified from their original form and/or genomic locus, or the promoter is not the native promoter for the operably linked nucleic acid molecule. Alternatively, the regulatory regions and/or a nucleic acid molecule provided herein may be entirely synthetic.

The termination region may be native with the transcriptional initiation region, may be native with the operably linked nucleic acid molecule, may be native with the cell host, or may be derived from another source (i.e., foreign or heterologous) to the promoter, the nucleic acid molecule, the cell host, or any combination thereof. In preparing the expression cassette, the various DNA fragments may be manipulated, so as to provide for the DNA sequences in the proper orientation. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

In some embodiments, a number of promoters are used in the expression cassettes provided herein. One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the present disclosure should not be limited to the use of constitutive promoters. Inducible promoters are also contemplated as part of the present disclosure. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. Synthetic promoters are also contemplated as part of the present disclosure, for example, the JeT promoter (see, WO/2002/012514).

In some embodiments, the promoters are selected based on the desired outcome. It is recognized that different applications can be enhanced by the use of different promoters in the expression cassettes to modulate the timing, location and/or level of expression of the polynucleotides disclosed herein. Such expression constructs may also contain, if desired, a promoter regulatory region (e.g., one conferring inducible, constitutive, environmentally- or developmentally-regulated, or cell- or tissue-specific/selective expression), a transcription initiation start site, a ribosome binding site, an RNA processing signal, a transcription termination site, and/or a polyadenylation signal.

In order to assess the expression of a co-stimulatory domain or CAR polypeptide comprising a co-stimulatory domain, the expression cassette can also contain either a selectable marker gene or a reporter gene, or both, to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes and fluorescent marker genes.

In specific embodiments, expression cassettes comprising nucleic acid molecules encoding CARs including at least one co-stimulatory domain, or an active variant thereof, disclosed herein are provided. As used herein a "CAR expression cassette" refers to an expression cassette comprising at least one nucleic acid molecule encoding a CAR. In some embodiments, a CAR expression cassette encodes a CAR without a co-stimulatory domain. A CAR expression cassette can also encode a CAR comprising a co-stimulatory domain as disclosed herein, or can encode a CAR comprising a co-stimulatory domain that is not disclosed herein. For example, in some embodiments an expression cassette comprises one or more sequences encoding an extracellular ligand-binding domain and an intracellular stimulatory domain comprising a co-stimulatory domain, or an active variant thereof, as disclosed herein. In specific embodiments, the extracellular ligand-binding domain is specific for an antigen of a cancer cell, such as, for example, an antigen specific for B cell lymphoma.

In a specific embodiment, the expression cassette encodes a CAR comprising an anti-CD19 scFv, the Novel1 co-stimulatory domain (SEQ ID NO: 5), or an active variant thereof, and a CD3ξ signaling domain. In other embodiments, the expression cassette encodes a CAR comprising an anti-CD19 scFv, the Novel3 co-stimulatory domain (SEQ ID NO: 6), or an active variant thereof, and a CD3ξ signaling domain. In other embodiments, the expression cassette encodes a CAR comprising an anti-CD19 scFv, the Novel5 co-stimulatory domain (SEQ ID NO: 7), or an active variant thereof, and a CD3ξ signaling domain. In other embodiments, the expression cassette encodes a CAR comprising an anti-CD19 scFv, the Novel6 co-stimulatory domain (SEQ ID NO: 8), or an active variant thereof, and a CD3ξ signaling domain. It is contemplated that these expression cassettes can be engineered to have specificity for any suitable disease-specific antigen or molecule.

In other specific embodiments, expression cassettes comprising nucleic acid molecules encoding an inducible regulatory construct including at least one co-stimulatory domain disclosed herein, or an active variant thereof, are provided. As used herein, a "regulatory expression cassette" refers to an expression cassette comprising a nucleic acid molecule encoding an inducible regulatory construct. An expression cassette can be both a CAR expression cassette and a regulatory expression cassette. In some embodiments a single expression cassette can comprise a nucleotide sequence encoding a CAR that does not comprise a co-stimulatory domain of any one of SEQ ID NOs: 5-8, or active fragments or variants thereof, and a nucleotide sequence encoding an inducible regulatory construct as described herein.

For example, in some embodiments, expression cassettes comprise sequences encoding a binding domain and at least one co-stimulatory domain, or an active variant thereof, as disclosed herein, wherein a small molecule, antibody, or other molecule binds to the binding domain to induce dimerization of two inducible regulatory constructs. In some embodiments, such dimerization initiates the co-stimulatory signal to the cell to promote proliferation, survival, and/or cytokine secretion. In some embodiments, wherein the binding domain can bind a small molecule, the binding domain comprises an analogue of FKBP12 (e.g., comprising an F36V substitution) and the small molecule is rimiducid (i.e., AP1903). Any binding domains known in the art to be useful in such inducible regulatory constructs, such as CAR-T cell safety switches and the like, are contemplated in the present disclosure.

In a specific embodiment, the expression cassette encodes an inducible regulatory construct comprising a binding domain and the Novel1 co-stimulatory domain (SEQ ID NO: 5), or an active variant thereof. In other embodiments, the expression cassette encodes an inducible regulatory construct comprising a binding domain and the Novel13 co-stimulatory domain (SEQ ID NO: 6), or an active variant thereof. In other embodiments, the expression cassette encodes an inducible regulatory construct comprising a binding domain and the Novel5 co-stimulatory domain (SEQ ID NO: 7), or an active variant thereof. In other embodiments, the expression cassette encodes an inducible regulatory construct comprising a binding domain and the Novel6 co-stimulatory domain (SEQ ID NO: 8), or an active variant thereof.

Also provided herein are vectors comprising the nucleic acid molecules encoding the novel co-stimulatory domains of the present disclosure. In some embodiments, vectors comprise a nucleic acid molecule encoding the novel co-stimulatory domains or an expression cassette as disclosed herein. In some embodiments, nucleic acids encoding the co-stimulatory domains disclosed herein are cloned into a number of types of vectors. For example, in some embodiments the nucleic acid is cloned into a vector including, but not limited to a plasmid, a phagemid, a phage derivative, an animal virus, and a cosmid. Vectors of particular interest include expression vectors, replication vectors, probe generation vectors, and sequencing vectors.

In specific embodiments, nucleic acid molecules encoding a co-stimulating domain are provided on viral vectors, such as retroviral vectors, lentiviral vectors, adenoviral vectors, and adeno-associated viral (AAV) vectors. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

2.3 Chimeric Antigen Receptors (CARs) and Inducible Regulatory Constructs

Provided herein are genetically-modified cells expressing a cell surface chimeric antigen receptor (CAR). Generally, a CAR of the present disclosure will comprise at least an extracellular domain and an intracellular domain. In some embodiments, the extracellular domain comprises a target-specific binding element otherwise referred to as a ligand-binding domain or moiety. In some embodiments, the intracellular domain, or cytoplasmic domain, comprises at least one co-stimulatory domain, or active variant thereof, as disclosed herein, and one or more signaling domains such as, for example, CD3 ξ. For example, in some embodiments, the CARs disclosed herein comprise an intracellular domain comprising at least one co-stimulatory domain, such as those provided in SEQ ID NOs: 5-8, or an active variant thereof. In specific embodiments, the CARs disclosed herein comprise at least two co-stimulatory domains, wherein at least one of the co-stimulatory domains are set forth in SEQ ID NOs: 5-8, or an active fragment or variant disclosed herein.

In some embodiments, a CAR of the present disclosure comprises an extracellular, target-specific binding element otherwise referred to as a ligand-binding domain or moiety. The choice of ligand-binding domain depends upon the type and number of ligands that define the surface of a target cell. For example, the ligand-binding domain may be chosen to recognize a ligand that acts as a cell surface marker on target cells associated with a particular disease state. Thus, examples of cell surface markers that may act as ligands for the ligand-binding domain in the CAR of the present disclosure can include those associated with viral, bacterial and parasitic infections, autoimmune disease, and cancer cells. In some embodiments, the CAR of the present disclosure is engineered to target a tumor antigen of interest by way of engineering a desired ligand-binding moiety that specifically binds to an antigen on a tumor cell. In the context of the present disclosure, "tumor antigen" refers to antigens that are common to specific hyperproliferative disorders such as cancer.

In some embodiments, the extracellular ligand-binding domain of the CAR is specific for any tumor antigen or epitope of interest. As non-limiting examples, in some embodiments the antigen of the target is a tumor-associated surface antigen, such as ErbB2 (HER2/neu), carcinoembryonic antigen (CEA), epithelial cell adhesion molecule (Ep-CAM), epidermal growth factor receptor (EGFR), EGFR variant III (EGFRvIII), CD19, CD20, CD30, CD40, disialoganglioside GD2, ductal-epithelial mucine, gp36, TAG-72, glycosphingolipids, glioma-associated antigen, B-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate specific antigen (PSA), PAP, NY-ESO-1, LAGA-1a, p53, prostein, PSMA, surviving and telomerase, prostate-carcinoma tumor antigen-1 (PCTA-1), MAGE, ELF2M, neutrophil elastase, ephrin B2, CD22, insulin growth factor (IGF1)-1, IGF-II, IGFI receptor, mesothelin, a major histocompatibility complex (MHC) molecule presenting a tumor-specific peptide epitope, 5T4, ROR1, Nkp30, NKG2D, tumor stromal antigens, the extra domain A (EDA) and extra domain B (EDB) of fibronectin and the A1 domain of tenascin-C (TnC A1) and fibroblast associated protein (fap); a lineage-specific or tissue specific antigen such as CD3, CD4, CD8, CD24, CD25, CD33, CD34, CD133, CD138, CTLA-4, B7-1 (CD80), B7-2 (CD86), endoglin, a major histocompatibility complex (MHC) molecule, BCMA (CD269, TNFRSF 17), CS1, or a virus-specific surface antigen such as an HIV-specific antigen (such as HIV gp120); an EBV-specific antigen, a CMV-specific antigen, a HPV-specific antigen such as the E6 or E7 oncoproteins, a Lasse Virus-specific antigen, an Influenza Virus-specific antigen, as well as any derivate or variant of these surface markers. In a particular embodiment of the present disclosure, the ligand-binding domain is specific for CD19.

In some embodiments, the extracellular domain of a chimeric antigen receptor further comprises an autoantigen (see, Payne et al. (2016) *Science*, Vol. 353 (6295): 179-184), which can be recognized by autoantigen-specific B cell receptors on B lymphocytes, thus directing T cells to specifically target and kill autoreactive B lymphocytes in antibody-mediated autoimmune diseases. Such CARs can be referred to as chimeric autoantibody receptors (CAARs), and the incorporation of one or more co-stimulatory domains described herein into such CAARs is encompassed by the present disclosure.

In some embodiments, a CAR disclosed herein further comprises a transmembrane domain which links the extracellular ligand-binding domain or autoantigen with the intracellular signaling and co-stimulatory domains. In some embodiments, the transmembrane domain is a CD8a transmembrane polypeptide.

The intracellular signaling domain of a CAR of the present disclosure is responsible for activation of at least one of the normal effector functions of the cell in which the CAR has been placed and/or activation of proliferative and cell survival pathways. The term "effector function" refers to a specialized function of a cell. Effector function of a T cell, for example, may be cytolytic activity or helper activity including the secretion of cytokines. An intracellular signaling domain, such as CD3ξ, can provide an activation signal to the cell in response to binding of the extracellular domain. As discussed, the activation signal can induce an effector function of the cell such as, for example, cytolytic activity or cytokine secretion.

In some embodiments, the intracellular domain includes one or more intracellular co-stimulatory domains, such as those described herein, which transmit a co-stimulatory signal which promotes cell proliferation, cell survival, and/or cytokine secretion after binding of the extracellular domain. In some embodiments, such intracellular co-stimulatory domains include, without limitation, any co-stimulatory domain disclosed herein or those domains known in the art, such as, for example, a CD28 domain, a 4-1BB domain, an OX-40 domain, an ICOS domain, or a CD27 domain.

Also provided herein are genetically-modified cells expressing an inducible regulatory construct. In some embodiments, an inducible regulatory construct is a transmembrane or intracellular construct that is expressed in a cell which provides an inducible co-stimulatory signal to promote cell proliferation, cell survival, and/or cytokine secretion. In some embodiments, inducible regulatory constructs comprise one or more co-stimulatory domains, such as those described herein and/or others known in the art, which provide a co-stimulatory signal upon activation. Generally, a co-stimulatory signal can be induced, for example, by homodimerization of two inducible regulatory construct polypeptides. An inducible regulatory construct typically comprises a binding domain which allows for homodimerization following binding of a small molecule, an antibody, or other molecule that allows for homodimerization of two construct polypeptides. Dimerization can initiate the co-stimulatory signal to the cell to promote proliferation, survival, and/or cytokine secretion. In some embodiments, wherein the binding domain binds a small molecule, the binding domain comprises an analogue of FKBP12 (e.g., comprising an F36V substitution) and the small molecule is rimiducid (i.e., AP1903). Any binding domains known in the art to be useful in such inducible regulatory constructs, such as CAR-T cell safety switches and the like, are contemplated in the present disclosure.

In particular embodiments, the intracellular signaling domain of a CAR of the present disclosure comprises a signaling domain derived from CD3 and at least one novel co-stimulatory domain, such as SEQ ID NO: 5-8, or an active variant thereof.

In other particular embodiments, the inducible regulatory constructs disclosed herein comprise a binding domain, which allows for dimerization of two constructs, and at least one novel co-stimulatory domain, such as SEQ ID NO: 5-8, or an active variant thereof.

2.4 Methods for Producing Recombinant Viral Vectors

In some embodiments, the present disclosure provides recombinant AAV vectors for use in the methods of the present disclosure. Recombinant AAV vectors are typically produced in mammalian cell lines such as HEK-293. Because the viral cap and rep genes are removed from the vector to prevent its self-replication to make room for the therapeutic gene(s) to be delivered (e.g. the endonuclease gene), it is necessary to provide these in trans in the packaging cell line. In addition, it is necessary to provide the "helper" (e.g. adenoviral) components necessary to support replication (Cots D, Bosch A, Chillon M (2013) *Curr. Gene Ther.* 13(5): 370-81). Frequently, recombinant AAV vectors are produced using a triple-transfection in which a cell line is transfected with a first plasmid encoding the "helper" components, a second plasmid comprising the cap and rep genes, and a third plasmid comprising the viral ITRs containing the intervening DNA sequence to be packaged into the virus. Viral particles comprising a genome (ITRs and intervening gene(s) of interest) encased in a capsid are then isolated from cells by freeze-thaw cycles, sonication, detergent, or other means known in the art. Particles are then purified using cesium-chloride density gradient centrifugation or affinity chromatography and subsequently delivered to the gene(s) of interest to cells, tissues, or an organism such as a human patient. Accordingly, methods are provided herein for producing recombinant AAV vectors comprising at least one nucleic acid sequence encoding a co-stimulatory domain described herein, such as SEQ ID NOs: 5-8, or active variants thereof. Likewise, methods are provided herein for producing recombinant AAV vectors encoding CARs or inducible regulatory constructs which include at least one co-stimulatory domain described herein, such as SEQ ID NOs: 5-8, or active variants thereof.

In some embodiments, genetic transfer is accomplished via lentiviral vectors. Lentiviruses, in contrast to other retroviruses, in some contexts may be used for transducing certain non-dividing cells. Non-limiting examples of lentiviral vectors include those derived from a lentivirus, such as Human Immunodeficiency Virus 1 (HIV-1), HIV-2, an Simian Immunodeficiency Virus (SIV), Human T-lymphotropic virus 1 (HTLV-1), HTLV-2 or equine infection anemia virus (E1AV). For example, lentiviral vectors have been generated by multiply attenuating the HIV virulence genes, for example, the genes env, vif, vpr, vpu and nef are deleted, making the vector safer for therapeutic purposes. Lentiviral vectors are known in the art, see Naldini et al., (1996 and 1998); Zufferey et al., (1997); Dull et al., 1998, U.S. Pat. Nos. 6,013,516; and 5,994,136). In some embodiments, these viral vectors are plasmid-based or virus-based, and are configured to carry the essential sequences for incorporating foreign nucleic acid, for selection, and for transfer of the nucleic acid into a host cell. Known lentiviruses can be readily obtained from depositories or collections such as the American Type Culture Collection ("ATCC"; 10801 University Blvd., Manassas, Va. 20110-2209), or isolated from known sources using commonly available techniques.

In specific embodiments, lentiviral vectors are prepared using a plasmid encoding the gag, pol, tat, and rev genes cloned from human immunodeficiency virus (HIV) and a second plasmid encoding the envelope protein from vesicular stomatitis virus (VSV-G) used to pseudotype viral particles. A transfer vector, such as the pCDH-EF1-MCS vector, can be used with a suitable promoter such as the JeT promoter or the EF1 promoter. CAR-signaling domains, such as the co-stimulatory domains disclosed herein, and active variants thereof, can then be inserted downstream of the promoter, followed by an IRES and GFP. All three plasmids can then be transfected into lentivirus cells, such as the Lenti-X-293T cells, and lentivirus can then be harvested, concentrated and screened after a suitable incubation time. Accordingly, methods are provided herein for producing recombinant lentiviral vectors comprising at least one nucleic acid sequence a co-stimulatory domain described herein, such as SEQ ID NOs: 5-8, or active variants thereof. Likewise, methods are provided herein for producing recombinant lentiviral vectors encoding a CAR or an inducible regulatory construct which includes at least one co-stimulatory domain described herein, such as SEQ ID NOs: 5-8, or active variants thereof.

2.5 Genetically-Modified Cells and Populations Thereof Comprising Novel Co-Stimulatory Domains Provided herein are cells genetically-modified to contain at least one novel co-stimulatory domain, such as SEQ ID NO: 5-8, or an active variant thereof, as disclosed herein. In specific embodiments, the genetically-modified cell comprises a nucleic acid molecule encoding a CAR or an inducible regulatory construct incorporating at least one novel co-stimulatory domain described herein, such as SEQ ID NO: 5-8, or an active variant thereof. In different variations of the present disclosure, a nucleic acid molecule or expression cassette which encodes a novel co-stimulatory domain described herein is present within the genome of the genetically-modified cell or, alternatively, is not integrated into the genome of the cell. In some embodiments where the nucleic acid molecule or expression cassette is not integrated into the genome, the nucleic acid molecule or expression cassette is present in the genetically-modified cell in a recombinant DNA construct, in an mRNA, in a viral genome, or other nucleic acid which is not integrated into the genome of the cell. In particular embodiments, the genetically-modified cell can comprise a nucleic acid molecule encoding a co-stimulatory domain described herein and further comprise at least one expression cassette disclosed herein comprising a nucleotide sequence encoding a CAR that does not comprise a co-stimulatory domain disclosed herein and/or a nucleotide sequence encoding an inducible regulatory construct.

In some genetically-modified cells embodied herein, the nucleic acid molecule encoding a CAR or an inducible regulatory construct incorporating at least one novel co-stimulatory domain described herein, is positioned with the endogenous T cell receptor alpha gene of the cell. In some of these embodiments, the nucleic acid molecule is positioned within the endogenous T cell receptor alpha constant region gene, such as within exon 1 of the T cell receptor alpha constant region gene.

In specific embodiments, the cells comprising the novel co-stimulatory domains, or active variants thereof, are eukaryotic cells. In particular embodiments, the cells comprising the novel co-stimulatory domains, or active variants thereof, are T cells or NK cells, particularly human T cells or NK cells. In some embodiments, the cells are primary T cells or primary NK cells.

T cells and NK cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present disclosure, any number of T cell and NK cell lines available in the art may be used. In some embodiments of the present disclosure, T cells and NK cells are obtained from a unit of blood collected from a subject using any number of techniques known to the skilled artisan. In one embodiment, cells from the circulating blood of an individual are obtained by apheresis.

Genetically-modified cells comprising the novel co-stimulatory domains disclosed herein, or active variants thereof, can exhibit increased proliferation when compared to appropriate control cells without the novel co-stimulatory domain, or active variant thereof. In some embodiments, cells comprising the novel co-stimulatory domains disclosed herein, or active variants thereof, further exhibit increased activation and proliferation in vitro or in vivo following stimulation with an appropriate antigen. For example, cells, such as CAR-T cells and CAR-NK cells, can exhibit increased activation, proliferation, and/or increased cytokine secretion compared to a control cell without the novel co-stimulatory domains disclosed herein, or active variants thereof. Increased cytokine secretion can include the increased secretion of IFN-γ, IL-2, TNF-α, among others. Methods for measuring cell activation and cytokine production are well known in the art, and some suitable methods are provided in the examples herein.

The present disclosure further provides a population of genetically-modified cells comprising a plurality of a genetically-modified cells described herein, which comprise in their genome a nucleic acid molecule encoding a CAR or an inducible regulatory construct incorporating at least one novel co-stimulatory domain described herein, such as SEQ ID NO: 5-8, or an active variant thereof. Thus, in various embodiments of the invention, a population of genetically-modified cells is provided wherein at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or up to 100%, of cells in the population are a genetically-modified cell comprising a novel co-stimulatory domain disclosed herein. In certain embodiments, a population of genetically-modified cells is provided wherein at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or up to 100%, of cells in the population express a CAR comprising a novel co-stimulatory domain described herein. In other embodiments, a population of genetically-modified cells is provided wherein at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or up to 100%, of cells in the population express an inducible regulatory construct comprising a novel co-stimulatory domain disclosed herein and a CAR which does not comprise a co-stimulatory domain described herein.

2.6 Methods for Producing Genetically-Modified Cells

The present disclosure provides methods for producing genetically-modified cells comprising the novel co-stimulatory domains disclosed herein, or active variants thereof. In specific embodiments, methods are provided for modifying the cell to comprise a nucleic acid sequence molecule encoding a CAR incorporating at least one novel co-stimulatory domain, such as SEQ ID NOs: 5-8, or an active variant thereof. In other embodiments, methods are provided for modifying the cell to comprise a nucleic acid molecule encoding an inducible regulatory construct incorporating at least one novel co-stimulatory domain, such as SEQ ID NOs: 5-8, or an active variant thereof. In different aspects of the present disclosure, a nucleic acid molecule or expression cassette encoding a novel co-stimulatory domain disclosed herein, or an active variant thereof, is integrated into the genome of the cell or, alternatively, is not integrated into the genome of the cell.

In some embodiments, DNA or RNA encoding the novel co-stimulatory domains (or CARs or inducible regulatory constructs) disclosed herein is introduced into a cell using any technology known in the art. In specific embodiments, vectors or expression cassettes comprising the nucleic acids encoding the novel co-stimulatory domains (or CARs or inducible regulatory constructs) disclosed herein is introduced into a cell using a viral vector. Such vectors are known in the art and include lentiviral vectors, adenoviral vectors, and adeno-associated virus (AAV) vectors (reviewed in Vannucci, et al. (2013 *New Microbiol.* 36:1-22). Recombinant AAV vectors useful in the present disclosure can have any serotype that allows for transduction of the virus into the cell and insertion of the nuclease gene into the cell and, in particular embodiments, into the cell genome. In particular embodiments, recombinant AAV vectors have a serotype of AAV2 or AAV6. Recombinant AAV vectors can also be self-complementary such that they do not require second-strand DNA synthesis in the host cell (McCarty, et al. (2001) *Gene Ther.* 8:1248-54).

In some embodiments, nucleic acid molecules or expression cassettes disclosed herein are delivered into a cell in the form of DNA (e.g., circular or linearized plasmid DNA or PCR products) or RNA. In some embodiments wherein the engineered nuclease genes are delivered in DNA form (e.g. plasmid) and/or via a viral vector (e.g. AAV or lentiviral vector), they are operably linked to a promoter or found on an expression cassette disclosed herein. In some embodiments, the promoter is a viral promoter such as endogenous promoters from the viral vector (e.g. the LTR of a lentiviral vector) or the well-known cytomegalovirus- or SV40 virus-early promoters. In other embodiments, the promoter is a synthetic promoter, such as the JeT promoter. In certain embodiments, genes encoding the novel co-stimulatory domains or CARs disclosed herein are operably linked to a promoter that drives gene expression preferentially in the target cell (e.g., a human T cell).

In some embodiments, nucleic acid molecules or expression cassettes encoding co-stimulatory domains (or CARs or inducible regulatory constructs) disclosed herein, are coupled covalently or non-covalently to a nanoparticle or encapsulated within such a nanoparticle using methods known in the art (Sharma, et al. (2014) *Biomed Res Int.* 2014). A nanoparticle is a nanoscale delivery system whose length scale is <1 μm, preferably <100 nm. Such nanoparticles may be designed using a core composed of metal, lipid, polymer, or biological macromolecule, and multiple copies of the nucleic acid molecules or expression cassettes can be attached to or encapsulated with the nanoparticle core. This increases the copy number of the DNA that is delivered to each cell and, so, increases the intracellular expression of each engineered nuclease to maximize the likelihood that the co-stimulatory domains (or CARs or inducible regulatory constructs) will be expressed. The surface of such nanoparticles may be further modified with polymers or lipids (e.g., chitosan, cationic polymers, or cationic lipids) to form a core-shell nanoparticle whose surface confers additional functionalities to enhance cellular delivery and uptake of the payload (Jian et al. (2012) *Biomaterials.* 33(30): 7621-30). Nanoparticles may additionally be advantageously coupled to targeting molecules to direct the nanoparticle to the appropriate cell type and/or increase the likelihood of cellular uptake. Examples of such targeting molecules include antibodies specific for cell-surface receptors and the natural ligands (or portions of the natural ligands) for cell surface receptors.

In some embodiments, nucleic acid molecules or expression cassettes encoding co-stimulatory domains (or CARs or inducible regulatory constructs) disclosed herein, are encapsulated within liposomes or complexed using cationic lipids (see, e.g., LIPOFECTAMINE, Life Technologies Corp., Carlsbad, Calif.; Zuris et al. (2015) *Nat Biotechnol.* 33: 73-80; Mishra et al. (2011) *J Drug Deliv.* 2011:863734). The liposome and lipoplex formulations can protect the payload from degradation, and facilitate cellular uptake and delivery efficiency through fusion with and/or disruption of the cellular membranes of the cells.

In some embodiments, nucleic acid molecules or expression cassettes encoding co-stimulatory domains (or CARs or inducible regulatory constructs) disclosed herein, are encapsulated within polymeric scaffolds (e.g., PLGA) or complexed using cationic polymers (e.g., PEI, PLL) (Tamboli et al. (2011) *Ther Deliv.* 2(4): 523-536). In some embodiments, nucleic acid molecules or expression cassettes encoding co-stimulatory domains (or CARs or inducible regulatory constructs) disclosed herein, are combined with amphiphilic molecules that self-assemble into micelles (Tong et al. (2007) *J Gene Med.* 9(11): 956-66). Polymeric micelles may include a micellar shell formed with a hydrophilic polymer (e.g., polyethyleneglycol) that can prevent aggregation, mask charge interactions, and reduce nonspecific interactions outside of the cell.

In some embodiments, nucleic acid molecules or expression cassettes encoding co-stimulatory domains (or CARs or inducible regulatory constructs) disclosed herein, are formulated as emulsions for delivery to the cell. The term "emulsion" refers to, without limitation, any oil-in-water, water-in-oil, water-in-oil-in-water, or oil-in-water-in-oil dispersions or droplets, including lipid structures that can form as a result of hydrophobic forces that drive apolar residues (e.g., long hydrocarbon chains) away from water and polar head groups toward water, when a water immiscible phase is mixed with an aqueous phase. These other lipid structures include, but are not limited to, unilamellar, paucilamellar, and multilamellar lipid vesicles, micelles, and lamellar phases. Emulsions are composed of an aqueous phase and a lipophilic phase (typically containing an oil and an organic solvent). Emulsions also frequently contain one or more surfactants. Nanoemulsion formulations are well known, e.g., as described in US Patent Application Nos. 2002/0045667 and 2004/0043041, and U.S. Pat. Nos. 6,015,832, 6,506,803, 6,635,676, and 6,559,189, each of which is incorporated herein by reference in its entirety.

In some embodiments, nucleic acid molecules or expression cassettes encoding co-stimulatory domains (or CARs or inducible regulatory constructs) disclosed herein, are covalently attached to, or non-covalently associated with, multifunctional polymer conjugates, DNA dendrimers, and polymeric dendrimers (Mastorakos et al. (2015) *Nanoscale.* 7(9): 3845-56; Cheng et al. (2008) *J Pharm Sci.* 97(1): 123-43). The dendrimer generation can control the payload capacity and size, and can provide a high payload capacity. Moreover, display of multiple surface groups can be leveraged to improve stability and reduce nonspecific interactions.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means. Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection. Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362. Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In some embodiments, the invention further provides for the introduction of the nucleic acid molecules or expression cassettes disclosed herein into the T cell receptor alpha gene. In certain embodiments, the nucleic molecule or expression cassettes are introduced into a recognition sequence present in the T cell receptor alpha constant region gene, which comprises the coding sequences for the T cell receptor alpha subunit. As such, introduction of the nucleic acid molecules or expression cassettes disrupts expression of the endogenous T cell receptor alpha subunit, and consequently disrupts expression of the endogenous T cell receptor. In particular embodiments, such recognition sequences can be present within exon 1 of the T cell receptor alpha constant region gene.

In particular embodiments, introducing a nucleic acid molecule encoding a co-stimulatory domain disclosed herein into a cell, such as a T cell or NK cell, can increase activation, proliferation, and/or cytokine secretion of the cell when compared to a control cell without the co-stimulatory domain disclosed herein. In some embodiments, activation, proliferation, and/or cytokine secretion of a cell can be increased in vitro or in vivo by introducing a nucleic acid molecule encoding a co-stimulatory domain disclosed herein.

In some embodiments, introduction of at least one novel co-stimulatory domain, or an active fragment or variant thereof, into a cell, such as a T cell or NK cell, prolong the period of cell proliferation and/or expansion of the cell population, and/or delay cell exhaustion, when compared to control cells without the novel co-stimulatory domain disclosed herein. Methods of measuring cell expansion and exhaustion (such as T cell or NK cell expansion and exhaustion) are known in the art and disclosed elsewhere herein.

2.7 Pharmaceutical Compositions

In some embodiments, the present disclosure provides a pharmaceutical composition comprising a genetically-modified cell, or a population of genetically-modified cells, of the present disclosure and a pharmaceutically-acceptable carrier. Such pharmaceutical compositions can be prepared in accordance with known techniques. See, e.g., Remington, *The Science And Practice of Pharmacy* (21$^{st}$ ed. 2005). In the manufacture of a pharmaceutical formulation according to the present disclosure, cells are typically admixed with a pharmaceutically acceptable carrier and the resulting composition is administered to a subject. The carrier must, of course, be acceptable in the sense of being compatible with any other ingredients in the formulation and must not be deleterious to the subject. In some embodiments, pharmaceutical compositions of the present disclosure further comprises one or more additional agents useful in the treatment of a disease in the subject. In additional embodiments, where the genetically-modified cell is a genetically-modified human T cell or NK cell (or a cell derived therefrom), pharmaceutical compositions of the present disclosure further include biological molecules, such as cytokines (e.g., IL-2, IL-7, IL-15, and/or IL-21), which promote in vivo cell proliferation and engraftment. Pharmaceutical compositions comprising genetically-modified cells of the present disclosure can be administered in the same composition as an additional agent or biological molecule or, alternatively, can be co-administered in separate compositions.

The present disclosure also provides genetically-modified cells, or populations thereof, described herein for use as a medicament. The present disclosure further provides the use of genetically-modified cells or populations thereof described herein in the manufacture of a medicament for treating a disease in a subject in need thereof. In one such aspect, the medicament is useful for cancer immunotherapy in subjects in need thereof.

In some embodiments, the pharmaceutical compositions and medicaments of the present disclosure are useful for treating any disease state that can be targeted by T cell adoptive immunotherapy. In a particular embodiment, the pharmaceutical compositions and medicaments of the present disclosure are useful as immunotherapy in the treatment of cancer. Non-limiting examples of cancer which may be treated with the pharmaceutical compositions and medicaments of the present disclosure are carcinomas, lymphomas, sarcomas, melanomas, blastomas, leukemias, and germ cell tumors, including but not limited to cancers of B-cell origin, neuroblastoma, osteosarcoma, prostate cancer, renal cell carcinoma, rhabdomyosarcoma, liver cancer, gastric cancer, bone cancer, pancreatic cancer, skin cancer, cancer of the head or neck, breast cancer, lung cancer, cutaneous or intraocular malignant melanoma, renal cancer, uterine cancer, ovarian cancer, colorectal cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, environmentally induced cancers including those induced by asbestos, multiple myeloma, Hodgkin lymphoma, non-Hodgkin's lymphomas, acute myeloid lymphoma, chronic myelogenous leukemia, chronic lymphoid leukemia, immunoblastic large cell lymphoma, acute lymphoblastic leukemia, mycosis fungoides, anaplastic large cell lymphoma, and T-cell lymphoma, and any combinations of said cancers. In certain embodiments, cancers of B-cell origin include, without limitation, B-lineage acute lymphoblastic leukemia, B-cell chronic lymphocytic leukemia, B-cell lymphoma, diffuse large B cell lymphoma, pre-B ALL (pediatric indication), mantle cell lymphoma, follicular lymphoma, marginal zone lymphoma, Burkitt's lymphoma, and B-cell non-Hodgkin's lymphoma.

2.8 Methods of Administering Genetically-Modified Cells

Another aspect disclosed herein is the administration of the genetically-modified cells of the present disclosure to a subject in need thereof. In particular embodiments, the pharmaceutical compositions described herein are administered to a subject in need thereof. For example, an effective amount of a population of cells comprising a novel co-stimulatory domain described herein, or an active variant thereof, can be administered to a subject having a disease. In particular embodiments, the disease can be cancer, such as a cancer of B-cell origin. Thus, the present disclosure also provides a method for providing a T cell-mediated immune response to a target cell population or tissue in a mammal, comprising the step of administering to the mammal a CAR-T cell, wherein the CAR comprises an extracellular ligand-binding domain that specifically interacts with a predetermined target, such as a tumor antigen, and an intracellular domain that comprises at least one signaling domain, such as CD3ξ, and at least one novel co-stimulatory signaling domain described herein, or active variant thereof. In other embodiments, the CAR does not comprise a novel co-stimulatory domain described herein, but the cell further comprises an inducible regulatory construct which comprises at least one novel co-stimulatory domain described herein, wherein dimerization of the inducible regulatory construct initiates a co-stimulatory signal to the cell. In such embodiments, the method further comprises the administration of a small molecule, antibody, or other molecule which induces dimerization of the inducible regulatory construct in order to induce a proliferative and/or survival signal in the CAR-T cell in order to promote cell proliferation and expansion of the CAR-T cell population in vivo. The administered CAR-T cells are able to reduce the proliferation, reduce the number, or kill target cells in the recipient. Unlike antibody therapies, genetically-modified cells of the present disclosure are able to replicate and expand in vivo, resulting in long-term persistence that can lead to sustained control of a disease.

Examples of possible routes of administration include parenteral, (e.g., intravenous (IV), intramuscular (IM), intradermal, subcutaneous (SC), or infusion) administration. Moreover, the administration may be by continuous infusion or by single or multiple boluses. In specific embodiments, one or both of the agents is infused over a period of less than about 12 hours, 6 hours, 4 hours, 3 hours, 2 hours, or 1 hour. In still other embodiments, the infusion occurs slowly at first and then is increased over time.

In some embodiments, a genetically-modified cell of the present disclosure targets a tumor antigen for the purposes of treating cancer. Such cancers can include, without limitation, carcinomas, adenocarcinomas, lymphomas, sarcomas, melanomas, blastomas, leukemias, and germ cell tumors, including but not limited to cancers of B-cell origin, neuroblastoma, osteosarcoma, prostate cancer, renal cell carcinoma, rhabdomyosarcoma, liver cancer, gastric cancer, bone cancer, pancreatic cancer, skin cancer, cancer of the head or neck, breast cancer, lung cancer, cutaneous or intraocular malignant melanoma, renal cancer, uterine cancer, ovarian cancer, colorectal cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, environmentally induced cancers including those induced by asbestos, multiple myeloma, Hodgkin lymphoma, non-Hodgkin's lymphomas, acute myeloid lymphoma, chronic myelogenous leukemia, chronic lymphoid leukemia, immunoblastic large cell lymphoma, acute lymphoblastic leukemia, mycosis fungoides, anaplastic large cell lymphoma, and T-cell lymphoma, and any combinations of said cancers. In certain embodiments, cancers of B-cell origin include, without limitation, B-lineage acute lymphoblastic leukemia, B-cell chronic lymphocytic leukemia, B-cell lymphoma, diffuse large B cell lymphoma, pre-B ALL (pediatric indication), mantle cell lymphoma, follicular lymphoma, marginal zone lymphoma, Burkitt's lymphoma, and B-cell non-Hodgkin's lymphoma.

In some of these embodiments wherein cancer is treated with the presently disclosed genetically-modified cells, the subject administered the genetically-modified cells is further administered an additional therapeutic, such as radiation, surgery, or a chemotherapeutic agent.

When an "effective amount" or "therapeutic amount" is indicated, the precise amount of the compositions of the present disclosure to be administered can be determined by a physician with consideration of individual differences in age, weight, tumor size (if present), extent of infection or metastasis, and condition of the patient (subject). In some embodiments, a pharmaceutical composition comprising the genetically-modified cells described herein is administered at a dosage of $10^4$ to $10^9$ cells/kg body weight, including all integer values within those ranges. In further embodiments, the dosage is $10^5$ to $10^6$ cells/kg body weight, including all integer values within those ranges. In some embodiments, cell compositions are administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In some embodiments, administration of genetically-modified cells of the present disclosure reduce at least one symptom of a target disease or condition. For example, administration of genetically-modified cells of the present disclosure can reduce at least one symptom of a cancer, such as cancers of B-cell origin. Symptoms of cancers, such as cancers of B-cell origin, are well known in the art and can be determined by known techniques.

EXPERIMENTAL

This disclosure is further illustrated by the following examples, which should not be construed as limiting. Those skilled in the art will recognize, or be able to ascertain, using no more than routine experimentation, numerous equivalents to the specific substances and procedures described herein. Such equivalents are intended to be encompassed in the scope of the claims that follow the examples below.

Example 1

Production of Lentiviral Vectors for Expression of CARs with Novel Co-Stimulatory Domains The purpose of this study was to evaluate and characterize novel co-stimulatory domains that were developed to promote CAR-T cell expansion and cytokine secretion following antigen stimulation.

As shown in FIG. 1, four novel co-stimulatory domains were engineered which comprise two TRAF-binding motifs. These domains are referred to as Novel1 (N1; SEQ ID NO: 5), Novel3 (N3; SEQ ID NO: 6), Novel5 (N5; SEQ ID NO: 7), and Novel6 (N6; SEQ ID NO: 8). In order to evaluate each novel co-stimulatory domain, lentiviral vectors were used to prepare anti-CD19 CAR-T cells. Each CAR comprised, from 5' to 3', a signal peptide (SEQ ID NO: 16), an anti-CD19 scFv (SEQ ID NO: 17) having the heavy chain and light chain variable regions of the FMC63 antibody linked by a $(G_4S)_3$ polypeptide linker, a CD8 hinge region and transmembrane domain (SEQ ID NO: 18), and an intracellular region comprising two intracellular signaling domains. An SV40 polyadenylation (polyA) sequence (SEQ ID NO: 22) was positioned 3' downstream of the CAR sequence. Some lentiviral vectors encoded an anti-CD19 CAR whose intracellular region comprised: (i) a novel co-stimulatory domain, and (ii) a CD3-ξ signaling domain (SEQ ID NO: 19). A negative control vector was prepared that encoded a CAR lacking a co-stimulatory domain (Null), and additional vectors were prepared that encoded CARs having CD28 (SEQ ID NO: 20) or 4-1BB (SEQ ID NO: 21) co-stimulatory domains and a CD3-ξ signaling domain. The lentiviral vectors prepared for this study are summarized in Table 1. Each CAR is illustrated in FIG. 2, and their respective sequences are set forth in SEQ ID NOs: 22-28.

TABLE 1

| Lentiviral Vector | Co-Stimulatory Domain | Activation Domain | CAR SEQ ID NO: |
|---|---|---|---|
| 1 | — | CD3ξ | 22 |
| 2 | CD28ξ | CD3ξ | 23 |
| 3 | 4-1BB | CD3ξ | 24 |
| 4 | Novel1 | CD3ξ | 25 |
| 5 | Novel3 | CD3ξ | 26 |
| 6 | Novel2 | CD3ξ | 27 |
| 7 | Novel6 | CD3ξ | 28 |

Lentiviral vectors were prepared with a $2^{nd}$ generation approach, using a plasmid encoding gag, pol, tat, and rev cloned from human immunodeficiency virus (HIV). A second plasmid, encoding the envelope protein from vesicular stomatitis virus (VSV-G) was used to pseudotype viral particles. The transfer vector pCDH-EF1-MCS (purchased from System Biosciences) was modified to contain the JeT promoter (SEQ ID NO: 32) rather than the EF1 promoter, and CAR-signaling variants were cloned downstream of the promoter, followed by and IRES and GFP. All three plasmids were transfected into Lenti-X-293T cells (purchased from ClonTech/Takara), and lentivirus was harvested from supernatants 3 d later. Viral particles were concentrated using Lenti-X concentrator (ClonTech/Takara) and quantified, using the Lenti-X qRT-PCR Titration kit (ClonTech/Takeda) to determine the number of viral genomes/ml, as well as titration on 293T cells (ATCC) to determine transducible units/ml.

Example 2

Expression of Chimeric Antigen Receptors Comprising Novel Co-Stimulatory Domains in Human T Cells and Characterization in Antigen-Induced Stress Test 1. Preparation of CAR-T Cells and Antigen-Induced Stress Test The purpose of this study was to evaluate the novel co-stimulatory domains in an antigen-induced stress. Briefly, lentiviral vectors were prepared as described in Example 1. To prepare donor human T cells for lentiviral transduction, T cells were stimulated in ImmunoCult anti-CD2/CD3/CD28 multimers (StemCell Technologies) and 20 ng/ml of IL-2 for 4 days. Cells were then collected and deposited into separate wells for transduction with individual lentiviral vectors. 5 Transducible Units per T cell were added to cultures. Transduction was performed in X-VIVO 15 medium (Lonza) supplemented with only IL-2 (20 ng/ml) and 8 µg/ml of polybrene (Sigma). Co-incubation of vector and T cells was carried out overnight prior to medium replacement (X-Vivo 15+20 ng/ml IL-2+5% normal human serum).

Beginning 4 days following lentiviral transduction, CAR expression was confirmed by GFP analysis (FIG. 3). A sample of each lentivirus-transduced T cell culture was obtained and GFP signal was measured on a Becton-Dickinson LSR:Fortessa flow cytometer. The GFP T cell population in each culture is identified by the region entitled CAR-GFP+ in FIG. 3, and the frequency of GFP+ events is listed on each dot plot.

Subsequently, $5 \times 10^4$ CAR-T cells were cultivated with an equivalent number of Raji cells. At the times indicated in FIGS. 4 (d3, 6, 10, 14, 17, and 20), cell number and viability were measured by automated cell counting and trypan blue exclusion. CAR-T cells were identified as $CD4^+$ or $CD8^+$ using antibodies against human CD4 and CD8, as well as GFP signal using flow cytometry. CAR-T numbers were calculated and $1 \times 10^5$ CAR-T cells were re-cultured with $5 \times 10^4$ additional Raji cells (2:1 effector:target ratio). $CD4^+$, $CD8^+$, and overall number of CAR-T cells were tracked and plotted over time. At each time point, 50 µl of culture supernatants were collected and stored at $-20°$ C. for a three-plex cytokine secretion assay. Cytokine levels in supernatants were measured using Ultrasensitive human IL-2, TNFα, and IFNγ magnetic bead kits (Life Technologies) in accord with the manufacturer's recommendations. Data were acquired using a Luminex MagPix instrument.

In a second study, CAR-T cells containing our novel co-stimulatory domains were constructed as described above and $1 \times 10^5$ CAR-T cells were cultivated with $1 \times 10^5$ Raji tumor cells. At the times indicated on the X axes of FIG. 6, cell number and viability were measured by automated cell counting and trypan blue exclusion. CAR-T cells were identified using antibodies against human CD4 and CD8 as well as GFP signal using flow cytometry. CAR-T numbers were calculated and $1 \times 10^5$ CAR-T cells were re-cultured with $1 \times 10^5$ additional Raji cells. Note that in FIG. 6, the target:effector ratios were adjusted to 1:1 and Raji cells were added to the culture more frequently, at d3, 5, 7, 10, 12, 14, 17, 19, 21, 24, 26, 28, and 31. $CD4^+$, $CD8^+$, and overall number of CAR-T cells were tracked and plotted over time.

4 days after transduction, but prior to co-culture with Raji cells, T cell cultures were assessed for CAR-GFP expression by flow cytometry as previously described. T cells were transduced at an MOI of 5 transducible units per cell and approximately similar efficiencies were observed for all lentiviral samples.

2. Results of Experiment #1

CAR-T cell numbers were measured over time and plotted in FIG. 4. Differences in CAR-T numbers were evident from d10 onward. CAR-T cells with 41BBz signaling domains exhibited more sustained proliferation than those with CD28z domains. The BB null control exhibited the lowest levels of CAR-T expansion in this experiment. Novel domains N5 and N6 exhibited high levels of sustained proliferation. No preference for CD4 (FIG. 4B) or CD8 (FIG. 4C) T cell expansion was observed, as each subset proliferated at similar rates. In order of descending performance in this proliferation assay, the results are as follows: N6>N5>41BBz>N1>>BBnull=CD28z>N3

Figure 5A:
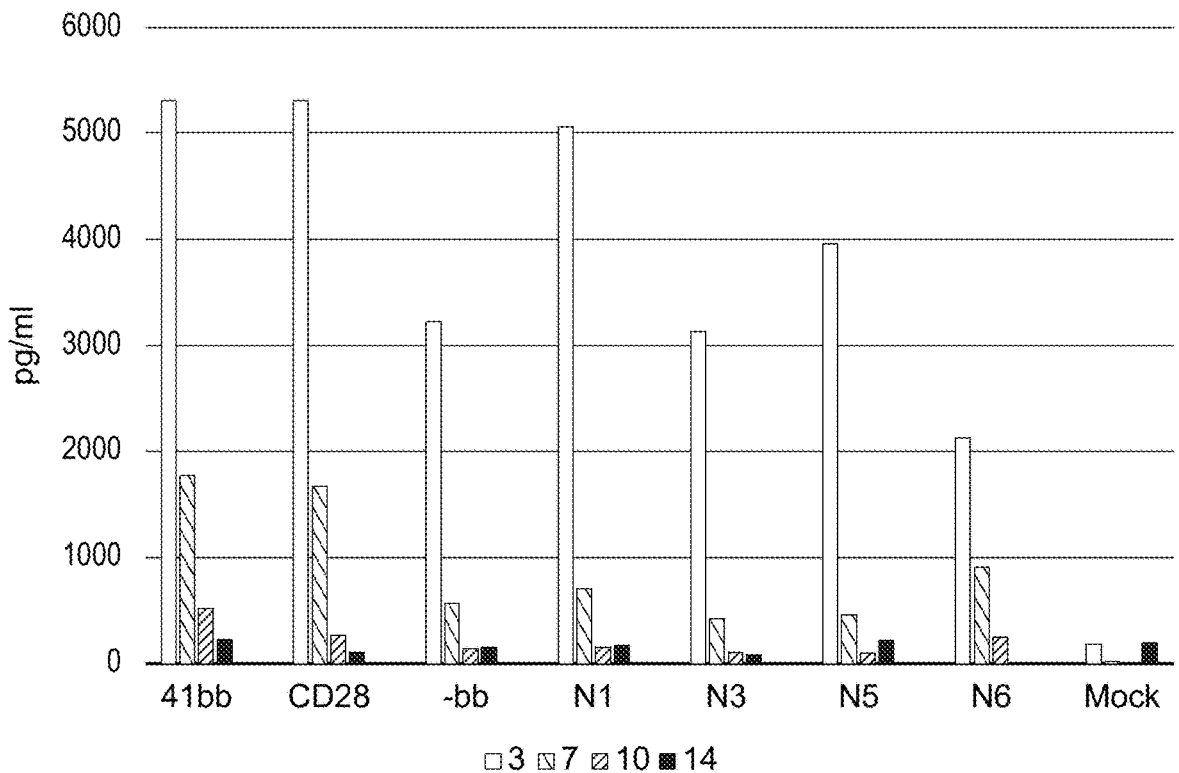
Figure 5B:
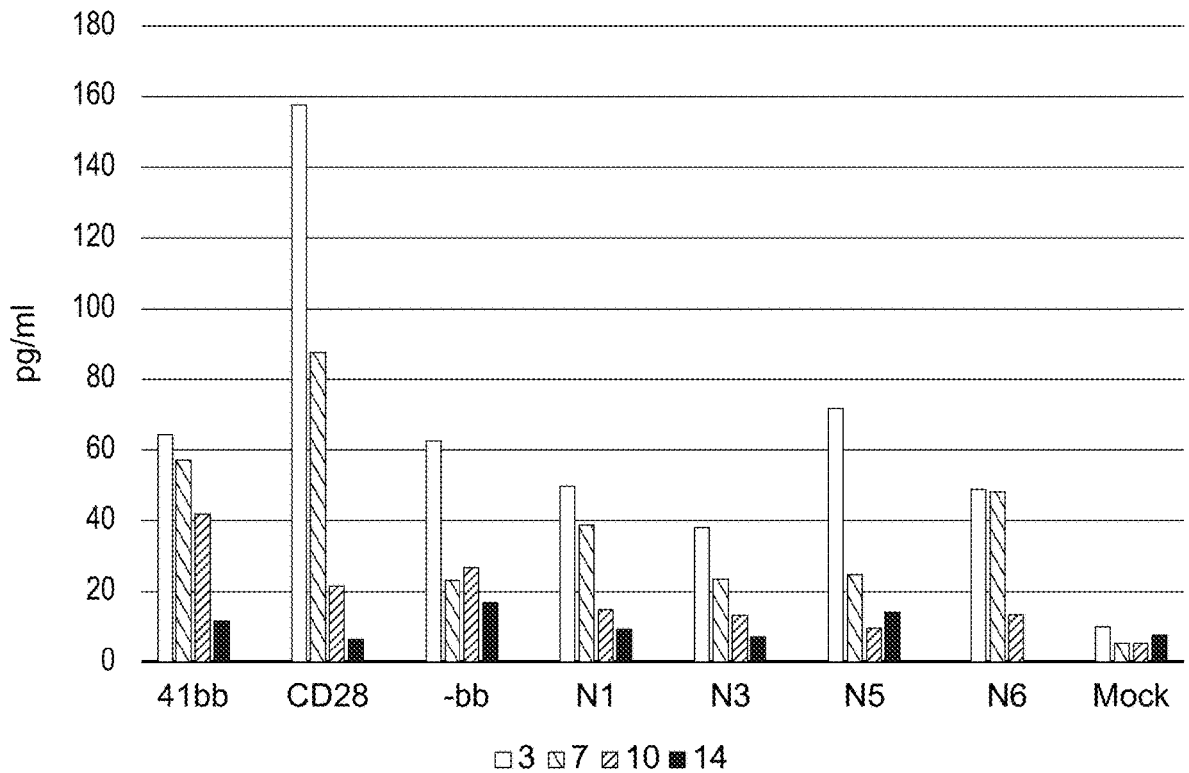

Secretion of IFNγ, TNFα, and IL-2 were measured by Luminex multiplex assay and appear in FIGS. 5A, 5B, and 5C, respectively. In general, secretion levels of all cytokines decreased over time. Ranking of the domains in terms of IFNγ secretion at d3 is as follows: 41BBz=CD28z>N1>N5>BBnull=N3>N6. Levels of IFNγ decreased by 50% or greater in all experimental groups at the d7 time point and continued to decrease for the remainder of the experiment. Ranking the domains in terms of TNFα secretion produces the following list: CD28z>N5=41BBz.BBnull>N1=N6>N3. Between d3 and 7 of culture, the level of TNFα production decreases by approximately 50% in CD28z, BBnull, N3, and N5 cultures while 41BBz, N1, and N6 cultures maintain TNFα production levels through d7. Production of IL-2, on the other hand, was low in all novel domain co-cultures, when compared to 41BBz and CD28z. IL-2 measurements may be confounded by high rates of IL-2 consumption by rapidly proliferating T cells present in some cultures (See FIG. 4).

3. Results of Experiment #2

Figure 6A:
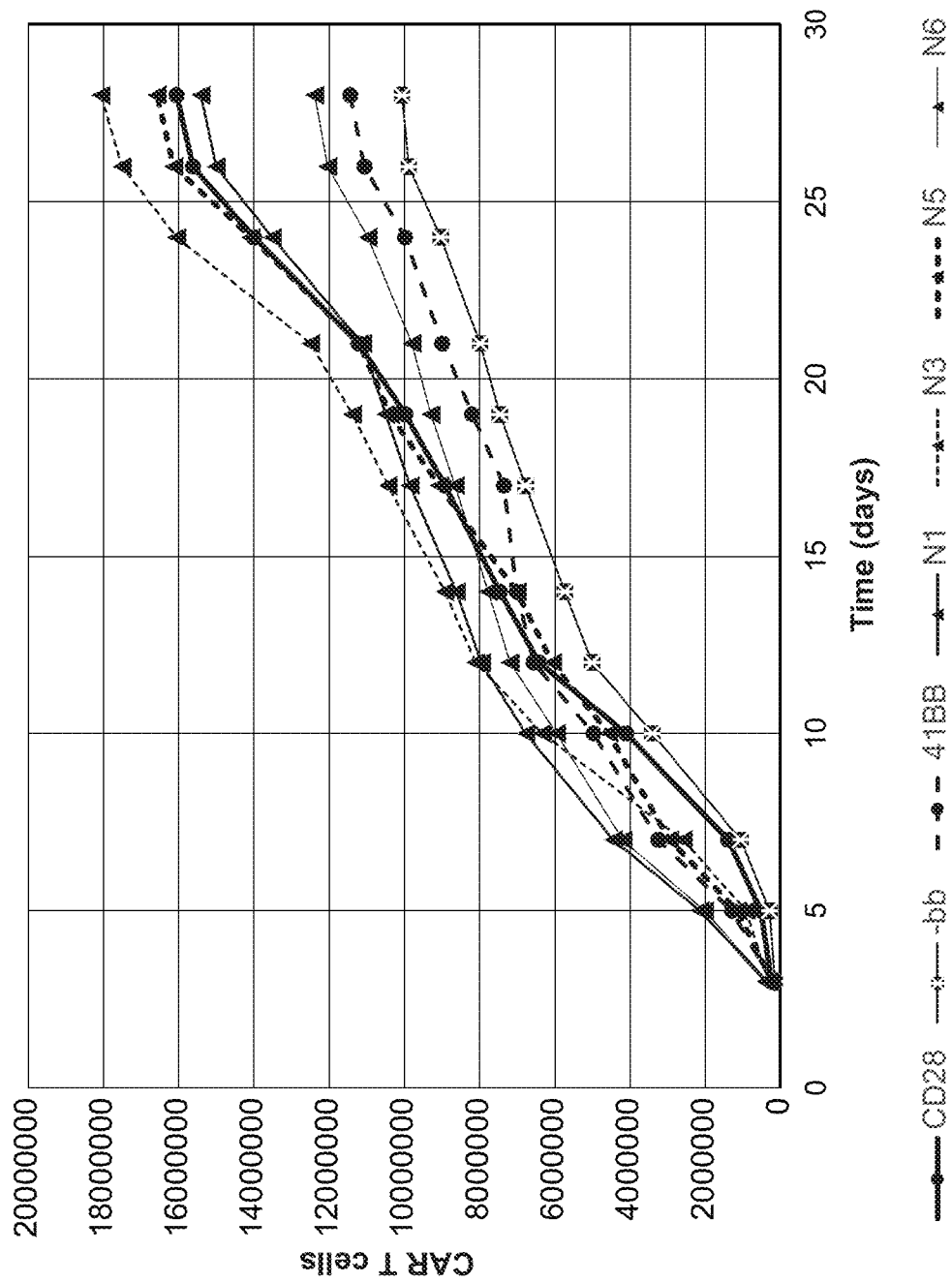

In the second experiment (FIG. 6), using more frequent antigen encounter and a higher target:effector ratio, the results were as follows, in order of descending performance: N3>N5>CD28z>N1>N6>41BBz>BB null. In this experiment, CAR-T cells expanded continuously throughout the culture period. CD4 CAR-T cells ceased expanding after approximately 12 days in Raji co-culture (FIG. 6B), while the CD8 CAR-T cells continued expanding (FIG. 6C).

4. Conclusions

Several novel signaling domains perform as well or better than 41BBz and/or CD28z under relatively lower (FIG. 4) or higher (FIG. 6) antigen burden. CARs carrying the N5 signaling domain outperformed 41BBz and CD28z under both conditions. N5 appears to perform the same as 41BBz in the CD4 compartment in both experiments while N5 outperforms 41BBz in the CD8 compartment in both experiments.

Example 3

Stress Test Using AAV for Targeted Insertion of CAR with 41BB, N1, or N6 Co-Stimulatory Domains 1. Preparation of CAR-T Cells and Antigen-Induced Stress Test In order to evaluate novel intracellular signaling domains, CAR-T cells were produced and their responses to antigen encounter were measured. To produce CAR-T cells, T cells were isolated from an apheresis sample collected from healthy human donors using Stem Cell Technologies CD3 positive selection kit. Two different donors were used in this assay, designated K799 and z4100. T cells were activated and expanded for 3 days using Immunocult anti-CD2/3/28 (StemCell Tech) prior to nucleofection (Lonza 4D nucleofector) with TRC1-2×87EE. Immediately after nucleofection, cells were transduced with AAV6 vectors encoding anti-CD19 CARs featuring different intracellular signaling domains. CAR variants included in this experiment comprised 4-1BB, N1, or N6 co-stimulatory domains. In all vectors, CAR expression was driven by the JeT promoter. Each CAR donor template was flanked by 5' and 3' homology arms, which have homology to the regions upstream and downstream of the TRC 1-2×0.87EE recognition sequence. CAR donor templates were further flanked by 5' and 3' inverted terminal repeats. The donor templates for each CAR are illustrated in FIG. 7, and the sequences of the vectors used to generate AAVs encoding the CD19-4-1BB CAR, the CD19-N1 CAR, and the CD19-N6 CAR, are provided in SEQ ID NOs: 29-31, respectively.

Figure 8A:
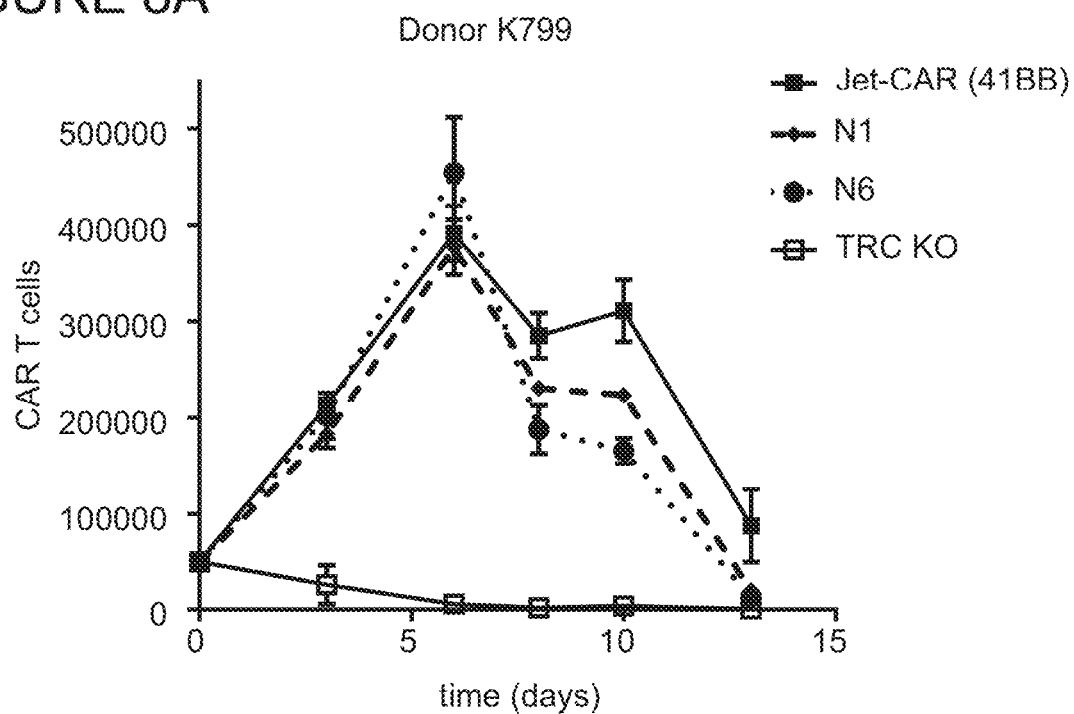
FIGS. 8A and 8B show CAR-T proliferation over time in response to antigen using CAR-T cells prepared from two different donors. Proliferation was measured for CAR-T cells comprising the 4-1BB, N1, or N6 co-stimulatory domains. Novel costimulatory signaling domains were found to support levels of proliferation that are equal to or better than those levels supported by 4-1BB signaling.

The multiplicity of infection was 50,000. 5 days post-nucleofection/transduction, non-edited CD3+ cells were removed by magnetic depletion (StemCell Tech CD3 positive selection kit). Cells were then assessed for purity of the CD3-fraction, and for CAR expression by flow cytometry, using anti-CD3-BrillianViolet-711 (Biolegend), and CD19-Fc-biotin (Acro) followed by streptavidin-PE (BioLegend). The following day, co-cultures containing T cells and K562 engineered to express CD19 ("K19" cells) were assembled. CD19-Fc+ frequencies determined in the above flow cytometry assay were used to calculate the input number of CAR-T cells and establish an effector:target (E:T) ratio of 2:1. At days 3, 6, 8, and 10 of coculture, samples were acquired for flow cytometric evaluation of tumor cell and CAR-T cell numbers in the co-culture. The numbers of CAR-T cells at each time are plotted in FIG. 8 as a demonstration of CAR-T expansion following antigen encounter. Using the calculated number of CAR-T cells as well as the remaining tumor cells detected at each time point, the necessary number of fresh K19 cells were added back to the co-culture in order to re-establish the E:T of 2:1. In addition, a parallel coculture plate was set up with variable E:T ratios (2:1, 1:1, and 1:2). Samples of these co-cultures were taken at 24 h and 72 h and the number of CD19+ cells was determined by flow cytometry. The results appear in FIG. 9. The number of CD19+ cells surviving co-culture with CAR-T cells serves as an indicator of target cell killing.

2. Results of Antigen-Induced Stress Test

Figure 8B:
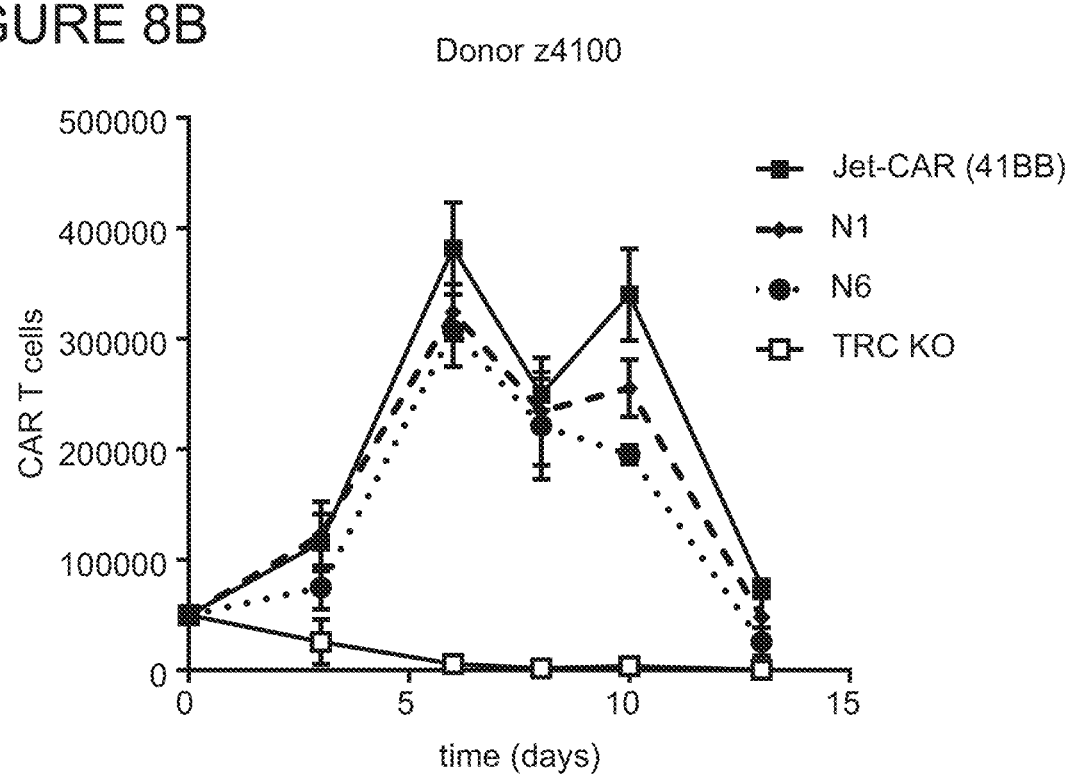
Figure 9A:
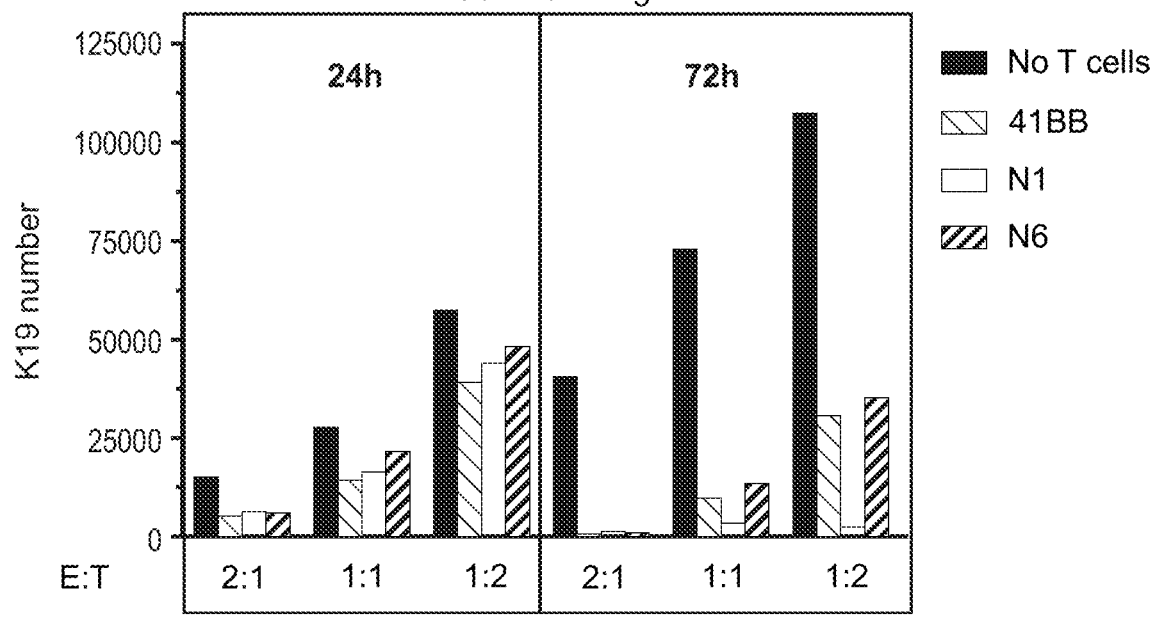
FIGS. 9A and 9B show killing of K19 cells at various effector:target (E:T) ratios at 24 hr and 72 hr of coculture with CAR-T cells comprising the 4-1BB, N1, or N6 co-stimulatory domains.
Figure 9B:
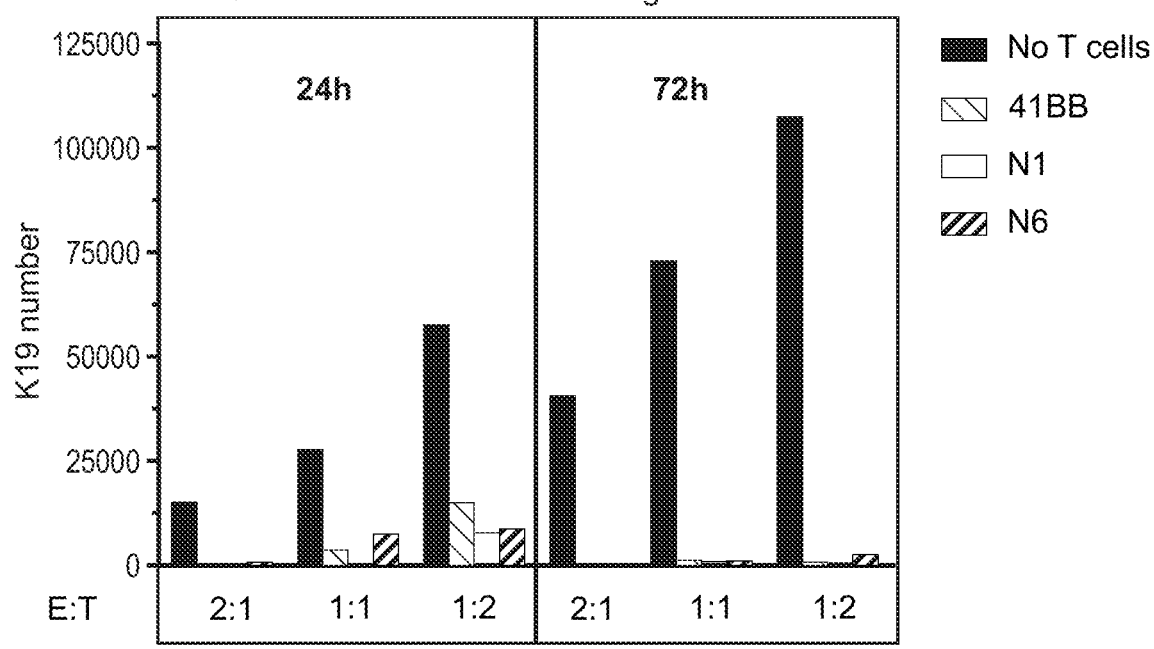

Input T cell populations were normalized to the frequency of CAR+ cells and equivalent numbers of CAR-T cells were challenged with K19 targets at an E:T of 2. Proliferation of CAR-T cells was assessed for T cells produced from donor K799 (FIG. 8A) and donor z4100 (FIG. 8B). Cells containing TRAC edits, but no CAR insertion (TRC KO) cells did not proliferate in response to antigen encounter. In contrast, CAR-T cells produced using the 4-1BB signaling domain proliferated robustly for the first week of coculture before contracting by d12. CAR-T cells produced with N1 or N6 variants exhibited proliferation rates that were not found to be substantially different from the rate supported by 4-1BB. Killing of CD19+ target cells was also assessed at various E:T ratios at 24 and 72 h of the coculture, at which times culture samples were analyzed for the number of remaining CD19+ cells and the results plotted against a control well that contained the same number of K19 cells, but no CAR-T cells. K19 numbers lower than the No T cell control are interpreted as cell killing. CAR-T cells produced using material from donor K799 displayed little cytolytic potential at the 24 h time point, demonstrating noticeable killing only at the least stringent E:T ratio of 2:1 (FIG. 9, Panel A). By 72 h, however, extensive killing was observed at all E:T ratios. N1 and N6 were comparable or superior to 4-1BB. N1 appeared to be superior in cytolytic activity compared to 4-1BB. Extensive killing was observed at both 24 and 72 h time points in the cocultures containing CAR-T cells produced from donor z4100 (FIG. 9B). As above, N1 and N6 were comparable or superior in terms of cytolytic activity when compared to 4-1BB. In general, more extensive killing was observed from CAR-T cells produced from donor z4100. It is important to note that the CD4:CD8 ratio in donor K799 is nearly 3:1, while the ratio in z4100 is 1:1. A sample containing a fixed number of total CAR-T cells (as is the case in these experiments) will therefore differ in their respective numbers of cytotoxic CD8+ T cells with z4100 containing nearly twice as many CD8+ T cells, providing an explanation for the enhanced killing activity observed in cells derived from this donor.

3. Conclusions

Novel costimulatory signaling domains were found to support levels of proliferation and target cell killing that are equal to or better than those levels supported by 4-1BB signaling. Importantly, we demonstrate this feature of N1 and N6 here in CAR-T cells produced with our targeted insertion strategy in addition to other data in which CAR was delivered by randomly-inserting lentiviral vectors. This method reduces the likelihood that differences in CAR-T responses to antigen can be ascribed to differences in integrated copy number between different CAR-T preparations. Importantly, both random and targeted insertion strategies indicated that N6, especially, is a viable alternative to the costimulatory support provided by native 4-1BB.

Example 4

Proliferation Assay in CAR-T Cells Having 41BB, N1, or N6 as the Co-Stimulatory Domain 1. Preparation of CAR-T Cells with Co-Stimulatory Domains and Proliferation Assay CAR elements featuring novel costimulatory domains were cloned out of lentiviral transfer vectors and ligated into the pDI vector. Expression of the CAR element is controlled by the JeT promoter and the element is flanked by TRAC homology arms to enable targeted gene insertion. This donor template is flanked by inverted terminal repeat sequences to enable packaging into AAV6 particles. These plasmids were first linearized by restriction endonuclease digestion and ethanol precipitation. Primed T cells were then nucleofected with TRC1-2×87EE, a linearized CAR plasmid, and STING siRNA to reduce toxicity mediated by intracellular nucleic acid sensors. Nucleic acid delivery was carried out using a Lonza 4D nucleofector. Edited T cells were grown in XVIVO-15 medium (Lonza) supplemented with 5% pooled human serum and 30 ng/ml IL-2 (Gibco). Cultures were carried out for 7 days prior to magnetic depletion of non-edited CD3+ cells using a human CD3 positive selection kit (StemCell Technologies). Cells were rested overnight in 2 ng/ml of IL-2 prior to labeling with 2 μM CellTrace Violet (Life Technologies) in accordance with the manufacturers' recommendations. CellTrace Violet (CTV) is a substrate for intracellular esterases and functions much like carboxyfluoroscein-succinimidyl ester (CFSE). CTV diffuses across membranes into the cytoplasm, where it is cleaved by esterase enzymes, which are abundant in the cytoplasm of live cells. The cleavage product does not diffuse across cell membranes, reacts very strongly with free amino groups found in cytoplasmic proteins, and is fluorescent. When labeled cells divide, the fluorescent cytoplasmic proteins are evenly divided between the daughter cells, resulting in two cells that are each half as bright as the parental generation. By comparing CTV fluorescence to temporal (such as a day 0 control) or biological controls (e.g. non-stimulated cells), rates of proliferation of various cell populations can be measured using flow cytometry by comparing frequencies of CTV dim events. CTV-labeled CD3-fractions of T cells expressing either no CAR, CAR-4-1BB, CAR-N1, or CAR-N6 were then challenged with antigen-bearing tumor cells. For this assay, K562 cells stably expressing CD19 were used at two different effector-to-target (E:T) ratios, 2:1 and 1:1. Importantly, the CAR+ frequency was determined for each co-culture using biotinylated CD19-Fc and streptavidin-PE. Input numbers of T cells were normalized based on their CAR+ frequencies. Cocultures of T cells and CD19+K562s were carried out for 5 days prior to flow cytometric analysis. CD4-PE and CD8-APC antibodies (BioLegend) were used to positively identify T cells. Data were acquired and analyzed using FlowJo software (TreeStar) and proliferation assessed by dye dilution.

2. Results of Proliferation Assay

Figure 10A:
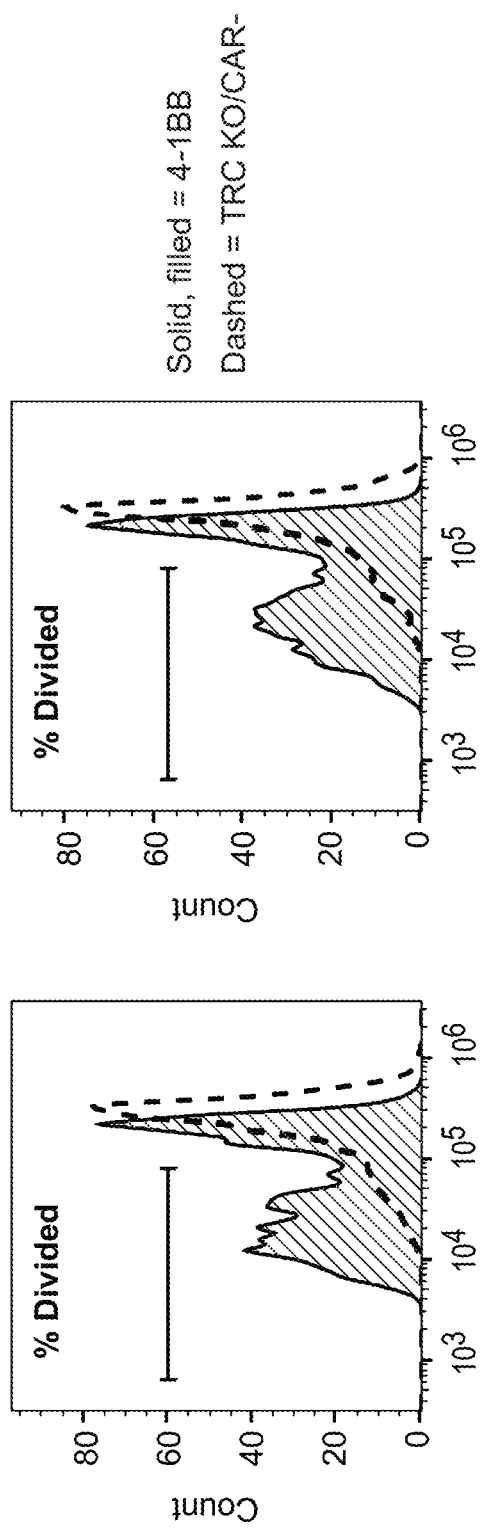
Figure 10B:
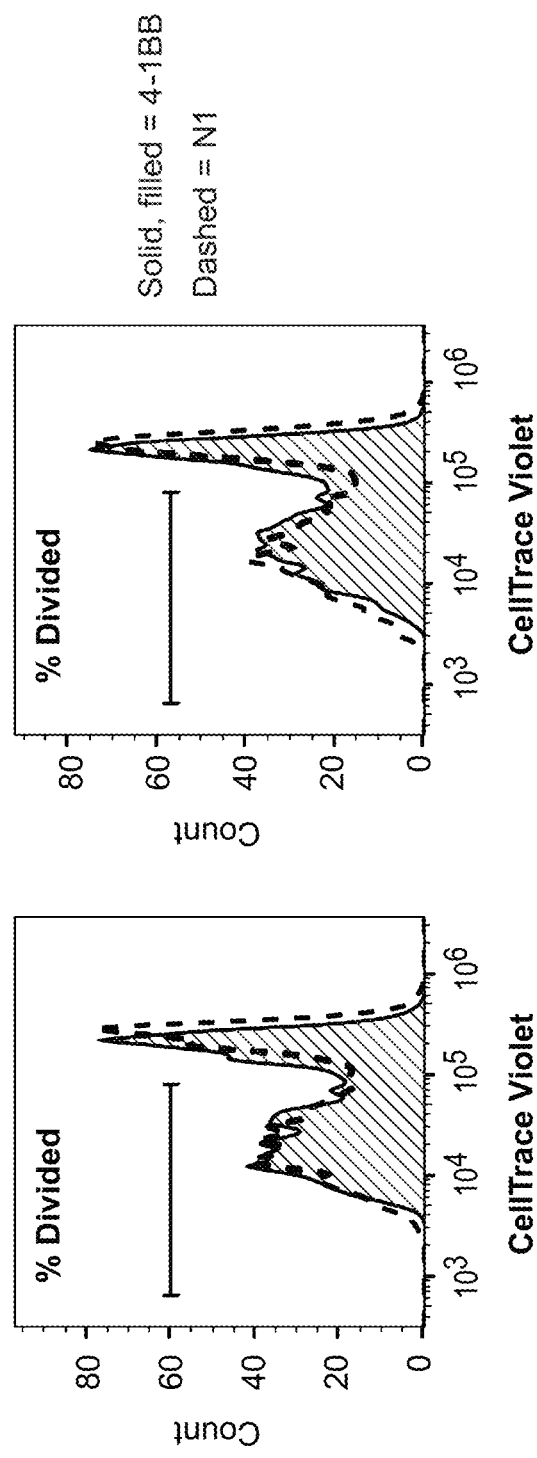
Figure 12B:
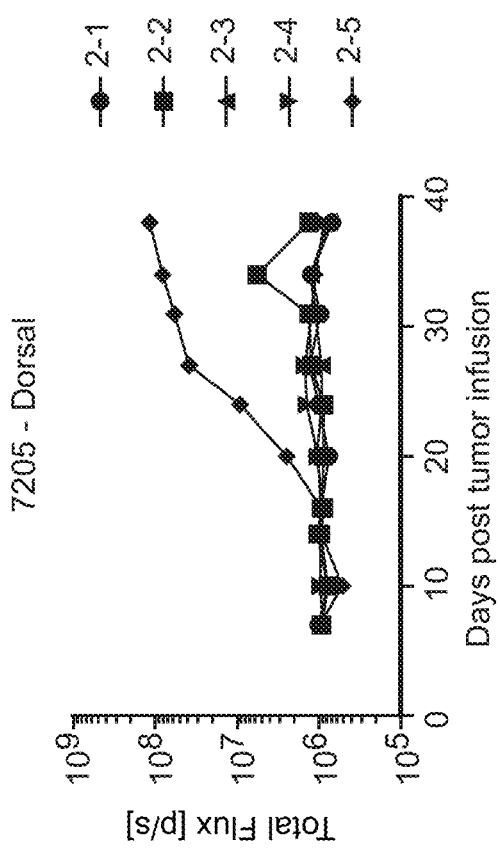
FIGS. 12A-12G show values of dorsal and ventral total flux observed in vivo in mice following engraftment and growth of Raji-ffluc cells and subsequent treatment with TCR KO cells, or CAR T cells bearing the 7205, 7206, or 4-1BB CAR constructs.
Figure 12D:
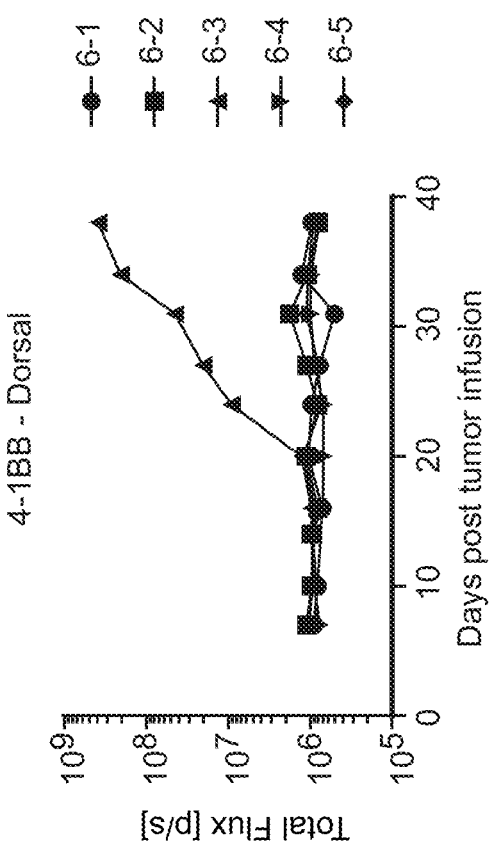
Figure 12A:
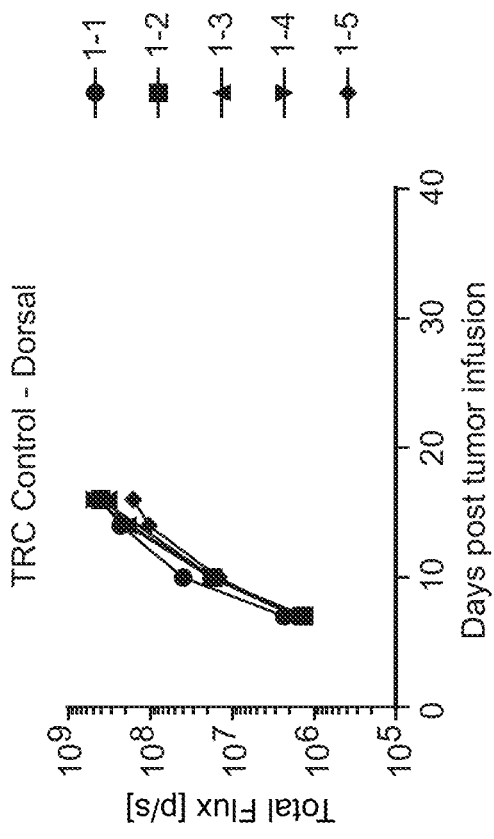
Figure 12C:
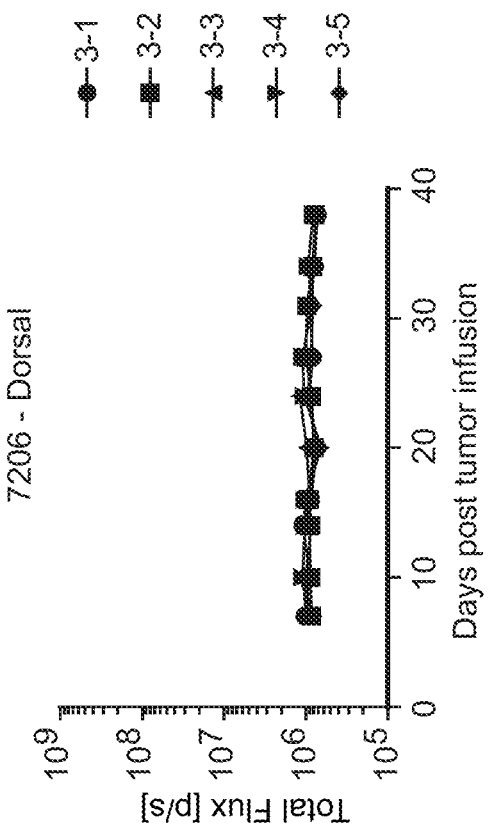
Figure 12E:
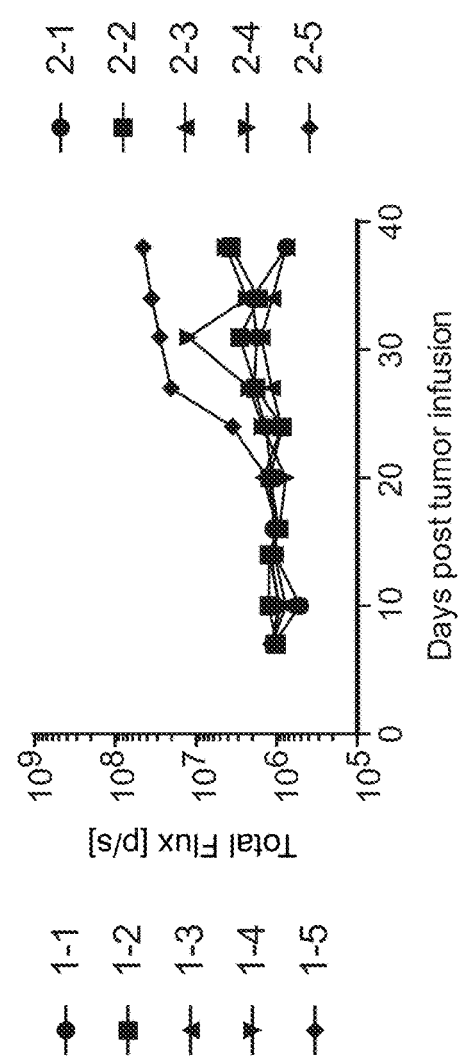
Figure 12G:
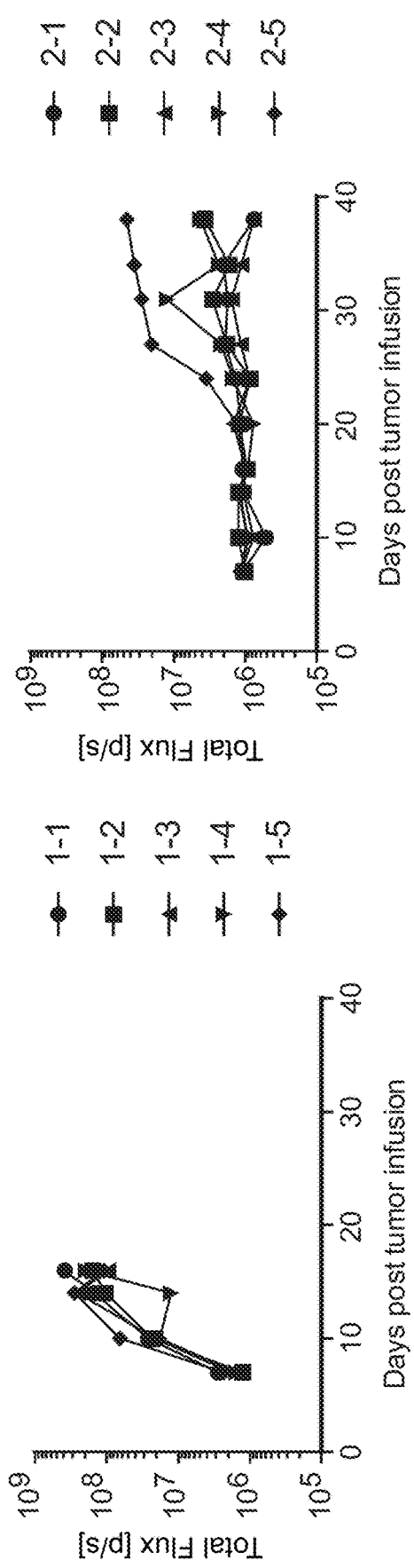
Figure 12F:
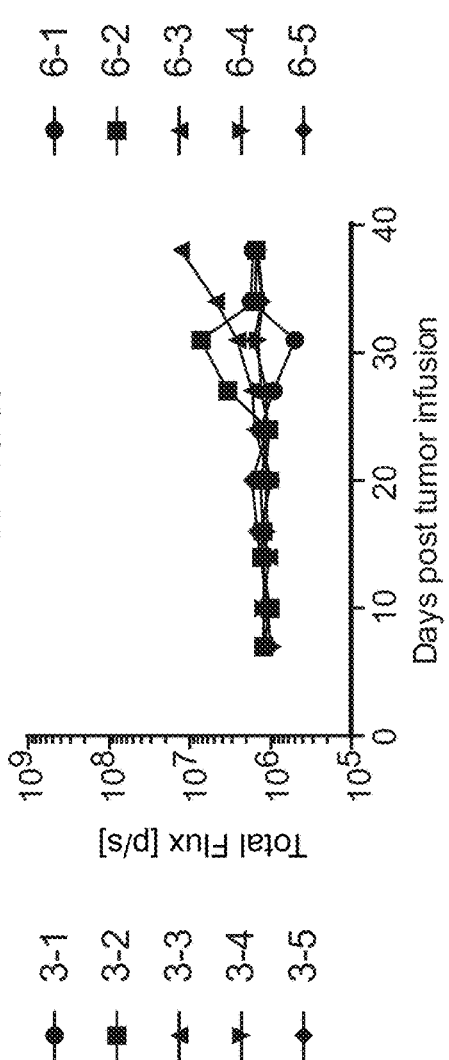
Figure 12H:
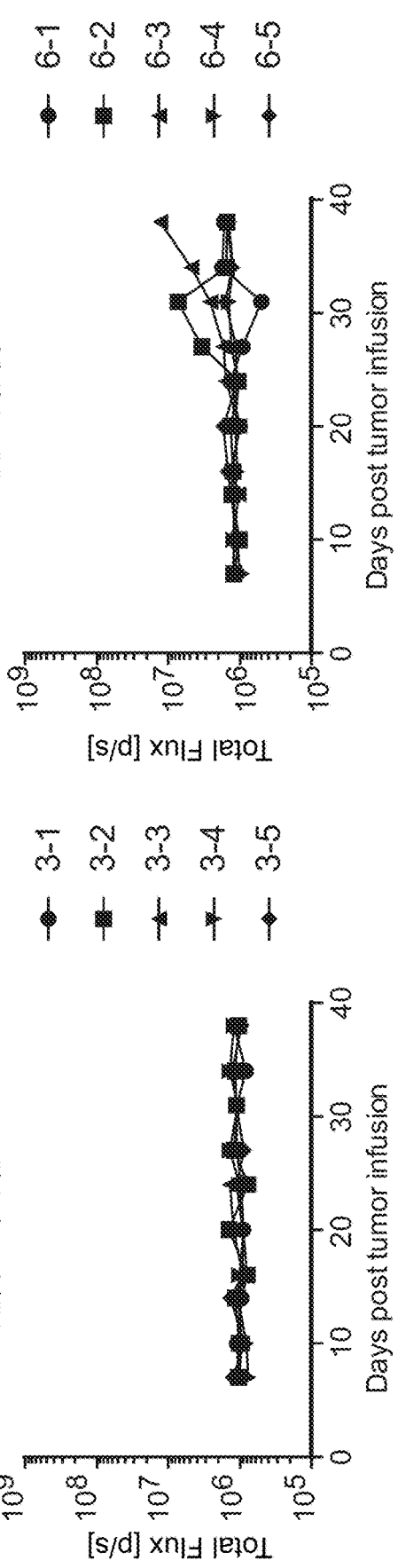
FIG. 12H shows ventral flux following treatment with 4-1BB CAR T cells.

The results from the proliferation assay appear in FIG. 10. The overlaid histograms in FIG. 10A depict the proliferation of CAR-4-1BB CAR-T cells and a lack of proliferation in negative control TRC KO T cells at two different E:T ratios. Slightly more than half of the CAR-4-1BB T cells proliferated in response to CD19+ target cells while 13% divided in the control samples. The overlaid histograms in FIG. 10B show the proliferation rates of CAR-4-1BB cells versus CAR-N1 cells. Approximately equal frequencies of divided cells appear in each culture. The overlaid histograms in FIG. 10C show proliferation rates of CAR-4-1BB T cells in comparison to CAR-N6 T cells. N6 supports proliferation in 77% of cells while 4-1BB supports proliferation in 56% of cells. A table of the frequencies of divided cells in each culture appears below.

TABLE 2

Frequency of dividing CAR-T cells in co-culture with antigen tumor cells.

| Signaling variant | % divided |
| --- | --- |
| 4-1BB | 56.2 |
| N1 | 55.1 |
| N6 | 77.4 |
| TRC- (CAR-) | 13.3 |

3. Conclusions

Lentiviral screens identified N6 as a lead candidate in an effort to identify alternative and/or superior signaling domains to incorporate into a CAR construct. This experiment demonstrated the ability of novel signaling domains to function in a single-copy targeted insertion scenario rather than the random insertion/variable copy number scenario typical of lentiviral delivery. These data support demonstrate that functional signaling variants can be designed and delivered. Importantly, N6 was particularly found to outperform 4-1BB as a costimulatory signal transducer in conjunction with CD3z following encounter with antigen.

Example 5

Efficacy of CAR T Cells Bearing 4-1BB and N6 Co-Stimulatory Domains in a Murine Xenograft Model of Disseminated B Cell Lymphoma 1. Preparation of CAR-T Cells and Injection into Tumor-Bearing Mice The purpose of this study was to evaluate the efficacy of CAR T cells engineered to express anti-CD19 CAR constructs containing the N6 co-stimulatory domain and compare these cells to CAR T cells with a 4-1BB co-stimulatory domain built into the CAR.

Anti-CD19 CAR sequences featuring 4-1BB or N6 co-stimulatory domains were cloned into the pDI plasmid and used to produce AAV6 viral vectors. Expression of the CAR element was controlled by the JeT promoter and the transgene was flanked by TRAC homology arms to enable targeted gene insertion into the TRAC locus when this donor template was delivered in conjunction with the TRC1-2× 0.87EE site-specific endonuclease. This CAR transgene donor template was flanked by inverted terminal repeat sequences to enable packaging into AAV6 particles.

For the N6 co-stimulatory domain, two different CAR transgenes were produced and packaged into different AAV vectors for testing. These two N6-containing CAR elements contained different polyadenylation (PolyA) sequences utilized at the 3' end of the CAR transgene to evaluate whether these PolyA sequences impacted the function of the CAR T cells. The polyA sequence utilized in the 7241 (4-1BB) and 7205 (N6) constructs was an SV40 polyA sequence comprising SEQ ID NO: 33. The polyA sequence utilized in the 7206 (N6) construct is an SV40 bi-polyA sequence having a first sequence comprising SEQ ID NO: 34 and a second sequence comprising SEQ ID NO: 35. Table 3 outlines the features of the CAR constructs used in this study, which are illustrated in FIG. 11. The sequences of the vectors used to generate AAVs encoding the 7241 (4-1BB) construct, the 7205 (N6) construct, and the 7206 (N6) construct, are provided in SEQ ID NOs: 36-38, respectively.

TABLE 3

| AAV Vectors | | | | | |
| --- | --- | --- | --- | --- | --- |
| Name of AAV Vector | Promoter | scFv | Co-Stimulatory Domain | Activation Domain | PolyA Sequence |
| 7205 | JeT | FMC63 | Novel6 (N6) | CD3ζ | SV40 PolyA |
| 7206 | JeT | FMC63 | Novel6 (N6) | CD3ζ | SV40 Bi-PolyA |
| 7241 | JeT | FMC63 | 4-1BB | CD3ζ | SV40 PolyA |

Primed T cells were electroporated with TRC1-2×87EE mRNA. Nucleic acid delivery was carried out using a Lonza 4D Nucleofector. After electroporation, cells were mock transduced, or transduced with AAV6 vectors bearing donor templates with anti-CD19 CAR transgenes including either 4-1BB or N6 co-stimulatory domains.

Edited T cells were grown in XVIVO-15 medium (Lonza) supplemented with 5% pooled human serum and 30 ng/ml IL-2 (Gibco). Cells were cultured for 5 days prior to magnetic depletion of non-edited CD3+ cells using a human CD3 positive selection kit (StemCell Technologies). Cells were cultured for an additional 3 days.

NSG mice (n=5 per group) were injected with 2e5 Raji cells expressing firefly luciferase (Raji-ffluc). Three days later, mice were injected with 1e6 control TCR KO cells each, or 1e6 CAR T cells produced using 7205 (N6), 7206 (N6), or 7241 (4-1BB) vectors. On the indicated days, live mice were injected i.p. with Luciferin substrate (150 mg/kg in saline), anesthetized, and Luciferase activity measured after 7 min using IVIS Spectrum (Perkin Elmer, Waltham, Mass.). Data was analyzed and exported using Living Image software 4.5.2 (Perkin Elmer, Waltham, Mass.). Luminescence signal intensity in the images is represented by radiance in p/sec/cm2/sr. Total flux was also calculated using Living Image software 4.5.2 (Perkin Elmer, Waltham, Mass.) using the entire animal as the region of interest. Mice were monitored for symptoms of disease progression and were euthanized when necessary according to pre-defined criteria.

2. Results of Murine Xenograft Model

Figure 13A:
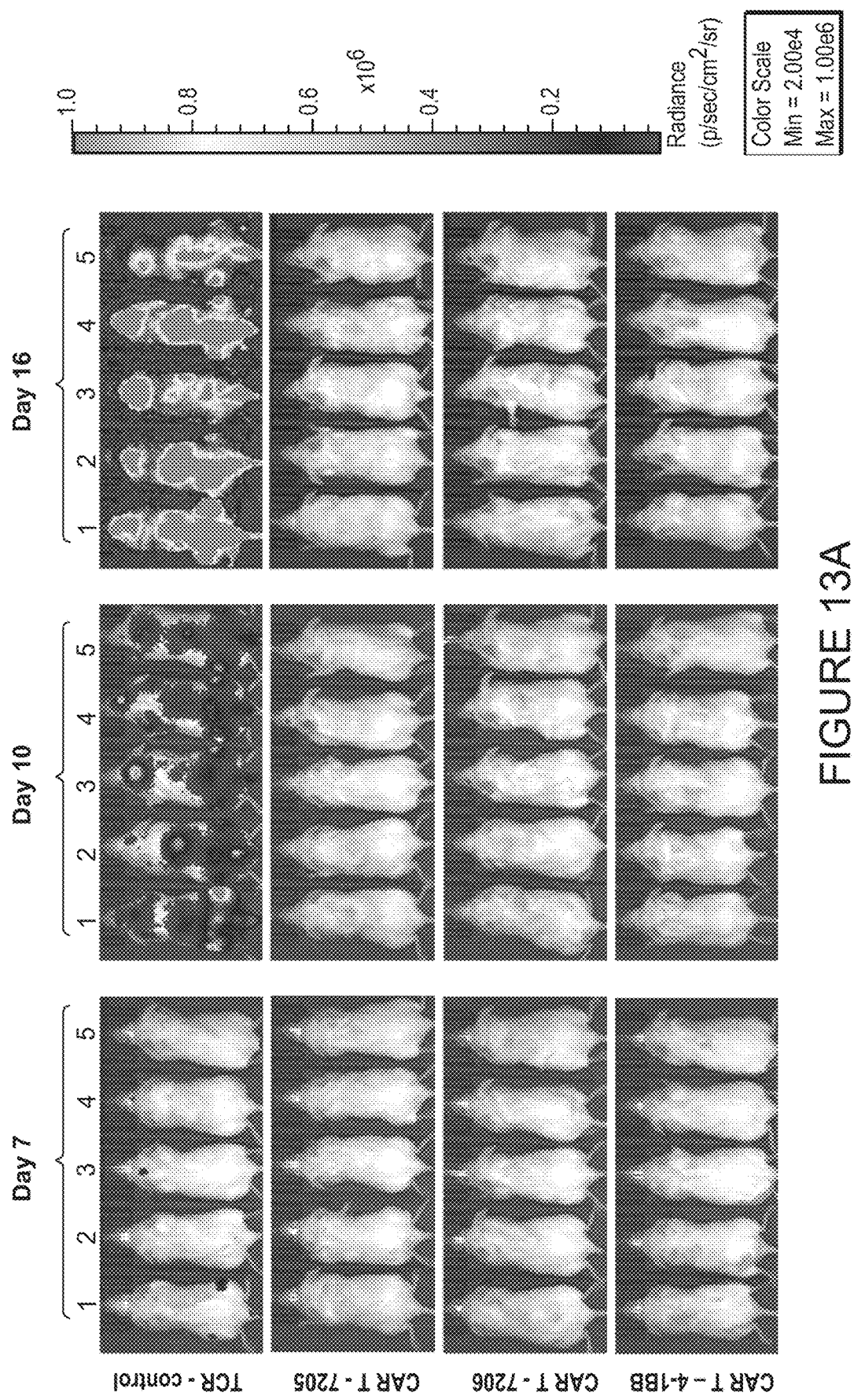
FIGS. 13A-13D show imaging of dorsal and ventral total flux observed in vivo in mice following engraftment and growth of Raji-ffluc cells and subsequent treatment with TCR KO cells, or CAR T cells bearing the 7205, 7206, or 4-1BB CAR constructs.
Figure 13B:
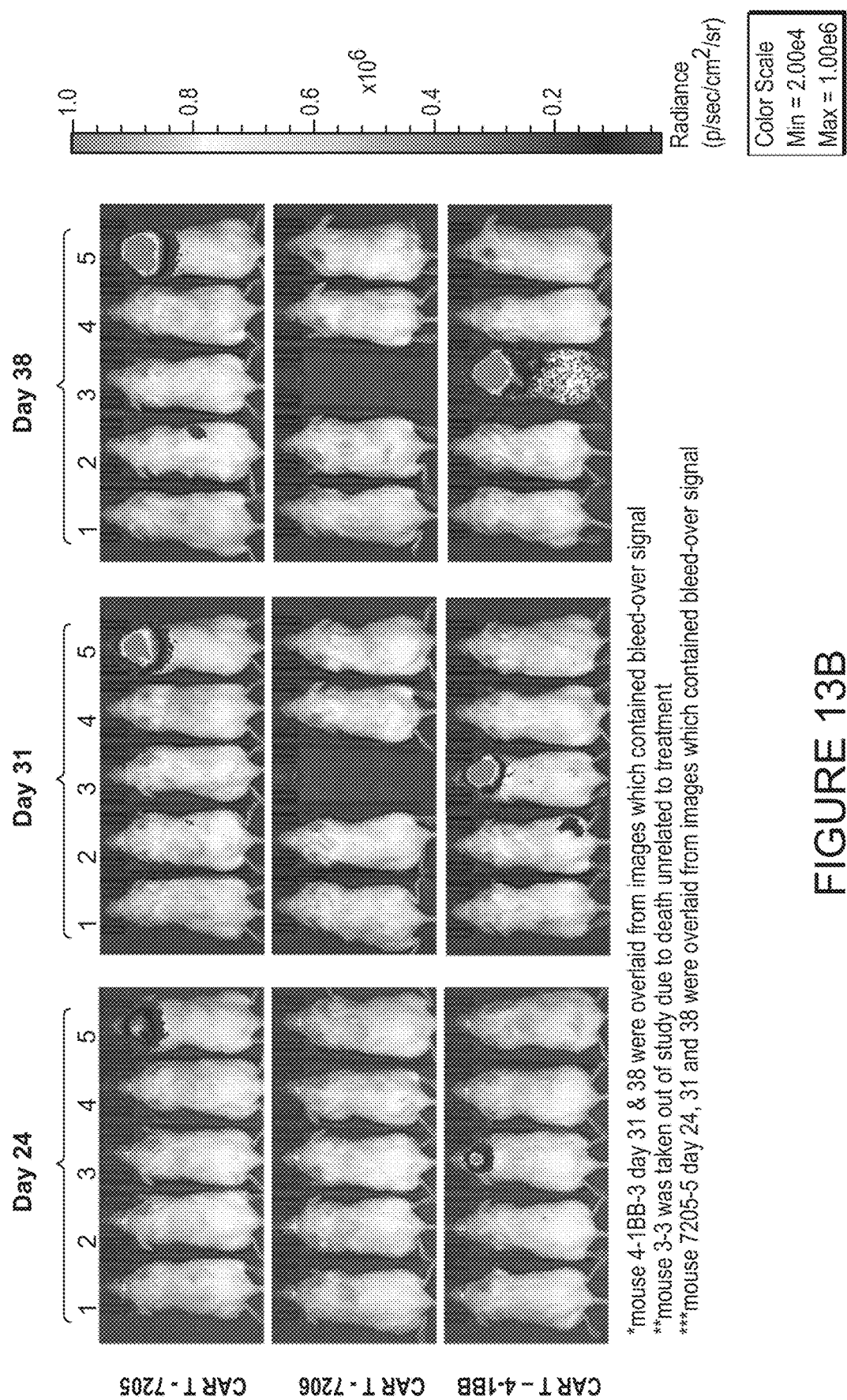
Figure 13C:
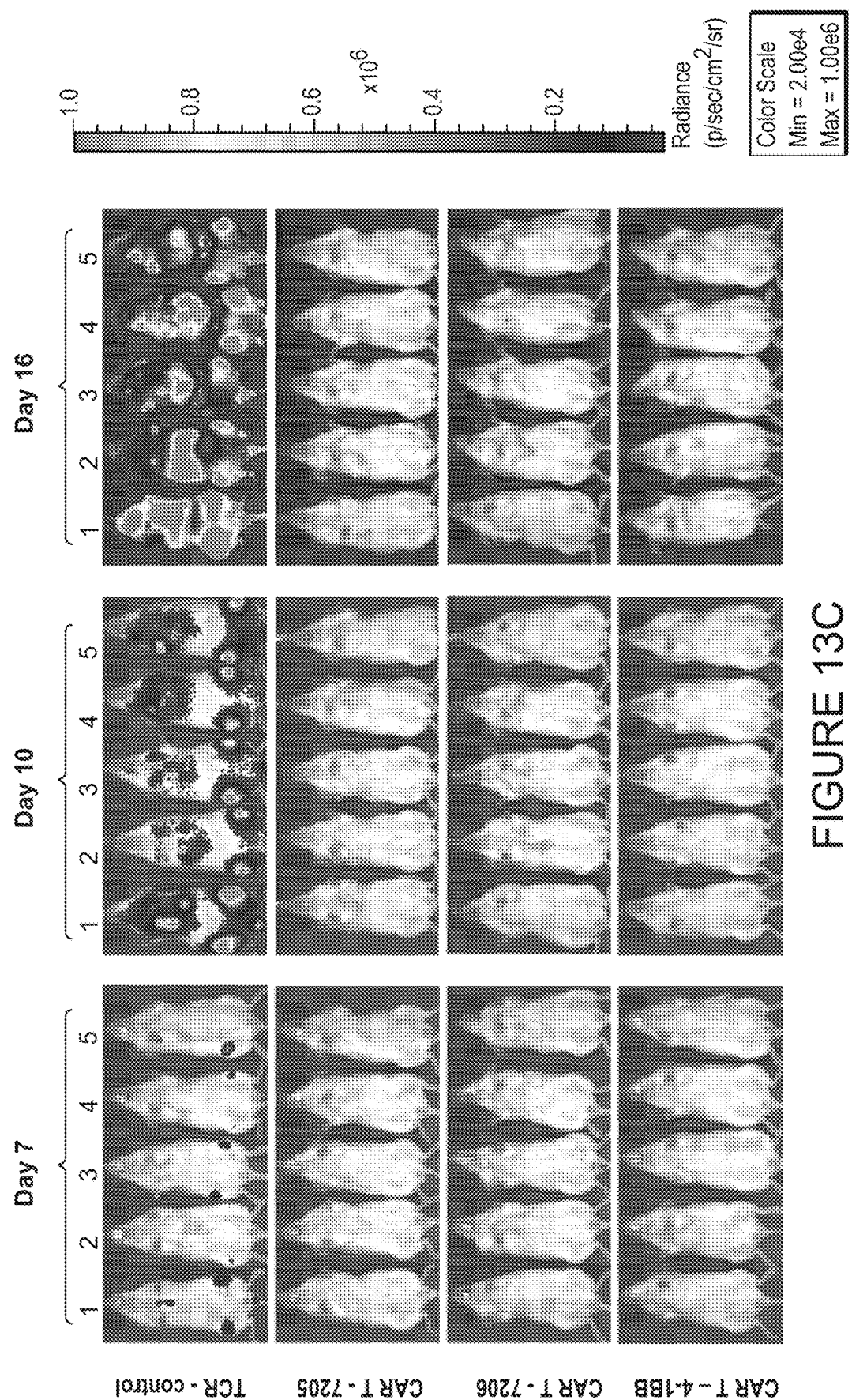
Figure 13D:
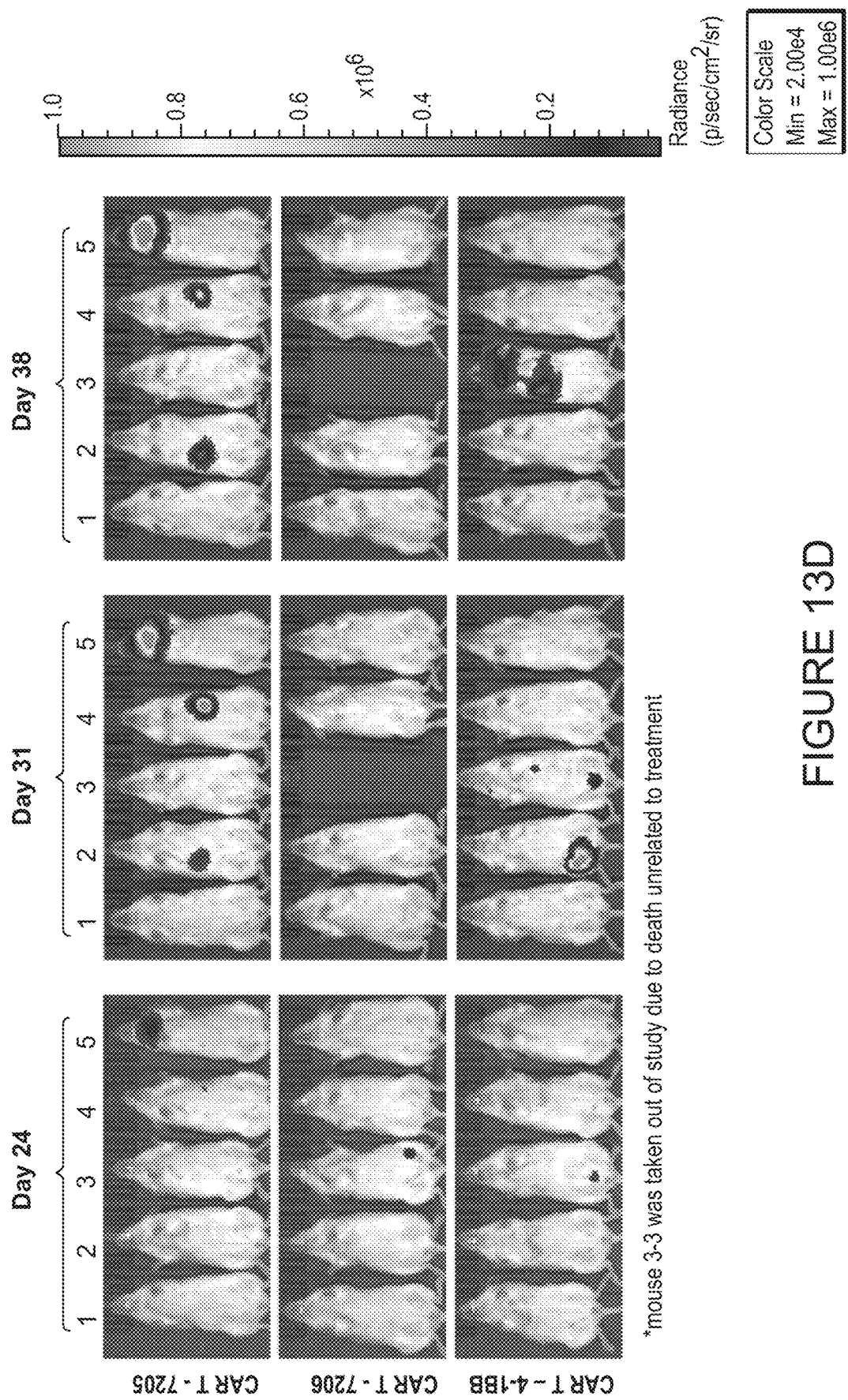
Figure 14:
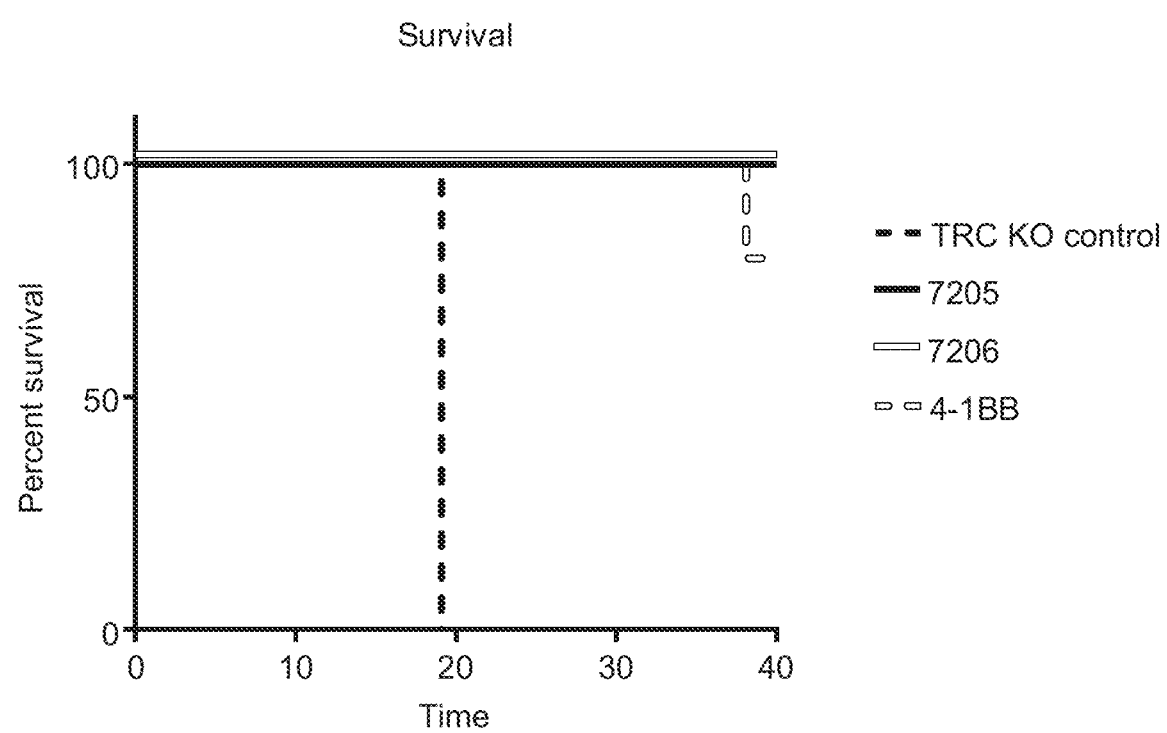
FIG. 14 shows a survival curve of mice following engraftment and growth of Raji-ffluc cells and subsequent treatment with TCR KO cells, or CAR T cells bearing the 7205, 7206, or 4-1BB CAR constructs.

The result of the murine xenograft model of disseminated B cell lymphoma evaluating the efficacy of the CAR constructs described in Table 3 are displayed in FIGS. 12-14.

Engraftment and growth of Raji-ffluc cells in control mice receiving TCR KO cells was visible by ventral and dorsal imaging of mice at day 7 post-injection of Raji-ffluc, and rapid outgrowth of Raji cells was observed in these mice as indicated by increasing luminescence signal at Day 10 and Day 16 (FIG. 12, FIG. 13A, and FIG. 13C). In contrast, treatment of mice with CAR T cells bearing the 7205 (N6), 7206 (N6), and 7241 (4-1BB) constructs resulted in delayed tumor growth (FIG. 12 and FIG. 13). Raji outgrowth was detected starting at approximately Day 20 in a subset of mice in the 7205 (N6) and 7241 (4-1BB) CART groups, as evidenced by dorsal and ventral imaging of the animals. However, in the 7206 (N6) CAR T treatment group, appreciable tumor growth was not observed during the 40 day study.

As shown in FIG. 14, all 5 mice in the TRC KO control group were euthanized at day 19 due to the rapid onset of disease-related symptoms including complete hind-limb paralysis. However, treatment with CAR T cells produced using the 7205 (N6) and 7206 (N6) vectors enhanced survival of the mice, with all mice in these groups remaining alive at day 40 (one mouse in the 7206 group was removed from the study due to death unrelated to tumor growth or CAR T infusion). Mice treated with the 7241 4-1BB-containing CAR construct also extended this survival time of mice in this treatment group, with one mouse requiring euthanization at day 38, and the other four mice remaining alive through study day 40.

3. Conclusions

Treatment of mice engrafted with Raji-ffluc CD19+ cells with anti-CD19 CAR T cells expressing second generation CARs bearing the N6 co-stimulatory domain (in both the 7205 and the 7206 configurations) resulted in pro-longed survival of mice and a dramatic reduction in tumor burden compared to mice receiving TCR KO cells. Importantly, through study day 40, the 7205 (N6) construct appeared to perform comparably to the 7241 4-1BB containing-CAR, and the 7206 (N6) construct appeared to outperform both the 7205 (N6) and the 7241 (4-1BB) configurations in terms of durable suppression of Raji cell outgrowth. Overall, these data confirm the in vitro findings that the N6 co-stimulatory domain is functional as a co-stimulatory domain and supports the ability of CAR T cells to kill CD19+ targets in vivo, in agreement with experiments evaluating the in vitro activity of the constructs. Furthermore, constructs bearing the N6 co-stimulatory domain matched or exceeded the activity of a CAR T construct with the 4-1BB co-stimulatory domain.

Example 6

Characterization of a Third-Generation CAR Comprising Multiple Co-Stimulatory Domains

1. Production of CAR T Cells Expressing a Third-Generation CAR

Further constructs were prepared in order to evaluate the novel co-stimulatory domains encompassed by the invention as part of a third-generation CAR, wherein the intracellular signaling domains include two co-stimulatory domains and a CD3-ξ signaling domain.

Figure 15:
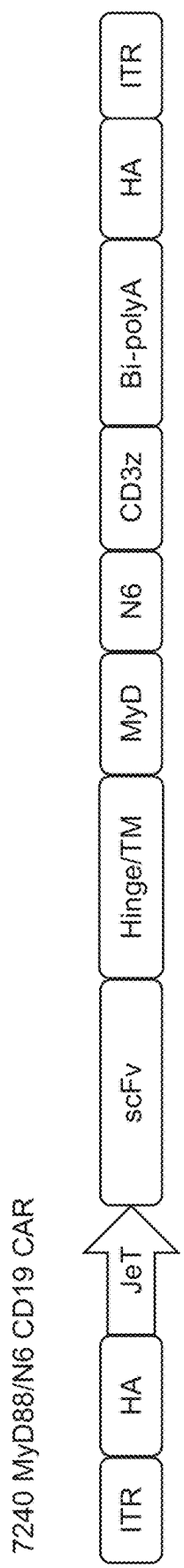
FIG. 15 shows the 7240 donor template construct comprising, from 5' to 3', a 5' inverted terminal repeat (ITR), a 5' homology arm, a promoter, coding sequences for an anti-CD19 scFv, a CD8 hinge and transmembrane domain, a MyD88 co-stimulatory domain, a Novel6 (N6) co-stimulatory domain, and a CD3 ξ intracellular signaling domain, an SV40 bi-polyA signal, a 3' homology arm, and a 3' ITR.
Figure 16A:
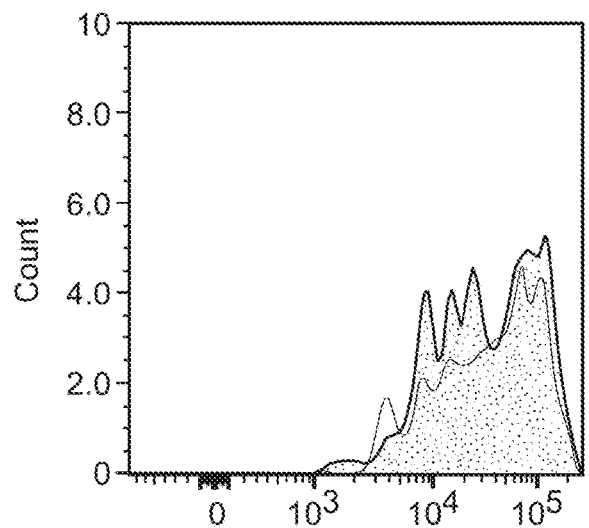
FIGS. 16A-16F show the results of a Cell Trace Violet proliferation assay using human T cells transfected to express an anti-CD19 CAR comprising the Novel6 (N6) co-stimulatory domain, or a CAR comprising both the MyD88 and Novel6 (N6) co-stimulatory domains. Transfected cells were labeled with Cell Trace Violet and co-cultured with CD19-negative K562 cells or engineered CD19-positive K562 cells (K19 cells). Proliferation was assessed by flow cytometry for CD4+ and CD8+ subsets of T cells.
Figure 16B:
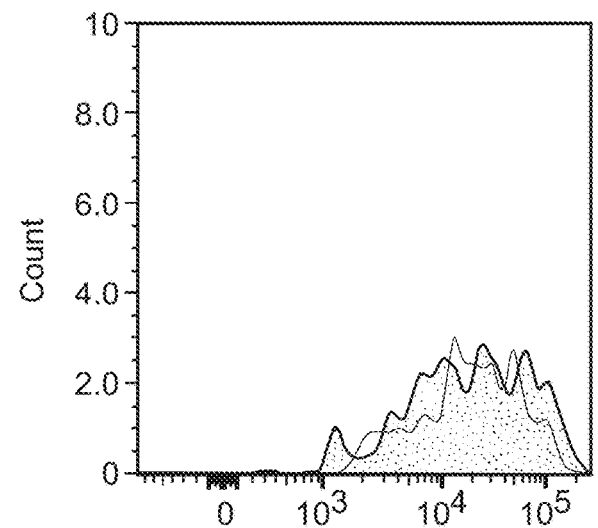
Figure 16C:
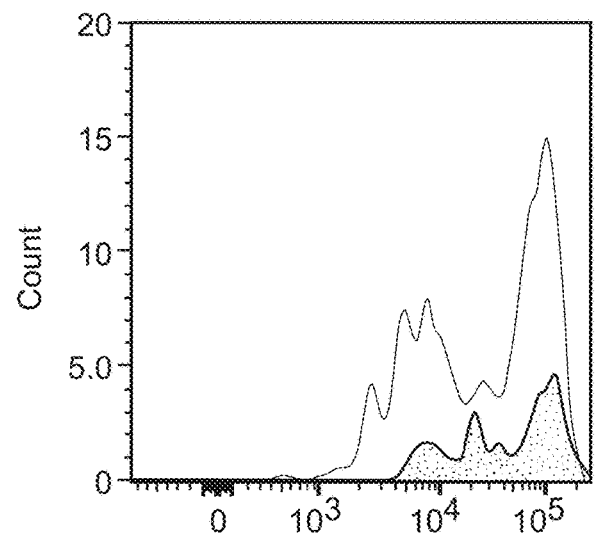
Figure 16D:
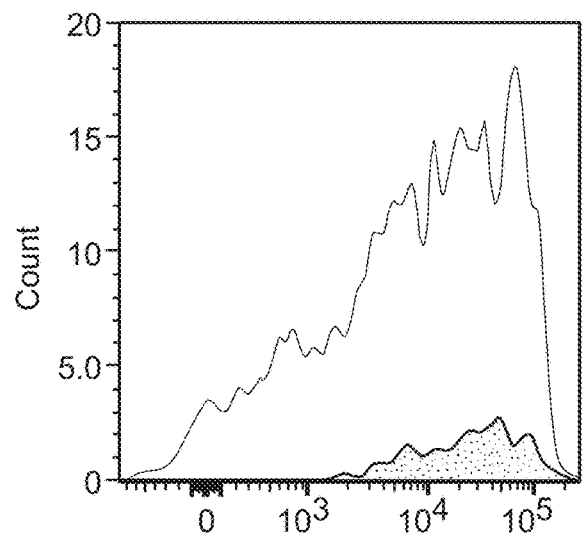
Figure 16E:
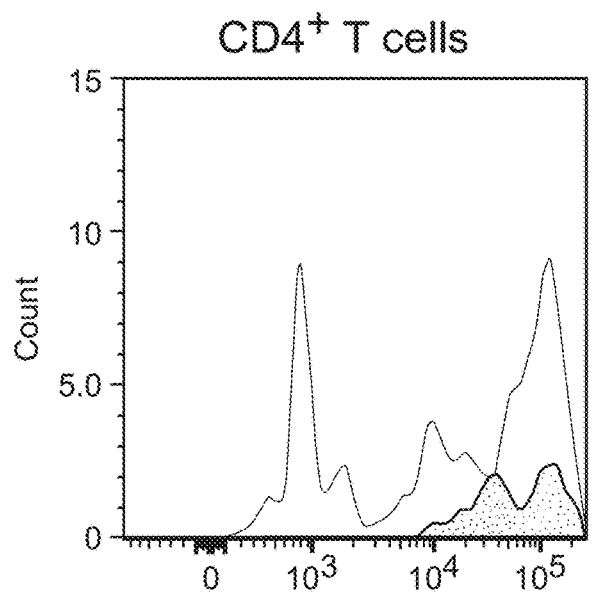
Figure 16F:
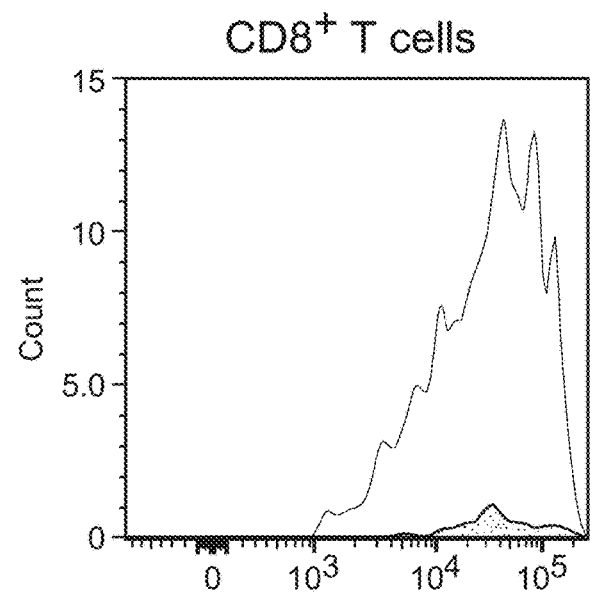

In certain examples, a third-generation anti-CD19 CAR was prepared which comprised, from 5' to 3', the signal sequence (SEQ ID NO: 16), FMC63-based CD19-specific scFv (SEQ ID NO: 17), and CD8 hinge and transmembrane domains (SEQ ID NO: 18) described above, followed by a MyD88 co-stimulatory domain (SEQ ID NO: 39; sequence obtained from WO 2016/036746), an N6 co-stimulatory domain (SEQ ID NO: 8), and a CD3-ξ signaling domain (SEQ ID NO: 19). The SV40 bi-polyA signal sequence comprising SEQ ID NO: 34 and SEQ ID NO: 35 was positioned 3' downstream of the CAR sequence. As described in previous examples, the sequence encoding this construct was cloned into the pDI plasmid, and expression of the CAR was controlled by the JeT promoter. Further, the transgene was flanked by TRAC homology arms to enable targeted gene insertion into the TRAC locus when this donor template was delivered in conjunction with the TRC1-2× 0.87EE site-specific endonuclease. This CAR transgene donor template was further flanked by inverted terminal repeat sequences. A MyD88/N6 CAR donor template is illustrated in FIG. 15, and the sequence of a vector comprising the donor template is provided as SEQ ID NO: 40.

In some experiments, the CAR donor template will be delivered as linearized DNA following linearization of the pDI plasmid. In other cases, the donor template will be packaged into AAV6 particles for viral delivery.

2. Evaluation of MyD88/N6 CAR T Cells for Cell Killing, Proliferation, and Cytokine Secretion In some experiments, MyD88/N6 CAR T cells are produced as described above in Example 4 by nucleofection of primed T cells with a linearized CAR template plasmid, the TRC 1-2×0.87EE meganuclease, and STING siRNA to reduce toxicity mediated by intracellular nucleic acid sensors. MyD88/N6 CAR T cells are further grown and expanded as described. MyD88/N6 CAR T cells are characterized for cell killing proficiency, proliferation, and cytokine secretion. To evaluate cell killing proficiency and proliferation, MyD88/N6 CAR T cells are subjected to an antigen-induced stress test as described in Example 3 above, wherein MyD88/N6 CAR T cells are co-cultured with K562 cells engineered to express CD19 ("K19" cells) at various effector:target ratios. Proliferation is also assessed as described in Example 4 by labeling cells with CellTrace Violet and co-culturing with antigen-bearing K19 cells at various effector:target ratios. Cytokine secretion (e.g., human IL-2, TNFα, and IFNγ) is determined as described in Example 2 above following co-culture with K19 cells at various effector:target ratios.

Similar experiments examining cell killing, proliferation, and cytokine secretion are conducted using transduction of recombinant AAV particles for delivery of the CAR donor template to primed T cells, which are further nucleofected with mRNA encoding the TRC 1-2×0.87EE meganuclease.

3. Proliferation of MyD88/N6 CAR T Cells

To compare the function of the N6 and MyD88/N6 co-stimulatory domains in CAR T cells, linearized plasmid DNA expressing the N6 co-stimulatory domain or the novel third-generation CAR containing the MyD88/N6 co-stimulatory domain were nucleofected into human T cells along with the TRC1-2×0.87EE site-specific endonuclease and STING siRNA. The MyD88/N6 CAR coding construct is illustrated in FIG. 15. The construct encoding the N6 CAR is referred to as 7206 and is provided as SEQ ID NO: 38. The construct encoding the MyD88/N6 CAR is referred to as 7240 and is provided as SEQ ID NO: 40.

After nucleofection, cells were grown in X-Vivo media (Lonza) supplemented with 5% FBS and 30 ng/ml IL-2 (Gibco) for 5 days. On day 5, remaining CD3$^+$ T cells were labeled using the human CD3 positive selection kit II (StemCell Technologies) and magnetically removed as per the manufacturer's recommendations. Remaining CD3-depleted fractions were re-suspended in X-Vivo media supplemented with 10 ng/ml IL-15 and 3 ng/ml IL-21 (Gibco) and grown for an additional 2 days. To prepare samples for the assay, $2e^6$ T cells from the N6 and MyD88/N6 conditions, as well as TRC1-2×0.87EE only treated control T cells, were labeled in vitro with a 2 µM solution of cell trace violet (CTV) solution. Post-incubation, CTV labeling consistency and CAR T cell frequencies were assessed on the Becton-Dickinson LSR:Fortessa flow cytometer after staining with CD19-Biotin Fc (Acro Biosystems) and Streptavidin PE (BD). For the proliferation assay, CAR T cell frequencies were normalized to 1% of the total T cell population added, with $2e^5$ total T cells ($2e^3$ CAR T cells) added to duplicate wells on a 96-well round bottom plate in X-Vivo media without cytokine supplementation. To assess antigen-specific CAR T cell proliferation, $4e^3$ K19 cells were added to one well with $4e^3$ K562 cells added to the second in order to calculate non-specific, background proliferation. Cells were mixed and incubated for a total of 6 days.

On day 6 post-co-culture, cells were spun down and washed twice with PBS. To analyze proliferation of individual T cell subsets, samples were stained with CD4 BV711 and CD8 BV785 antibodies (Biolegend), as well as ghost dye BV510 (TONBO biosciences) in order to exclude dead cells. After staining, samples were run and data was collected on the Becton-Dickinson LSR:Fortessa flow cytometer.

4. Results of Proliferation Studies

The results of the proliferation assay comparing the N6 and MyD88/N6 co-stimulatory domains are shown in FIG. 16. To gauge background proliferation of CAR negative populations, CTV dilution in T cells derived from the TRC-only nucleofected control sample were compared in wells co-cultured with either K19 or K562 cells. Importantly, both T cell subsets showed similar levels of non-specific proliferation in the presence of K19 (light shading) and K562 cells (dark shading), suggesting any proliferation was CD19-independent (FIGS. 16A and 16B). By comparison, both CD4$^+$ and CD8$^+$ T cells nucleofected with linearized plasmid DNA expressing the N6 co-stimulatory domain showed greater dilution of CTV in the presence of K19 cells compared to K562 controls, indicating substantial antigen-specific proliferation (FIGS. 16C and 16D). Notably, the same assessment done in T cells expressing the MyD88/N6 co-stimulatory domain also showed greater proliferation of CAR T cells in response to K19 cells (FIGS. 16E and 16F). The overall dilution of CTV was less in MyD88/N6 expressing T cells compared to CAR T cells expressing the N6 co-stimulatory domain alone; however, expression of either co-stimulatory domain resulted in greater dilution of CTV compared to TRC-only control T cells.

5. Conclusions

Nucleofection of primed T cells with linearized plasmid DNA expressing either the N6 or the third generation MyD88/N6 co-stimulatory domain resulted in CAR T cells that were able to proliferate, as indicated by dilution of CTV, in an antigen-specific manner. Furthermore, proliferation occurred in both CD4$^+$ and CD8$^+$ T cells subsets and above background seen in non-CAR expressing control cells. Collectively, this study demonstrated that both N6 and MyD88/N6 can function as co-stimulatory domains in CAR T cells.

Example 7

Characterization of Novel Co-Stimulatory Domains in an Inducible Construct

1. Production of CAR T Cells Expressing a First Generation CAR and an Inducible Construct Comprising a Novel Co-Stimulatory Domain Further constructs were prepared in order to evaluate the novel co-stimulatory domains encompassed by the invention as part of an inducible co-stimulatory construct, which is co-expressed with a first-generation anti-CD19 CAR comprising a CD3-ξ signaling domain.

In certain examples, a construct was prepared which comprised, from 5' to 3', an expression cassette for an inducible co-stimulatory construct, a T2A element, and a CAR expression cassette encoding a first-generation anti-CD19 CAR.

The first generation anti-CD19 CAR encoded by the CAR expression cassette included, from 5' to 3', the signal sequence (SEQ ID NO: 16), the FMC63-based CD19-specific scFv (SEQ ID NO: 17), and the CD8 hinge and transmembrane domains (SEQ ID NO: 18) described above, with an intracellular region comprising a CD3-ξ signaling domain (SEQ ID NO: 19). The SV40 bi-polyA signal sequence comprising SEQ ID NO: 34 and SEQ ID NO: 34 was positioned 3' downstream of the CAR sequence.

The inducible co-stimulatory construct included, from 5' to 3', either an N6 co-stimulatory domain alone (SEQ ID NO: 8), or a MyD88 domain (SEQ ID NO: 39) and an N6 domain (SEQ ID NO: 8) in tandem, followed by an Fv domain comprising two tandem ligand-binding FKBP12v36 domains (SEQ ID NO: 41; sequences obtained from WO 2015/123527), which bind the small molecule rimiducid to induce dimerization of the construct and activation of co-stimulatory signaling.

As described in previous examples, these constructs were cloned into the pDI plasmid, and expression of both the inducible co-stimulatory construct and the anti-CD19 CAR were controlled by the JeT promoter. Further, these constructs were flanked by TRAC homology arms to enable targeted gene insertion into the TRAC locus when delivered in conjunction with the TRC1-2×0.87EE site-specific endonuclease. These constructs were further flanked by inverted terminal repeat sequences.

In some experiments, the donor template will be delivered as linearized DNA following linearization of the pDI plasmid. In other cases, the donor template will be packaged into AAV6 particles for viral delivery.

Cells expressing the anti-CD19 CAR in conjunction with an inducible co-stimulatory construct having only the N6 co-stimulatory domain are referred to as iN6 CAR T cells. Cells expressing the anti-CD19 CAR in conjunction with an inducible co-stimulatory construct having both the MyD88 and N6 co-stimulatory domains are referred to as iMyD88/N6 CAR T cells.

2. Evaluation of CAR T Cells with Inducible Constructs for Cell Killing, Proliferation, and Cytokine Secretion In some experiments, iN6 CAR T cells or iMyD88/N6 CAR T cells are produced as described above in Example 4 by nucleofection of primed T cells with a linearized template plasmid, the TRC 1-2×0.87EE meganuclease, and STING siRNA to reduce toxicity mediated by intracellular nucleic acid sensors. iN6 CAR T cells or iMyD88/N6 CAR T cells are further grown and expanded as described.

iN6 CAR T cells and iMyD88/N6 CAR T cells are characterized for cell killing proficiency, proliferation, and cytokine secretion in both the presence and absence of the small molecule rimiducid, which induces dimerization of the inducible construct and initiates co-stimulatory signaling in the cell. To evaluate cell killing proficiency and proliferation, CAR T cells are subjected to an antigen-induced stress test as described in Example 3 above, wherein the CAR T cells are co-cultured with K562 cells engineered to express CD19 ("K19" cells) at various effector:target ratios. Proliferation is also assessed as described in Example 4 by labeling cells with CellTrace Violet and co-culturing with antigen-bearing K19 cells at various effector:target ratios. Cytokine secretion (e.g., human IL-2, TNFα, and IFNγ) is determined as described in Example 2 above following co-culture with K19 cells at various effector:target ratios.

Similar experiments examining cell killing, proliferation, and cytokine secretion are conducted using transduction of recombinant AAV particles for delivery of the donor template to primed T cells, which are further nucleofected with mRNA encoding the TRC 1-2×0.87EE meganuclease.

3. Proliferation of iMyD88/N6 CAR T Cells

Figure 17:
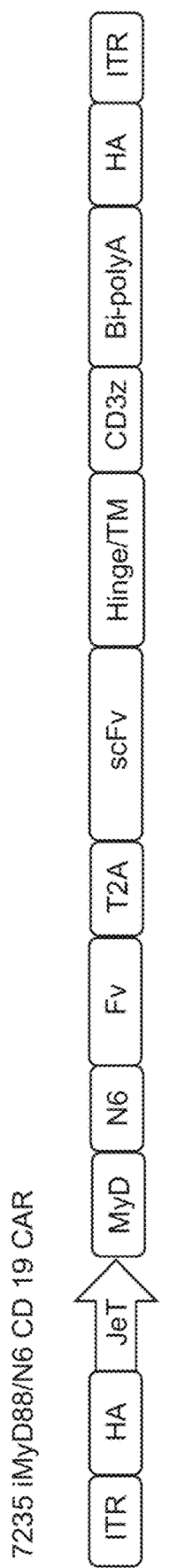
FIG. 17 shows the 7235 donor template construct comprising, from 5' to 3', a 5' inverted terminal repeat (ITR), a 5' homology arm, a promoter, coding sequences for a MyD88 co-stimulatory domain, a Novel6 (N6) co-stimulatory domain, and tandem ligand-binding FKBP12v36 domains (Fv), a T2A element, coding sequences for an anti-CD19 scFv, a CD8 hinge and transmembrane domain, and a CD3 ξ intracellular signaling domain, an SV40 bi-polyA signal, a 3' homology arm, and a 3' ITR.

To characterize the functionality of novel co-stimulatory domains in an inducible construct, primed T cells were nucleofected with linearized plasmid DNA expressing an iMyD88/N6 inducible co-stimulatory construct or, as a control, the N6 co-stimulatory domain expressed as part of the CAR. Cells were further nucleofected with the TRC1-2×0.87EE site-specific endonuclease and STING siRNA as described above. As a negative control, a separate sample was nucleofected with the TRC1-2×0.87EE site-specific endonuclease and STING siRNA only. The CAR donor template construct is illustrated in FIG. 17. As described above, the construct encoding the N6 CAR is referred to as 7206 and is provided as SEQ ID NO: 38. The construct encoding the iMyD88/N6 co-stimulatory domain is referred to as 7235 and is provided as SEQ ID NO: 42.

Post-nucleofection, T cell samples were rested for 6 hours in X-Vivo (Lonza) media supplemented with 5% FBS and 30 ng/ml IL-2 (Gibco). Samples were then split in half into separate wells, with one well receiving rimiducid at a final concentration of 5 nanomolar and the other well left untreated. Cells were subsequently incubated for 5 days. On day 5, remaining CD3+ T cells were labeled using the human CD3 positive selection kit II (StemCell Technologies) and magnetically removed as per the manufacturer's recommendations. Remaining CD3-depleted fractions were re-suspended in X-Vivo media supplemented with 10 ng/ml IL-15 and 3 ng/ml IL-21 (Gibco). Samples that had received rimiducid on day 0 post-nucleofection were spiked with fresh rimiducid at a final concentration of 5 nanomolar, while untreated samples were resuspended in cytokine supplemented X-Vivo alone. Cells were then incubated for an additional 2 days.

To prepare samples for the assay, $2e^6$ T cells from the iMyD88/N6 and N6 conditions that had or had not received rimiducid, as well as TRC1-2×0.87EE-only treated control T cells, were labeled in vitro with a 2 μM solution of cell trace violet (CTV) solution. Post-incubation, CTV labeling consistency and CAR T cell frequencies were assessed on the Becton-Dickinson LSR:Fortessa flow cytometer after staining with CD19-Biotin Fc (Acro Biosystems) and Streptavidin PE (BD). CAR T cell frequencies were normalized to 1% of the total T cell population added, with $2e^5$ total T cells ($2e^3$ CAR T cells) added to two separate wells on a 96-well round bottom plate in X-Vivo media without cytokine supplementation. One well then received $4e^3$ target K19 cells, while the other received $4e^3$ K562 cells as a control. Rimiducid was then added to samples that had received rimiducid on day 0 and day 5 post-nucleofection respectively. Cells were mixed and incubated for a total of 6 days.

On day 6 post-co-culture, samples were stained for flow cytometric analysis. To quantitate proliferation of individual T cell subsets, samples were stained with CD4 BV711 and CD8 BV785 antibodies (Biolegend), with the exclusion of dead cells during analysis occurring by addition of ghost dye BV510 (TONBO biosciences) to the staining cocktail. After staining, samples were run and data was collected on the Becton-Dickinson LSR:Fortessa flow cytometer.

4. Results of Proliferation Studies

The results of the proliferation assay comparing the novel inducible co-stimulatory construct iMyD88/N6 to the N6 CAR are shown in FIGS. 18-20. CD4+ and CD8+ T cells from non-CAR expressing TRC-only nucleofected cells showed similar levels of non-specific proliferation when co-cultured with either K19 (light shading) or K562 (dark shading) cells (FIGS. 18A and 18B).

Figure 19A:
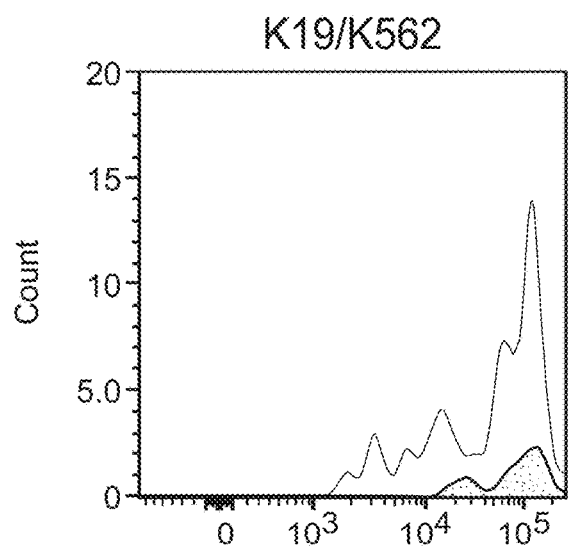
Figure 19B:
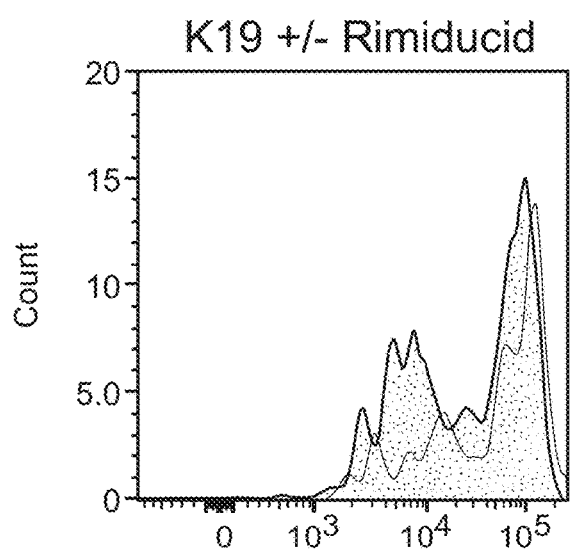
FIG. 19B shows the CD4+ subset of cells cultured on K19 cells in the presence or absence of rimiducid.
Figure 19C:
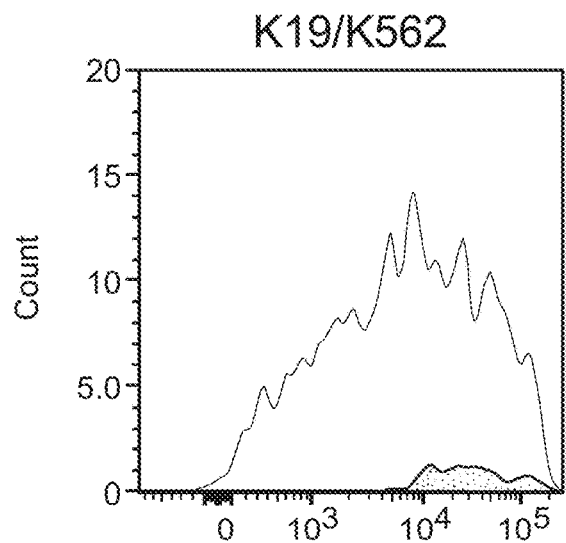
FIG. 19C shows the CD8+ subset of cells cultured on K19 or K562 cells.
Figure 19D:
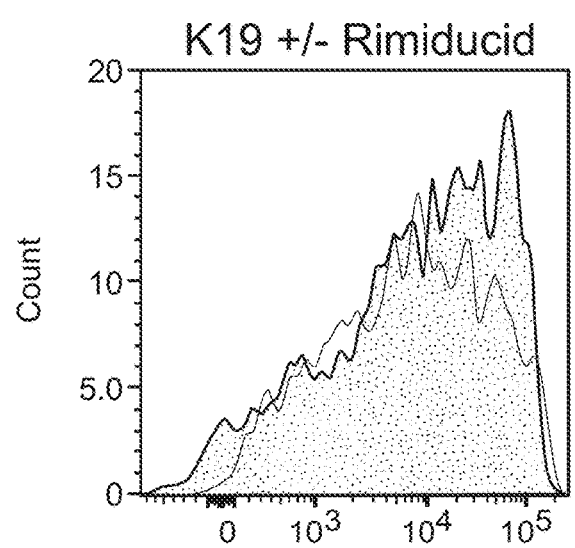
FIG. 19D shows the CD8+ subset of cells cultured on K19 cells in the presence or absence of rimiducid.

By contrast, proliferation of CAR T cells expressing an N6 CAR was antigen-dependent, as dilution of CTV was greater when co-cultured with K19 (light shading) as opposed to K562 (dark shading) cells (FIGS. 19A and 19C). Further, CAR T cells expressing the non-inducible N6 CAR showed substantial proliferation of both T cell subsets in the presence (dark shading) or absence (light shading) of rimiducid and K19 cells (FIGS. 19B and 19D), showing that rimiducid does not have any function in the absence of a switch-dependent co-stimulatory domain.

Figure 20A:
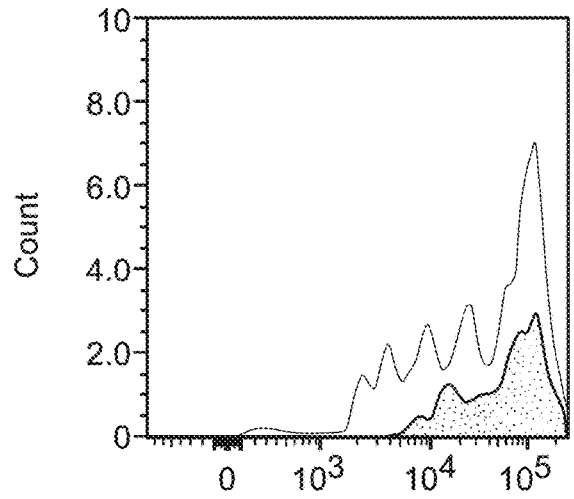
FIGS. 20A-20D show the show the results of a Cell Trace Violet proliferation assay using human T cells transfected to express an anti-CD19 CAR lacking a co-stimulatory domain in combination with an inducible construct comprising both the MyD88 and the Novel6 (N6) co-stimulatory domains (iMyD88/N6 CAR). Transfected cells were labeled with Cell Trace Violet and co-cultured with CD19-negative K562 cells or engineered CD19-positive K562 cells (K19 cells). Further, cells were assessed in K19 co-culture in the presence or absence of rimiducid. Proliferation was assessed by flow cytometry for CD4+ and CD8+ subsets of T cells.
Figure 20B:
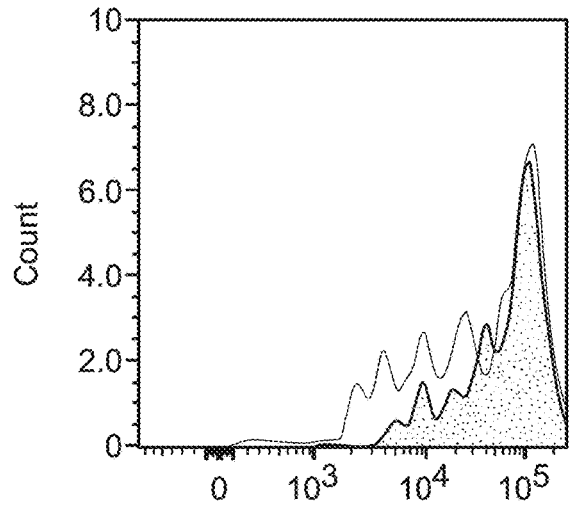
Figure 20C:
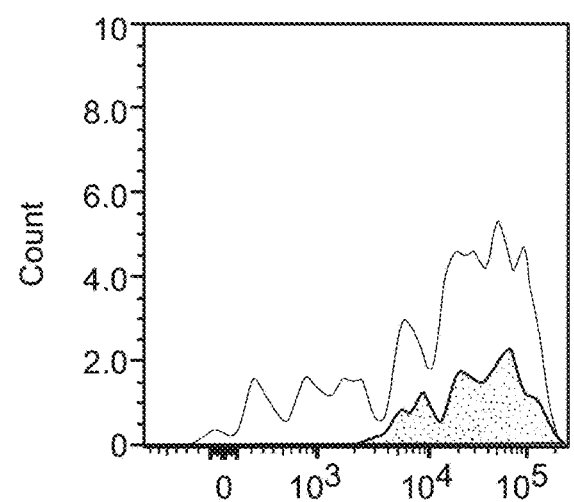
Figure 20D:
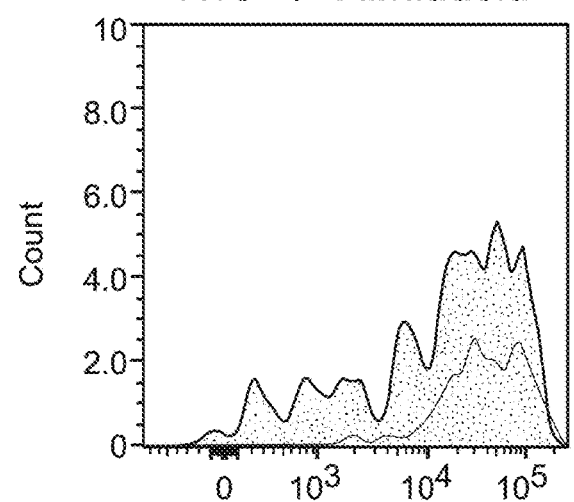

For the inducible co-stimulatory construct, proliferation of both CD4+ and CD8+ T cells expressing iMyD88/N6 was greater when co-cultured with K19 (light shading) cells compared to K562 control cells (dark shading) (FIGS. 20A and 20C). Importantly, increased CTV dilution was dependent on rimiducid (dark shading) compared to non-rimiducid treated samples (light shading) when cultured with K19 cells for both T cell subsets analyzed, supporting the inducible function of the iMyD88/N6 switch (FIGS. 20B and 20D).

5. Conclusions

The expression of the novel inducible co-stimulatory construct iMyD88/N6 on CAR T cells resulted in the proliferation of both $CD4^+$ and $CD8^+$ T cells that was antigen-dependent. Strikingly, dilution of CTV on cultured T cells was greatest in the presence of rimiducid, showing the inducible nature of the co-stimulatory domain constructs when expressed in CAR T cells. As rimiducid had no effect on CAR T cell proliferation when the co-stimulatory domain is expressed as part of the CAR, these data support the functionality of the novel switch co-stimulatory domains on CAR T cell function.

The invention claimed is:

1. A nucleic acid molecule comprising a nucleotide sequence encoding a co-stimulatory domain comprising an amino acid sequence set forth in SEQ ID NO: 8.

2. The nucleic acid molecule of claim 1, wherein said nucleotide sequence encodes a chimeric antigen receptor (CAR) comprising said co-stimulatory domain.

3. The nucleic acid molecule of claim 2, wherein said CAR comprises a CD3 ξ intracellular signaling domain.

4. The nucleic acid molecule of claim 1, wherein said nucleic acid molecule is an mRNA, a recombinant DNA construct, or a viral genome of a viral vector.

5. A recombinant DNA construct comprising the nucleic acid molecule of claim 1.

6. A viral vector comprising the nucleic acid molecule of claim 1.

7. The viral vector of claim 6, wherein said viral vector is a recombinant AAV vector.

8. A genetically-modified human T cell comprising in its genome an expression cassette comprising the nucleic acid molecule of claim 1.

9. The genetically-modified human T cell of claim 8, wherein said nucleic acid molecule comprises a nucleotide sequence encoding a CAR comprising said co-stimulatory domain.

10. A method for producing a genetically-modified human T cell comprising a CAR said method comprising introducing into a human T cell the nucleic acid molecule of claim 2 using a viral vector.

11. The method of claim 10, wherein said method further comprises
introducing into said human T cell a second nucleic acid molecule encoding an engineered nuclease,
wherein said engineered nuclease is expressed in said cell,
wherein said engineered nuclease recognizes and cleaves a recognition sequence in the genome of said cell to produce a cleavage site,
and wherein said nucleic acid molecule encoding said CAR is inserted into the genome of said human T cell at said cleavage site.

12. The method of claim 11, wherein said engineered nuclease is an engineered meganuclease, a recombinant zinc-finger nuclease (ZFN), a recombinant transcription activator-like effector nuclease (TALEN), a CRISPR/Cas nuclease, or a megaTAL nuclease.

13. The method of claim 12, wherein said engineered nuclease is an engineered meganuclease.

14. The method of claim 11, wherein said nucleic acid molecule encoding said CAR comprises sequences homologous to sequences flanking said cleavage site, such that said nucleic acid molecule is inserted into the genome of said cell at said cleavage site by homologous recombination.

15. A pharmaceutical composition comprising a pharmaceutically-acceptable carrier and the genetically-modified human T cell of claim 9.

16. The nucleic acid molecule of claim 2, wherein said CAR comprises a CD8 hinge region and a CD8 transmembrane domain.

17. The nucleic acid molecule of claim 2, wherein said CAR comprises a CD19-specific antigen-binding domain.

18. The nucleic acid molecule of claim 2, wherein said CAR comprises an amino acid sequence set forth in SEQ ID NO: 28.

19. The genetically-modified human T cell of claim 9, wherein said CAR comprises a CD3 ξ intracellular signaling domain.

20. The genetically-modified human T cell of claim 9, wherein said CAR comprises a CD8 hinge region and a CD8 transmembrane domain.

21. The genetically-modified human T cell of claim 9, wherein said CAR comprises a CD19-specific antigen-binding domain.

22. The genetically-modified human T cell of claim 9, wherein said CAR comprises an amino acid sequence set forth in SEQ ID NO: 28.

23. The method of claim 11, wherein said nucleic acid molecule encoding said CAR is introduced into said human T cell using a recombinant AAV vector, and wherein said second nucleic acid molecule encoding said engineered nuclease is an mRNA.

* * * * *